(12) United States Patent
Summa et al.

(10) Patent No.: US 7,981,879 B2
(45) Date of Patent: Jul. 19, 2011

(54) HIV INTEGRASE INHIBITORS

(75) Inventors: Vincenzo Summa, Rome (IT); Paola Pace, Rome (IT)

(73) Assignee: Instituto di Ricerchi di Biologia Molecolare P. Angeletti S.p.A., Rome (IT)

( * ) Notice: Subject to any disclaimer, the term of this patent is extended or adjusted under 35 U.S.C. 154(b) by 819 days.

(21) Appl. No.: 11/887,305

(22) PCT Filed: Mar. 22, 2006

(86) PCT No.: PCT/GB2006/001062
§ 371 (c)(1),
(2), (4) Date: Sep. 27, 2007

(87) PCT Pub. No.: WO2006/103399
PCT Pub. Date: Oct. 5, 2006

(65) Prior Publication Data
US 2009/0253681 A1    Oct. 8, 2009

Related U.S. Application Data

(60) Provisional application No. 60/666,897, filed on Mar. 31, 2005.

(51) Int. Cl.
*A61P 31/00* (2006.01)
*A61K 31/553* (2006.01)
*C07D 498/04* (2006.01)

(52) U.S. Cl. ............ 514/211.05; 514/211.1; 540/490; 540/552

(58) Field of Classification Search ............ 514/211.05, 514/211.1; 540/490, 552
See application file for complete search history.

(56) References Cited

U.S. PATENT DOCUMENTS

| | | |
|---|---|---|
| 6,262,055 B1 | 7/2001 | Young et al. |
| 6,306,891 B1 | 10/2001 | Selnick et al. |
| 6,380,249 B1 | 4/2002 | Young et al. |
| 6,841,558 B2 | 1/2005 | Anthony et al. |
| 6,919,351 B2 | 7/2005 | Anthony et al. |
| 6,921,759 B2 | 7/2005 | Anthony et al. |
| 7,037,908 B2 | 5/2006 | Naidu et al. |
| 7,115,601 B2 | 10/2006 | Naidu et al. |
| 7,135,467 B2 | 11/2006 | Walker et al. |
| 7,157,447 B2 | 1/2007 | Naidu et al. |
| 7,169,780 B2 | 1/2007 | Crescenzi et al. |
| 7,173,022 B2 | 2/2007 | Naidu et al. |
| 7,176,196 B2 | 2/2007 | Naidu et al. |
| 7,192,948 B2 | 3/2007 | Banville et al. |
| 7,211,572 B2 | 5/2007 | Miyazaki et al. |
| 7,217,713 B2 | 5/2007 | Crescenzi et al. |
| 7,232,819 B2 | 6/2007 | Di Francesco et al. |
| 7,273,859 B2 | 9/2007 | Naidu |
| 7,279,487 B2 | 10/2007 | Egbertson et al. |
| 7,414,045 B2 | 8/2008 | Crescenzi et al. |
| 7,419,969 B2 | 9/2008 | Naidu et al. |
| 7,435,734 B2 | 10/2008 | Crescenzi et al. |
| 7,459,452 B2 | 12/2008 | Di Francesco et al. |
| 7,491,819 B1 | 2/2009 | Naidu et al. |
| 7,511,037 B2 | 3/2009 | Naidu et al. |
| 2003/0229079 A1 | 12/2003 | Payne et al. |
| 2004/0204498 A1 | 10/2004 | Walker et al. |
| 2004/0229892 A1 | 11/2004 | Naidu et al. |
| 2004/0229909 A1 | 11/2004 | Kiyama et al. |
| 2005/0010048 A1 | 1/2005 | Zhuang et al. |
| 2005/0054645 A1 | 3/2005 | Miyazaki et al. |
| 2006/0046985 A1 | 3/2006 | Crescenzi et al. |
| 2006/0106007 A1 | 5/2006 | Naidu et al. |
| 2006/0276466 A1 | 12/2006 | Naidu et al. |
| 2007/0083045 A1 | 4/2007 | Di Francesco et al. |
| 2007/0123524 A1 | 5/2007 | Crescenzi et al. |
| 2007/0149556 A1 | 6/2007 | Mikamiyama et al. |

FOREIGN PATENT DOCUMENTS
WO  WO 2005/061490 A1  7/2005
WO  WO 2007/064316 A1  6/2007

OTHER PUBLICATIONS

Pearl, L. et al. "A structural model for the retroviral proteases", Nature, 1987, vol. 329, pp. 351-354.
Power, M. et al. "Nucleotide Sequence of SRV-1, a Type D Simian Acquired Immune Deficiency Syndrome Retrovirus", Science, 1986, vol. 231, pp. 1567-1572.
Ratner, L. et al. "Complete nucleotide sequence of the AIDS virus, HTLV-III", Nature, 1985, vol. 313, pp. 277-284. Thornber, C. "Isosterism and Molecular Modification in Drug Design", Chemical Society Reviews, 1979, vol. 8, pp. 563-580.
Toh, H. et al. "Close structural resemblance between putative polymerase of a *Drosophila* transposable genetic element 17.6 and pol gene product of Moloney murine leukaemia virus", The EMBO Journal, 1985, vol. 4, pp. 1267-1272.

*Primary Examiner* — Brenda L Coleman
(74) *Attorney, Agent, or Firm* — Kenneth R. Walton; Sheldon O. Heber

(57) ABSTRACT

Compounds of Formula I are inhibitors of FHV integrase and inhibitors of FHV replication (I), wherein m, n, X, $R^1$, $R^2$, $R^3$, $R^4$, $R^5$, $R^6$, $R^7$; $R^8$, $R^9$ and $R^{10}$ are defined herein. The compounds are useful for the prophylaxis or treatment of infection by HTV and the prophylaxis, treatment, or delay in the onset of AIDS. The compounds are employed against HTV infection and ADDS as compounds per se or in the form of pharmaceutically acceptable salts. The compounds and their salts can be employed as ingredients in pharmaceutical compositions, optionally in combination with other antivirals, immunomodulators, antibiotics or vaccines.

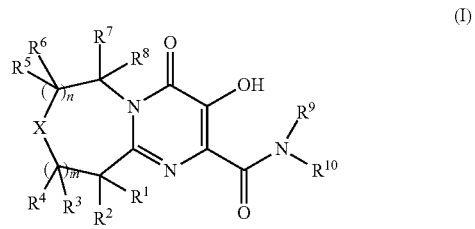

(I)

14 Claims, No Drawings

HIV INTEGRASE INHIBITORS

CROSS-REFERENCE TO RELATED APPLICATIONS

This application is a 371 application of International Application No. PCT/GB2006/001062 filed on Mar. 22, 2006, which claims the benefit of U.S. Provisional Application No. 60/666,897, filed Mar. 31, 2005, the disclosure of which is incorporated by reference herein in its entirety.

FIELD OF THE INVENTION

The present invention is directed tetrahydropyrazinopyrimidine carboxamides and related compounds and pharmaceutically acceptable salts thereof, their synthesis, and their use as inhibitors of the HIV integrase enzyme. The compounds and pharmaceutically acceptable salts thereof of the present invention are useful for the prophylaxis or treatment of infection by HIV and for the prophylaxis, treatment, or delay in the onset of AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:
U.S. Pat. No. 6,380,249, U.S. Pat. No. 6,306,891, and U.S. Pat. No. 6,262,055 disclose 2,4-dioxobutyric acids and acid esters useful as HIV integrase inhibitors.

US 2003/0229079 (corresponding to WO 01/00578) discloses 1-(aromatic- or heteroaromatic-substituted)-3-(heteroaromatic substituted)-1,3-propanediones useful as HIV integrase inhibitors.

US 2003/0055071 (corresponding to WO 02/30930), US 2004/0034221 (corresponding to WO 02/30426), and US 2004/0044207 (corresponding to WO 02/55079) each disclose certain 8-hydroxy-1,6-naphthyridine-7-carboxamides as HIV integrase inhibitors.

US 2005/010048 (corresponding to WO 02/036734) discloses certain aza- and polyaza-naphthalenyl ketones to be NV integrase inhibitors.

US2004/229909 (corresponding to WO 2003/016275) discloses certain compounds having integrase inhibitory activity.

WO 03/35076 discloses certain 5,6-dihydroxypyrimidine-4-carboxamides as HIV integrase inhibitors, and US 2005/025774 (corresponding to WO 03/35077) discloses certain N-substituted 5-hydroxy-6-oxo-1,6-dihydropyrimidine-4-carboxamides as HIV integrase inhibitors.

WO 03/062204 discloses certain hydroxynaphthyridinone carboxamides that are useful as HIV integrase inhibitors.

US 2004/204498 (corresponding to WO 2004/062613) and US 2004/229892 (corresponding to WO 2004/096128) disclose certain pyrimidine carboxamides that are useful as HIV integrase inhibitors.

WO 2005/016927 discloses certain nitrogenous condensed ring compounds that are HIV integrase inhibitors.

WO 2005/061490 discloses certain hydroxypyrimidinone derivatives having HIV integrase inhibitory activity. Various pyrimidinone compounds useful as HIV integrase inhibitors are also disclosed in WO 2005/115398, WO 2005/118589, WO 2005/118590, WO 2005/118593, and US 2005/0256109.

SUMMARY OF THE INVENTION

The present invention is directed to tetrahydropyrazinopyrimidine carboxamides and related compounds. These compounds are useful in the inhibition of HIV integrase, the prophylaxis or treatment of infection by HIV, and the prophylaxis, treatment, or delay in the onset of AIDS and/or ARC, either as compounds or their pharmaceutically acceptable salts or hydrates (when appropriate), or as pharmaceutical composition ingredients, whether or not in combination with other HIV antivirals, anti-infectives, immunomodulators, antibiotics or vaccines. More particularly, the present invention includes compounds of Formula I, and pharmaceutically acceptable salts thereof:

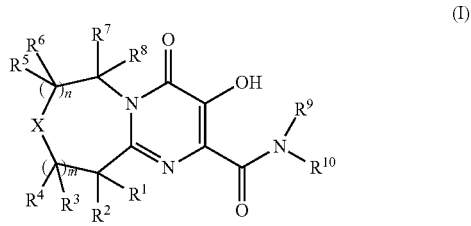

wherein:
X is $N(R^K)$, O, S, S(O), $S(O)_2$,

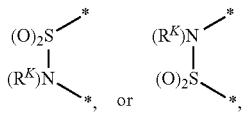

where each * denotes the point of attachment to the rest of the molecule;
$R^K$ is:
(1) H,
(2) $C_{1-6}$ alkyl,
(3) $C_{1-6}$ alkyl substituted with T, wherein T is $CO_2R^A$, CN, $SO_2R^A$, $N(R^D)R^E$, $C(O)N(R^D)R^E$, $N(R^A)$—C(O)C(O)—$N(R^D)R^E$, $N(R^A)$—$C(O)R^B$, $N(R^A)$—$SO_2R^B$, $N(R^A)$—$SO_2N(R^D)R^E$, or $N(R^A)$—$CO_2R^B$,
(4) $C_{1-6}$ haloalkyl,
(5) $C(O)R^A$,
(6) C(O)—$C_{1-6}$ haloalkyl,
(7) $CO_2R^A$,
(8) C(O)—U,
(9) C(O)—$C_{1-6}$ alkylene-U,
(10) $C(O)N(R^D)R^E$,
(11) C(O)—$C_{1-6}$ alkylene-$N(R^D)R^E$,
(12) C(O)C(O)—U,
(13) C(O)C(O)—$C_{1-6}$ alkylene-U,
(14) C(O)C(O)—$N(R^D)R^E$,
(15) C(O)C(O)—$C_{1-6}$ alkylene-$N(R^D)R^E$,
(16) $SO_2R^A$,
(17) $SO_2$—U,
(18) $SO_2$—$C_{1-6}$ alkylene-U,
(19) $SO_2N(R^D)R^E$,
(20) CycB,
(21) $C_{1-6}$ alkyl substituted with U, or
(22) $C_{1-6}$ alkyl substituted with $C(O)N(R^A)$—$C_{1-6}$ alkylene-U,
wherein U is CycB, AryB, or HetB;
m and n are each independently integers equal to zero, 1, or 2, with the proviso that m+n is zero, 1, or 2;
$R^1$ is:
(1) H,
(2) $C_{1-6}$ alkyl,
(3) $C_{1-6}$ haloalkyl,
(4) $C_{1-6}$ alkyl substituted with V, wherein V is OH, O—$C_{1-6}$ alkyl, O—$C_{1-6}$ haloalkyl, $SR^A$, $S(O)R^A$, $SO_2R^A$, $N(R^D)R^E$, $C(O)N(R^D)R^E$, $N(R^A)$—C(O)C(O)—$N(R^D)R^E$, $N(R^A)$—$C(O)R^B$, $N(R^A)$—$SO_2R^B$, $N(R^A)$—$C_{1-6}$ alkylene-$SO_2R^B$, $N(R^A)C(O)$—$C_{1-6}$ alkylene-$SO_2R^B$, $N(R^A)$—$SO_2N(R^D)R^E$, $N(R^A)$—$CO_2R^B$, or $N(R^A)$—$C(O)N(R^D)R^E$,
(5) $C_{1-6}$ alkyl substituted with W, wherein W is CycA, AryA, HetA, O—$C_{1-6}$ alkylene-CycA, O—$C_{1-16}$ alkylene-AryA, O—$C_{1-16}$ alkylene-HetA, $S(O)_j$—$C_{1-6}$ alkylene-CycA, $S(O)_j$—$C_{1-6}$ alkylene-AryA, $S(O)_j$—$C_{1-6}$ alkylene-HetA, $N(R^A)$—C(O)-AryA, or $N(R^A)$—C(O)-HetA,
(6) $N(R^A)$—$SO_2R^B$,
(7) $N(R^A)$—$SO_2N(R^D)R^E$,
(8) $N(R^A)$—$CO_2R^B$,
(9) $N(R^D)R^E$,
(10) $N(R^C)R^A$,
(11) $N(R^A)$—$C(O)R^B$,
(12) $N(R^C)$—$C(O)R^A$,
(13) $S(O)_jR^F$,
(14) $OR^F$,
(16) CycA,
(17) AryA,
(18) HetA,
(19) $N(R^A)$—C(O)-CycA,
(20) $N(R^A)$—C(O)-AryA,
(21) $N(R^A)$—C(O)-HetA,
(22) $N(R^A)$—C(O)—$N(R^D)R^E$,
(23) $N(R^C)$—C(O)-CycA,
(24) $N(R^C)$—C(O)-AryA,
(25) $N(R^C)$—C(O)-HetA,
(26) $N(R^C)$—C(O)—$N(R^D)R^E$,
(27) $N(R^A)$—C(O)C(O)-CycA,
(28) $N(R^A)$—C(O)C(O)-AryA,
(29) $N(R^A)$—C(O)C(O)-HetA,
(30) $N(R^A)$—C(O)C(O)—$N(R^D)R^E$,
(31) $N(R^C)$—C(O)C(O)-CycA,
(32) $N(R^C)$—C(O)C(O)-AryA,
(33) $N(R^C)$—C(O)C(O)-HetA, or
(34) $N(R^C)$—C(O)C(O)—$N(R^D)R^E$;
each j is independently an integer equal to zero, 1, or 2;
$R^2$ is H or $C_{1-6}$ alkyl; or alternatively $R^1$ and $R^2$ together with the ring carbon atom to which they are both attached form (i) a 3- to 7-membered saturated carbocyclic ring or (ii) a 4- to 7-membered saturated heterocyclic ring containing 1 or 2 heteroatoms independently selected from N, O and S, where independently each N is optionally substituted with $C_{1-6}$ alkyl and each S is optionally oxidized to S(O) or $S(O)_2$; (note: the ring formed by the joining of $R^1$ and $R^2$ provides a spiro ring system)
each $R^3$ is independently H or $C_{1-6}$ alkyl, and each $R^4$ is independently H or $C_{1-6}$ alkyl; or alternatively $R^3$ and $R^4$ attached to the same carbon atom together form oxo or thioxo;
each $R^5$ is independently H or $C_{1-6}$ alkyl, and each $R^6$ is independently H or $C_{1-6}$ alkyl; or alternatively $R^5$ and $R^6$ attached to the same carbon atom together form oxo or thioxo;
$R^7$ is H or $C_{1-6}$ alkyl;
$R^8$ is H or $C_{1-6}$ alkyl; or alternatively $R^7$ and $R^8$ together form oxo or thioxo;
$R^9$ is H or $C_{1-6}$ alkyl;
$R^{10}$ is $C_{1-6}$ alkyl substituted with CycC, AryC or HetC;
each $R^A$ is independently H or $C_{1-6}$ alkyl;
each $R^B$ is independently H or $C_{1-6}$ alkyl;
$R^C$ is $C_{1-6}$ alkyl substituted with CycA, AryA, or HetA; or alternatively, when X is $N(R^K)$ and $R^1$ includes the $N(R^C)$ moiety, $R^C$ and $R^K$ together with (i) the N atom to which $R^K$ is attached, (ii) the N atom to which $R^C$ is attached, (iii) the ring carbon to which $R^1$ is attached, and (iv) the zero, 1 or 2 ring carbons between X and the ring carbon to which $R^1$ is attached, form a fused 5- to 7-membered diazacycloalkyl ring, wherein the portion of the fused ring obtained from $R^C$ and $R^K$ is a 1- to 4-membered methylene chain optionally substituted with oxo or $C_{1-6}$ alkyl;
each $R^D$ and $R^E$ are each independently H or $C_{1-6}$ alkyl, or together with the nitrogen to which they are both attached form a 4- to 7-membered saturated heterocyclic ring optionally containing a heteroatom in addition to the nitrogen attached to $R^D$ and $R^E$ selected from N, O, and S, where the S is optionally oxidized to S(O) or $S(O)_2$, and wherein the saturated heterocyclic ring is optionally substituted with 1 or 2 substituents each of which is independently $C_{1-6}$ alkyl or $S(O)_2$—$C_{1-6}$ alkyl;
$R^F$ is $C_{1-6}$ alkyl, or alternatively, when X is $N(R^K)$ and $R^1$ is $SR^F$ or $OR^F$, $R^F$ and $R^K$ together with (i) the N atom to which $R^K$ is attached, (ii) the S or O atom to which $R^F$ is attached, (iii) the ring carbon to which $R^1$ is attached, and (iv) the zero, 1 or 2 ring carbons between X and the ring carbon to which $R^1$ is attached, form a fused 5- to 7-membered oxyazacycloalkyl or thioazacycloalkyl ring, wherein the portion of the fused ring obtained from $R^F$ and $R^K$ is a 1- to 4-membered methylene chain;

each CycA is independently $C_{3-8}$ cycloalkyl which is optionally substituted with a total of from 1 to 6 substituents, wherein:
(i) from zero to 6 substituents are each independently:
(1) halogen,
(2) CN
(3) $C_{1-6}$ alkyl,
(4) OH,
(5) O—$C_{1-6}$ alkyl,
(6) $C_{1-6}$ haloalkyl, or
(7) O—$C_{1-6}$ haloalkyl, and
(ii) from zero to 2 substituents are each independently:
(1) CycD,
(2) AryD,
(3) HetD, or
(4) $C_{1-6}$ alkyl substituted with CycD, AryD, or HetD;

CycB and CycC each independently have the same definition as CycA;

each AryA is independently aryl which is optionally substituted with a total of from 1 to 5 substituents, wherein:
(i) from zero to 5 substituents are each independently:
(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(3) O—$C_{1-16}$ alkyl,
(4) $C_{1-6}$ haloalkyl,
(5) O—$C_{1-16}$ haloalkyl,
(6) OH,
(7) halogen,
(8) CN,
(9) $NO_2$,
(10) $N(R^A)R^B$,
(11) $C(O)N(R^A)R^B$,
(12) $C(O)R^A$,
(13) C(O)—$C_{1-16}$ haloalkyl,
(14) $C(O)OR^A$,
(15) $OC(O)N(R^A)R^B$,
(16) $SR^A$,
(17) $S(O)R^A$,
(18) $S(O)_2R^A$,
(19) $S(O)_2N(R^A)R^B$,
(20) $N(R^A)S(O)_2R^B$,
(21) $N(R^A)S(O)_2N(R^A)R^B$,
(22) $N(R^A)C(O)R^B$,
(23) $N(R^A)C(O)N(R^A)R^B$,
(24) $N(R^A)C(O)$—$C(O)N(R^A)R^B$, or
(25) $N(R^A)CO_2R^B$, and
(ii) from zero to 2 substituents are each independently:
(1) CycD,
(2) AryD,
(3) HetD, or
(4) $C_{1-6}$ alkyl substituted with CycD, AryD, or HetD;

AryB and AryC each independently have the same definition as AryA;

each HetA is independently a heteroaryl which is optionally substituted with a total of from 1 to 5 substituents, wherein:
(i) from zero to 5 substituents are each independently:
(1) $C_{1-6}$ alkyl,
(2) $C_{1-6}$ alkyl substituted with OK, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(3) O—$C_{1-16}$ alkyl,
(4) $C_{1-6}$ haloalkyl,
(5) O—$C_{1-6}$ haloalkyl,
(6) OH,
(7) oxo,
(8) halogen,
(9) CN,
(10) $NO_2$,
(11) $N(R^A)R^B$,
(12) $C(O)N(R^A)R^B$,
(13) $C(O)R^A$,
(14) C(O)—$C_{1-6}$ haloalkyl,
(15) $C(O)OR^A$,
(16) $OC(O)N(R^A)R^B$,
(17) $SR^A$,
(18) $S(O)R^A$,
(19) $S(O)_2R^A$,
(20) $S(O)_2N(R^A)R^B$,
(21) $N(R^A)S(O)_2R^B$,
(22) $N(R^A)S(O)_2N(R^A)R^B$,
(23) $N(R^A)C(O)R^B$,
(24) $N(R^A)C(O)N(R^A)R^B$,
(25) $N(R^A)C(O)$—$C(O)N(R^A)R^B$, or
(26) $N(R^A)CO_2R^B$, and
(ii) from zero to 2 substituents are each independently:
(1) CycD,
(2) AryD,
(3) HetD, or
(4) $C_{1-6}$ alkyl substituted with CycD, AryD, or HetD;

HetB and HetC each independently have the same definition as HetA;

each CycD is independently a $C_{3-8}$ cycloalkyl which is optionally substituted with from 1 to 4 substituents each of which is independently halogen, $C_{1-6}$ alkyl, OH, O—$C_{1-6}$ alkyl, or $C_{1-6}$ haloalkyl;

each AryD is independently phenyl or naphthyl, wherein the phenyl or naphthyl is optionally substituted with from 1 to 5 substituents each of which is independently any one of the substituents (1) to (25) as set forth above in part (i) of the definition of AryA;

each HetD is independently a 5- or 6-membered heteroaromatic ring containing from 1 to 4 heteroatoms independently selected from N, O and S, wherein the heteroaromatic ring is optionally substituted with from 1 to 4 substituents each of which is independently halogen, $C_{1-6}$ alkyl, $C_{1-6}$ haloalkyl, O—$C_{1-6}$ alkyl, O—$C_{1-6}$ haloalkyl, or hydroxy;

each aryl is independently (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic;

each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or S(O)$_2$;

The present invention also includes pharmaceutical compositions containing a compound of Formula I or a pharmaceutically acceptable salt thereof. The present invention further includes methods for the treatment of AIDS, the delay in the onset of AIDS, the prophylaxis of AIDS, the prophylaxis of infection by HIV, and the treatment of infection by HIV.

Other embodiments, aspects and features of the present invention are either further described in or will be apparent from the ensuing description, examples and appended claims.

DETAILED DESCRIPTION OF THE INVENTION

The present invention includes compounds of Formula I above, and pharmaceutically acceptable salts thereof. These compounds and their pharmaceutically acceptable salts are HIV integrase inhibitors (e.g., HIV-1 integrase inhibitors).

A first embodiment of the present invention (i.e., Embodiment E1) is a compound of Formula I, or a pharmaceutically acceptable salt thereof, wherein all of the variables are as originally defined (i.e., as defined for Formula I in the Summary of the Invention), and provided that:

(A) when m is zero and X is O, then $R^1$ is not H or $C_{1-6}$ alkyl;

(B) when m is zero, X is O, and the —X[—C($R^5R^6$)$_n$C($R^7R^8$)]-moiety is —OCH$_2$— or —OCH$_2$CH$_2$— or —OCH$_2$CH$_2$CH$_2$—, then $R^1$ and $R^2$ do not together form a ring (C) when X is N($R^K$) and $R^K$ is:

(1) H,
(2) $C_{1-6}$ alkyl,
(3) $C_{1-6}$ alkyl substituted with T, wherein T is CO$_2R^A$, CN, SO$_2R^A$, N($R^D$)$R^E$, C(O)N($R^D$)$R^E$, or N($R^A$)—C(O)$R^B$,
(4) $C_{1-6}$ haloalkyl,
(5) C(O)$R^A$,
(6) C(O)—$C_{1-6}$ haloalkyl,
(8) C(O)—U and U is AryB or HetB,
(9) C(O)—$C_{1-6}$ alkylene-U
(10) C(O)N($R^D$)$R^E$,
(11) C(O)—$C_{1-6}$ alkylene-N($R^D$)$R^E$,
(14) C(O)C(O)—N($R^D$)$R^E$ (except when $R^D$ and $R^E$ together with the N to which they are both attached form a saturated heterocyclic ring),
(16) SO$_2R^A$,
(18) SO$_2$—$C_{1-6}$ alkylene-U, or
(21) $C_{1-6}$ alkyl substituted with U (except when $C_{1-6}$ alkyl substituted with U is CH$_2$-HetB, and HetB is a 5-membered heteroaromatic ring containing from 2 to 4 heteroatoms independently selected from 1 to 4 N atoms, zero or 1 O atom, and zero or 1 S atom, wherein the heteroaromatic ring is attached to the —CH$_2$— moiety via a ring carbon atom and is optionally substituted with a methyl group, and m is zero and the —C($R^5R^6$)$_n$C($R^7R^8$)— moiety is —CH$_2$CH$_2$—), then $R^1$ is:

(4) $C_{1-6}$ alkyl substituted with V, wherein V is S(O)$R^A$, N($R^A$)—C(O)C(O)—N($R^D$)$R^E$, N($R^A$)—SO$_2R^B$, N($R^A$)—$C_{1-6}$ alkylene-SO$_2R^B$, N($R^A$)C(O)—$C_{1-6}$ alkylene-SO$_2R^B$, N($R^A$)—SO$_2$N($R^D$)$R^E$, N($R^A$)—CO$_2R^B$, or N($R^A$)—C(O)N($R^D$)$R^E$ when N($R^A$)—C(O)N($R^D$)$R^E$ is other than NH—C(O)NH$_2$, (5) $C_{1-6}$ alkyl substituted with W, wherein W is O—$C_{1-6}$ alkylene-CycA, O—$C_{1-6}$ alkylene-AryA, O—$C_{1-6}$ alkylene-HetA, S(O)$_j$—$C_{1-6}$ alkylene-CycA, S(O)$_j$—$C_{1-6}$ alkylene-AryA, S(O)$_j$—$C_{1-6}$ alkylene-HetA, N($R^A$)—C(O)-AryA, or N($R^A$)—C(O)-HetA, (7) N($R^A$)—SO$_2$N($R^D$)$R^E$ when $R^D$ and $R^E$ together with the N to which they are both attached form an optionally substituted saturated heterocyclic ring,

(10) N($R^C$)$R^A$ when $R^C$ and $R^K$ are involved in the formation of an optionally substituted fused diazacycloalkyl ring,

(12) N($R^C$)—C(O)$R^A$ when $R^C$ and $R^K$ are involved in the formation of an optionally substituted fused diazacycloalkyl ring,

(13) S(O)$_j R^F$ when $R^F$ and $R^K$ are involved in the formation of a fused thioazacycloalkyl ring,

(14) O$R^F$ when $R^F$ and $R^K$ are involved in the formation of a fused oxyazacycloalkyl ring,

(16) CycA,

(21) N($R^A$)—C(O)-HetA,

(22) N($R^A$)—C(O)—N($R^D$)$R^E$ when $R^D$ and $R^E$ together with the N to which they are both attached form an optionally substituted saturated heterocyclic ring,

(23) N($R^C$)—C(O)-CycA when $R^C$ and $R^K$ are involved in the formation of an optionally substituted fused diazacycloalkyl ring,

(24) N($R^C$)—C(O)-AryA when $R^C$ and $R^K$ are involved in the formation of an optionally substituted fused diazacycloalkyl ring,

(25) N($R^C$)—C(O)-HetA,

(26) N($R^C$)—C(O)—N($R^D$)$R^E$ when (i) $R^D$ and $R^E$ together with the N to which they are both attached form a optionally substituted saturated heterocyclic ring or (ii) $R^C$ and $R^K$ are involved in the formation of an optionally substituted fused diazacycloalkyl ring),

(27) N($R^A$)—C(O)C(O)-CycA,
(28) N($R^A$)—C(O)C(O)-AryA,
(29) N($R^A$)—C(O)C(O)-HetA,
(30) N($R^A$)—C(O)C(O)—N($R^D$)$R^E$,
(31) N($R^C$)—C(O)C(O)-CycA,
(32) N($R^C$)—C(O)C(O)-AryA,
(33) N($R^C$)—C(O)C(O)-HetA, or
(34) N($R^C$)—C(O)C(O)—N($R^D$)$R^E$; or (D) when m is zero, the —C($R^5R^6$)$_n$C($R^7R^8$)— moiety is —CH$_2$CH$_2$—, X is N($R^K$), $R^K$ is CH$_2$-HetB, and HetB is a 5-membered heteroaromatic ring containing from 2 to 4 heteroatoms independently selected from 1 to 4 N atoms, zero or 1 O atom, and zero or 1 S atom, wherein the heteroaromatic ring is attached to the —CH$_2$— moiety via a ring carbon atom and is optionally substituted with a methyl group, then either:

(d1) $R^1$ is as defined in proviso C, or
(d2) $R^1$ and $R^2$ are both methyl, R9 is H, and R10 is 4-fluorobenzyl.

A second embodiment of the present invention (Embodiment E2) is a compound of Formula I, or a pharmaceutically acceptable salt thereof, wherein all of the variables are as originally defined, and provided that:

(A) when m is zero and X is O, then $R^1$ is not H or $C_{1-6}$ alkyl;

(B) when m is zero, X is O, and the —X[—C($R^5R^6$)$_n$C($R^7R^8$)]-moiety is —OCH$_2$— or —OCH$_2$CH$_2$— or —OCH$_2$CH$_2$CH$_2$—, then $R^1$ and $R^2$ do not together form a ring;

(C) when X is N($R^K$) and $R^K$ is:
(1) H,
(2) $C_{1-6}$ alkyl, (3) $C_{1-6}$ alkyl substituted with T, wherein T is $CO_2R^A$, CN, $SO_2R^A$, $N(R^D)R^E$, $C(O)N(R^D)R^E$,
(4) $C_{1-6}$ haloalkyl,
(5) $C(O)R^A$,
(6) $C(O)$—$C_{1-6}$ haloalkyl,
(8) $C(O)$—U and U is AryB or HetB,
(9) $C(O)$—$C_{1-6}$ alkylene-U
(10) $C(O)N(R^D)R^E$,
(11) $C(O)$—$C_{1-6}$ alkylene-$N(R^D)R^E$,
(14) $C(O)C(O)$—$N(R^D)R^E$ (except when $R^D$ and $R^E$ together with the N to which they are both attached form a saturated heterocyclic ring),
(16) $SO_2R^A$,
(18) $SO_2$—$C_{1-6}$ alkylene-U, or
(21) $C_{1-6}$ alkyl substituted with U,
then $R^1$ is:
(4) $C_{1-6}$ alkyl substituted with V, wherein V is $S(O)R^A$, $N(R^A)$—$C(O)C(O)$—$N(R^D)R^E$, $N(R^A)$—$C_{1-6}$ alkylene-$SO_2R^B$, $N(R^A)C(O)$—$C_{1-6}$ alkylene-$SO_2R^B$, $N(R^A)$—$SO_2N(R^D)R^E$, $N(R^A)$—$CO_2R^B$, or $N(R^A)$—$C(O)N(R^D)R^E$ when $N(R^A)$—$C(O)N(R^D)R^E$ is other than NH—C(O)NH$_2$,
(5) $C_{1-6}$ alkyl substituted with W, wherein W is O—$C_{1-6}$ alkylene-CycA, O—$C_{1-6}$ alkylene-AryA, O—$C_{1-6}$ alkylene-HetA, $S(O)_j$—$C_{1-6}$ alkylene-CycA, $S(O)_j$—$C_{1-6}$ alkylene-AryA, $S(O)_j$—$C_{1-6}$ alkylene-HetA, $N(R^A)$—C(O)-AryA, or $N(R^A)$—C(O)-HetA,
(7) $N(R^A)$—$SO_2N(R^D)R^E$ when $R^D$ and $R^E$ together with the N to which they are both attached form an optionally substituted saturated heterocyclic ring,
(10) $N(R^C)R^A$ when $R^C$ and $R^K$ are involved in the formation of an optionally substituted fused diazacycloalkyl ring,
(12) $N(R^C)$—$C(O)R^A$ when $R^C$ and $R^K$ are involved in the formation of an optionally substituted fused diazacycloalkyl ring,
(13) $S(O)_j R^F$ when $R^F$ and $R^K$ are involved in the formation of a fused thioazacycloalkyl ring,
(14) $OR^F$ when $R^F$ and $R^K$ are involved in the formation of a fused oxyazacycloalkyl ring,
(16) CycA,
(21) $N(R^A)$—C(O)-HetA,
(22) $N(R^A)$—C(O)—$N(R^D)R^E$ when $R^D$ and $R^E$ together with the N to which they are both attached form an optionally substituted saturated heterocyclic ring,
(23) $N(R^C)$—C(O)-CycA when $R^C$ and $R^K$ are involved in the formation of an optionally substituted fused diazacycloalkyl ring,
(24) $N(R^C)$—C(O)-AryA when $R^C$ and $R^K$ are involved in the formation of an optionally substituted fused diazacycloalkyl ring,
(25) $N(R^C)$—C(O)-HetA,
(26) $N(R^C)$—C(O)—$N(R^D)R^E$ when (i) $R^D$ and $R^E$ together with the N to which they are both attached form a optionally substituted saturated heterocyclic ring or (ii) $R^C$ and $R^K$ are involved in the formation of an optionally substituted fused diazacycloalkyl ring),
(27) $N(R^A)$—C(O)C(O)-CycA,
(28) $N(R^A)$—C(O)C(O)-AryA,
(29) $N(R^A)$—C(O)C(O)-HetA,
(30) $N(R^A)$—C(O)C(O)—$N(R^D)R^E$,
(31) $N(R^C)$—C(O)C(O)-CycA,
(32) $N(R^C)$—C(O)C(O)-AryA,
(33) $N(R^C)$—C(O)C(O)-HetA, or
(34) $N(R^C)$—C(O)C(O)—$N(R^D)R^E$.

A third embodiment of the present invention (Embodiment E3) is a compound of Formula I, or a pharmaceutically acceptable salt thereof, wherein all of the variables are as originally defined, and provided that:

(A) when X is O, then $R^1$ is not H or $C_{1-6}$ alkyl;

(B) when X is O, and the —X[—$C(R^5R^6)_n C(R^7R^8)$]-moiety is —$OCH_2$— or —$OCH_2CH_2$— or —$OCH_2CH_2CH_2$—, then $R^1$ and $R^2$ do not together form a ring; or (C) when X is $N(R^K)$, then $R^1$ is:
(27) $N(R^A)$—C(O)C(O)-CycA,
(28) $N(R^A)$—C(O)C(O)-AryA,
(29) $N(R^A)$—C(O)C(O)-HetA,
(30) $N(R^A)$—C(O)C(O)—$N(R^D)R^E$,
(31) $N(R^C)$—C(O)C(O)-CycA,
(32) $N(R^C)$—C(O)C(O)-AryA,
(33) $N(R^C)$—C(O)C(O)-HetA, or
(34) $N(R^C)$—C(O)C(O)—$N(R^D)R^E$.

A fourth embodiment of the present invention (Embodiment E4) is a compound of Formula I, or a pharmaceutically acceptable salt thereof, wherein the integer m is equal to 1 and the integer n is equal to 1, or m is zero and n is 2, or m is zero and n is 1, or m is 1 and n is zero, or m is zero and n is zero; and all other variables are as originally defined (i.e., as defined for Formula I in the Summary of the invention) or as defined in any of the preceding embodiments. In an aspect of this embodiment, m=n=1. In another aspect of this embodiment, m=0 and n=2. In another aspect, m=0 and n=1. In another aspect, m=1 and n=0. In another aspect m=n=0.

It is understood that when m=0 the ring carbon substituted with $R^1$ and $R^2$ is directly attached to X by a single bond, and when n=0 the ring carbon substituted with $R^7$ and $R^8$ is directly attached to X by a single bond. Accordingly, the compounds represented by values of m and n set forth in Embodiment E4 are compounds of Formula I-A (i.e., m=n=0), I—B (m=1; n=0), I—C (m=0; n=1), I-D (m=n=1), or I-E (m=0; n=2):

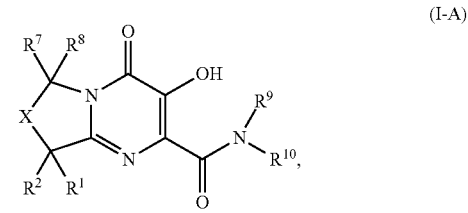

(I-A)

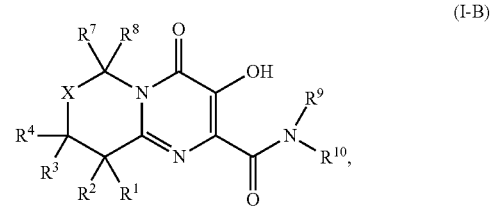

(I-B)

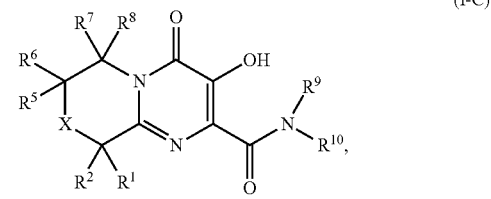

(I-C)

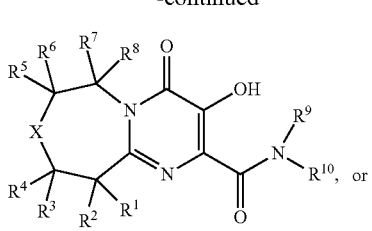

(I-D)

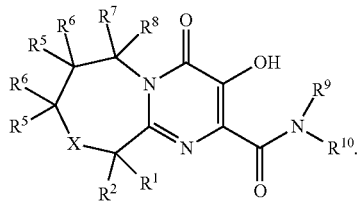

(I-E)

A fifth embodiment of the present invention (Embodiment E5) is a compound of Formula I, or a pharmaceutically acceptable salt thereof, wherein X is N($R^K$) or O; and all other variables are as originally defined or as defined in any of the preceding embodiments. In an aspect of this embodiment, X is N($R^K$).

A sixth embodiment of the present invention (Embodiment E6) is a compound of Formula I, or a pharmaceutically acceptable salt thereof, wherein $R^9$ is H or $C_{1-4}$ alkyl; $R^{10}$ is:
(1) $CH_2$-phenyl or $CH_2$-HetC, wherein the phenyl is optionally substituted with a total of from 1 to 3 substituents, wherein (i) from zero to 3 substituents are each independently bromo, chloro, fluoro, $C_{1-4}$ alkyl, $CF_3$, C(O)$NH_2$, C(O)NH($C_{1-4}$ alkyl), C(O)N($C_{1-4}$ alkyl)$_2$, S—$C_{1-4}$ alkyl, $SO_2$—$C_{1-4}$ alkyl, or $SO_2$N($C_{1-14}$ alkyl)$_2$, and (ii) from zero to 1 substituent is a heteroaromatic selected from the group consisting of imidazolyl, triazolyl, oxadiazolyl, pyrrolyl, and pyrazolyl, wherein the heteroaomatic ring is optionally substituted with 1 or 2 substituents each of which is independently Cl, Br, F, $C_{1-4}$ alkyl, $CF_3$, O—$C_{1-4}$ alkyl, $OCF_3$, or OH,
(2) $CH_2$-HetC, wherein HetC is a heteroaryl which is (i) a 5- or 6-membered heteroaromatic ring containing a total of from 1 to 4 heteroatoms independently selected from 1 to 4 N atoms, zero to 1 O atom, and zero to 1 S atom, or (ii) a 9 or 10-membered bicyclic, fused ring system in which one ring is a benzene ring and the other ring is a 5- or 6-membered heteroaromatic ring containing from 1 to 3 heteroatoms independently selected from zero to 3 N atoms, zero to 1 O atom, and zero to 1 S atom, wherein the heteroaryl is optionally substituted with from 1 to 3 substituents each of which is independently Cl, Br, F, or $C_{1-4}$ alkyl; and all other variables are as originally defined or as defined in any one of the preceding embodiments. In an aspect of this embodiment, $R^9$ is H and the definition of $R^{10}$ is unchanged.

A seventh embodiment of the present invention (Embodiment E7) is a compound of Formula I, or a pharmaceutically acceptable salt thereof, wherein $R^9$ is H or $C_{1-4}$ alkyl; $R^{10}$ is:
(1) $CH_2$-phenyl wherein the phenyl is optionally substituted with a total of from 1 to 2 substituents wherein (i) from zero to 2 substituents are each independently bromo, chloro, fluoro, $CH_3$, $CF_3$, C(O)$NH_2$, C(O)NH($CH_3$), C(O)N($CH_3$)$_2$, $SCH_3$, $SO_2CH_3$, or $SO_2$N($CH_3$)$_2$, and (ii) from zero to 1 substituent is oxadiazolyl optionally substituted with $CH_3$, or
(2) $CH_2$-HetC, wherein HetC is a heteroaryl which is quinolinyl, indazolyl, benzoxazolyl, isoquinolinyl, cinnolinyl, quinazolinyl, benzopyranyl, wherein the heteroaryl is optionally substituted with from 1 to 3 substituents each of which is independently Cl, Br, F, or $C_{1-4}$ alkyl;
and all other variables are as originally defined or as defined in any one of the preceding embodiments. In an aspect of this embodiment, $R^9$ is H and the definition of $R^{10}$ is unchanged.

An eighth embodiment of the present invention (Embodiment E8) is a compound of Formula I, or a pharmaceutically acceptable salt thereof, wherein $R^9$ is H; $R^{10}$ is 4-fluorobenzyl, 3-chloro-4-fluorobenzyl, 3-chloro-4-methylbenzyl, 4-fluoro-3-methylbenzyl, 3-chlorobenzyl, 4-fluoro-2-methylsulfonylbenzyl, 3-bromo-4-fluorobenzyl, 4-fluoro-2-[(methylamino)carbonyl]benzyl, 2-methylthiobenzyl, 4-fluoro-2-[(3-methyl)-1,2,4-oxadiazol-5-yl]benzyl, or [(5-fluoro)quinolin-8-yl]methyl; and all other variables are as originally defined or as defined in any one of the preceding embodiments.

A ninth embodiment of the present invention (Embodiment E9) is a compound of Formula I, or a pharmaceutically acceptable salt thereof, wherein $R^9$ is H; $R^{10}$ is 4-fluorobenzyl; and all other variables are as originally defined or as defined in any one of the preceding embodiments.

A tenth embodiment of the present invention (Embodiment E10) is a compound of Formula I, or a pharmaceutically acceptable salt thereof, wherein:
X is N($R^K$) or O;
$R^K$ is:
(1) H,
(2) $C_{1-4}$ alkyl,
(3) $C_{1-4}$ alkyl substituted with T, wherein T is $CO_2R^A$, CN, N($R^D$)$R^E$, or C(O)N($R^D$)$R^E$,
(4) C(O)$R^A$,
(5) C(O)—$C_{1-4}$ fluoroalkyl,
(6) $CO_2R^A$,
(7) $SO_2R^A$,
(8) $SO_2$-AryB,
(9) $SO_2$N($R^D$)$R^E$,
(10) C(O)N($R^D$)$R^E$,
(11) C(O)C(O)—N($R^D$)$R^E$,
(12) C(O)—$C_{1-4}$ alkylene-N($R^D$)$R^E$,
(13) CycB,
(14) $C_{1-4}$ alkyl substituted with U, wherein U is CycB, AryB, or HetB, or
(15) $C_{1-4}$ alkyl substituted with C(O)N($R^A$)—$C_{1-4}$ alkylene-HetB;
$R^1$ is:
(1) H,
(2) $C_{1-4}$ alkyl,
(3) $C_{1-4}$ alkyl substituted with V, wherein V is OH, O—$C_{1-4}$ alkyl, $SR^A$, S(O)$R^A$, $SO_2R^A$, N($R^D$)$R^E$, C(O)N($R^D$)$R^E$, N($R^A$)—C(O)C(O)—N($R^D$)$R^E$, N($R^A$)—C(O)$R^B$, N($R^A$)—$SO_2R^B$, N($R^A$)—$C_{1-4}$ alkylene-$SO_2R^B$, N($R^A$)C(O)—$C_{1-4}$ alkylene-$SO_2R^B$, N($R^A$)—$SO_2$N($R^D$)$R^E$, or N($R^A$)—$CO_2R^B$,
(4) $C_{1-4}$ alkyl substituted with W, wherein W is CycA, AryA, HetA, O—$C_{1-4}$ alkylene-AryA, O—$C_{1-4}$ alkylene-HetA, or N($R^A$)—C(O)-HetA,
(5) N($R^A$)—$SO_2R^B$,
(6) N($R^A$)—$SO_2$N($R^D$)$R^E$,
(7) N($R^A$)—$CO_2R^B$,
(8) N($R^D$)$R^E$,
(9) N($R^C$)$R^A$,
(10) N($R^A$)—C(O)$R^B$,
(11) N($R^C$)—C(O)$R^A$,

(12) $SR^F$, $S(O)R^F$, or $S(O)_2R^F$,
(13) $N(R^A)$—C(O)-HetA,
(14) $N(R^C)$—C(O)—$N(R^D)R^E$, or
(15) $N(R^A)$—C(O)C(O)—$N(R^D)R^E$, or
(16) $N(R^C)$—C(O)C(O)—$N(R^D)R^E$;

$R^2$ is H or $C_{1-4}$ alkyl; or alternatively $R^1$ and $R^2$ together with the ring carbon atom to which they are both attached form (i) a 3- to 6-membered saturated carbocyclic ring or (ii) a 6-membered saturated heterocyclic ring containing 1 heteroatom selected from N, O and S, where the N is optionally substituted with $C_{1-4}$ alkyl and the S is optionally oxidized to $S(O)$ or $S(O)_2$;

each $R^3$ is independently H or $C_{1-4}$ alkyl, and each $R^4$ is independently H or $C_{1-4}$ alkyl; or alternatively $R^3$ and $R^4$ attached to the same carbon atom together form oxo;

each $R^5$ is independently H or $C_{1-4}$ alkyl, and each $R^6$ is independently H or $C_{1-4}$ alkyl; or alternatively $R^5$ and $R^6$ attached to the same carbon atom together form oxo;

$R^7$ is H or $C_{1-4}$ alkyl;

$R^8$ is H or $C_{1-4}$ alkyl; or alternatively $R^7$ and $R^8$ together form oxo;

$R^9$ is H or $C_{1-4}$ alkyl;

$R^{10}$ is $C_{1-4}$ alkyl substituted with CycC, AryC or HetC;

each $R^A$ is independently H or $C_{1-4}$ alkyl;

each $R^B$ is independently H or $C_{1-4}$ alkyl;

$R^C$ is $C_{1-4}$ alkyl substituted with CycA, AryA, or HetA; or alternatively, when X is $N(R^K)$ and $R^1$ includes the $N(R^C)$ moiety, $R^C$ and $R^K$ together with (i) the N atom to which $R^K$ is attached, (ii) the N atom to which $R^C$ is attached, (iii) the ring carbon to which $R^1$ is attached, and (iv) the zero, 1 or 2 ring carbons between X and the ring carbon to which $R^1$ is attached, form a fused 5- or 6-membered diazacycloalkyl ring; wherein the portion of the fused ring obtained from $R^C$ and $R^K$ is a 1- to 3-membered methylene chain optionally substituted with oxo or $C_{1-4}$ alkyl;

each $R^D$ and $R^E$ are independently H or $C_{1-4}$ alkyl, or together with the nitrogen to which they are both attached form a 5- or 6-membered saturated heterocyclic ring optionally containing a heteroatom in addition to the nitrogen attached to $R^C$ and $R^D$ selected from N, O, and S, where the S is optionally oxidized to $S(O)$ or $S(O)_2$, and wherein the saturated heterocyclic ring is optionally substituted with 1 or 2 substituents each of which is independently $C_{1-4}$ alkyl or $S(O)_2$—$C_{1-4}$ alkyl;

$R^F$ is $C_{1-4}$ alkyl, or alternatively, when X is $N(R^K)$ and $R^1$ is $SR^F$, $R^F$ and $R^K$ together with (i) the N atom to which $R^K$ is attached, (ii) the S atom to which $R^F$ is attached, (iii) the ring carbon to which $R^1$ is attached, and (iv) the zero, 1 or 2 ring carbons between X and the ring carbon to which $R^1$ is attached, form a fused 5- or 6-membered thioazacycloalkyl ring, wherein the portion of the fused ring obtained from $R^F$ and $R^K$ is a 1- to 3-membered methylene chain;

each CycA is independently a $C_{3-6}$ cycloalkyl which is optionally substituted with 1 or 2 substituents each of which is independently $C_{1-4}$ alkyl, OH, or O—$C_{1-4}$ alkyl;

CycB is a $C_{3-6}$ cycloalkyl which is optionally substituted with 1 or 2 substituents each of which is independently $C_{1-4}$ alkyl, OH, or O—$C_{1-4}$ alkyl;

CycC is a $C_{3-6}$ cycloalkyl which is optionally substituted with 1 or 2 substituents each of which is independently $C_{1-4}$ alkyl, OH, or O—$C_{1-4}$ alkyl;

each AryA is independently phenyl or naphthyl, wherein the phenyl or naphthyl is optionally substituted with from 1 to 3 substituents each of which is independently:

(1) $C_{1-4}$ alkyl, which is optionally substituted with OH, O—$C_{1-4}$ alkyl, O—$C_{1-4}$ haloalkyl, CN, $N(R^A)R^B$, C(O)$N(R^A)R^B$, $C(O)R^A$, $CO_2R^A$, $SR^A$, $S(O)R^A$, $SO_2R^A$, or $SO_2N(R^A)R^B$,
(2) O—$C_{1-4}$ alkyl,
(3) $C_{1-4}$ haloalkyl,
(4) O—$C_{1-4}$ haloalkyl,
(5) OH,
(6) halogen,
(7) CN,
(8) $NO_2$,
(9) $N(R^A)R^B$,
(10) $C(O)N(R^A)R^B$,
(11) $C(O)R^A$,
(12) C(O)—$C_{1-4}$ haloalkyl,
(13) $CO_2R^A$,
(14) $SR^A$,
(15) $S(O)R^A$,
(16) $SO_2R^A$, or
(17) $SO_2N(R^A)R^B$, AryB independently has the same definition as AryA;

AryC is phenyl or naphthyl, wherein the phenyl or naphthyl is:
  (i) optionally substituted with from 1 to 3 substituents each of which is independently any one of the substituents (1) to (17) as set forth above in the definition of AryA, and
  (ii) optionally substituted with:
    (1) AryD,
    (2) HetD,
    (3) CycD, or
    (4) $C_{1-4}$ alkyl substituted with CycD, AryD or HetD;

each HetA is independently a 5- or 6-membered heteroaromatic ring containing from 1 to 4 heteroatoms independently selected from zero to 4 N atoms, zero or 1 O atom, and zero or 1 S atom, wherein each N is optionally in the form of an oxide, and wherein the heteroaromatic ring is optionally substituted with from 1 to 3 substituents each of which is independently halogen, $C_{1-4}$ alkyl, or OH;

HetB is a 5- or 6-membered heteroaromatic ring containing from 1 to 4 heteroatoms independently selected from zero to 4 N atoms, zero or 1 O atom, and zero or 1 S atom, wherein the heteroaromatic ring is optionally substituted with from 1 to 3 substituents each of which is independently halogen, $C_{1-4}$ alkyl, or OH;

HetC is a 5- or 6-membered heteroaromatic ring containing from 1 to 4 heteroatoms independently selected from zero to 4 N atoms, zero or 1 O atom, and zero or 1 S atom, wherein each N is optionally in the form of an oxide, and wherein the heteroaromatic ring is:
  (i) optionally substituted with from 1 to 3 substituents each of which is independently halogen, $C_{1-4}$ alkyl, or OH; and
  (ii) optionally substituted with AryD, HetD, CycD, or $C_{1-4}$ alkyl substituted with AryD, HetD or CycD;

each CycD is independently a $C_{3-6}$ cycloalkyl which is optionally substituted with 1 or 2 substituents each of which is independently $C_{1-4}$ alkyl, OH, or O—$C_{1-4}$ alkyl;

each AryD is independently phenyl or naphthyl, wherein the phenyl or naphthyl is optionally substituted with from 1 to 3 substituents each of which is independently any one of the substituents (1) to (17) as set forth above in the definition of AryA; and each HetD is independently a 5- or 6-membered heteroaromatic ring containing from 1 to 4 heteroatoms independently selected from zero to 4 N atoms, zero or 1 O atom, and zero or 1 S atom, wherein the heteroaromatic ring is optionally substituted with from 1 to 3 substituents each of which is independently halogen, $C_{1-4}$ alkyl, or OH.

An eleventh embodiment of the present invention (Embodiment E11) is a compound of Formula I wherein the variables are as defined in Embodiment E10, and provided that:

(A) when m is zero and X is O, then $R^1$ is not H or $C_{1-4}$ alkyl;

(B) when m is zero, X is O, and the —X[—C($R^5R^6$)$_n$C($R^7R^8$)]-moiety is —OCH$_2$— or —OCH$_2$CH$_2$— or —OCH$_2$CH$_2$CH$_2$—, then $R^1$ and $R^2$ do not together form a ring;

(C) when X is N($R^K$) and $R^K$ is:
(1) H,
(2) $C_{1-4}$ alkyl,
(3) $C_{1-4}$ alkyl substituted with T, wherein T is CO$_2R^A$, CN, N($R^D$)$R^E$, or C(O)N($R^D$)$R^E$,
(4) C(O)$R^A$,
(5) C(O)—$C_{1-4}$ fluoroalkyl,
(7) SO$_2R^A$,
(10) C(O)N($R^D$)$R^E$,
(11) C(O)C(O)—N($R^D$)$R^E$ (except when $R^D$ and $R^E$ together with the N to which they are both attached form a saturated heterocyclic ring),
(12) C(O)—$C_{1-4}$ alkylene-N($R^D$)$R^E$, or
(14) $C_{1-4}$ alkyl substituted with U (except when $C_{1-4}$ alkyl substituted with U is CH$_2$-HetB, and HetB is a 5-membered heteroaromatic ring containing from 2 to 4 heteroatoms independently selected from 1 to 4 N atoms, zero or 1 O atom, and zero or 1 S atom, wherein the heteroaromatic ring is attached to the —CH$_2$— moiety via a ring carbon atom and is optionally substituted with a methyl group, and m is zero and the —C($R^5R^6$)$_n$C($R^7R^8$)— moiety is —CH$_2$CH$_2$—), then $R^1$ is:
(3) $C_{1-4}$ alkyl substituted with V, wherein V is S(O)$R^A$, N($R^A$)—C(O)C(O)—N($R^D$)$R^E$, N($R^A$)—SO$_2R^B$, N($R^A$)—$C_{1-4}$ alkylene-SO$_2R^B$, N($R^A$)C(O)—$C_{1-4}$ alkylene-SO$_2R^B$, N($R^A$)—SO$_2$N($R^D$)$R^E$, or N($R^A$)—CO$_2R^B$,
(4) $C_{1-4}$ alkyl substituted with W, wherein W is O—$C_{1-4}$ alkylene-AryA, O—$C_{1-4}$ alylene-HetA, or N($R^A$)—C(O)-HetA,
(6) N($R^A$)—SO$_2$N($R^D$)$R^E$ when $R^D$ and $R^E$ together with the N to which they are both attached form an optionally substituted saturated heterocyclic ring,
(9) N($R^C$)$R^A$ when $R^C$ and $R^K$ are involved in the formation of an optionally substituted fused diazacycloalkyl ring,
(11) N($R^C$)—C(O)$R^A$ when $R^C$ and $R^K$ are involved in the formation of an optionally substituted fused diazacycloalkyl ring,
(12) S$R^F$, S(O)$R^F$, or S(O)$_2R^F$ when $R^F$ and $R^K$ are involved in the formation of a fused thioazacycloalkyl ring,
(13) N($R^A$)—C(O)-HetA,
(14) N($R^C$)—C(O)—N($R^D$)$R^E$ when (i) $R^D$ and $R^E$ together with the N to which they are both attached form a optionally substituted saturated heterocyclic ring or (ii) $R^C$ and $R^K$ are involved in the formation of an optionally substituted fused diazacycloalkyl ring),
(15) N($R^A$)—C(O)C(O)—N($R^D$)$R^E$, or
(16) N($R^C$)—C(O)C(O)—N($R^D$)$R^E$; or (D) when m is zero, the —C($R^5R^6$)$_n$C($R^7R^8$)— moiety is —CH$_2$CH$_2$—, X is N($R^K$), $R^K$ is CH$_2$-HetB, and HetB is a 5-membered heteroaromatic ring containing from 2 to 4 heteroatoms independently selected from 1 to 4 N atoms, zero or 1 O atom, and zero or 1 S atom, wherein the heteroaromatic ring is attached to the —CH$_2$— moiety via a ring carbon atom and is optionally substituted with a methyl group, then either:
(d1) $R^1$ is as defined in proviso C, or
(d2) $R^1$ and $R^2$ are both methyl, R9 is H, and R10 is 4-fluorobenzyl.

A twelfth embodiment of the present invention (Embodiment E12) is a compound of Formula I, or a pharmaceutically acceptable salt thereof, wherein all of the variables are as defined in Embodiment E10, and provided that:

(A) when m is zero and X is O, then $R^1$ is not H or $C_{1-4}$ alkyl;

(B) when m is zero, X is O, and the —X[—C($R^5R^6$)$_n$C($R^7R^8$)]-moiety is —OCH$_2$— or —OCH$_2$CH$_2$— or —OCH$_2$CH$_2$CH$_2$—, then $R^1$ and $R^2$ do not together form a ring;

(C) when X is N($R^K$) and $R^K$ is:
(1) H,
(2) $C_{1-4}$ alkyl,
(3) $C_{1-4}$ alkyl substituted with T, wherein T is CO$_2R^A$, CN, N($R^D$)$R^E$, or C(O)N($R^D$)$R^E$,
(4). C(O)$R^A$,
(5) C(O)—$C_{1-4}$ fluoroalkyl,
(7) SO$_2R^A$,
(10) C(O)N($R^D$)$R^E$,
(11) C(O)C(O)—N($R^D$)$R^E$ (except when $R^D$ and $R^E$ together with the N to which they are both attached form a saturated heterocyclic ring),
(12) C(O)—$C_{1-4}$ alkylene-N($R^D$)$R^E$, or
(14) $C_{1-4}$ alkyl substituted with U,
then $R^1$ is:
(3) $C_{1-4}$ alkyl substituted with V, wherein V is S(O)$R^A$, N($R^A$)—C(O)C(O)—N($R^D$)$R^E$, N($R^A$)—SO$_2R^B$, N($R^A$)—$C_{1-4}$ alkylene-SO$_2R^B$, N($R^A$)C(O)—$C_{1-4}$ alkylene-SO$_2R^B$, N($R^A$)—SO$_2$N($R^D$)$R^E$, or N($R^A$)—CO$_2R^B$,
(4) $C_{1-4}$ alkyl substituted with W, wherein W is O—$C_{1-4}$ alkylene-AryA, O—$C_{1-4}$ alkylene-HetA, or N($R^A$)—C(O)-HetA,
(6) N($R^A$)—SO$_2$N($R^D$)$R^E$ when $R^D$ and $R^E$ together with the N to which they are both attached form an optionally substituted saturated heterocyclic ring,
(9) N($R^C$)$R^A$ when $R^C$ and $R^K$ are involved in the formation of an optionally substituted fused diazacycloalkyl ring,
(11) N($R^C$)—C(O)$R^A$ when $R^C$ and $R^K$ are involved in the formation of an optionally substituted fused diazacycloalkyl ring,
(12) S(O)$_jR^F$ when $R^F$ and $R^K$ are involved in the formation of a fused thioazacycloalkyl ring,
(13) N($R^A$)—C(O)-HetA,
(14) N($R^C$)—C(O)—N($R^D$)$R^E$ when (i) $R^D$ and $R^E$ together with the N to which they are both attached form a optionally substituted saturated heterocyclic ring or (ii) $R^C$ and $R^K$ are involved in the formation of an optionally substituted fused diazacycloalkyl ring),
(15) N($R^A$)—C(O)C(O)—N($R^D$)$R^E$, or
(16) N($R^C$)—C(O)C(O)—N($R^D$)$R^E$.

A thirteenth embodiment of the present invention (Embodiment E13) is a compound of Formula I, or a pharmaceutically acceptable salt thereof, wherein all of the variables are as defined in Embodiment E10, and provided that:

(A) when X is O, then $R^1$ is not H or $C_{1-4}$ alkyl;

(B) when X is O, and the —X[—C($R^5R^6$)$_n$C($R^7R^8$)]-moiety is —OCH$_2$— or —OCH$_2$CH$_2$— or —OCH$_2$CH$_2$CH$_2$—, then $R^1$ and $R^2$ do not together form a ring; or (C) when X is N($R^K$), then $R^1$ is:
(15) N($R^A$)—C(O)C(O)—N($R^D$)$R^E$, or
(16) N($R^C$)—C(O)C(O)—N($R^D$)$R^E$.

A fourteenth embodiment of the present invention (Embodiment E14) is a compound of Formula I, or a pharmaceutically acceptable salt thereof, which is a compound of Formula II, III, IV, V, VI, or VII:

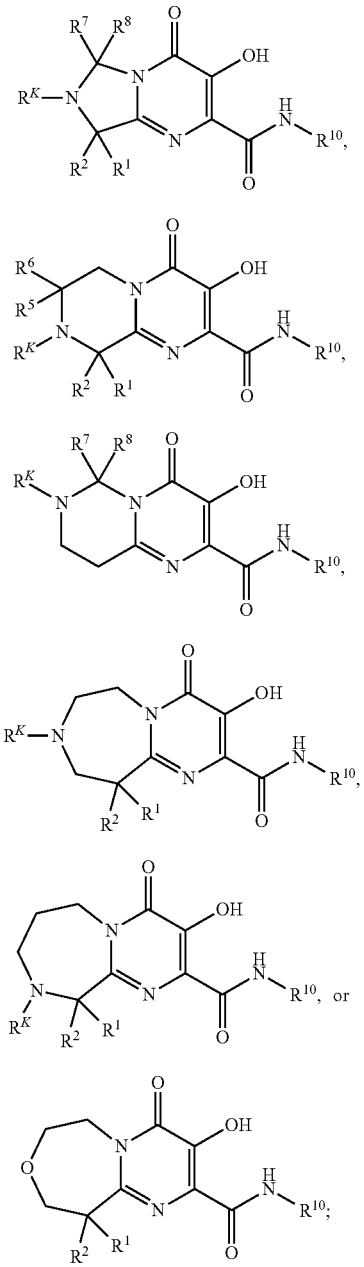

and all other variables are as defined in any one of Embodiments E10, E11, E12 and E13.

A fifteenth embodiment of the present invention (Embodiment E15) is a compound of any one of Formulas II, III, V and VI, or a pharmaceutically acceptable salt thereof, wherein: $R^1$ and $R^2$ are both methyl (except in Formula IV where $R^1$ and $R^2$ are both H); $R^5$, $R^6$, $R^7$ and $R^8$ are each H; $R^{10}$ is 4-fluorobenzyl; $R^K$ is CH$_2$-HetB; and HetB is a 5-membered heteroaromatic ring containing from 2 to 4 heteroatoms independently selected from 1 to 4 N atoms, zero or 1 O atom, and zero or 1 S atom, wherein the heteroaromatic ring is attached to the —CH$_2$— moiety via a ring carbon atom and is optionally substituted with a methyl group. In an aspect of this embodiment, the compound is a compound of Formula II, or a pharmaceutically acceptable salt thereof. In another aspect of this embodiment, the compound is a compound of Formula III, or a pharmaceutically acceptable salt thereof. In another aspect of this embodiment, the compound is a compound of Formula IV, or a pharmaceutically acceptable salt thereof. In another aspect of this embodiment, the compound is a compound of Formula V, or a pharmaceutically acceptable salt thereof. In another aspect of this embodiment, the compound is a compound of Formula VI, or a pharmaceutically acceptable salt thereof.

A sixteenth embodiment of the present invention (Embodiment E16) is a compound of any one of Formulas II, III, V, VI and VII, or a pharmaceutically acceptable salt thereof, wherein: $R^1$ is N($R^A$)—C(O)C(O)—N($R^D$)$R^E$ or N($R^C$)—C(O)C(O)—N($R^D$)$R^E$; $R^2$ is H; and all other variables are as defined in Embodiment E10. In an aspect of this embodiment, the compound is a compound of Formula II, or a pharmaceutically acceptable salt thereof. In another aspect of this embodiment, the compound is a compound of Formula III, or a pharmaceutically acceptable salt thereof. In another aspect of this embodiment, the compound is a compound of Formula V, or a pharmaceutically acceptable salt thereof. In another aspect of this embodiment, the compound is a compound of Formula VI, or a pharmaceutically acceptable salt thereof. In another aspect of this embodiment, the compound is a compound of Formula VII, or a pharmaceutically acceptable salt thereof.

A seventeenth embodiment of the present invention (Embodiment E17) is a compound of Formula I, or a pharmaceutically acceptable salt thereof, wherein:

X is N($R^K$) or O;

$R^K$ is:
(1) H,
(2) C$_{1-4}$ alkyl,
(3) (CH$_2$)$_{1-2}$-T, wherein T is CO$_2R^A$, CN, N($R^D$)$R^E$, or C(O)N($R^D$)$R^E$,
(4) C(O)$R^A$,
(5) C(O)—(CH$_2$)$_{0-2}$—CF$_3$,
(6) CO$_2R^A$,
(7) SO$_2R^A$,
(8) SO$_2$-AryB,
(9) SO$_2$N($R^D$)$R^E$,
(10) C(O)N($R^D$)$R^E$,
(11) C(O)C(O)—N($R^D$)$R^E$,
(12) C(O)—(CH$_2$)$_{1-2}$—N($R^D$)$R^E$,
(13) CycB,
(14) (CH$_2$)$_{1-2}$—U, wherein U is CycB, AryB, or HetB, or
(15) (CH$_2$)$_{1-2}$C(O)N($R^A$)—(CH$_2$)$_{1-2}$-HetB;

$R^1$ is:
(1) H,
(2) C$_{1-4}$ alkyl,
(3) (CH$_2$)$_{1-2}$—V, wherein V is OH, O—C$_{1-4}$ alkyl, S$R^A$, S(O)$R^A$, SO$_2R^A$, N($R^D$)$R^E$, C(O)N($R^D$)$R^E$, N($R^A$)—C(O)C(O)—N($R^D$)$R^E$, N($R^A$)—C(O)$R^B$, N($R^A$)—SO$_2R^B$, N($R^A$)—C$_{1-4}$ alkylene-SO$_2R^B$, N($R^A$)C(O)—C$_{1-4}$ alkylene-SO$_2R^B$, N($R^A$)—SO$_2$N($R^D$)$R^E$, or N($R^A$)—CO$_2R^B$,
(4) (CH$_2$)$_{1-2}$—W, wherein W is CycA, AryA, HetA, O—(CH$_2$)$_{1-2}$-AryA, O—(CH$_2$)$_{1-2}$-HetA, or N($R^A$)—C(O)-HetA,
(5) N($R^A$)—SO$_2R^B$,
(6) N($R^A$)—SO$_2$N($R^D$)$R^E$,
(7) N($R^A$)—CO$_2R^B$,
(8) N($R^D$)$R^E$, (9) N(R^C)R^A,
(10) N(R^A)—C(O)R^B,
(11) N(R^C)—C(O)R^A,
(12) SR^F,
(13) N(R^A)—C(O)-HetA,
(14) N(R^C)—C(O)—N(R^D)R^E,
(15) N(R^A)—C(O)C(O)—N(R^D)R^E or
(16) N(R^C)—C(O)C(O)—N(R^D)R^E;

R² is H or C$_{1-4}$ alkyl; or alternatively R¹ and R² together with the ring carbon atom to which they are both attached form cyclopropyl, cyclobutyl, cyclopentyl, cyclohexyl, or oxacyclohexyl (alternatively known in the art as tetrahydropyranyl);

each R³ is H, and each R⁴ is H; or alternatively R³ and R⁴ attached to the same carbon atom together form oxo;

each R⁵ is H, and each R⁶ is H; or alternatively R⁵ and R⁶ attached to the same carbon atom together form oxo;

R⁷ is H;

R⁸ is H; or alternatively R⁷ and R⁸ together form oxo;

R⁹ is H;

R¹⁰ is CH₂-CycC, CH₂-AryC or CH₂-HetC;

each R^A is independently H or C$_{1-4}$ alkyl;

each R^B is independently H or C$_{1-4}$ alkyl;

R^C is (CH₂)$_{1-2}$-CycA, (CH₂)$_{1-2}$-AryA, or (CH₂)$_{1-2}$-HetA; or alternatively, when X is N(R^K), R^C and R^K together with (i) the N atom to which R^K is attached, (ii) the N atom to which R^C is attached, (iii) the ring carbon to which R¹ is attached, and (iv) the zero, 1 or 2 ring carbons between X and the ring carbon to which R¹ is attached, form a fused 5- or 6-membered diazacycloalkyl ring; wherein the portion of the fused ring obtained from R^C and R^K is a 1- to 3-membered methylene chain optionally substituted with oxo;

each R^D and R^E are independently H or C$_{1-4}$ alkyl, or together with the nitrogen to which they are both attached form a 5- or 6-membered saturated heterocyclic ring selected from the group consisting of

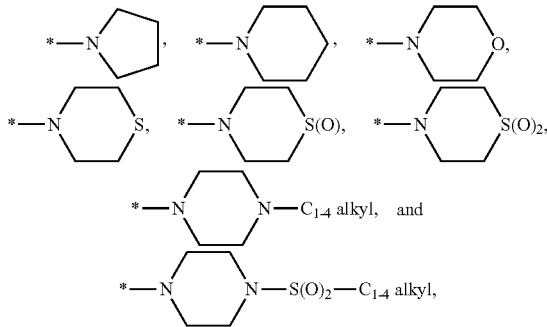

wherein * denotes the point of attachment to the rest of the molecule;

R^F is C$_{1-4}$ alkyl, or alternatively, when X is N(R^K) and R¹ is SR^F, R^F and R^K together with (i) the N atom to which R^K is attached, (ii) the S atom to which R^F is attached, (iii) the ring carbon to which R¹ is attached, and (iv) the zero, 1 or 2 ring carbons between X and the ring carbon to which R¹ is attached, form a fused 5- or 6-membered thioazacycloalkyl ring, wherein the portion of the fused ring obtained from R^F and R^K is a 1- to 3-membered methylene chain;

each CycA is independently a C$_{3-6}$ cycloalkyl;

CycB is a C$_{3-6}$ cycloalkyl;

CycC is a C$_{3-6}$ cycloalkyl;

AryA, AryB and AryC are each independently phenyl which is optionally substituted with 1 or 2 substituents each of which is independently bromo, chloro, fluoro, C$_{1-4}$ alkyl, CF₃, C(O)NH₂, C(O)NH(C$_{1-4}$ alkyl), C(O)N(C$_{1-4}$ alkyl)₂, S—C$_{1-4}$ alkyl, SO₂—C$_{1-4}$ alkyl, or SO₂N(C$_{1-4}$ alkyl)₂; and HetA, HetB, and HetC are each independently a 5- or 6-membered heteroaromatic ring selected from the group consisting of pyrrolyl, pyrazolyl, imidazolyl, triazolyl, tetrazolyl, oxazolyl, thiazolyl, isooxazolyl, isothiazolyl, furanyl, thienyl, oxadiazolyl, pyridinyl, pyridinyl N-oxide, pyrimidinyl, pyridazinyl, and pyrazinyl, wherein the heteroaromatic ring is optionally substituted with from 1 or 2 substituents each of which is independently a C$_{1-4}$ alkyl;

and the integers m and n are as originally defined or as defined in Embodiment E4. In an aspect of this embodiment, X is N(R^K).

An eighteenth embodiment of the present invention (Embodiment E18) is a compound of Formula I as defined in Embodiment E17, or a pharmaceutically acceptable salt thereof, wherein provisos A, B, C and D as set forth in Embodiment E11 are applied. In an aspect of this embodiment, X is N(R^K).

A nineteenth embodiment of the present invention (Embodiment E19) is a compound of Formula I as defined in Embodiment E17, or a pharmaceutically acceptable salt thereof, wherein provisos A, B and C as set forth in Embodiment E12 are applied. In an aspect of this embodiment, X is N(R^K).

A twentieth embodiment of the present invention (Embodiment E20) is a compound of Formula I as defined in Embodiment E17, or a pharmaceutically acceptable salt thereof, wherein provisos A, B and C as set forth in Embodiment E13 are applied. In an aspect of this embodiment, X is N(R^K).

It is understood that the definitions of variables in the provisos set forth in Embodiments E11, E12 and E13 can be customized in the provisos in Embodiments E18, E19 and E20 so that the definitions therein match (i.e., are consistent with) the definitions of the variables in Embodiment E17. For example, part (3) of the definition of R^K in Embodiment E17 recites "(CH₂)$_{1-2}$-T". Accordingly, the reference to "C$_{1-4}$ alkyl substituted with T" in part (3) of the definition of R^K in proviso C of Embodiment E11 can be rewritten here to refer to "(CH₂)$_{1-2}$-T".

A twenty-first embodiment of the present invention (Embodiment E21) is a compound of Formula I, or a pharmaceutically acceptable salt thereof, wherein:

X is N(R^K) or O;

R^K is:

(1) H, (2) C$_{1-4}$ alkyl, (3) (CH₂)$_{1-2}$-T, wherein T is CO₂H, CO₂CH₃, CO₂CH₂CH₃, CN, N(CH₃)₂, N(CH₂CH₃)₂, C(O)NH₂, C(O)NH(CH₃), C(O)N(CH₃)₂, C(O)NH(CH₂CH₃), C(O)N(CH₂CH₃)₂,

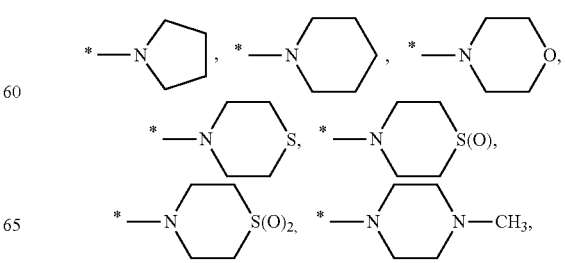

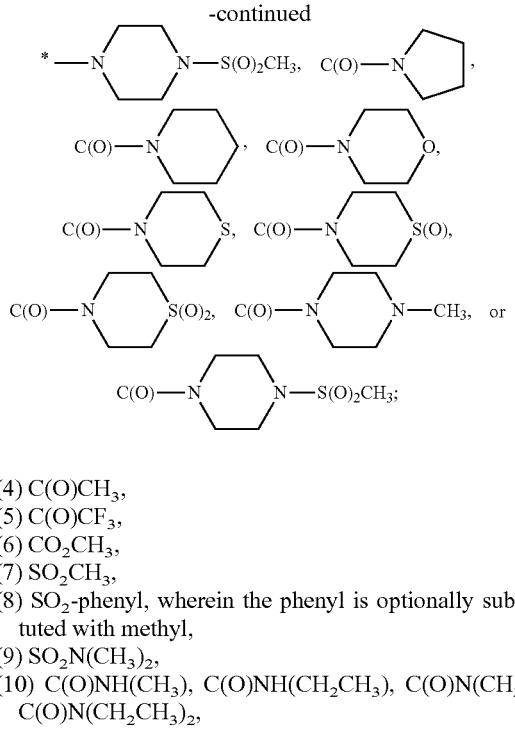

(4) C(O)CH₃,
(5) C(O)CF₃,
(6) CO₂CH₃,
(7) SO₂CH₃,
(8) SO₂-phenyl, wherein the phenyl is optionally substituted with methyl,
(9) SO₂N(CH₃)₂,
(10) C(O)NH(CH₃), C(O)NH(CH₂CH₃), C(O)N(CH₃)₂, C(O)N(CH₂CH₃)₂,

(11) C(O)C(O)—N(CH₃)₂,

(12) C(O)—(CH₂)₁₋₂—N(CH₃)₂,
(13) cyclopropyl, cyclobutyl, cyclopentyl, or cyclohexyl,

(14) (CH₂)₁₋₂—U, wherein U is cyclopropyl, cyclopentyl, cyclohexyl, phenyl, or a heteroaromatic ring selected from the group consisting of pyrazolyl, triazolyl, tetrazolyl, oxazolyl, isoxazolyl, thiazolyl, isothiazolyl, oxadiazolyl, pyridinyl, and pyrazinyl, wherein the heteroaromatic ring is optionally substituted with methyl,
(15) (CH₂)₁₋₂C(O)N(H)—(CH₂)₁₋₂-pyridinyl,
(16) (CH₂)₁₋₂C(O)N(H)—(CH₂)₁₋₂-pyrimidinyl,
(17) (CH₂)₁₋₂C(O)N(H)—(CH₂)₁₋₂-pyrazinyl,
(18) (CH₂)₁₋₂C(O)N(CH₃)—(CH₂)₁₋₂-pyridinyl,
(19) (CH₂)₁₋₂C(O)N(CH₃)—(CH₂)₁₋₂-pyrimidinyl, or
(20) (CH₂)₁₋₂C(O)N(CH₃)—(CH₂)₁₋₂-pyrazinyl;

$R^1$ is:
(1) H,
(2) $C_{1-4}$ alkyl,
(3) (CH₂)₁₋₂—V, wherein V is OH, OCH₃, SCH₃, SO₂CH₃, N(CH₃)₂, C(O)NH₂, C(O)NH(CH₃), C(O)N(CH₃)₂, C(O)NH(CH₂CH₃), C(O)N(CH₂CH₃)₂,

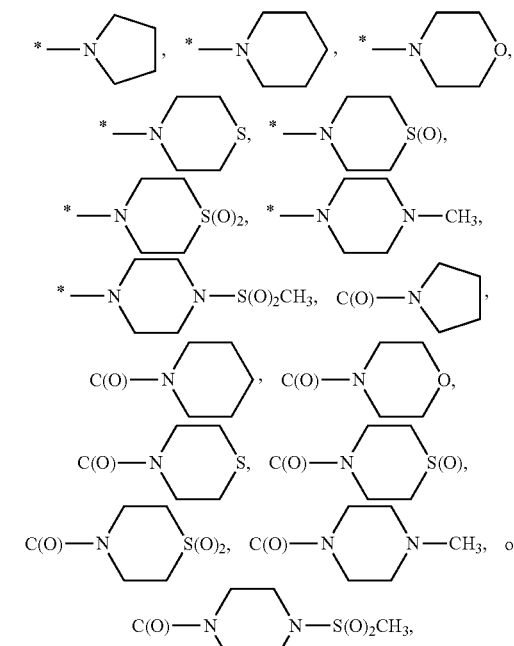

N(CH₃)—C(O)C(O)—N(CH₃)₂, N(CH₃)—C(O)CH₃, N(CH₃)—SO₂CH₃, N(CH₃)CH₂SO₂CH₃, N(CH₃)C(O)CH₂SO₂CH₃, N(CH₃)—SO₂N(CH₃)₂, or N(CH₃)—CO₂CH₃, (4) (CH₂)₁₋₂—W, wherein W is OCH₂-phenyl or N(CH₃)—C(O)-HetA,
(5) N(H)—SO₂CH₃,
(6) N(CH₃)—SO₂CH₃,
(7) N(CH₃)—SO₂N(CH₃)₂, (8) 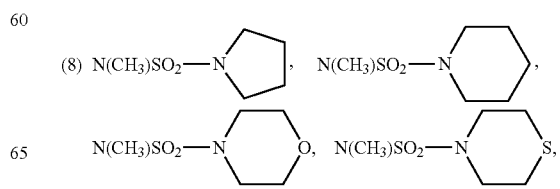

-continued

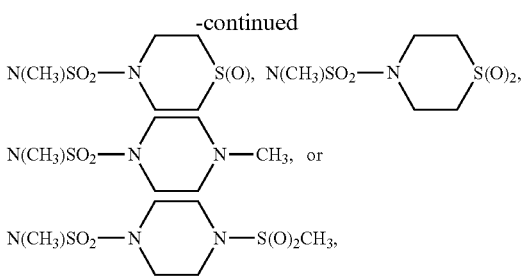

(9) N(CH$_3$)—CO$_2$CH$_3$,
(10) NH(CH$_2$CH(CH$_3$)$_2$),
(11) NH(CH$_3$),
(12) NH(CH$_2$CH$_3$),
(13) N(CH$_3$)$_2$,
(14) N(CH$_2$CH$_3$)$_2$,
(15) N(R$^C$)CH$_3$,
(16) NH(R$^C$),
(17) NH—C(O)CH$_3$,
(18) N(CH$_3$)—C(O)CH$_3$,
(19) N(CH$_2$CH$_3$)—C(O)CH$_3$,
(20) N(CH$_2$CH(CH$_3$)$_2$)—C(O)CH$_3$,
(21) N(R$^C$)—C(O)CH$_3$,
(22) SR$^F$, S(O)R$^F$, or S(O)$_2$R$^F$,
(23) N(CH$_3$)—C(O)-HetA,
(24) N(R$^C$)—C(O)—N(R$^D$)R$^E$,
(25) N(H)—C(O)C(O)—N(CH$_3$)$_2$,
(26) N(CH$_3$)—C(O)C(O)—N(CH$_3$)$_2$,
(27) N(CH$_2$CH$_3$)—C(O)C(O)—N(CH$_3$)$_2$,
(28) N[CH(CH$_3$)$_2$]—C(O)C(O)—N(CH$_3$)$_2$,
(29) N[CH$_2$CH(CH$_3$)$_2$)]C(O)C(O)—N(CH$_3$)$_2$,

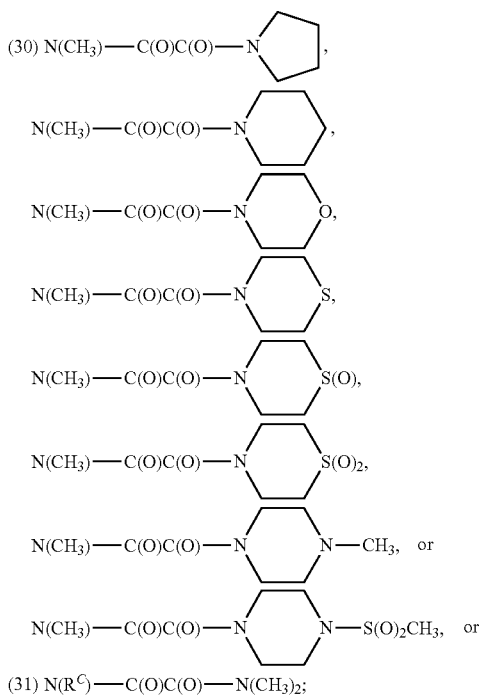

R$^2$ is H or C$_{1-4}$ alkyl; or alternatively R$^1$ and R$^2$ together with the ring carbon atom to which they are both attached form cyclopropyl, cyclopentyl, cyclohexyl, or tetrahydropyran-4-yl;

each R$^3$ is H, and each R$^4$ is H; or alternatively R$^3$ and R$^4$ attached to the same carbon atom together form oxo;

each R$^5$ is H, and each R$^6$ is H; or alternatively R$^5$ and R$^6$ attached to the same carbon atom together form oxo;

R$^7$ is H;

R$^8$ is H; or alternatively R$^7$ and R$^8$ together form oxo;

R$^9$ is H;

R$^{10}$ is CH$_2$-phenyl, wherein the phenyl is optionally substituted with 1 or 2 substituents each of which is independently bromo, chloro, fluoro, CH$_3$, CF$_3$, C(O)NH$_2$, C(O)NH(CH$_3$), C(O)N(CH$_3$)$_2$, SCH$_3$, SO$_2$CH$_3$, or SO$_2$N(CH$_3$)$_2$;

R$^C$ is CH$_2$-cyclohexyl or CH$_2$-phenyl where the phenyl is optionally substituted with 1 or 2 substituents each of which is independently bromo, chloro, fluoro, methyl, ethyl, CF$_3$, C(O)NH$_2$, C(O)NH(CH$_3$), C(O)NH(CH$_2$CH$_3$), C(O)N(CH$_3$)$_2$, SCH$_3$, SO$_2$CH$_3$, or SO$_2$N(CH$_3$)$_2$; or alternatively:

(a) when X is N(R$^K$), R$^1$ is N(R$^C$)—C(O)C(O)—N(CH$_3$)$_2$, and m=n=1, then R$^C$ and R$^K$ together with (i) the N atom to which R$^K$ is attached, (ii) the N atom to which R$^C$ is attached, (iii) the ring carbon to which R$^1$ is attached, and (iv) and the ring carbon between X and the ring carbon to which R$^1$ is attached, form a fused 6-membered diazacycloalkyl ring; wherein the portion of the fused ring obtained from R$^C$ and R$^K$ is —CH$_2$CH$_2$—, (b) when X is N(R$^K$), R$^1$ is N(R$^C$)—C(O)CH$_3$, m=0, and n=1, then R$^C$ and R$^K$ together with (i) the N atom to which R$^K$ is attached, (ii) the N atom to which R$^C$ is attached, and (iii) the ring carbon to which R$^1$ is attached, form a fused 5-membered diazacycloalkyl ring; wherein the portion of the fused ring obtained from R$^C$ and R$^K$ is —C(O)CH$_2$— or —CH$_2$C(O)—, or (c) when X is N(R$^K$), R$^1$ is N(R$^C$)CH$_3$, and m=n=1, then R$^C$ and R$^K$ together with (i) the N atom to which R$^K$ is attached, (ii) the N atom to which R$^C$ is attached, (iii) the ring carbon to which R$^1$ is attached, and (iv) and the ring carbon between X and the ring carbon to which R$^1$ is attached, form a fused 6-membered diazacycloalkyl ring; wherein the portion of the fused ring obtained from R$^C$ and R$^K$ is —C(O)CH$_2$— or —CH$_2$C(O)—; and R$^F$ is CH$_3$, or alternatively, when X is N(R$^K$), R$^1$ is SR$^F$, and m=n=0, R$^F$ and R$^K$ together with (i) the N atom to which R$^K$ is attached, (ii) the S atom to which R$^F$ is attached, and (iii) the ring carbon to which R$^1$ is attached, form a fused 5-membered thioazacycloalkyl ring, wherein the portion of the fused ring obtained from R$^F$ and R$^K$ is —CH$_2$CH$_2$—;

HetA is a heteroaromatic ring selected from the group consisting of pyrazolyl, triazolyl, tetrazolyl, oxazolyl, isoxazolyl, thiazolyl, isothiazolyl, oxadiazolyl, pyridinyl, pyridinyl N-oxide, and pyrazinyl, wherein the heteroaromatic ring is optionally substituted with methyl;

and the integers m and n are as originally defined or as defined in Embodiment E4. In an aspect of this embodiment, X is N(R$^K$).

A twenty-second embodiment of the present invention (Embodiment E22) is a compound of Formula I as defined in Embodiment E21, or a pharmaceutically acceptable salt thereof, wherein provisos A, B, C and D as set forth in Embodiment E11 are applied. In an aspect of this embodiment, X is N(R$^K$).

A twenty-third embodiment of the present invention (Embodiment E23) is a compound of Formula I as defined in Embodiment E21, or a pharmaceutically acceptable salt thereof, wherein provisos A, B and C as set forth in Embodiment E12 are applied. In an aspect of this embodiment, X is N(R$^K$).

A twenty-fourth embodiment of the present invention (Embodiment E24) is a compound of Formula I as defined in Embodiment E21, or a pharmaceutically acceptable salt thereof, wherein provisos A, B and C as set forth in Embodiment E13 are applied. In an aspect of this embodiment, X is N(R$^K$).

It is understood that the definitions of variables in the provisos set forth in Embodiments E11, E12 and E13 can be customized in the provisos in Embodiments E22, E23 and E24 so that the definitions therein match the definitions in Embodiment E21.

A first class of the present invention includes compounds of Formula VIII and pharmaceutically acceptable salts thereof:

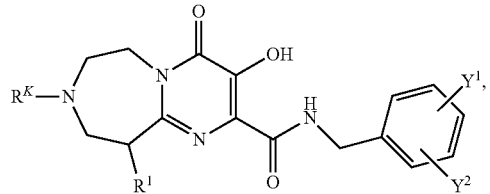

(VIII)

wherein:
R$^K$ is:
(1) H,
(2) methyl,
(3) ethyl,
(4) isopropyl,
(5) C(O)CH$_3$,
(6) SO$_2$CH$_3$,
(7) C(O)C(O)—N(CH$_3$)$_2$,
(8) cyclopropyl
(9) cyclopentyl,
(10) CH$_2$-cyclopropyl,
(11) CH$_2$-phenyl, or
(12) CH$_2$CH$_2$-phenyl;
R$^1$ is:
(1) H,
(2) methyl,
(3) ethyl,
(4) isopropyl,
(5) N(H)—SO$_2$CH$_3$,
(6) N(CH$_3$)—SO$_2$CH$_3$,
(7) N(CH$_3$)—SO$_2$N(CH$_3$)$_2$,
(8) N(CH$_3$)—CO$_2$CH$_3$,
(9) NH(CH$_2$CH(CH$_3$)$_2$),
(10) NH(CH$_3$),
(11) NH(CH$_2$CH$_3$),
(12) N(CH$_3$)$_2$,
(13) N(CH$_2$CH$_3$)$_2$,
(14) N(H)R$^C$,
(15) N(R$^C$)CH$_3$,
(16) NH—C(O)CH$_3$,
(17) N(CH$_3$)—C(O)CH$_3$,
(18) N(CH$_2$CH$_3$)—C(O)CH$_3$,
(19) N(CH$_2$CH(CH$_3$)$_2$)—C(O)CH$_3$,
(20) N(R$^C$)—C(O)CH$_3$,

(21) N(CH$_3$)C(O)— 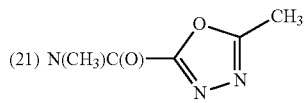

(22) N(H)—C(O)C(O)—N(CH$_3$)$_2$,
(23) N(CH$_3$)—C(O)C(O)—N(CH$_3$)$_2$,
(24) N(CH$_2$CH$_3$)—C(O)C(O)—N(CH$_3$)$_2$,
(25) N[CH$_2$CH(CH$_3$)$_2$]-C(O)C(O)—N(CH$_3$)$_2$,

(26) N(CH$_3$)—C(O)C(O)—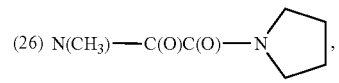,

(26) N(CH$_3$)—C(O)C(O)—,

(27) N(CH$_3$)—C(O)C(O)—,

(28) N(CH$_3$)—C(O)C(O)—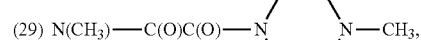,

(29) N(CH$_3$)—C(O)C(O)—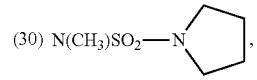,

(30) N(CH$_3$)SO$_2$—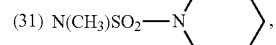,

(31) N(CH$_3$)SO$_2$—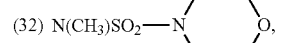,

(32) N(CH$_3$)SO$_2$—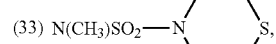,

(33) N(CH$_3$)SO$_2$—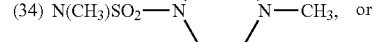,

(34) N(CH$_3$)SO$_2$—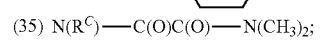, or

(35) N(R$^C$)—C(O)C(O)—N(CH$_3$)$_2$;

R$^C$ is CH$_2$-cyclohexyl, CH$_2$-phenyl, or CH$_2$-phenyl where the phenyl is para-substituted with fluoro; and Y$^1$ and Y$^2$ are each independently H, Br, Cl, F, CH$_3$, C(O)NH(CH$_3$), C(O)N(CH$_3$)$_2$, SCH$_3$, SO$_2$CH$_3$, or SO$_2$N(CH$_3$)$_2$.

A sub-class of the first class includes the compounds as defined therein, and pharmaceutically acceptable salts thereof, wherein proviso C as set forth in Embodiment E11 is applied. Another sub-class of the first class includes the compounds as defined therein, and pharmaceutically acceptable salts thereof, wherein proviso C as set forth in Embodiment E12 is applied. Another sub-class of the first class includes the compounds as defined therein, and pharmaceutically acceptable salts thereof, wherein proviso C as set forth in Embodiment E13 is applied. It is understood that the definitions of variables in the proviso C set forth in Embodiments E11, E12, and E13 can be customized in the provisos included in these sub-classes so that the definitions therein match the definitions set forth in the first class.

A second class of the present invention includes compounds of Formula I and pharmaceutically acceptable salts thereof:

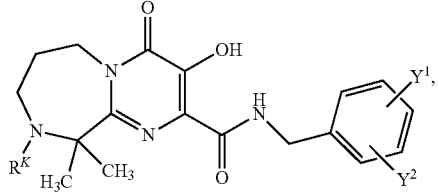
(IX)

wherein:
$R^K$ is H or $C_{1-3}$ alkyl, $CH_2$-phenyl, or $CH_2$-pyridinyl; and
$Y^1$ and $Y^2$ are each independently H, Br, Cl, F, $CH_3$, $C(O)NH(CH_3)$, $C(O)N(CH_3)_2$, $SCH_3$, $SO_2CH_3$, or $SO_2N(CH_3)_2$.

A sub-class of the second class includes compounds of Formula IX, and pharmaceutically acceptable salts thereof, wherein $R^K$ is H or $C_{1-3}$ alkyl; and all other variables are as originally defined in the second class.

Another sub-class of the second class includes compounds of Formula IX, and pharmaceutically acceptable salts thereof, wherein $R^K$ is $C_{1-3}$ alkyl, $CH_2$-phenyl, or $CH_2$-pyridinyl; and all other variables are as originally defined in the second class.

A third class of the present invention includes compounds of Formula X and pharmaceutically acceptable salts thereof:

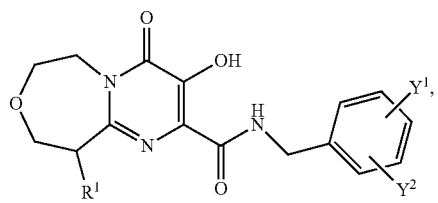
(X)

wherein:
$R^1$ is:
(1) H,
(2) $N(CH_3)$—$SO_2N(CH_3)_2$,
(3) $NH(CH_3)$,
(4) $NH(CH_2CH_3)$,
(5) $NH(CH_2CH(CH_3)_2)$,
(6) $N(CH_3)_2$,
(7) $N(CH_2CH_3)_2$,
(8) $N(CH_3)$—$C(O)CH_3$,
(9) $N(CH_2CH_3)$—$C(O)CH_3$,
(10) $N(CH_2CH(CH_3)_2)$—$C(O)CH_3$,

(11) 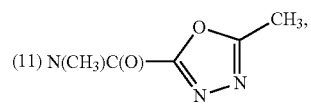

(12) $N(H)$—$C(O)C(O)$—$N(CH_3)_2$,
(13) $N(CH_3)$—$C(O)C(O)$—$N(CH_3)_2$,
(14) $N(CH_2CH_3)$—$C(O)C(O)$—$N(CH_3)_2$,
(15) $N(CH(CH_3)_2)$—$C(O)C(O)$—$N(CH_3)_2$,

(16) $N(CH_3)$—$C(O)C(O)$—N⟨pyrrolidinyl⟩,
(17) $N(CH_3)$—$C(O)C(O)$—N⟨piperidinyl⟩,
(18) $N(CH_3)$—$C(O)C(O)$—N⟨morpholinyl⟩ O,
(19) $N(CH_3)$—$C(O)C(O)$—N⟨thiomorpholinyl⟩ S,
(20) $N(CH_3)$—$C(O)C(O)$—N⟨N-methylpiperazinyl⟩—$CH_3$,
(21) $N(CH_3)SO_2$—N⟨pyrrolidinyl⟩,
(22) $N(CH_3)SO_2$—N⟨piperidinyl⟩,
(23) $N(CH_3)SO_2$—N⟨morpholinyl⟩ O,
(24) $N(CH_3)SO_2$—N⟨thiomorpholinyl⟩ S, or
(25) $N(CH_3)SO_2$—N⟨N-methylpiperazinyl⟩—$CH_3$; and $Y^1$ and $Y^2$ are each independently H, Br, Cl, F, $CH_3$, $C(O)NH(CH_3)$, $C(O)N(CH_3)_2$, $SCH_3$, $SO_2CH_3$, or $SO_2N(CH_3)_2$.

A sub-class of the third class includes the compounds of Formula X, and pharmaceutically acceptable salts thereof, wherein $R^1$ is other than H; i.e., $R^1$ is any one of the groups (2) to (25) as originally defined in the third class; and all other variables are as originally defined in the third class.

A fourth class of the present invention includes compounds of Formula XI and pharmaceutically acceptable salts thereof:

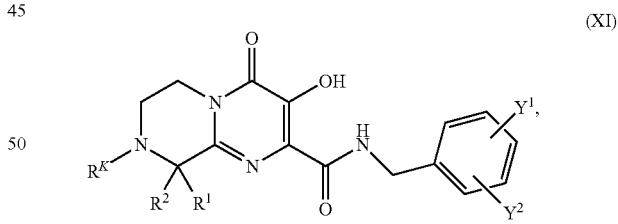
(XI)

wherein:
$R^K$ is:
(1) H,
(2) methyl,
(3) ethyl,
(4) isopropyl,
(5) $CH_2CO_2H$,
(6) $CH_2CN$,
(7) $CH_2CH_2NH(CH_3)$, $CH_2CH_2NH(CH_2CH_3)$, $CH_2CH_2N(CH_3)_2$ or $CH_2CH_2N(CH_2CH_3)_2$,
(8) $CH_2C(O)NH_2$,
(9) $CH_2C(O)NH(CH_3)$,
(10) $CH_2C(O)N(CH_3)_2$,

(11) 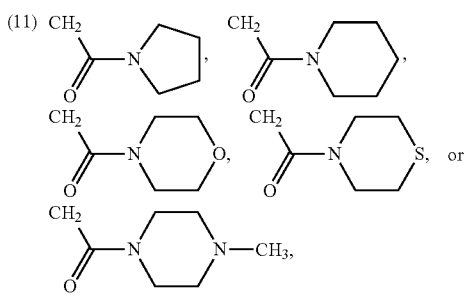

(12) $C(O)CH_3$,
(13) $C(O)CF_3$,
(14) $CO_2CH_3$,
(15) $SO_2CH_3$,

(16) 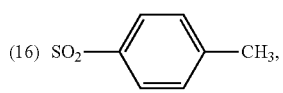

(17) $SO_2N(CH_3)_2$,
(18) $C(O)NH(CH_3)$, $C(O)NH(CH_2CH_3)$, $C(O)N(CH_3)_2$, or $C(O)N(CH_2CH_3)_2$,

(19) 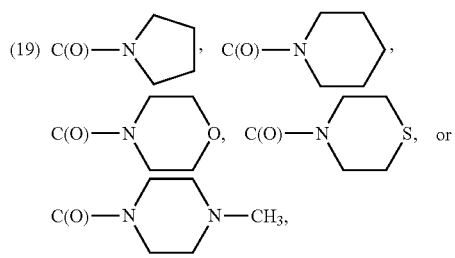

(20) $C(O)C(O)-N(CH_3)_2$,
(21) $C(O)CH_2N(CH_3)_2$,
(22) $CH_2$-phenyl,
(23) $CH_2$-pyridinyl,
(24) $CH_2CH_2$-pyridinyl,

(25) 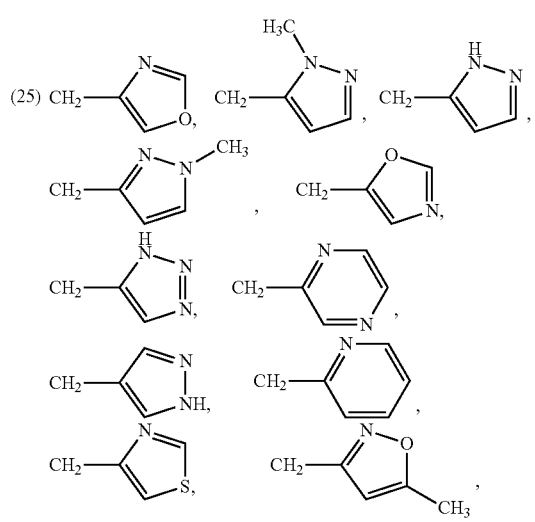

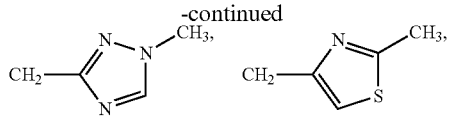

(24) 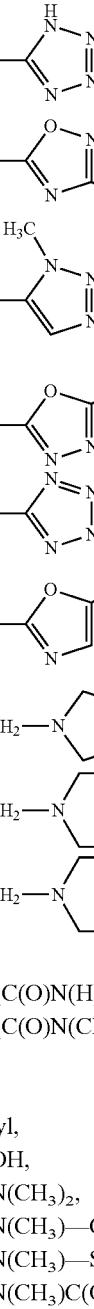

(25) $CH_2C(O)N(H)CH_2$-pyridinyl, or
(26) $CH_2C(O)N(CH_3)CH_2$-pyridinyl;

$R^1$ is:
(1) H,
(2) methyl,
(3) $CH_2OH$,
(4) $CH_2N(CH_3)_2$,
(5) $CH_2N(CH_3)-C(O)C(O)-N(CH_3)_2$,
(6) $CH_2N(CH_3)-SO_2CH_3$,
(7) $CH_2N(CH_3)C(O)CH_2-SO_2CH_3$,
(8) $CH_2N(CH_3)-SO_2N(CH_3)_2$,
(9) $CH_2SCH_3$,
(10) $CH_2SO_2CH_3$,
(11) $CH_2OCH_2$-phenyl,

(12) $CH_2N(CH_3)C(O)$-2-pyridyl, or

(13) 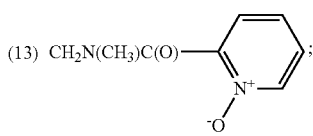

R² is H or methyl; or alternatively R¹ and R² together with the ring carbon atom to which they are both attached form cyclopropyl or tetrahydropyran-4-yl; and Y¹ and Y² are each independently H, Br, Cl, F, $CH_3$, C(O)NH($CH_3$), C(O)N($CH_3$)$_2$, $SCH_3$, $SO_2CH_3$, or $SO_2N(CH_3)_2$.

A sub-class of the fourth class includes the compounds as defined therein, and pharmaceutically acceptable salts thereof, wherein provisos C and D as set forth in Embodiment E11 is applied. Another sub-class of the fourth class includes the compounds as defined therein, and pharmaceutically acceptable salts thereof, wherein proviso C as set forth in Embodiment E12 is applied. Another sub-class of the fourth class includes the compounds as defined therein, and pharmaceutically acceptable salts thereof, wherein proviso C as set forth in Embodiment E13 is applied. It is understood that the definitions of variables in the provisos C and D set forth in Embodiments E11, E12, and E13 can be customized in the provisos included in these sub-classes so that the definitions therein match the definitions set forth in the fourth class.

A fifth class of the present invention includes compounds of Formula XII and pharmaceutically acceptable salts thereof:

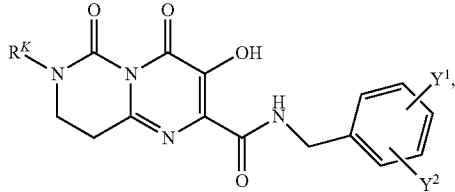

(XII)

wherein:

$R^K$ is $C_{1-3}$ alkyl, $CH_2$-phenyl, $CH_2$-pyridinyl, or (CO)$CH_3$; and

Y¹ and Y² are each independently H, Br, Cl, F, $CH_3$, C(O)NH($CH_3$), C(O)N($CH_3$)$_2$, $SCH_3$, $SO_2CH_3$, or $SO_2N(CH_3)_2$.

A sixth class of the present invention includes compounds of Formula XIII, XIV, and XV, and pharmaceutically acceptable salts thereof:

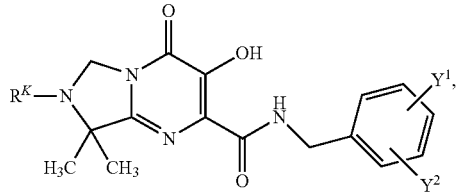

(XIII)

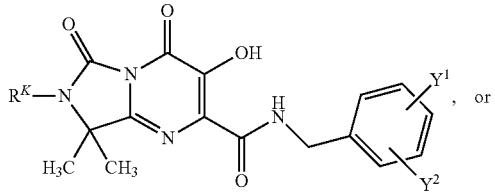

(XIV)

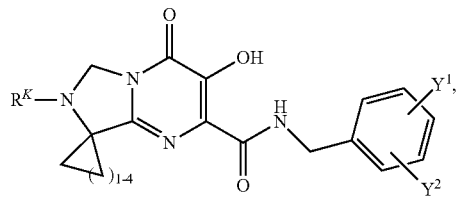

(XV)

wherein:

$R^K$ is $C_{1-3}$ alkyl, $CH_2$-phenyl, or $CH_2$-pyridinyl; and

Y¹ and Y² are each independently H, Br, Cl, F, $CH_3$, C(O)NH($CH_3$), C(O)N($CH_3$)$_2$, $SCH_3$, $SO_2CH_3$, or $SO_2N(CH_3)_2$. A sub-class of the sixth class includes compounds of Formula XV, and pharmaceutically acceptable salts thereof.

Another embodiment of the present invention is a compound, or a pharmaceutically acceptable salt thereof, selected from the group consisting of the compounds set forth in Table 1 below.

Another embodiment of the present invention is a compound, or a pharmaceutically acceptable salt thereof, selected from Compounds 1-4, 6, 7, 9-39 and 41-185.

Another embodiment of the present invention is a compound, or a pharmaceutically acceptable salt thereof, selected from Compounds 60, 61, 63, 64, 69, 71, 72, 75, 76, 82, 84, 85, 86, 87, 89, 91, 92, 110, 113-136, 138, 142-150, 153-157, 180 and 181.

Another embodiment of the present invention is a compound, or a pharmaceutically acceptable salt thereof, selected from Compounds 87, 116-119, 121, 123-136, 142-150, 154-157, 180 and 181. Another embodiment of the present invention is a compound, or a pharmaceutically acceptable salt thereof, selected from Compounds 116-119, 121, 123-136, 142-150, 154-157, 180 and 181. The compounds in these two embodiments have exhibited excellent potency in the integrase assay (Example 32) and in the spread assay (Example 33). It is believed that these compounds are active against clinical mutants that have been generated with approved HIV reverse transcriptase inhibitors and protease inhibitors.

Another embodiment of the present invention is a compound of Formula I, or a pharmaceutically acceptable salt thereof, as originally defined or as defined in any of the foregoing embodiments, classes, or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. A compound or salt of 100% purity is one which is free of detectable impurities as determined by one or more standard methods of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, non-nucleoside HIV reverse transcriptase inhibitors, and nucleoside HIV reverse transcriptase inhibitors.

(e) A pharmaceutical combination which is (i) a compound of Formula I and (ii) an anti-HIV agent selected from the group consisting of HIV antiviral agents, immunomodulators, and anti-infective agents; wherein the compound of Formula I and the anti-HIV agent are each employed in an amount that renders the combination effective for the inhibition of HIV integrase, for the treatment or prophylaxis of infection by HIV, or for the treatment, prophylaxis or delay in the onset of AIDS.

(f) The combination of (e), wherein the anti-HIV agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject an effective amount of a compound of Formula I.

(h) A method for the treatment or prophylaxis of infection by HIV in a subject in need thereof which comprises administering to the subject an effective amount of a compound of Formula I.

(i) The method of (h), wherein the compound of Formula I is administered in combination with an effective amount of at least one antiviral selected from the group consisting of HIV protease inhibitors, non-nucleoside HIV reverse transcriptase inhibitors, and nucleoside HIV reverse transcriptase inhibitors.

(j) A method for the treatment, prophylaxis, or delay in the onset of AIDS in a subject in need thereof which comprises administering to the subject an effective amount of a compound of Formula I.

(k) The method of (j), wherein the compound is administered in combination with an effective amount of at least one antiviral selected from the group consisting of HIV protease inhibitors, non-nucleoside HIV reverse transcriptase inhibitors, and nucleoside HIV reverse transcriptase inhibitors.

(l) A method of inhibiting HIV integrase in a subject in need thereof which comprises administering to the subject the pharmaceutical composition of (a), (b), (c) or (d) or the combination of (e) or (f).

(m) A method for the treatment or prophylaxis of infection by HIV in a subject in need thereof which comprises administering to the subject the pharmaceutical composition of (a), (b), (c) or (d) or the combination of (e) or (f).

(n) A method for the treatment, prophylaxis, or delay in the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) the inhibition of HIV integrase, (b) treatment or prophylaxis of infection by HIV, or (c) treatment, prophylaxis, or delay in the onset of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

The present invention also includes prodrugs of the compounds of Formula I. The term "prodrug" refers to a derivative of a compound of Formula I, or a pharmaceutically acceptable salt thereof, which is converted in vivo into Compound I. Prodrugs of compounds of Formula I can exhibit enhanced solubility, absorption, and/or lipophilicity compared to the compounds per se, thereby resulting in increased bioavailability and efficacy. The in vivo conversion of the prodrug can be the result of an enzyme-catalyzed chemical reaction, a metabolic chemical reaction, and/or a spontaneous chemical reaction (e.g., solvolysis). The prodrug can be, for example, a derivative of a hydroxy group such as an ester (—OC(O)R), a carbonate ester (—OC(O)OR), a phosphate ester (—O—P(=O)(OH)$_2$), or an ether (—OR). Other examples include the following: When the compound of Formula I contains a carboxylic acid group, the prodrug can be an ester or an amide, and when the compound of Formula I contains a primary amino group, the prodrug can be an amide, carbamate, imine, or a Mannich base. One or more functional groups in Compound I can be derivatized to provide a prodrug thereof. Conventional procedures for the selection and preparation of suitable prodrug derivatives are described, for example, in *Design of Prodrugs*, edited by H. Bundgaard, Elsevier, 1985; C. S. Larsen and J. Ostergaard, "Design and application of prodrugs" in: *Textbook of Drug Design and Discovery*, 3$^{rd}$ edition, edited by C. S. Larsen, 2002, pp. 410-458; and Beaumont et al., *Current Drug Metabolism* 2003, vol. 4, pp. 461-458; the disclosures of each of which are incorporated herein by reference in their entireties. Prodrugs of compounds of Formula I can also be selected and prepared by application of the descriptions in WO 2005/070901 and WO 2005/117904, both herein incorporated by reference in their entireties.

As used herein, the term "alkyl" refers to any linear or branched chain alkyl group having a number of carbon atoms in the specified range. Thus, for example, "C$_{1-6}$ alkyl" (or "C$_1$-C$_6$ alkyl") refers to all of the hexyl alkyl and pentyl alkyl isomers as well as n-, iso-, sec- and t-butyl, n- and isopropyl, ethyl and methyl. As another example, "C$_{1-4}$ alkyl" refers to n-, iso-, sec- and t-butyl, n- and isopropyl, ethyl and methyl.

The term "alkylene" refers to any divalent linear or branched chain aliphatic hydrocarbon radical (or alternatively an "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The terms "cycloalkyl" refers to any cyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or 1). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "diazacycloalkyl" means a saturated cyclic ring consisting of two nitrogens and one or more carbon atoms (e.g., imidazolidinyl, pyrazolidinyl, or piperazinyl).

The term "oxyazacycloalkyl" means a saturated cyclic ring consisting of an oxygen atom, a nitrogen atom, and one or more carbon atoms.

The term "thioazacycloalkyl" means a saturated cyclic ring consisting of a sulfur atom, a nitrogen atom, and one or more carbon atoms.

The term "1- to 4-membered methylene chain" means a divalent radical of formula —$(CH_2)_{1-4}$—.

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

When any variable (e.g., $R^A$, $R^B$, or AryD) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "is optionally substituted with from 1 to 5 substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound.

Any of the various carbocyclic and heterocyclic rings and ring systems defined herein may be attached to the rest of the compound at any ring atom (i.e., any carbon atom or any heteroatom) provided that a stable compound results. Suitable aryls include phenyl, 9- and 10-membered bicyclic, fused carbocyclic ring systems, and 11- to 14-membered tricyclic fused carbocyclic ring systems, wherein in the fused carbocyclic ring systems at least one ring is aromatic. Suitable aryls include, for example, phenyl, naphthyl, tetrahydronaphthyl (tetralinyl), indenyl, anthracenyl, and fluorenyl. Suitable heteroaryls include 5- and 6-membered heteroaromatic rings and 9- and 10-membered bicyclic, fused ring systems, wherein the heteroaromatic ring or the bicyclic, fused ring system contains from 1 to 4 heteroatoms selected from N, O and S. Suitable 5- or 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Suitable heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, and quinazolinyl. Suitable saturated heterocyclics include 4- to 7-membered saturated heterocyclic rings containing 1 or 2 heteroatoms selected from N, O and S. Suitable 4- to 7-membered saturated heterocyclics include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. The foregoing are representative of saturated heterocyclics that may be formed by the joining of $R^1$ and $R^2$ together with the ring carbon to which they are both attached. Saturated heterocyclics that may be formed by the joining of $R^D$ and $R^E$ together with the nitrogen to which they are both attached include, for example, azetidinyl, pyrrolidinyl, piperidinyl, morpholinyl, thiomorpholinyl, piperazinyl, azepanyl, diazepanyl, and thiazinanyl.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers or enantiomers. All isomeric forms of these compounds, whether isolated or in mixtures, are within the scope of the present invention.

As would be recognized by one of ordinary skill in the art, certain of the compounds of the present invention can exist as tautomers. All tautomeric forms of these compounds, whether isolated or in mixtures, are within the scope of the present invention.

In instances where a hydroxy (—OH) substituent(s) is(are) permitted on a heteroaromatic ring and keto-enol tautomerism is possible, it is understood that the substituent might in fact be present, in whole or in part, in the keto form, as exemplified here for a hydroxypyridinyl substituent:

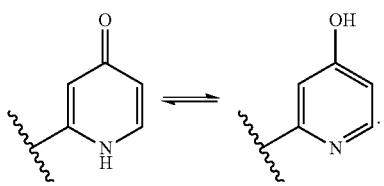

Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

The compounds of the present inventions are useful in the inhibition of HIV integrase (e.g., HIV-1 integrase), the prophylaxis or treatment of infection by HIV and the prophylaxis, treatment or the delay in the onset of consequent pathological conditions such as AIDS. The prophylaxis of AIDS, treating AIDS, delaying the onset of AIDS, the prophylaxis of infection by V, or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention can be commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Certain compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administered" or "administering") in reference to a compound of the invention mean providing the compound or a prodrug of the compound to the individual in need of treatment or prophylaxis. When a compound of the invention or a prodrug thereof is provided in combination with one or more other active agents (e.g., antiviral agents useful for the prophylaxis or treatment of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (or, alternatively, "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of the inhibition of HIV integrase, the prophylaxis or treatment of HIV infection, or the prophylaxis or treatment or delay in the onset of AIDS, the compounds of the present invention, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21$^{st}$ edition, Lippincott Williams & Wilkins, 2005.

The compounds of this invention can be administered orally in a dosage range of about 0.001 to about 1000 mg/kg of mammal (e.g., human) body weight per day in a single dose or in divided doses. One preferred dosage range is about 0.01 to about 500 mg/kg body weight per day orally in a single dose or in divided doses. Another preferred dosage range is about 0.1 to about 100 mg/kg body weight per day orally in single or divided doses. For oral administration, the compositions can be provided in the form of tablets or capsules containing about 1.0 to about 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more anti-HIV agents useful in the treatment of HIV infection or AIDS. An "anti-HIV agent" is any agent which is directly or indirectly effective in the inhibition of HIV integrase or another enzyme required for HIV replication or infection, the treatment or prophylaxis of HIV infection, and/or the treatment, prophylaxis or delay in the onset of AIDS. It is understood that an anti-HIV agent is effective in treating, preventing, or delaying the onset of HIV infection or AIDS and/or diseases or conditions arising therefrom or associated therewith. For example, the compounds of this invention may be effectively administered, whether at periods of pre-exposure and/or post-exposure, in combination with effective amounts of one or more HIV antivirals, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, HIV protease inhibitors (e.g., indinavir, atazanavir, lopinavir optionally with ritonavir, saquinavir, or nelfmavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). It will be understood that the scope of combinations of the compounds of this invention with HIV antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of HIV infection or AIDS. The HIV antivirals and other agents will typically be employed in these combinations in their conventional dosage ranges and regimens as reported in the art, including, for example, the dosages described in the *Physicians' Desk Reference*, 57$^{th}$ edition, Thomson PDR, 2003, or the 59$^{th}$ edition thereof, 2005. The dosage ranges for a compound of the invention in these combinations are the same as those set forth above. It is understood that pharmaceutically acceptable salts of the compounds of the invention and/or the other agents (e.g., indinavir sulfate) can be used as well.

Abbreviations employed herein include the following: AcOH=acetic acid; Bn=benzyl; BOC or Boc=t-butyloxycarbonyl; Bz=benzoyl; CBZ=carbobenzoxy (alternatively, benzyloxycarbonyl); CDI=carbonyldiimidazole; DCM=dichloromethane; DDQ=2,3-dichloro-5,6-dicyano-1,4-benzoquinone; DEAD=diethylazodicarboxylate; DMAD=dimethylacetylenedicarboxylate; DMF=N,N-dimethylformamide; EDC=1-ethyl-3-(3-dimethylaminopropyl) carbodiimide; ES MS=electrospray mass spectroscopy; Et=ethyl; EtOAc=ethyl acetate; EtOH=ethanol; HMDO=hexamethyl disiloxane; HOBT or HOBt=1-hydroxy benzotriazole hydrate; Me=methyl; MeOH=methanol; MsCl=methanesulfonyl chloride; NMP=N-methylpyrrolidinone; NMR=nuclear magnetic resonance; Ph=phenyl; Py=pyridine; RP HPLC=reverse phase high performance liquid chromatography; t-Bu=tert-butyl; SFC=supercritical fluid chromatography; TBAF=tetrabutylammonium fluoride; TFA=trifluoroacetic acid; THF=tetrahydrofuran; TsOH=toluenesulfonic acid.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme A depicts the synthesis of 3-hydroxy-8,9,9-substituted-4-oxo-6,7,8,9-tetrahydro-4H-pyrazino[1,2-a]pyrimidine-2-carboxamides. Reductive alkylation of the amino derivative 1-1 with chloroacetaldeyde using standard chemistry (such as that described in Jerry March, *Advanced Organic Chemistry*, 3$^{rd}$ edition, John Wiley & Sons, 1985, pp. 798-800) can afford 2-substituted-5,6-dihydroxypyrimidine-4-carboxamide 1-2. Intramolecular alkylation of 1-2 with cesium carbonate provides tetrahydropyrazinopyrimidine carboxamide 1-3. Acylation or sulfonylation [see, e.g., the description in Jerry March, *Advanced Organic Chemistry*, 3$^{rd}$ edition, John Wiley & Sons, 1985, pp. 370-371 (acylation) and p. 445 (sulfonylation)] of the nitrogen at the 8 position of 1-3 followed by hydrolysis (e.g., with a base such as NaOH) provides the desired compound 1-4. Alternatively, protection of the 3-hydroxy with a suitable protective group (e.g., benzyl chloride or benyzl bromide; further description on suitable protective groups is in T. W. Greene & P. G. M. Wuts, *Protective Groups in Organic Synthesis*, 3$^{rd}$ edition, John Wiley & Sons, 1999, pp. 249-287) followed by alkylation of the nitrogen [see, e.g., the description in Jerry March, *Advanced Organic Chemistry*, 3$^{rd}$ edition, John Wiley & Sons, 1985, pp. 377-379] provides the desired 1-4. Another alternative is alkylation of 1-3 to 1-4-a by reductive amination using standard chemistry.

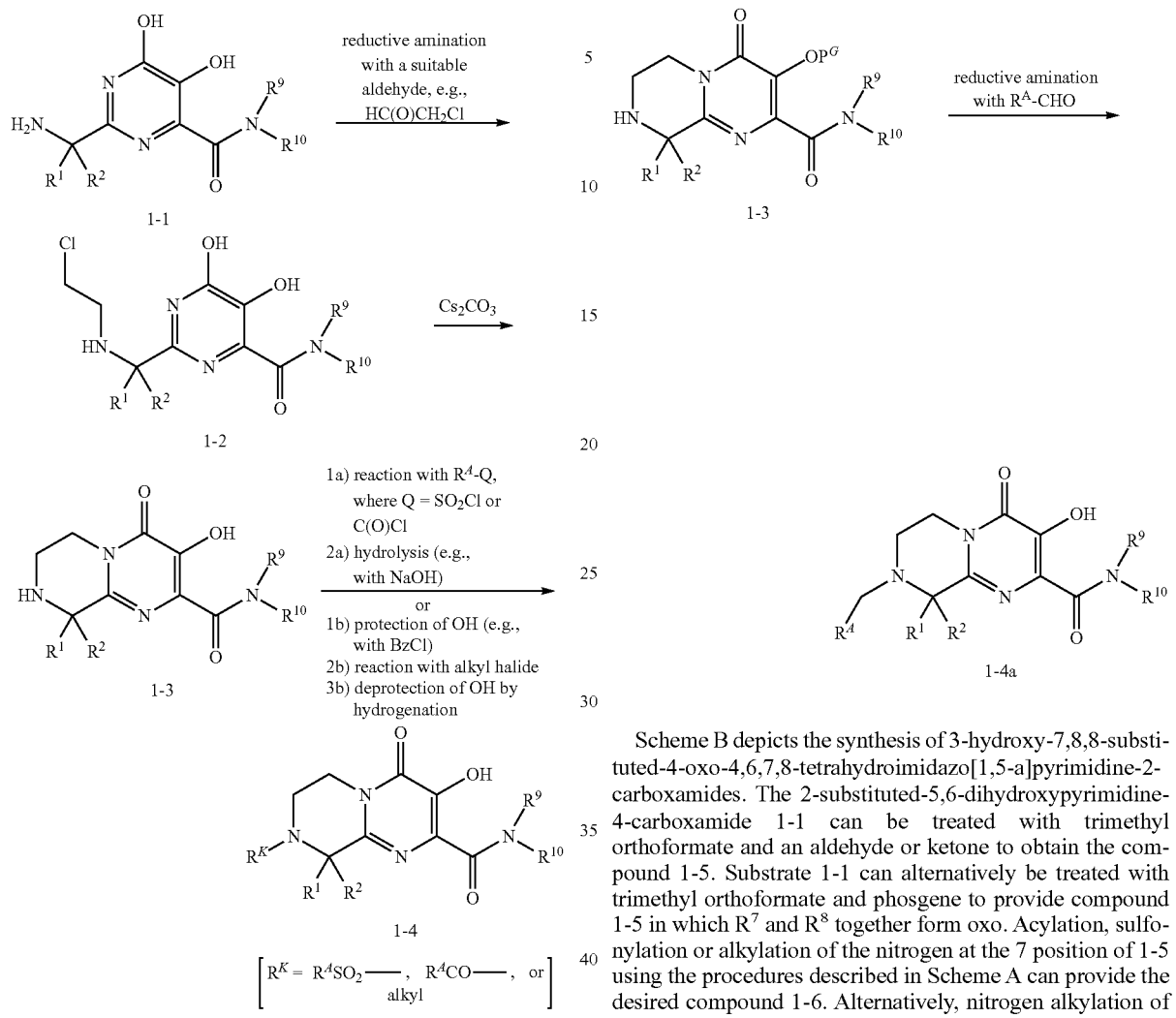

Scheme B depicts the synthesis of 3-hydroxy-7,8,8-substituted-4-oxo-4,6,7,8-tetrahydroimidazo[1,5-a]pyrimidine-2-carboxamides. The 2-substituted-5,6-dihydroxypyrimidine-4-carboxamide 1-1 can be treated with trimethyl orthoformate and an aldehyde or ketone to obtain the compound 1-5. Substrate 1-1 can alternatively be treated with trimethyl orthoformate and phosgene to provide compound 1-5 in which $R^7$ and $R^8$ together form oxo. Acylation, sulfonylation or alkylation of the nitrogen at the 7 position of 1-5 using the procedures described in Scheme A can provide the desired compound 1-6. Alternatively, nitrogen alkylation of 1-5 to desired 1-6a can be achieved by reductive amination.

-continued

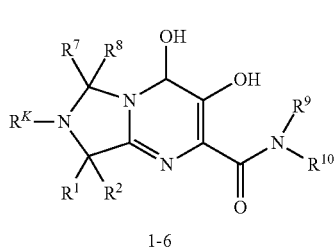

1-6

[$R^K$ = $R^4SO_2$——, $R^4CO$——, or alkyl]

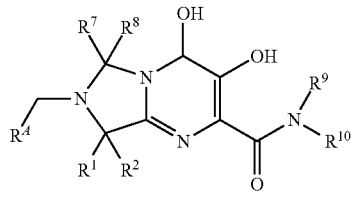

1-6a

Scheme C depicts the synthesis of 3-hydroxy-9,10,10-substituted-4-oxo-4,6,7,8,9,10-hexahydropyrimido[1,2-a][1,4]diazepine-2-carboxamides. The 2-substituted-5,6-dihydroxypyrimidine-4-carboxamide 1-7 can be obtained by reductive alkylation of the amino derivative 1-1 with a benzyl protected hydroxyalkyl aldehyde (exemplified in Scheme C with 3-(benzyloxy)propanal) followed by removal of the benzyl protective group by, e.g., hydrogenolysis. Intramolecular cyclization under Mitsunobu conditions (e.g., treatment with DEAD in the presence of $PPh_3$) provides 3-hydroxy-10,10-substituted-4-oxo-4,6,7,8,9,10-hexahydropyrimido[1,2-a][1,4]diazepine-2-carboxamide 1-8. Acylation, sulfonylation, or alkylation of the nitrogen at the 9 position of 1-8 can then provide the desired compound 1-9. Alternatively, reductive amination can provide desired compound 1-9a.

Scheme C:

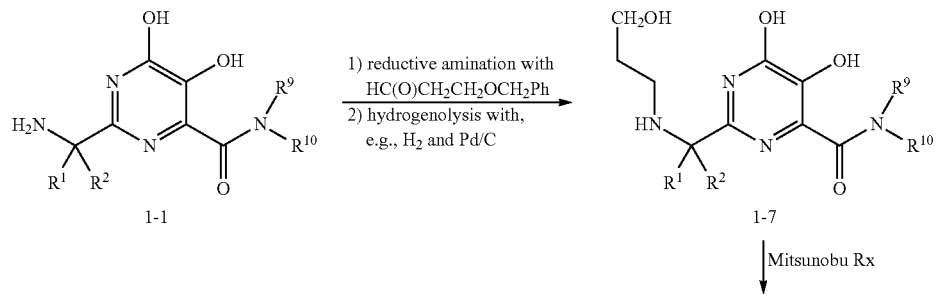

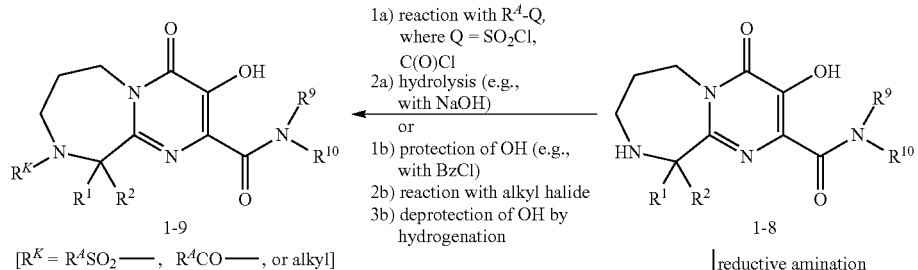

[$R^K$ = $R^4SO_2$——, $R^4CO$——, or alkyl]

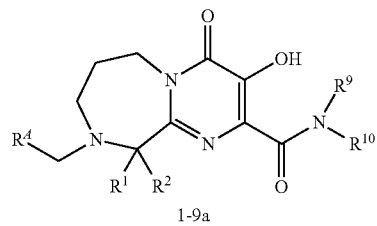

1-9a

Scheme D depicts the synthesis of 10-substituted-3-hydroxy-8-substituted-4-oxo-4,6,7,8,9,10-hexahydropyrimido[1,2-d][1,4]diazepine-2-carboxamides. Amide 1-10 can be prepared in accordance with WO 2001/090082. The amidoxime 1-11 can be obtained by thioamidation of the amide 1-10 with $P_4S_{10}$ followed by treatment with hydroxylamine. Reaction of the amidoxime 1-11 with dimethylacetylenedicarboxylate, followed by cyclization at high temperature in a suitable solvent (e.g., toluene, xylenes (individually or mixtures), chlorobenzene, or an alkyl alcohol such as MeOH) can provide the methyl ester 1-12. The methyl ester 1-12 can then be treated with DDQ, followed by treatment with benzylamine or a N-benzyl-N-alkylamine to obtain compound 1-13. The benzyl group of 1-13 can be removed by hydrogenolysis, after which the methyl ester can be converted to amide 1-14 by treatment with a suitable amine. Acylation, sulfonylation or reductive amination of the secondary amine at the 10 position of 1-14 using standard chemistry can provide compound 1-15. Removal of the Boc protective group (e.g., by treatment with an acid such as TFA) from 1-15 followed by acylation or sulfonylation and then hydrolysis (e.g., with NaOH) can provide the desired 1-16. Alternatively, removal of the Boc protective group form 1-15 followed by reductive amination can provide the desired 1-16a.

Scheme D

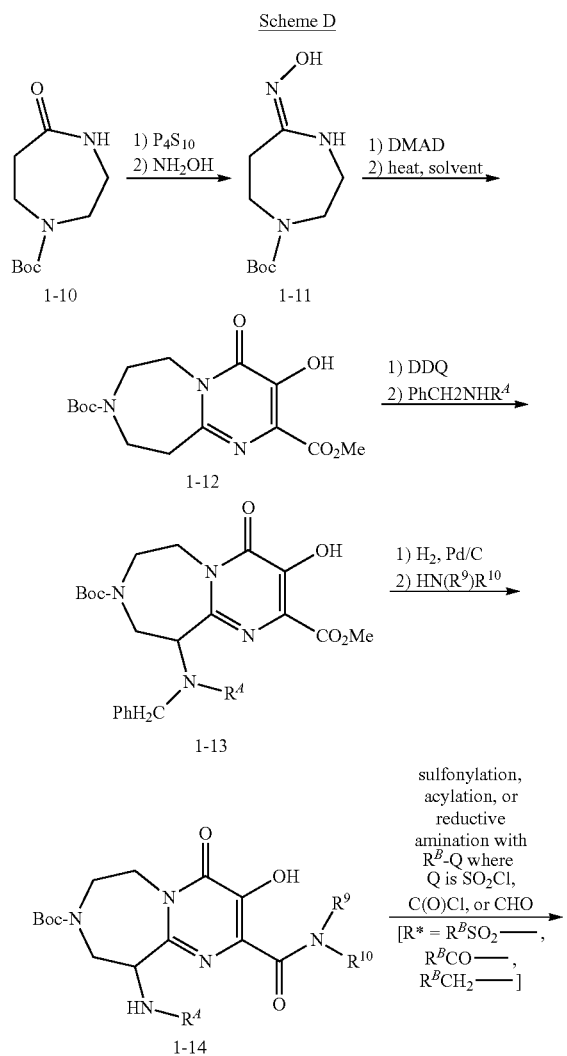

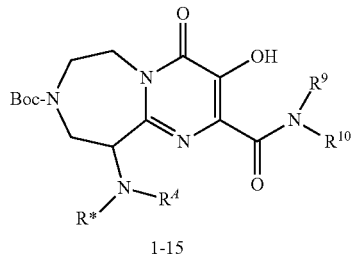

1-15

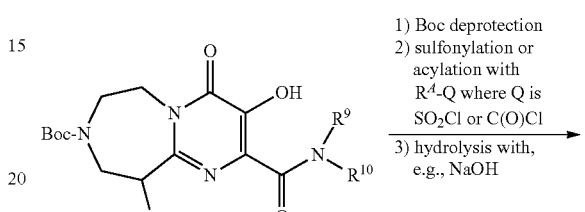

1) Boc deprotection
2) sulfonylation or acylation with $R^A$-Q where Q is $SO_2Cl$ or C(O)Cl
3) hydrolysis with, e.g., NaOH 1-15

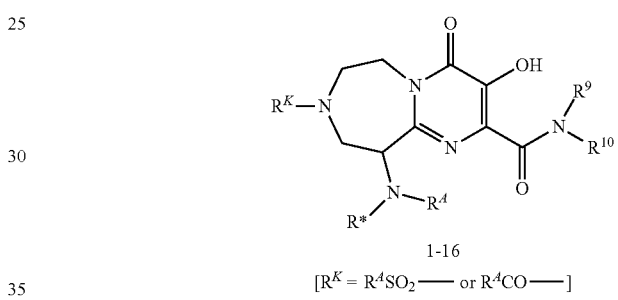

1-16

$[R^K = R^A SO_2—$ or $R^A CO—]$

Alternative:

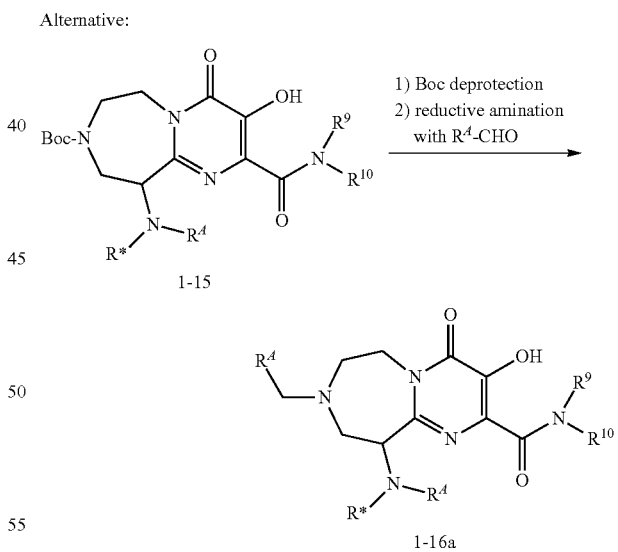

1-15

1-16a

Scheme E shows an alternative approach to Scheme D for the preparation of compound 1-16. The intermediate compound 1-13 is first deprotected, followed by acylation, sulfonylation or reductive amination using standard chemistry to give 1-17. Hydrogenolysis of 1-17 followed by acylation, sulfonylation or reductive amination using standard chemistry provides compound 1-18, and then coupling 1-18 with the appropriate amine affords the desired compound 1-16 or 1-16a.

Scheme E

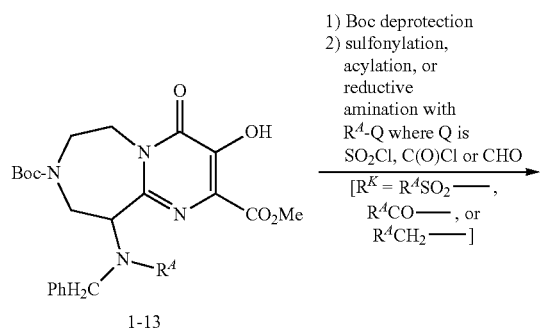

1-13

1) Boc deprotection
2) sulfonylation, acylation, or reductive amination with $R^A$-Q where Q is $SO_2Cl$, C(O)Cl or CHO
[$R^K = R^A SO_2$——,
$R^A CO$——, or
$R^A CH_2$——]

1) $H_2$, Pd/C
2) sulfonylation, acylation, or reductive amination with $R^B$-Q where Q is $SO_2Cl$, C(O)Cl or CHO
[$R^* = R^B SO_2$——,
$R^B CO$——,
$R^B CH_2$——]

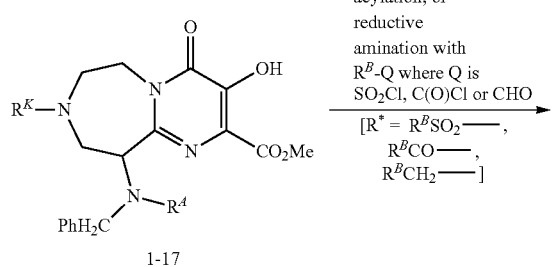

1-17

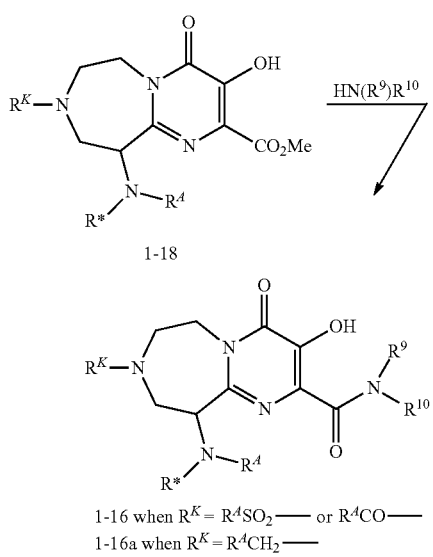

1-18

HN($R^9$)$R^{10}$ 1-16 when $R^K = R^A SO_2$—— or $R^A CO$——
1-16a when $R^K = R^A CH_2$——

The first two steps of Scheme E can be conducted in the reverse order as shown in Scheme F, wherein the intermediate compound 1-13 is first subject to hydrogenolysis and then the methyl ester is converted to the desired amide by coupling with the appropriate amine to obtain the compound 1-19. Acylation, sulfonylation or reductive amination using standard chemistry followed by Boc deprotection step gives 1-20.

Scheme F

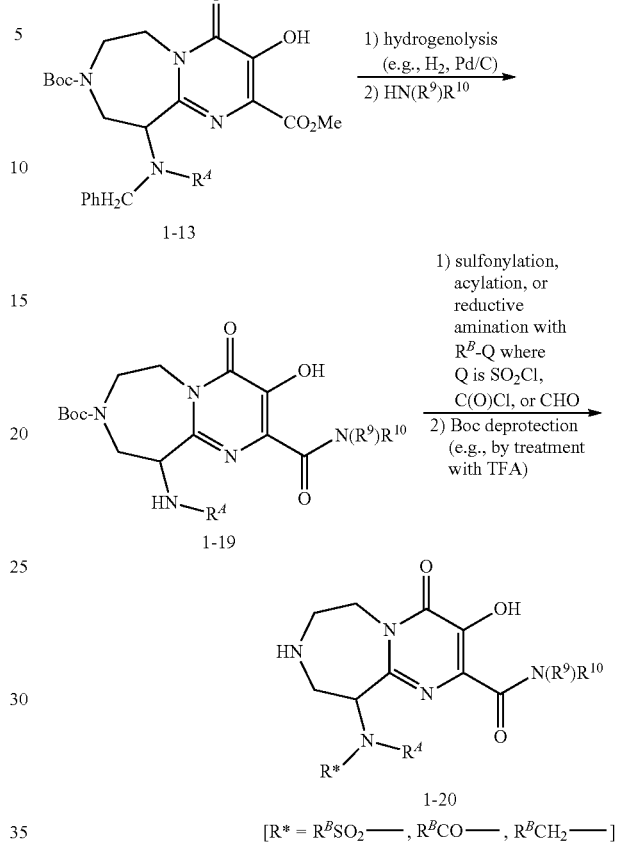

1-13

1) hydrogenolysis (e.g., $H_2$, Pd/C)
2) HN($R^9$)$R^{10}$ 1-19

1) sulfonylation, acylation, or reductive amination with $R^B$-Q where Q is $SO_2Cl$, C(O)Cl, or CHO
2) Boc deprotection (e.g., by treatment with TFA)

1-20

[$R^* = R^B SO_2$——, $R^B CO$——, $R^B CH_2$——]

Scheme G depicts the synthesis of 10-substituted-3-hydroxy-8-substituted-4-oxo-4,6,7,8,9,10-hexahydropyrimido[1,2-d][1,4]diazepine-2-carboxamides. Nitrile 1-21 (prepared in the manner described in *Eur. J. Org. Chem.* 1999, 9: 2127-2135) is treated with hydroxylamine to obtain amidoxime 1-22, which is then treated with dimethylacetylenedicarboxylate, and then cyclized at high temperature in a suitable solvent (e.g., toluene, xylenes (individually or in mixtures), chlorobenzene, or an alkyl alcohol such as MeOH) to obtain the pyrimidine methyl ester. The 5-hydroxy in the pyrimidine methyl ester intermediate is then protected using, e.g., benzoic anhydride to afford methyl ester 1-23. Ester 1-23 can be converted into an amide by coupling with an appropriate amine followed by the Boc deprotection with a suitable acid (e.g., TFA) to generate the free amino compound 1-24. Reductive amination of amine 1-24 with chloroacetaldehyde followed by ring closure with KO-t-Bu can provide the cyclized compound 1-25. Boc protection of the nitrogen in the 8 position of 1-25 and removal of the benzyl group by hydrogenolysis produces alcohol 1-26, which can be activated with MsCl (e.g., at room temperature in the presence of TEA and a suitable solvent such as $CHCl_3$) and then displaced with an appropriate benzylamine (e.g., coupling with the amine in a suitable solvent such as acetonitrile at elevated temperature and then ageing the reaction mixture until completion of the reaction) to afford amine compound 1-27. Removal of the Boc (e.g., with TFA), followed by sulfonylation, acylation or reductive amination of the secondary amine in the 8-position of the bicyclic system, and then removal of the benzyl group by hydrogenolysis affords amino compound 1-28. Sulfonylation, acylation or reductive amination of the secondary amine can then afford the desired compound 1-29. Alternatively, alcohol 1-26, after activation with MsCl, can be displaced with sodium thiomethoxide to afford after Boc deprotection compound 1-27a. Reductive amination of the secondary amine in the 8-position of the bicyclic system and oxidation of the thioether affords compound 1-28.

Scheme G:

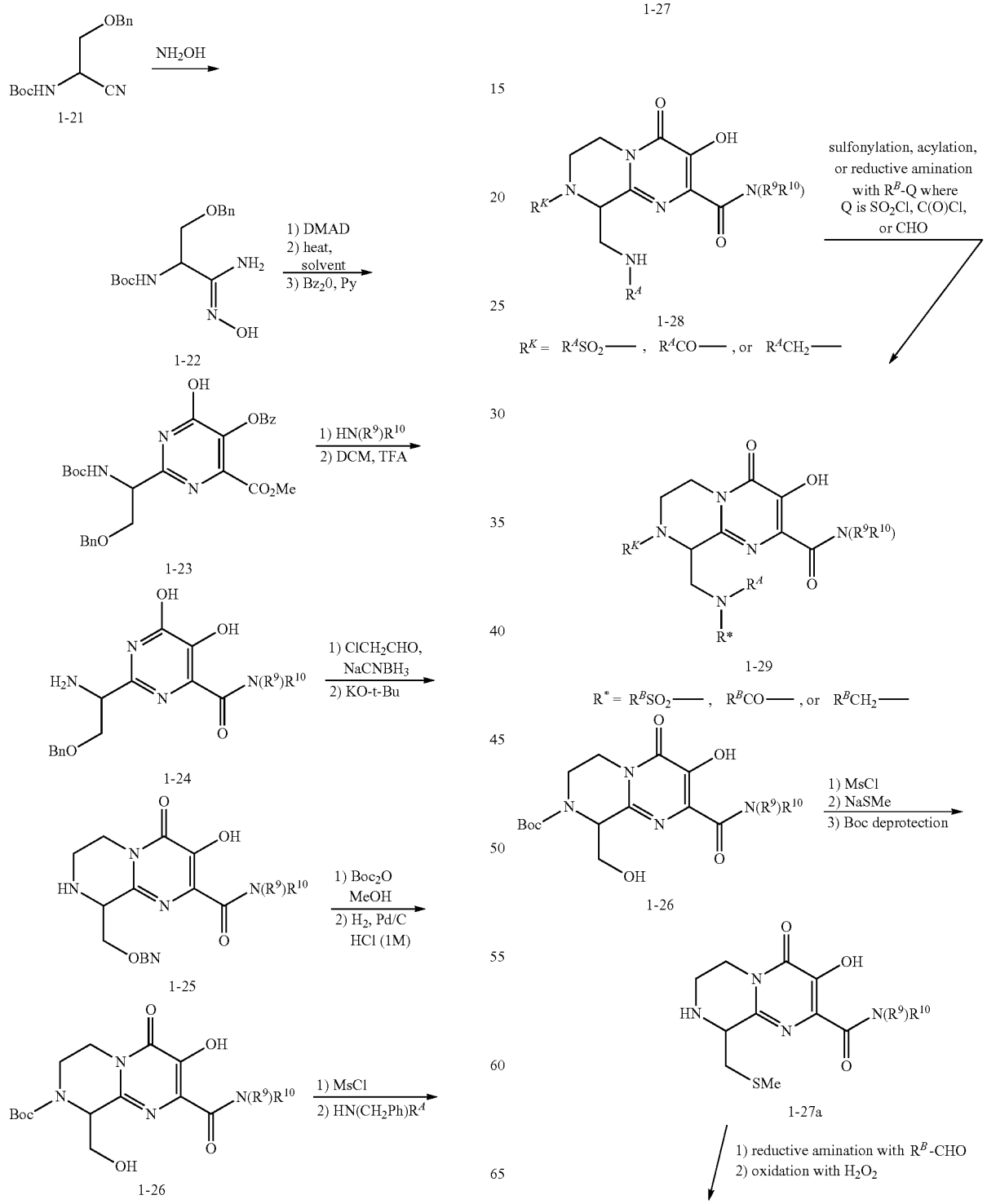

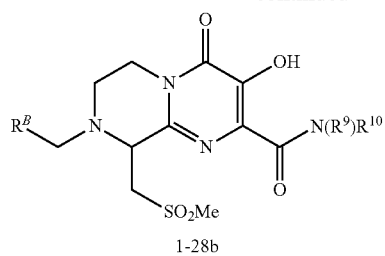

1-28b

Scheme H depicts the synthesis of 8-substituted-3-hydroxy-4-oxo-4,6,7,8,9,10-hexahydropyrimido[1,2-d][1,4]diazepine-2-carboxamides. The intermediate compound 1-12 is first deprotected (e.g., by treating with an acid such as TFA), followed by acylation, sulfonylation or reductive amination using standard chemistry to give 1-30. Coupling with the appropriate amine produces the compound 1-31.

Scheme H:

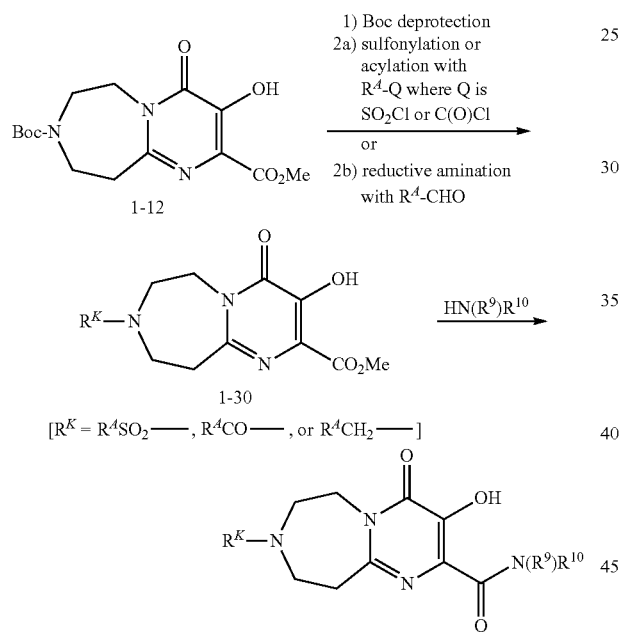

Scheme I depicts the synthesis of 10-substituted-3-hydroxy-4-oxo-6,7,9,10-tetrahydro-4H-pyrimido[1,2-d][1,4]oxazepine-2-carboxamides. Thioamidation of 4-oxacaprolactam 1-32 with $P_4S_{10}$ followed by treatment with hydroxylamine affords amidoxime 1-33. Reaction of the amidoxime 1-33 with dimethylacetylenedicarboxylate, followed by cyclization at high temperature in a suitable solvent provides the methyl ester 1-34, which can be benzoylated and then brominated (e.g., with N-bromosuccinimide) to obtain compound 1-35. The bromoderivative can then be treated with benzyl amine or the appropriate N-benzyl-N-alkylamine to obtain, after hydrogenative removal of the benzyl group, compound 1-36. Acylation, sulfonylation or reductive amination of the secondary amine at the 10 position of 1-36 using standard chemistry provides compound 1-37. Coupling of the appropriate amine to 1-37 produces the compound 1-38.

Scheme I:

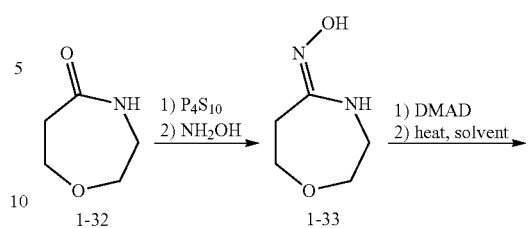

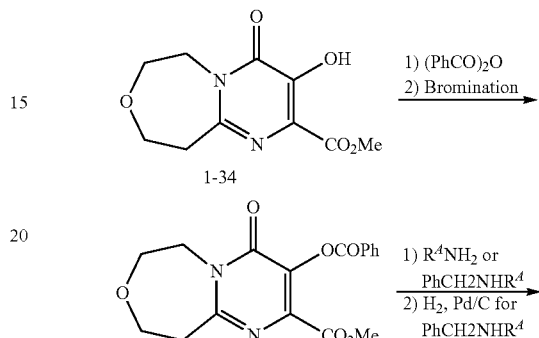

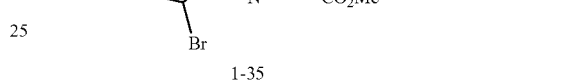

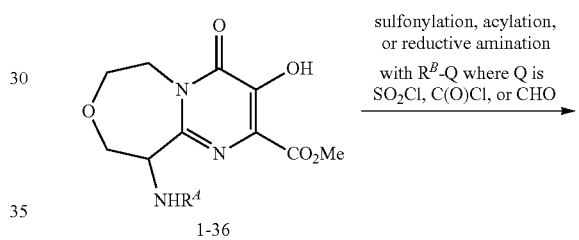

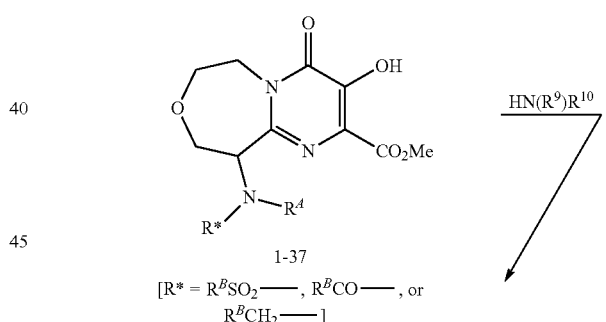

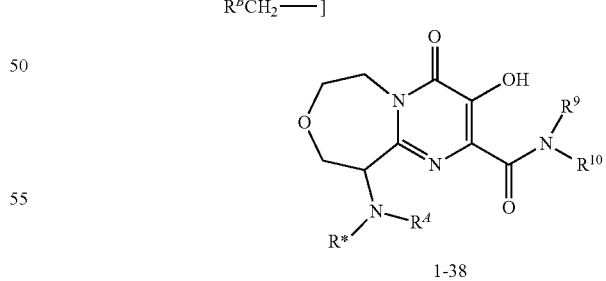

Scheme J depicts a method for preparing 3-hydroxy-4,7-dioxo-6,7,8,9-tetrahydro-4H-pyrazino[1,2-a]pyrimidine-2-carboxamides and 3-hydroxy-4,7,7-trioxo-8,9-dihydro-4H-pyrimido[2,1-d][1,2,5]thiadiazine-2-carboxamides. The amino group at the 2-position of pyrimidine carboxamide 1-1 is sulfonylated/acylated with halomethylsulfonyl halide/haloacetyl halide to afford sulfonylated/acylated intermediate 1-40, which can then undergo internal alkylation via treatment with cesium carbonate to afford the desired bicyclic 1-41.

Scheme J

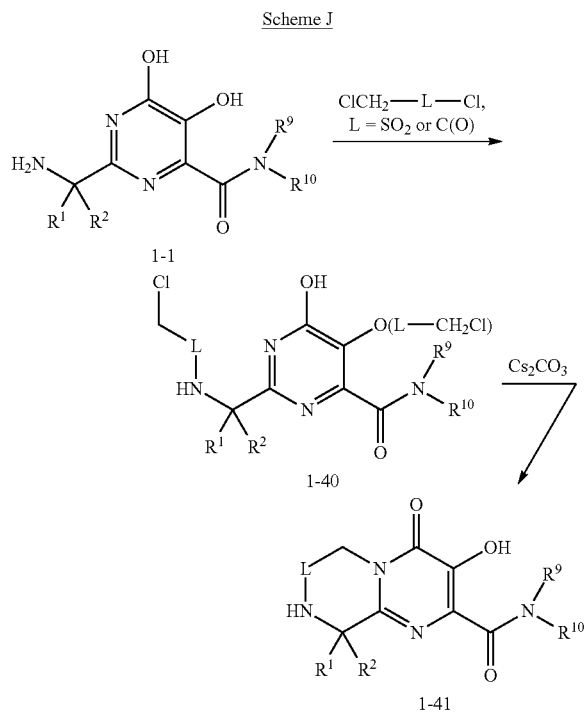

Scheme K

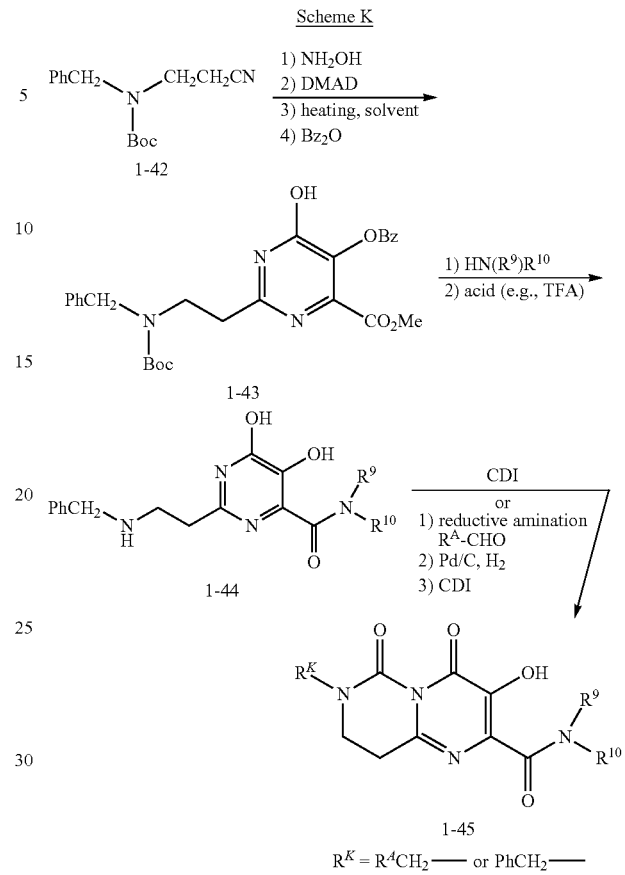

Scheme K depicts a method for preparing 3-hydroxy-4,6-dioxo-6,7,8,9-tetrahydro-4H-pyrimido[1,6-a]pyrimidine-2-carboxamides. The Boc-protected aminonitrile 1-42 (which can be prepared from commercially available starting materials using known chemistry) is first treated with hydroxylamine to obtain the corresponding amidoxime, which is then reacted with DMAD and the resulting adduct cyclized to a dihydroxypyrimdine methyl ester at elevated temperature in a suitable solvent. The 3-hydroxy group on the pyrimidine ring can then be protected by treating with benzoyl anhydride to afford 1-43. Coupling 1-43 with a suitable amine with concomitant removal of Bz followed by acid treatment to remove the Boc protective group provides 1-44, which can be cyclized to form the desired compound 1-45 by (i) acylation with CDI (to give the 7-benzyl derivative) or (ii) reductive amination with a suitable aldehyde, hydrogenolysis to remove the benzyl group, and then acylation and cyclization with CDI.

Scheme L:

Scheme L depicts an alternative synthesis for the preparation of 3-hydroxy-8,9,9-substituted-4-oxo-6,7,8,9-tetrahydro-4H-pyrazino[1,2-a]pyrimidine-2-carboxamides. The core hydroxyl group can readily be protected, for instance using a benzyl protection group, and then the nitrogen alkylated with bromoacetonitrile to give the required nitrile 1-46. Nitrile 1-46 can then undergo a [3+2]-cycloaddition, typically with concurrent deprotection of the hydroxyl group, to provide tetrazole 1-47 using sodium azide in the presence of catalytic triethylamine hydrochloride in a high boiling solvent like NMP. After transient protection of the phenolic hydroxyl group, the tetrazole can be alkylated which after deprotection of the hydroxyl group provides isomeric tetrazoles 1-48 and 1-49. Alternatively, nitrile 1-46 can be reacted with hydroxylamine to yield an amide oxime, which in turn can be reacted with various anhydrides to provide, following deprotection, the 1,2,4-oxadiazoles 1-50.

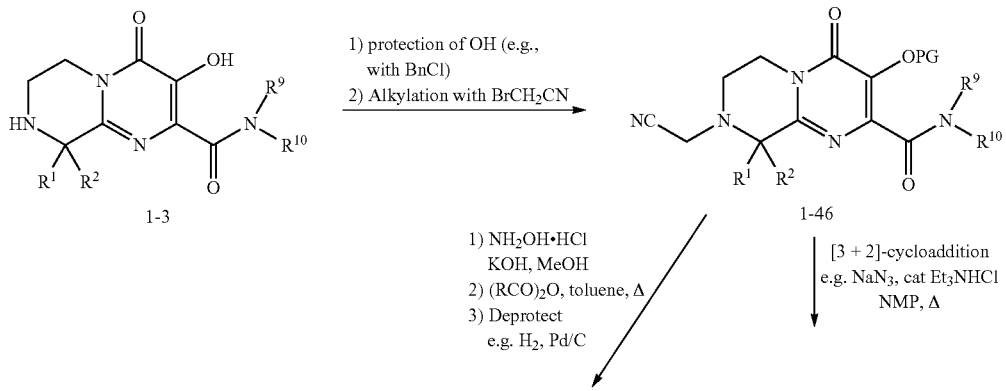

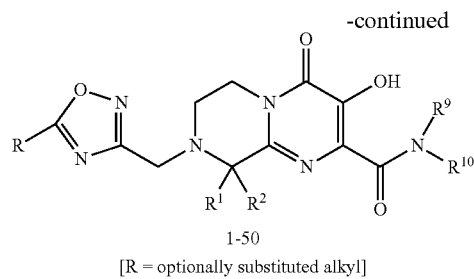

1-50
[R = optionally substituted alkyl]

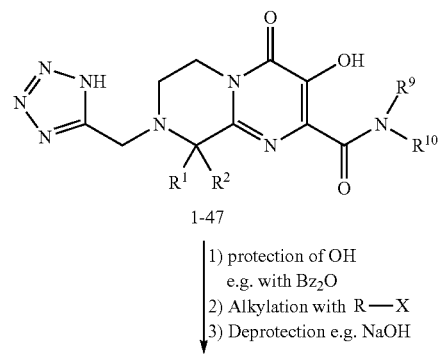

1-47

1) protection of OH
   e.g. with Bz₂O
2) Alkylation with R—X
3) Deprotection e.g. NaOH

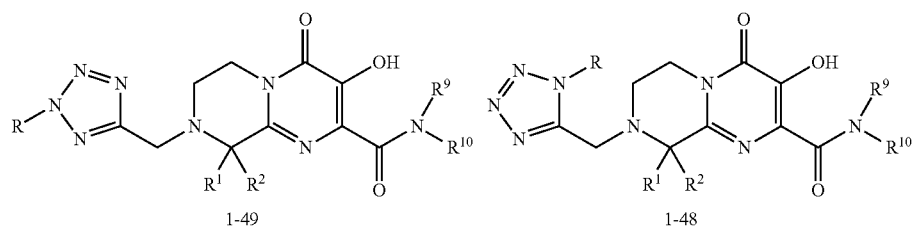

1-49                1-48

Scheme M depicts additional routes for the preparation of 3-hydroxy-8,9,9-substituted-4-oxo-6,7,8,9-tetrahydro-4H-pyrazino[1,2-a]pyrimidine-2-carboxamides. After protection of the core hydroxyl group, substrate 1-3 is alkylated with propargyl bromide to give the alkynee 1-51. Alkyne 1-51 can then undergo a [3+2]-cycloaddition with a nitrile oxide generated in situ from a nitro-compound in the presence of an isocyanate and a base, to yield isoxazole 1-52 after deprotection of the hydroxyl group. Alternatively, the [3+2]-cycloaddition can be performed with trimethylsilyldiazomethane to give, after removal of the silicon group using reagents such as TBAF, the isomeric [1,2,3]-triazoles 1-52 and 1-53.

Scheme M:

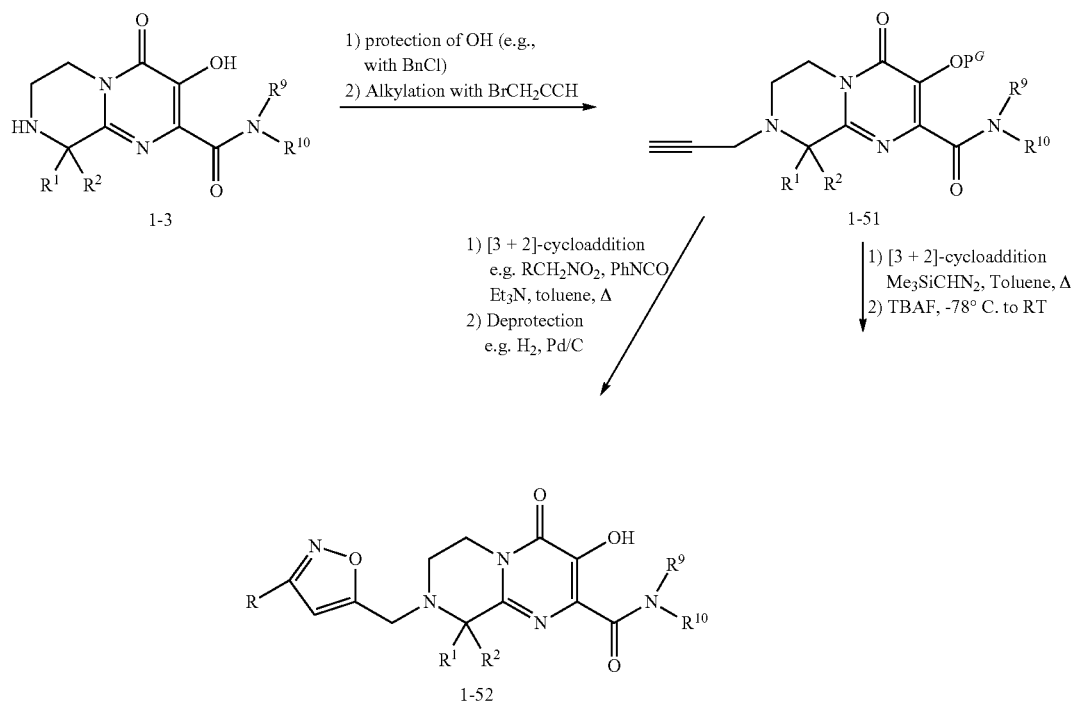

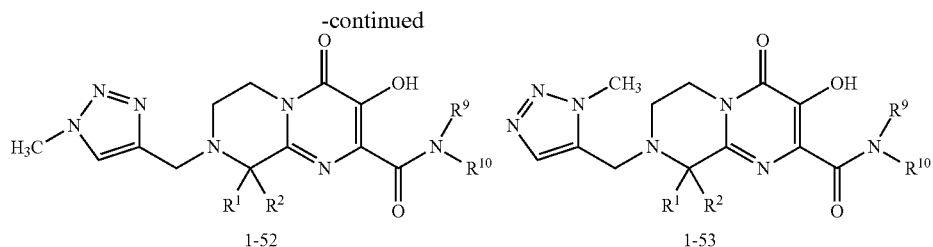

1-52    1-53

Additional methods for preparing 3-hydroxy-8,9,9-substituted-4-oxo-6,7,8,9-tetrahydro-4H-pyrazino[1,2-a]pyrimidine-2-carboxamides are shown in Scheme N, wherein, after protection of the hydroxyl group, alkylation with an alkyl bromoacetate gives the intermediate 1-54, which can either be: reacted with an amide oxime to yield the corresponding 1,2,4-oxadiazole 1-55; or alternatively hydrolyzed to the corresponding carboxylic acid and coupled to various amines, giving after deprotection of the hydroxyl group, amides such as 1-56. A specific example of the latter would be coupling to propargyl amine which would yield compound 1-57. In this case, a further reaction is possible upon treatment with a mercury (II) salt, such as mercuric acetate, in acetic acid at 100° C. which after removal of the protecting group provides the oxazole derivatives 1-58. Alternatively, the ester intermediate 1-54 can be reacted with hydrazine hydrate and then cyclized with various ortho esters to give after deprotection 1,3,4-oxadiazoles such as 1-59.

Scheme N:

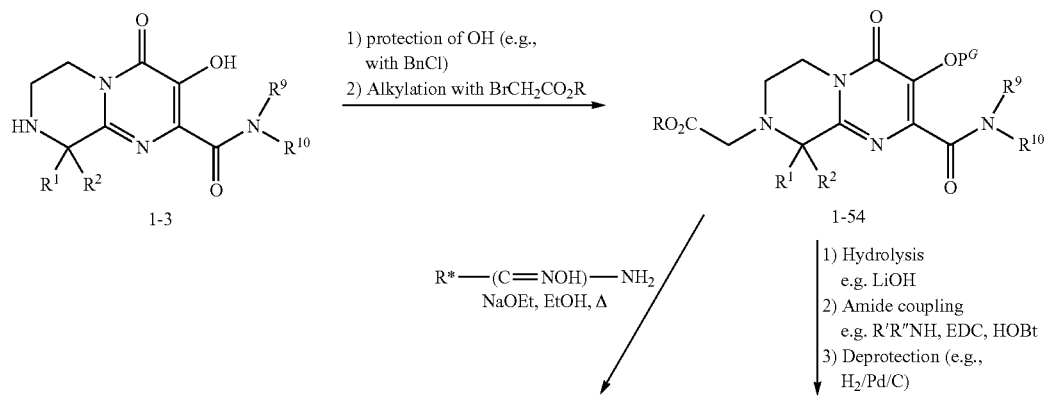

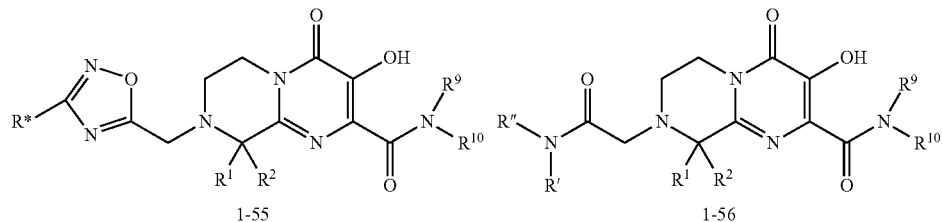

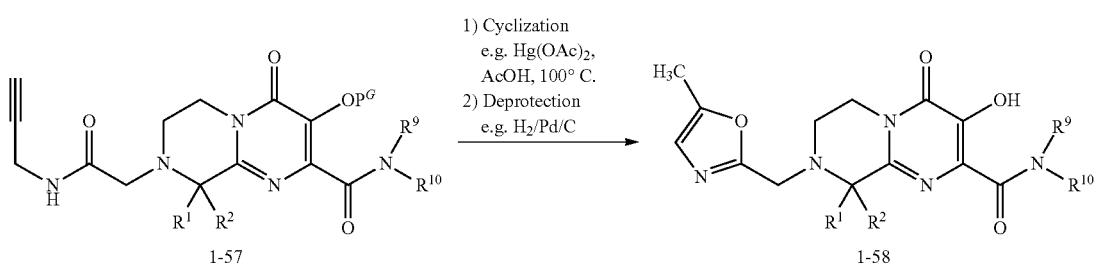

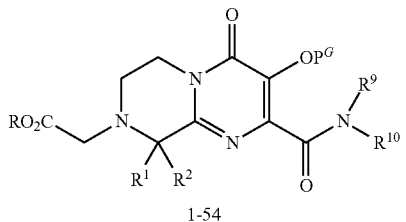

-continued

1) NH₂NH₂·H₂O MeOH, Δ
2) Cyclization e.g. R*C(OCH₃)₃, TsOH, Toluene, Δ
3) Deprotection e.g. H₂/Pd/C

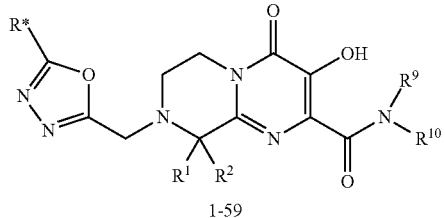

1-54

1-59

[ R = alkyl
R′,R″ = H, alkyl, aryl, arylalkyl, heteroarylalkyl, or together form a heterocycle
R* = H, alkyl, aryl, aryl, arylalkyl, heteroaryl, heteroarylalkyl, etc. ]

In the methods for preparing compounds of the present invention set forth in the foregoing schemes, functional groups in various moieties and substituents (in addition to those already explicitly noted in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. The protecting groups may be removed at a convenient subsequent stage using methods known in the art. Alternatively the interfering group can be introduced into the molecule subsequent to the reaction step of concern.

The following examples serve only to illustrate the invention and its practice. The examples are not to be construed as limitations on the scope or spirit of the invention.

Example 1

N-(4-Fluorobenzyl)-3-hydroxy-9,9-dimethyl-4-oxo-6,7,8,9-tetrahydro-4H-pyrazino[1,2-a]pyrimidine-2-carboxamide (Entry No. 41 in Table 1)

Step 1: 2-{1-[(2-Chloroethyl)amino]-1-methylethyl}-N-(4-fluorobenzyl)-5,6-dihydroxypyrimidine-4-carboxamide To a methanolic solution of 2-(1-amino-1-methylethyl)-N-(4-fluorobenzyl)-5,6-dihydroxypyrimidine-4-carboxamide hydrochloride (prepared as described in WO2003035076 A1) Et₃N (1 eq.), chloroacetaldehyde (2 eq.), AcOH (ca. 1.5 eq.) were added and subsequently NaBH₃CN (1.5 eq.). The reaction mixture was stirred at room temperature overnight. To drive the reaction to completion a few drops of TFA were added and stirring was prolonged for a further 1.5 hours. MeOH was removed under reduced pressure to yield the title amine as crude. MS (ES) C₁₇H₂₀ClFN₄O₃ requires 383. Found: 384 (M+H⁺).

Step 2: N-(4-Fluorobenzyl)-3-hydroxy-9,9-dimethyl-4-oxo-6,7,8,9-tetrahydro-4H-pyrazino[1,2-a]pyrimidine-2-carboxamide 2-{1-[(2-Chloroethyl)amino]-1-methylethyl}-N-(4-fluorobenzyl)-5,6-dihydroxypyrimidine-4-carboxamide (1 eq.) was dissolved in 1,4-dioxane and Cs₂CO₃ (1 eq.) was added. The reaction mixture was stirred at 100° C. overnight, then cooled to room temperature and the solvent was removed under reduced pressure. The resulting brown oil was suspended in MeOH, filtered and the filtrate was evaporated to give a residue that was purified on Cation Exchange Resin (Varian Mega Bond Elute SCX). After washing with MeOH, the product was collected eluting with 2N NH₃ solution in MeOH. The fractions containing the desired material were concentrated under reduced pressure to yield, after trituration with Et₂O the title compound as a yellow solid. A small portion of this crude was purified by RP HPLC (C₁₈, 5 μM, H₂O/MeCN with 1% of TFA as eluant) affording the pure product as TFA salt. ¹H NMR (400 MHz, d₆-DMSO) δ 9.41 (bs, 1H), 7.37 (dd, J=8.6 Hz, J=5.7 Hz, 2H), 7.17 (t, J=8.6 Hz, 2H), 4.48 (d, J=6.4 Hz, 2H), 3.74 (t, J=5.5 Hz, 2H), 3.06 (t, J=5.5 Hz, 2H), 1.46 (s, 6H); MS (ES) C₁₇H₁₉FN₄O₃ requires: 346. Found: 347 (M+H⁺).

Example 2

N-(4-Fluorobenzyl)-3-hydroxy-9,9-dimethyl-8-[(1-methyl-1H-pyrazol-3-yl)methyl]-4-oxo-6,7,8,9-tetrahydro-4H-pyrazino[1,2-a]pyrimidine-2-carboxamide (Entry No. 61 in Table 1)

To a solution of N-(4-fluorobenzyl)-3-hydroxy-9,9-dimethyl-4-oxo-6,7,8,9-tetrahydro-4H-pyrazino[1,2-a]pyrimidine-2-carboxamide (prepared as described in Example 1, Step 1-2) in MeOH and AcOH (5 eq.) was added 1-methyl-1H-pyrazole-3-carbaldehyde (2 eq.) and then NaBH₃CN (1.5 eq.). The mixture was left to stir for 48 hours at room temperature during which time further additions of the aldehyde (1.5 eq.) was necessary to drive the reaction to completion. After concentration under reduced pressure the crude residue was purified by RP HPLC (C₁₈, 5 μM, H₂O/MeCN with 1% of TFA as eluant) affording the title product as TFA salt. ¹H-NMR (300 MHz, d₆-DMSO) δ 12.32 (bs, 1H), 9.51 (t, J=6.3 Hz, 1H), 7.74 (d, J=1.5 Hz, 1H), 7.38 (dd, J=8.6 Hz, J=5.7 Hz, 2H), 7.18 (t, J=8.6 Hz, 2H), 6.36 (d, J=1.5 Hz, 1H), 4.49 (d, J=6.3 Hz, 2H), 4.14 (br. S, 2H), 3.86 (m, 5H), 3.37 (bs, 2H), 1.77 (s, 6H); MS (ES) C₂₂H₂₅FN₆O₃ requires 440. Found: 441 (M+H⁺).

Example 3

N-(4-Fluorobenzyl)-3-hydroxy-9,9-dimethyl-8-[(5-methylisoxazol-3-yl)methyl]-4-oxo-6,7,8,9-tetrahydro-4H-pyrazino[1,2-a]pyrimidine-2-carboxamide (Entry No. 67 in Table 1)

Step 1: 3-(Benzyloxy)-N-(4-fluorobenzyl)-9,9-dimethyl-4-oxo-6,7,8,9-tetrahydro-4H-pyrazino[1,2-a]pyrimidine-2-carboxamide To a stirred solution of N-(4-fluorobenzyl)-3-hydroxy-9,9-dimethyl-4-oxo-6,7,8,9-tetrahydro-4H-pyrazino[1,2-a]pyrimidine-2-carboxamide (see Example 1) in DMF was added $K_2CO_3$ (2 eq.) followed by BnCl (1.1 eq.). The mixture was stirred at 65° C. overnight, after which time additional BnCl (0.3 eq.) was added and the mixture was left for a further 6 hours. The solvent was removed under reduced pressure and the brown oil was taken into EtOAc, washed with 1N HCl and brine, dried ($Na_2SO_4$) and evaporated under reduced pressure. The residue was purified by flash column chromatography, eluting with 2% MeOH/DCM to afford the title product. $^1$H NMR (300 MHz, d6-DMSO) δ 8.88 (t, J=6.2 Hz, 1H), 7.30-7.44 (m, 7H), 7.06 (t, J=8.8 Hz, 2H), 5.05 (s, 2H), 4.41 (d, J=6.2 Hz, 2H), 3.80 (t, J=5.4 Hz, 2H), 3.09 (br. s, 2H), 1.44 (s, 6H); MS (ES) $C_{24}H_{25}FN_4O_3$ requires 436. Found: 437 (M+H$^+$).

Step 2: N-(4-Fluorobenzyl)-3-hydroxy-9,9-dimethyl-8-[(5-methylisoxazol-3-yl)methyl]-4-oxo-6,7,8,9-tetrahydro-4H-pyrazino[1,2-a]pyrimidine-2-carboxamide To a stirred solution of 3-(benzyloxy)-N-(4-fluorobenzyl)-9,9-dimethyl-4-oxo-6,7,8,9-tetrahydro-4H-pyrazino[1,2-a]pyrimidine-2-carboxamide (prepared as described in Example 3, step 1) (1 eq.) in a mixture of 2-butanone/acetone was added $K_2CO_3$ (3.5 eq.) followed by 3-(chloromethyl)-5-methylisoxazole (2.5 eq.). The mixture was stirred at 70° C. for 15 days during which time further chloride (20 eq.) was added. The volatiles were removed under reduced pressure and the residue was taken up in EtOAc and was washed with brine, dried ($Na_2SO_4$) and concentrated under reduced pressure. MS (ES) $C_{29}H_{30}FN_5O_4$ requires 531. Found: 532 (M+H$^+$). The resulting crude was directly dissolved in MeOH and was stirred overnight under an $H_2$ atmosphere in the presence of 10% Pd/C. The catalyst was then filtered off through celite, and the filtrate was concentrated under reduced pressure and purified by RP HPLC ($C_{18}$, 5 μM, $H_2O$/MeCN with 1% of TFA as eluant) to afford the title product as TFA salt. $^1$H NMR (300 MHz, d6-DMSO) δ 12.22 (br. S, 1H), 9.45 (br. S, 1H), 7.38 (m, 2H), 7.17 (t, J=8.7 Hz, 2H), 6.23 (s, 1H), 4.49 (d, J=6.0 Hz, 2H), 3.8-3.65 (m, 4H), 2.90 (br. S, 2H), 2.39 (s, 3H), 1.58 (s, 6H); MS (ES) $C_{22}H_{24}FN_5O_4$ requires 441. Found: 442 (M+H$^+$).

Examples 4 and 5

N-(4-Fluorobenzyl)-3-hydroxy-9,9-dimethyl-4-oxo-8-(2H-tetrazol-5-ylmethyl)-6,7,8,9-tetrahydro-4H-pyrazino[1,2-a]pyrimidine-2-carboxamide (Entry No. 74 in Table 1)

Step 1: 3-(Benzyloxy)-8-(cyanomethyl)-N-(4-fluorobenzyl)-9,9-dimethyl-4-oxo-6,7,8,9-tetrahydro-4H-pyrazino[1,2-a]pyrimidine-2-carboxamide A mixture of 3-(benzyloxy)-N-(4-fluorobenzyl)-9,9-dimethyl-4-oxo-6,7,8,9-tetrahydro-4H-pyrazino[1,2-a]pyrimidine-2-carboxamide (see Example 3, Step 1), $K_2CO_3$ (2 eq.) and bromoacetonitrile (2 eq.) in DMF was heated at 70° C. overnight and was then cooled to room temperature. The solvent was removed under reduced pressure and the residue was taken up in EtOAc, washed with brine, dried ($Na_2SO_4$) and concentrated to yield the crude nitrile which was used in the next step without further purification. $^1$H NMR (300 MHz, d6-DMSO) δ 8.9 (t, J=6.2 Hz, 1H), 7.26-7.41 (m, 7H), 7.06 (t, J=8.8 Hz, 2H), 5.06 (s, 2H), 4.41 (d, J=6.2 Hz, 2H), 3.96 (s, 2H), 3.89 (t, J=5.2 Hz, 2H), 3.15 (t, J=5.2 Hz, 2H), 1.53 (s, 6H); MS (ES) $C_{26}H_{26}FN_5O_3$ requires 475. Found: 476 (M+H$^+$).

Step 2: N-(4-Fluorobenzyl)-3-hydroxy-9,9-dimethyl-4-oxo-8-(2H-tetrazol-5-ylmethyl)-6,7,8,9-tetrahydro-4H-pyrazino[1,2-a]pyrimidine-2-carboxamide The crude organic product obtained above (1 eq.), $Et_3NHCl$ (1.5 eq.) and $NaN_3$ (3 eq.) were dissolved in NMP and the reaction mixture was heated at reflux under N2 overnight. The mixture was then cooled to room temperature and the resulting mixture was purified by RP HPLC (C18, 5 μM, $H_2O$/MeCN with 1% of TFA as eluant) to isolate the title tetrazole as TFA salt.

$^1$H NMR (300 MHz, d6-DMSO) δ 12.18 (br. s, 1H), 9.44 (br. s, 1H), 7.37 (dd, J=8.6 Hz, J=5.5 Hz, 2H), 7.17 (t, J=8.6 Hz, 2H), 4.48 (d, J=6.4 Hz, 2H), 4.11 (s, 2H), 3.78 (br. s, 2H), 2.92 (br. s, 2H), 1.56 (s, 6H); MS (ES) $C_{19}H_{21}FN_8O_3$ requires 428. Found: 429 (M+H$^+$).

Also obtained and isolated by RP HPLC was 8-(cyanomethyl)-N-(4-fluorobenzyl)-3-hydroxy-9,9-dimethyl-4-oxo-6,7,8,9-tetrahydro-4H-pyrazino[1,2-a]pyrimidine-2-carboxamide (Entry No. 73 in Table 1). $^1$H NMR (300 MHz, d6-DMSO) δ 12.2 (br. s, 1H), 9.43 (br. s, 1H), 7.37 (dd, J=8.5 Hz, J=5.6 Hz, 2H), 7.16 (t, J=8.5 Hz, 2H), 4.47 (d, J=6.4 Hz, 2H), 3.93 (s, 2H), 3.83 (t, J=5.3 Hz, 2H), 3.11 (t, J=5.3 Hz, 2H), 1.54 (s, 6H); MS (ES) $C_{19}H_{20}FN_5O_3$ requires 385. Found: 386 (M+H$^+$).

Examples 6 and 7

N-(4-Fluorobenzyl)-3-hydroxy-9,9-dimethyl-8-[(2-methyl-2H-tetrazol-5-yl)methyl]-4-oxo-6,7,8,9-tetrahydro-4H-pyrazino[1,2-a]pyrimidine-2-carboxamide (Entry No. 87 in Table 1) and N-(4-Fluorobenzyl)-3-hydroxy-9,9-dimethyl-8-[(1-methyl-1H-tetrazol-5-yl)methyl]-4-oxo-6,7,8,9-tetrahydro-4H-pyrazino[1,2-a]pyrimidine-2-carboxamide (Entry No. 86 in Table 1)

Step 1: 2-{[(4-Fluorobenzyl)amino]carbonyl}-9,9-dimethyl-4-oxo-8-(1H-tetrazol-5-ylmethyl)-6,7,8,9-tetrahydro-4H-pyrazino[1,2-a]pyrimidin-3-yl benzoate To a solution N-(4-fluorobenzyl)-3-hydroxy-9,9-dimethyl-4-oxo-8-(2H-tetrazol-5-ylmethyl)-6,7,8,9-tetrahydro-4H-pyrazino[1,2-a]pyrimidine-2-carboxamide (see Example 4, Steps 1-2) and benzoic anhydride (0.9 eq.) in THF were added triethylamine (1.1 eq.) and diethylamino pyridine (3 mol %). The mixture was stirred at room temperature overnight and was then concentrated under reduced pressure. The residue was taken up in ethyl acetate and washed with brine, dried ($Na_2SO_4$) and concentrated under reduced pressure to yield the benzoylated material. MS (ES) $C_{26}H_{25}FN_8O_4$ requires 532. Found: 533 (M+H$^+$).

Step 2: N-(4-Fluorobenzyl)-3-hydroxy-9,9-dimethyl-8-[(1-methyl-1H-tetrazol-5-yl)methyl]-4-oxo-6,7,8,9-tetrahydro-4H-pyrazino[1,2-a]pyrimidine-2-carboxamide; N-(4-Fluorobenzyl)-3-hydroxy-9,9-dimethyl-8-[(2-methyl-2H-tetrazol-5-yl)methyl]-4-oxo-6,7,8,9-tetrahydro-4H-pyrazino[1,2-a]pyrimidine-2-carboxamide A solution of the crude organic product obtained above (1 eq.) in MeCN was treated with $K_2CO_3$ (3 eq.) and MeI (3 eq.) and the reaction was stirred at 45° C. overnight. The volatiles removed under reduced pressure and MeCN added followed by 1N NaOH (4 eq.). The mixture was stirred overnight at 30° C. The solvent was removed under reduced pressure and the residue was purified by RP HPLC (C18, 5 μM, $H_2O$/MeCN with 1% of TFA as eluant) affording the title isomeric tetrazoles in approximately 1:1 ratio as TFA salts.

N-(4-fluorobenzyl)-3-hydroxy-9,9-dimethyl-8-[(1-methyl-1H-tetrazol-5-yl)methyl]-4-oxo-6,7,8,9-tetrahydro-4H-pyrazino[1,2-a]pyrimidine-2-carboxamide shows: $^1$H NMR (600 MHz, $d_6$-DMSO) δ 12.18 (br. s, 1H), 9.46 (t, J=6.4 Hz, 1H), 7.37 (dd, J=8.6 Hz, J=5.7 Hz, 2H), 7.17 (t, J=8.6 Hz, 2H), 4.47 (d, J=6.4 Hz, 2H), 4.13 (s, 2H), 4.07 (s, 3), 3.70 (t, J=5.3 Hz, 2H), 2.80 (t, J=5.3 Hz, 2H), 1.61 (s, 6H); MS (ES) $C_{20}H_{23}FN_8O_3$ requires 442. Found: 443 (M+H$^+$).

N-(4-Fluorobenzyl)-3-hydroxy-9,9-dimethyl-8-[(2-methyl-2H-tetrazol-5-yl)methyl]-4-oxo-6,7,8,9-tetrahydro-4H-pyrazino[1,2-a]pyrimidine-2-carboxamide shows: $^1$H NMR (600 MHz, $d_6$-DMSO) δ 12.18 (br. s, 1H), 9.45 (t, J=6.4 Hz, 1H), 7.37 (dd, J=8.5 Hz, J=5.8 Hz, 2H), 7.17 (t, J=8.5 Hz, 2H), 4.48 (d, J=6.4 Hz, 2H), 4.35 (s, 3H), 4.07 (s, 2H), 3.70 (t, J=5.4 Hz, 2H), 3.03 (t, J=5.4 Hz, 2H), 1.59 (s, 6H); MS (ES) $C_{20}H_{23}FN_8O_3$ requires 442. Found: 443 (M+H$^+$).

Example 8

N-[4-fluoro-2-(methylsulfonyl)benzyl]-3-hydroxy-7,8,8-trimethyl-4-oxo-4,6,7,8-tetrahydroimidazo[1,5-a]pyrimidine-2-carboxamide (Entry No. 2 in Table 1)

2-(1-amino-1-methylethyl)-N-[4-fluoro-2-(methylsulfonyl)benzyl]-5,6-dihydroxypyrimidine-4-carboxamide (prepared as described in WO2003035076 A1) was taken in trimethyl orthoformate and treated with 1.1 eq. of formaldehyde. The mixture was aged at room temperature for 1 hour, and then an additional equivalent of formaldehyde was added, followed by 1.5 eq. of sodium cyanoborohydride and a few drops of acetic acid. Stirring was continued for one hour more, and the mixture was purified by RP HPLC (C$_{18}$, 5 μM, $H_2O$/MeCN with 1% of TFA as eluant) to afford the title compound as a white solid.

1H-NMR (400 MHz, DMSO-$d_6$) δ 12.2 (bs, 1H), 9.32 (t, J=6.4 Hz, 1H), 7.72 (d, J=7.54 Hz, 1H), 7.62-7.58 (m, 2H), 4.87 (d, J=6.5 Hz, 2H), 4.68 (s, 3H), 3.43 (s, 3H), 2.38 (s, 3H), 1.31 (s, 3H). MS (ES) $C_{18}H_{21}FN_4O_5S$ requires 424. Found: 425 (M+H$^+$).

Example 9

N-(4-fluorobenzyl)-3-hydroxy-10,10-dimethyl-4-oxo-4,6,7,8,9,10-hexahydro pyrimido[1,2-a][1,4]diazepine-2-carboxamide (Entry No. 175 in Table 1)

Step 1: N-(4-fluorobenzyl)-5,6-dihydroxy-2-{1-[(3-hydroxypropyl)amino]-1-methylethyl}pyrimidine-4-carboxamide A methanolic solution of 2-(1-amino-1-methylethyl)-N-(4-fluorobenzyl)-5,6-dihydroxypyrimidine-4-carboxamide (prepared as described in WO2003035076 A1) was treated with 3-(benzyloxy)propanal (1.5 eq.) and sodium cyanoborohydride (1.5 eq.). The mixture was stirred at room temperature overnight, solution was applied on a cation exchange resin. The resin was washed with methanol and desired product was eluted with 2 N ammonia solution in methanol. Evaporation of appropriate fractions followed by trituration with $Et_2O$ gave intermediate 2-(1-{[3-(benzyloxy)propyl]amino}-1-methylethyl)-N-(4-fluorobenzyl)-5,6-dihydroxypyrimidine-4-carboxamide. MS (ES) $C_{25}H_{29}FN_4O_4$ requires 468. Found: 469 (M+H$^+$). The crude organic product was taken in methanol, treated with 1 eq. of 6N HCl and stirred under hydrogen atmosphere in the presence of catalytic amount of 10% palladium on charcoal. After overnight stirring, mixture was filtered through celite, filtrate was concentrated under reduced pressure and purified by cation exchange resin. The resin was washed with methanol and desired product was eluted with 2 N ammonia solution in methanol. Evaporation of appropriate fractions followed by trituration with $Et_2O$ gave title compound as a pink solid. MS (ES) $C_{18}H_{23}FN_4O_4$ requires 378. Found: 379 (M+H$^+$).

Step 2: N-(4-fluorobenzyl)-3-hydroxy-10,10-dimethyl-4-oxo-4,6,7,8,9,10-hexahydropyrimido[1,2-a][1,4]diazepine-2-carboxamide Crude N-(4-fluorobenzyl)-5,6-dihydroxy-2-{1-[(3-hydroxypropyl)amino]-1-methylethyl}pyrimidine-4-carboxamide prepared as described in Step 1 was dissolved in THF, and treated with triphenylphosphine (1.5 eq.) and DEAD (1.5 eq.). The mixture was stirred under nitrogen, after 14 hours additional reagents (2 eq.) were necessary to complete reaction. Solvent was evaporated under vacuo and the residue loaded on cation exchange resin. The resin was washed with methanol and desired product was eluted with 2 N ammonia solution in methanol. Evaporation of appropriate fractions and further purification of the residue by RP HPLC (C$_{18}$, 5 μM, $H_2O$/MeCN with 1% of TFA as eluant) gave, after lyophilization, title compound as a white solid.

$^1$H NMR (300 MHz, 330 K, $d_6$-DMSO) δ 12.38 (1H, bs), 9.2 (1H, bs), 9.05 (1H, t, J=5.8 Hz), 7.38 (2H, dd, J=8.2 Hz, J=5.6 Hz), 7.16 (2H, t, J=8.8 Hz), 4.52 (2H, d, J=6.6 Hz), 4.52-4.42 (2H, m), 3.40-3.33 (2H, m), 2.05-1.95 (2H, m), 1.80 (6H, s); MS (ES) $C_{18}H_{21}FN_4O_3$ requires 360. Found: 361 (M+H$^+$).

Example 10

N-(4-fluorobenzyl)-3-hydroxy-9,10,10-trimethyl-4-oxo-4,6,7,8,9,10-hexahydropyrimido[1,2-a][1,4]diazepine-2-carboxamide (Entry 176 in Table 1)

A methanolic solution of 2-{[(4-fluorobenzyl)amino]carbonyl}-3-hydroxy-10,10-dimethyl-4-oxo-4,6,7,8,9,10-hexahydropyrimido[1,2-a][1,4]diazepin-9-ium trifluoroacetate (prepared as described in Example 9, Step 1-2) was treated with formaldehyde (1.5 eq.) and sodium cyanoborohydride (1.2 eq.). The mixture was stirred at room temperature 3 hours and then directly purified by RP HPLC (C$_{18}$, 5 μM, $H_2O$/MeCN with 1% of TFA as eluant) to give the title product as TFA salt, after lyophilization of the appropriate fractions.

$^1$H NMR (300 MHz, 330K, $d_6$-DMSO+TFA) δ 8.95 (1H, t, J=5.8 Hz), 7.38 (2H, dd, J=8.2 Hz, J=5.6 Hz), 7.16 (2H, t, J=8.8 Hz), 5.32-5.18 (2H, m), 4.52 (2H, d, J=6.6 Hz), 3.97-

3.80 (2H, m), 2.21-2.05 (2H, m), 2.8 (3H, s), 1.9 (3H, s), 1.85 (3H, s); MS (ES) $C_{19}H_{23}FN_4O_3$ requires 374. Found: 375 (M+H$^+$).

Example 11

N-(2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide and the corresponding (+) and (−) enantiomers (Entry Nos. 156 and 157 in Table 1)

Step 1: tert-Butyl 5-thioxo-1,4-diazepane-1-carboxylate tert-Butyl 5-oxo-1,4-diazepane-1-carboxylate, $P_4S_{10}$ (0.2 eq.), HMDO (2 eq.) and dichloromethane were combined and stirred magnetically at room temperature for 1 hour. The reaction mixture was then cooled to 0° C. and aqueous $K_2CO_3$ solution (1.26 mL of 5.3 M/mmol $P_4S_{10}$ taken) was added. A volume of acetone equal to one half of the reaction solvent was added to obtain a stirrable mixture, and the reaction mixture was stirred vigorously for 30 minutes at 0° C. Volatiles were evaporated, water and ethyl acetate were added, layers were separated and the organic phase was washed with water and brine. The organic extract was dried over $Na_2SO_4$ and evaporated, to afford the title compound. $^1$H NMR (300 MHz, CDCl$_3$) δ 8.7 (bs, 1H), 3.68-3.60 (m, 4H), 3.42-3.38 (m, 2H), 3.15-3.09 (m, 2H), 1.43 (s, 9H); MS (ES) $C_{10}H_{18}N_2O_2S$ requires 230. Found: 231 (M+H$^+$).

Step 2: tert-Butyl 5-(hydroxyimino)-1,4-diazepane-1-carboxylate

A solution of hydroxylamine hydrochloride (2 eq.) in methanol was added to an equimolar methanolic solution of potassium hydroxide. Potassium chloride was filtered off and the filtrate was added to a solution of the above tert-butyl 5-thioxo-1,4-diazepane-1-carboxylate (1 eq.) in methanol. The mixture was stirred at 55° C. overnight, then cooled to room temperature and the solvent was removed under reduced pressure. The residue was taken in chloroform, washed with brine, dried over $Na_2SO_4$ and concentrated under reduced pressure to give, after trituration with ethyl ether, the title amidoxime. $^1$H NMR (300 MHz, CDCl$_3$) δ 6.4-6.1 (bs, 1H), 5.8 (broad triplet, 1H), 3.6-3.5 (m, 4H), 3.35-3.22 (m, 2H), 2.5-2.4 (m, 2H), 1.45 (s, 9H); MS (ES) $C_{10}H_{19}N_3O_3$ requires 229. Found: 230 (M+H$^+$).

Step 3: 8-tert-butyl-2-methyl-3-hydroxy-4-oxo-6,7,9,10-tetrahydropyrimido[1,2-d][1,4]diazepine-2,8(4H)-dicarboxylate To a suspension of tert-butyl 5-thioxo-1,4-diazepane-1-carboxylate prepared in the previous step (1 eq.) in acetonitrile, dimethylacetylene dicarboxylate (1 eq.) was added in one portion and the mixture was stirred at room temperature for 1 hour. The solvent was removed under reduced pressure and the oily residue was taken in xylene and stirred overnight at 145° C. After cooling to room temperature, the solvent was evaporated under reduced pressure and residue was taken in ethyl acetate and treated with saturated solution of NaHCO$_3$. The aqueous phase was separated, washed with additional ethyl acetate, then carefully acidified with 2N HCl. The product was extracted in chloroform, and the organic solution was dried over $Na_2SO_4$ and concentrated under reduced pressure to afford title compound as a brown solid. $^1$H NMR (300 MHz, d$_6$-DMSO) δ 10.43 (s, 1H), 4.58-4.50 (m, 2H), 4.03 (s, 3H), 3.88-3.78 (m, 4H) 3.26-3.18 (m, 2H) 1.50 (s, 9H); MS (ES) $C_{15}H_{21}N_3O_6$ requires 339. Found: 340 (M+H$^+$).

Step 4: 8-tert-butyl 2-methyl 10-[benzyl(methyl)amino]-3-hydroxy-4-oxo-6,7,9,10-tetrahydropyrimido[1,2-d][1,4]diazepine-2,8(4H)-dicarboxylate To a solution of 8-tert-butyl 2-methyl 3-hydroxy-4-oxo-6,7,9,10-tetrahydro pyrimido[1,2-d][1,4]diazepine-2,8(4H)-dicarboxylate in dry dioxane, DDQ (2.2 eq.) was added and the mixture was aged for 2 days at 105° C. After cooling to room temperature, N-benzylmethylamine (7 eq.) was added and the mixture was aged at 65° C. for 6 hours. The reaction mixture was concentrated under vacuum and the resulting residue was dissolved in the minimum amount of MeOH and carefully acidified with glacial acetic acid. The solution was charged on a cartridge of cation exchange resin eluting first with MeOH and then with 1M ammonia in methanol. The eluate was concentrated under reduced pressure to get an oily residue that was taken in ethyl acetate and washed three times with saturated solution of NaHCO$_3$. Organic layers were concentrated to afford crude product as brown oil, which was used without further purification. MS (ES) $C_{23}H_{30}N_4O_6$ requires 458. Found: 459 (M+H$^+$).

Step 5: tert-butyl 2-{[(4-fluoro-3-methylbenzyl)amino]carbonyl}-3-hydroxy-10-(methylamino)-4-oxo-6,7,9,10-tetrahydropyrimido[1,2-d][1,4]diazepine-8(4H)-carboxylate 8-tert-butyl 2-methyl 10-[benzyl(methyl)amino]-3-hydroxy-4-oxo-6,7,9,10-tetrahydropyrimido[1,2-d][1,4]diazepine-2,8(4H)-dicarboxylate prepared as described in Step 4, was dissolved in MeOH, treated with 1 N HCl (1 eq.) and stirred overnight under an H$_2$ atmosphere in the presence of 10% Pd/C. The catalyst was filtered off through celite, and the filtrate was concentrated under reduced pressure. MS (ES) $C_{16}H_{24}N_4O_6$ requires 368. Found: 369 (M+H$^+$). The crude organic product was taken in methanol and treated with 1.2 eq. of 4-fluoro-3-methyl-benzylamine and resulting mixture was refluxed overnight. After cooling to room temperature, evaporation of volatiles under reduced pressure yielded title product which was directly taken in the next step. MS (ES) $C_{23}H_{30}FN_5O_5$ requires 475. Found: 476 (M+H$^+$).

Step 6: tert-butyl 10-[[(dimethylamino)(oxo)acetyl](methyl)amino]-2-{[(4-fluoro-3-methylbenzyl)amino]carbonyl}-3-hydroxy-4-oxo-6,7,9,10-tetrahydropyrimido[1,2-d][1,4]diazepine-8(4H)-carboxylate To a suspension tert-butyl 2-{[(4-fluoro-3-methylbenzyl)amino]carbonyl}-3-hydroxy-10-(methylamino)-4-oxo-6,7,9,10-tetrahydropyrimido[1,2-d][1,4]diazepine-8(4H)-carboxylate, triethylamine (2.5 eq.) and methyl chloro(oxo)acetate (2 eq.) were added and resulting mixture was stirred one hour at room temperature. Volatiles were evaporated under reduced pressure and residue was taken in methanol and treated with an excess of dimethylamine (2 M solution in methanol). The reaction mixture was stirred overnight at room temperature, yielding after evaporation of volatiles, title product which was further reacted in the next step. MS (ES) $C_{27}H_{35}FN_6O_7$ requires 574. Found: 575 (M+H$^+$).

Step 7: N-(2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide The compound of Step 6 was stirred in dichloromethane/trifluoroacetic acid (8/2 v/v) for 1 hour, then concentrated under reduced pressure and purified by RP HPLC ($C_{18}$, 5 μM, $H_2O$/MeCN with 1% of TFA as eluant) affording desired compound as trifluoroacetic salt. $^1$H NMR (300 MHz, $CD_3CN$) δ 12.68 (bs, 1H), 9.96 (bs, 1H), 7.50 (d, J=7.51 Hz, 1H), 7.45-7.41 (m, 1H), 7.21 (t, J=8.62 Hz, 1H), 5.55-5.46 (m, 2H), 4.75 (dd, J=14.6 Hz, J=6.8 Hz, 1H), 4.67 (dd, J=14.6 Hz, J=6.3 Hz, 1H), 4.24-4.05 (m, 3H), 3.96-3.92 (m, 1H), 3.39-3.36 (m, 1H), 3.24 (s, 3H), 3.19 (s, 3H), 3.18 (s, 3H), 2.46 (s, 3H); MS (ES) $C_{22}H_{27}FN_6O_5$ requires 474. Found: 475 (M+H$^+$).

N-(2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide has been resolved into its enantiomers by semipreparative chiral SFC using the following conditions: Solvents: $CO_2$, modifier: MeOH 30%, TFA 0.2%. Column: Chiracel OD-H 250×10 mm at 9.99 mL/min, P=100 bar, T=35° C.

The first eluate is the (+) enantiomer (EtOH, c=0.5, 25° C.) $[α]_D$=(+) 5.3

The second eluate is the (−) enantiomer (EtOH, c=0.5, 25° C.) $[α]_D$=(−) 5.0

Example 12

N-(8-cyclopropyl-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide and the corresponding (+) and (−) enantiomers (Entry Nos. 127 and 128 in Table 1)

N-(2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (prepared as described in Example 11, Step 1-7) was dissolved in methanol and treated with triethylamine (2 eq.), [(1-ethoxycyclopropyl)oxy](trimethyl)silane and acetic acid pH=5.5. To the mixture was then added NaCNBH$_3$ (4 eq.) and reaction was refluxed overnight. After cooling to room temperature, mixture was concentrated under reduced pressure and purified by prep RP HPLC ($C_{18}$, 5 μM, $H_2O$/MeCN with 1% of TFA as eluant) affording desired compound as a white solid. $^1$H NMR (300 MHz, $CD_3CN$) δ 12.67 (bs, 1H), 10.01 (bs, 1H), 7.49 (d, J=7.52 Hz, 1H), 7.45-7.40 (m, 1H), 7.21 (t, J=8.62 Hz, 1H), 5.51-5.41 (m, 2H), 4.76 (dd, J=14.6 Hz, J=6.86 Hz, 1H), 4.66 (dd, J=14.6 Hz, J=6.41 Hz, 1H), 4.27-4.00 (m, 4H), 3.51-3.36 (m, 2H), 3.27 (s, 3H), 3.19 (s, 3H), 3.17 (s, 3H), 2.46 (s, 3H), 1.37-1.31 (m, 2H), 1.19-1.10 (m, 2H); MS (ES) $C_{25}H_{31}FN_6O_5$ requires 514. Found: 515 (M+H$^+$).

N-(8-cyclopropyl-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide has been resolved into its enantiomers by semipreparative chiral SFC using the following conditions: Solvents: $CO_2$, modifier: MeOH 30%, TFA 0.2%. Column: Chiracel OD-H 250×10 mm at 9.99 mL/min, P=100 bar, T=35° C.

The first eluate is the (+) enantiomer (EtOH, c=0.7, 25° C.) $[α]_D$=(+) 32.9

The second eluate is the (−) enantiomer (EtOH, c=0.7, 25° C.) $[α]_D$=(−) 32.5

Example 13

N-(2-{[(3-chloro-4-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide and the corresponding (+) and (−) enantiomers (Entry Nos. 144 and 145 in Table 1)

Step 1: tert-butyl 2-{[(3-chloro-4-methylbenzyl)amino]carbonyl}-3-hydroxy-10-(methylamino)-4-oxo-6,7,9,10-tetrahydropyrimido[1,2-d][1,4]diazepine-8(4H)-carboxylate 8-tert-butyl 2-methyl 10-[benzyl(methyl)amino]-3-hydroxy-4-oxo-6,7,9,10-tetrahydropyrimido[1,2-d][1,4]diazepine-2,8(4H)-dicarboxylate (see Example 11, Steps 1-4) was dissolved in MeOH, treated with 1 N HCl (1 eq.) and stirred overnight under an $H_2$ atmosphere in the presence of 10% Pd/C. The catalyst was then filtered off through celite, and the filtrate was concentrated under reduced pressure. MS (ES) $C_{16}H_{24}N_4O_6$ requires 368. Found: 369 (M+H$^+$). The crude organic product was taken in methanol and treated with 1.2 eq. of 3-chloro-4-methyl-benzylamine and resulting mixture was refluxed overnight. After cooling to room temperature, evaporation of volatiles under reduced pressure yielded title product which was directly taken in the next step. MS (ES) $C_{23}H_{30}ClN_5O_5$ requires 491. Found: 492 (M+H$^+$).

Step 2: tert-butyl 2-{[(3-chloro-4-methylbenzyl)amino]carbonyl}-10-[[(dimethylamino)(oxo)acetyl](methyl)amino]-3-hydroxy-4-oxo-6,7,9,10-tetrahydropyrimido[1,2-d][1,4]diazepine-8(4H)-carboxylate To a suspension of the above prepared tert-butyl 2-{[(3-chloro-4-methylbenzyl)amino]carbonyl}-3-hydroxy-10-(methylamino)-4-oxo-6,7,9,10-tetrahydro pyrimido[1,2-d][1,4]diazepine-8(4H)-carboxylate was added triethylamine (2.5 eq.) and methyl chloro(oxo)acetate (2 eq.) and resulting mixture was stirred one hour at room temperature. Volatiles were evaporated under reduced pressure and residue was taken in methanol and treated with an excess of dimethylamine (2 M solution in methanol). The reaction mixture was stirred overnight at room temperature, yielding after evaporation of volatiles, crude product which was further reacted in the next step. MS (ES) $C_{27}H_{35}ClN_6O_7$ requires 590. Found: 591 (M+H$^+$).

Step 3: N-(2-{[(3-chloro-4-methylbenzyl)amino]carbonyl}-8-cyclopropyl-3-hydroxy-4-oxo-4,6,7,8,9,10-hexahydropyrimido[1,2-d][1,4]diazepin-10-yl)-N,N',N'-trimethylethanediamide The compound of Step 2 was stirred in dichloromethane/trifluoroacetic acid (8/2 v/v) for 1 hour, then concentrated under reduced pressure and triturated with diethyl ether. A portion of this material was purified by prep RP HPLC (C18, 5 μM, $H_2O$/MeCN with 1% of TFA as eluant) affording title compound as a white solid. $^1$H NMR (400 MHz, $CD_3CN$) δ 12.40 (bs, 1H), 9.78 (bs, 1H), 7.43 (s, 1H), 7.28-7.21 (m, 2H), 5.37-5.29 (m, 2H), 4.58 (dd, J=14.6 Hz, J=6.86 Hz, 1H), 4.47 (dd, J=14.6 Hz, J=6.41 Hz, 1H), 4.01-3.3.92 (m, 3H), 3.78-3.69 (m, 1H), 3.22-3.12 (m, 1H), 3.08 (s, 3H), 2.93 (s, 3H), 2.91 (s, 3H), 2.28 (s, 3H); MS (ES) $C_{22}H_{27}ClN_6O_5$ requires 490. Found: 491 (M+H$^+$). N-(2-{[(3-chloro-4-methylbenzyl)amino]carbonyl}-3-hydroxy-4,6,7,8,9,10-hexahydropyrimido[1,2-d][1,4]diazepin-10-yl)-N,N',N'-trimethylethanediamide has been resolved into its enantiomers by semipreparative chiral SFC using the following conditions:
Solvents: $CO_2$, modifier: MeOH 30%, TFA 0.2%
Column: Chiracel OD-H 250×10 mm at 10 mL/min, P=100 bar, T=35° C.
The first eluate is the (+) enantiomer (EtOH, c=0.2, 25° C.) $[\alpha]_D$=(+) 5.2
The second eluate is the (−) enantiomer (EtOH, c=0.2, 25° C.) $[\alpha]_D$=(−) 5.3

Example 14

N-(2-{[(3-chloro-4-methylbenzyl)amino]carbonyl}-8-cyclopropyl-3-hydroxy-4-oxo-4,6,7,8,9,10-hexahydropyrimido[1,2-d][1,4]diazepin-10-yl)-N,N',N'-trimethylethanediamide and the corresponding (+) and (−) enantiomers (Entry Nos. 115 and 116 in Table 1)

Crude organic product prepared as described in Example 13, Steps 1-3 was dissolved in methanol and treated with triethylamine (2 eq.), acetic acid until pH=5.5 and [(1-ethoxycyclopropyl)oxy]-(trimethyl)silane. To the mixture was then added $NaCNBH_3$ (4 eq.) and reaction was refluxed overnight. After cooling to room temperature, mixture was concentrated under reduced pressure and purified by prep RP HPLC ($C_{18}$, 5 μM, $H_2O$/MeCN with 1% of TFA as eluant) affording desired compound as a white solid. $^1$H NMR (300 MHz, $CD_3CN$) δ 12.54 (bs, 1H), 9.98 (bs, 1H), 7.63 (s, 1H), 7.49-7.42 (m, 2H), 5.49-5.40 (m, 2H), 4.76 (dd, J=14.6 Hz, J=6.86 Hz, 1H), 4.67 (dd, J=14.6 Hz, J=6.41 Hz, 1H), 4.12-3.92 (m, 4H), 3.26 (s, 3H), 3.19 (s, 3H), 3.16 (s, 3H), 2.70-2.52 (m, 2H), 1.92 (s, 3H) 1.25-1.01 (m, 4H); MS (ES) $C_{25}H_{31}ClN_6O_5$ requires 530. Found: 531 (M+H$^+$).

N-(2-{[(3-chloro-4-methylbenzyl)amino]carbonyl}-8-cyclopropyl-3-hydroxy-4-oxo-4,6,7,8,9,10-hexahydropyrimido[1,2-d][1,4]diazepin-10-yl)-N,N',N'-trimethylethanediamide has been resolved into its enantiomers by semipreparative chiral HPLC using the following conditions:
Solvents: a mixture 35:65 0.2% TFA in Hexanes:EtOH. Column: Chiralpack AD column, 250×46 mm at 10.0 mL/min, detected by absorption at 300 nm.
The first eluate is the (+) enantiomer (EtOH, c=0.7, 25° C.) $[\alpha]_D$=(+) 22.1
The second eluate is the (−) enantiomer (EtOH, c=0.7, 25° C.) $[\alpha]_D$=(−) 21.8

Example 15

N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide and the corresponding (+) and (−) enantiomers. (Entry Nos. 154 and 155 in Table 1)

Step 1: Methyl 10-[benzyl(methyl)amino]-3-hydroxy-8-methyl-4-oxo-4,6,7,8,9,10-hexahydropyrimido[1,2-d][1,4]diazepine-2-carboxylate 8-tert-butyl 2-methyl 10-[benzyl(methyl)amino]-3-hydroxy-4-oxo-6,7,9,10-tetrahydropyrimido[1,2-d][1,4]diazepine-2,8(4H)-dicarboxylate (prepared as described in Example 11, Step 1-4) was taken in $CH_2Cl_2$/TFA (8/2 v/v) and stirred at room temperature for 1 hour. Volatiles were evaporated and residue was triturated with diethyl ether. MS (ES) $C_{18}H_{22}N_4O_4$ requires 358. Found: 359 (M+H$^+$). The crude organic product was dissolved in MeOH and treated with formaldehyde (3 eq.) and triethylamine (3 eq.). Acetic acid was added until pH=5.5, followed by $NaCNBH_3$ (2 eq.), and resulting mixture was stirred overnight at room temperature. The reaction mixture was concentrated to a residue which was purified on Cation Exchange Resin (Varian Mega Bond Elute SCX). After washing with MeOH, the product was collected eluting with 2N $NH_3$ solution in MeOH. The fractions containing the desired material were concentrated under reduced pressure to yield the title compound as a yellow oil. MS (ES) $C_{19}H_{24}N_4O_4$ requires 372. Found: 373 (M+H$^+$).

Step 2: Methyl 10-[[(dimethylamino)(oxo)acetyl](methyl)amino]-3-hydroxy-8-methyl-4-oxo-4,6,7,8,9,10-hexahydropyrimido[1,2-d][1,4]diazepine-2-carboxylate Compound of Step 1 was dissolved in MeOH and 6 N HCl (2.5 eq.) and stirred overnight under an $H_2$ atmosphere in the presence of 10% Pd/C. The catalyst was then filtered off through celite, and the filtrate was concentrated under reduced pressure and triturated with diethyl ether to yield methyl 3-hydroxy-8-methyl-10-(methylamino)-4-oxo-4,6,7,8,9,10-hexahydropyrimido[1,2-d][1,4]diazepine-2-carboxylate as a yellow solid. MS (ES) $C_{12}H_{18}N_4O_4$ requires 282. Found: 283 (M+H$^+$). The crude product was taken in dichloromethane and treated with triethylamine (2.5 eq.) and methyl chloro(oxo)acetate (1.2 eq.). After stirring one hour at room temperature, solvent was removed under reduced pressure and residue was taken in methanol and treated with an excess of dimethyl amine (2 M solution in methanol) at room temperature overnight. Volatiles were evaporated under reduced pressure to the title compound. MS (ES) $C_{16}H_{23}N_5O_6$ requires 381. Found: 382 (M+H$^+$).

Step 3: N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide Methyl 10-[[(dimethylamino)(oxo)acetyl](methyl)amino]-3-hydroxy-8-methyl-4-oxo-4,6,7,8,9,10-hexahydropyrimido[1,2-d][1,4]diazepine-2-carboxylate prepared as described in Step 2 was dissolved in methanol and treated with 1.2 eq. of triethylamine and 1.2 eq. of 4-fluorobenzylamine. The reaction mixture was refluxed overnight, then cooled to room temperature and purified by RP HPLC ($C_{18}$, 5 μM, $H_2O$/MeCN with 1% of TFA as eluant) affording desired compound (trifluoroacetic salt) as a white solid. $^1$H NMR (300 MHz, $CD_3CN$) δ 12.4 (bs, 1H), 10.01 (bs, 1H), 7.63 (dd, J=8.6 Hz, J=5.7 Hz, 2H), 7.29 (t, J=8.6 Hz, 2H), 5.53-5.30 (m, 2H), 4.82-4.68 (m, 2H), 4.25-4.13 (m, 3H), 3.95 (bs, 1H), 3.48-3.42 (m, 1H), 3.25 (s, 3H), 3.20 (s, 3H), 3.19 (s, 3H), 3.13 (s, 3H); MS (ES) $C_{22}H_{27}FN_6O_5$ requires 474. Found: 475 (M+H$^+$).

N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide has been resolved into its enantiomers by semipreparative chiral SFC using the following conditions: Solvents: $CO_2$, modifier: 1:1 MeOH:EtOH 30%, TFA 0.2%. Column: Chiracel OD-H 250×10 mm at 9.99 mL/min, P=100 bar, T=35° C.
The first eluate is the (+) enantiomer (EtOH, c=0.7, 25° C.) $[\alpha]_D$=(+) 18.0
The second eluate is the (−) enantiomer (EtOH, c=0.7, 25° C.) $[\alpha]_D$=(−) 18.0

Example 16

N-(2-{[(4-fluoro-3-methylbenzyl)amino]carbonyl}-3-hydroxy-8-methyl-4-oxo-4,6,7,8,9,10-hexahydro-pyrimido[1,2-d][1,4]diazepin-10-yl)-N,N',N'-trimethylethanediamide and the corresponding (+) and (−) enantiomers (Entry Nos. 146 and 147 in Table 1)

The title product was prepared in the manner described in Step 3 of Example 15, wherein 3-methyl-4-fluorobenzylamine was used in place of 4-fluorobenzylamine. $^1$H NMR (300 MHz, $CD_3CN$) δ12.76 (bs, 1H), 9.75 (bs, 1H), 7.27 (d, J=7.52 Hz, 1H), 7.23-7.18 (m, 1H), 6.98 (t, J=8.6 Hz, 1H), 5.4-5.25 (m, 2H), 4.57-4.41 (m, 2H), 4.10-3.97 (m, 3H), 3.76-3.72 (m, 1H), 3.19-3.11 (m, 1H), 3.03 (s, 3H), 2.97 (s, 3H), 2.96 (s, 3H), 2.87 (s, 3H), 2.23 (s, 3H); MS (ES) $C_{23}H_{29}FN_6O_5$ requires 488. Found: 489 (M+H$^+$).

N-(2-{[(4-fluoro-3-methylbenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide has been resolved into its enantiomers by semipreparative chiral HPLC using the following conditions: Solvents: a mixture 35:65 0.2% TFA in Hexanes:EtOH. Column: Chiralpack AD column, 250×46 mm at 10.0 mL/min, detected by absorption at 300 nm.

The first eluate is the (+) enantiomer (EtOH, c=0.5, 25° C.) $[\alpha]_D$=(+) 16.0

The second eluate is the (−) enantiomer (EtOH, c=0.5, 25° C.) $[\alpha]_D$=(−) 16.0

Example 17

N-(2-{[(3-chloro-4-methylbenzyl)amino]carbonyl}-3-hydroxy-8-methyl-4-oxo-4,6,7,8,9,10-hexahydro-pyrimido[1,2-d][1,4]diazepin-10-yl)-N,N',N'-trimethylethanediamide and the corresponding (+) and (−) enantiomers (Entry Nos. 130 and 131 in Table 1)

The title product was prepared in the manner described in Step 3 of Example 15, wherein 3-chloro-4-methylbenzylamine was used in place of 4-fluorobenzylamine. $^1$H NMR (300 MHz, $CD_3CN$) δ 12.38 (bs, 1H), 9.78 (bs, 1H), 7.40 (s, 1H), 7.26-7.20 (m, 2H), 5.40-5.25 (m, 2H), 4.55 (dd, J=14.8 Hz, J=6.7 Hz, 1H), 4.46 (dd, J=14.8 Hz, J=6.2 Hz, 1H), 4.10-3.97 (m, 3H), 3.20-3.11 (m, 1H), 3.03 (s, 3H), 2.97 (s, 3H), 2.96 (s, 3H), 2.87 (s, 3H), 2.33 (s, 3H); MS (ES) $C_{23}H_{29}ClN_6O_5$ requires 504. Found: 505 (M+H$^+$).

N-(2-{[(3-chloro-4-methylbenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide has been resolved into its enantiomers by semipreparative chiral SFC using the following conditions: Solvents: $CO_2$, modifier: 1:1 MeOH:EtOH 30%, TFA 0.2%. Column: Chiracel OD-H 250×10 mm at 9.99 mL/min, P=100 bar, T=35° C.

The first eluate is the (+) enantiomer (EtOH, c=0.3, 25° C.) $[\alpha]_D$=(+) 6.8

The second eluate is the (−) enantiomer (EtOH, c—0.3, 25° C.) $[\alpha]_D$=(−) 7.0

Example 18

N-(8-ethyl-2-{[(4-fluoro-3-methylbenzyl)amino] carbonyl}-3-hydroxy-4-oxo-4,6,7,8,9,10-hexahydro-pyrimido[1,2-d][1,4]diazepin-10-yl)-N,N',N'-trimethylethanediamide and the corresponding (+) and (−) enantiomers (Entry Nos. 132 and 133 in Table 1)

Step 1: Methyl 10-[benzyl(methyl)amino]-8-ethyl-3-hydroxy-4-oxo-4,6,7,8,9,10-hexahydropyrimido[1,2-d][1,4]diazepine-2-carboxylate 8-tert-butyl 2-methyl 10-[benzyl(methyl)amino]-3-hydroxy-4-oxo-6,7,9,10-tetrahydropyrimido[1,2-d][1,4]diazepine-2,8(4H)-dicarboxylate (prepared as described in Example 11, Step 1-4) was taken in $CH_2Cl_2$/TFA (8/2 v/v) and stirred at room temperature for 1 hour. Volatiles were evaporated and residue was triturated with diethyl ether. MS (ES) $C_{18}H_{22}N_4O_4$ requires 358. Found: 359 (M+H$^+$). The crude organic product was dissolved in MeOH and treated with acetaldehyde (3 eq.) and triethylamine (3 eq.). Acetic acid was added until pH=5.5, followed by $NaCNBH_3$ (2 eq.), and resulting mixture was stirred overnight at room temperature. The reaction mixture was concentrated to a residue which was purified on Cation Exchange Resin (Varian Mega Bond Elute SCX). After washing with MeOH, the product was collected eluting with 2N $NH_3$ solution in MeOH. The fractions containing the desired material were concentrated under reduced pressure to yield the title compound as brown oil. MS (ES) $C_{20}H_{26}N_4O_4$ requires 386. Found: 387 (N+H$^+$).

Step 2: Methyl 10-[[(dimethylamino)(oxo)acetyl] (methyl)amino]-8-ethyl-3-hydroxy-4-oxo-4,6,7,8,9, 10-hexahydropyrimido[1,2-d][1,4]diazepine-2-carboxylate The compound of Step 1 was dissolved in MeOH and 6 N HCl (2.5 eq.) and stirred overnight under an $H_2$ atmosphere in the presence of 10% Pd/C. The catalyst was then filtered off through celite, and the filtrate was concentrated under reduced pressure and triturated with diethyl ether to yield methyl 8-ethyl-3-hydroxy-10-(methylamino)-4-oxo-4,6,7,8, 9,10-hexahydropyrimido[1,2-d][1,4]diazepine-2-carboxylate. MS (ES) $C_{13}H_{20}N_4O_4$ requires 296. Found: 297 (M+H$^+$). The latter compound was taken in dichloromethane and treated with triethylamine (2.5 eq.) and methyl chloro (oxo)acetate (1.2 eq.). After stirring one hour at room temperature, solvent was removed under reduced pressure and residue was taken in methanol and treated with an excess of dimethyl amine (2 M solution in methanol) at room temperature overnight. Volatiles were evaporated under reduced pressure yielding title compound which was used without purification in the next step. MS (ES) $C_{17}H_{25}N_5O_6$ requires 395. Found: 396 (M+H$^+$).

Step 3: N-(8-ethyl-2-{[(4-fluoro-3-methylbenzyl) amino]carbonyl}-3-hydroxy-4-oxo-4,6,7,8,9,10-hexahydropyrimido[1,2-d][1,4]diazepin-10-yl)-N,N', N'-trimethylethanediamide Crude methyl 10-[[(dimethylamino)(oxo)acetyl](methyl) amino]-8-ethyl-3-hydroxy-4-oxo-4,6,7,8,9,10-hexahydropyrimido[1,2-d][1,4]diazepine-2-carboxylate was dissolved in methanol and treated with 1.2 eq. of triethylamine and 1.2 eq. of 4-fluoro-3-methylbenzylamine. The reaction mixture was refluxed overnight, then cooled to room temperature and purified by RP HPLC ($C_{18}$, 5 μM, $H_2O$/MeCN with 1% of TFA as eluant) affording desired compound as a white solid. $^1$H NMR (300 MHz, CD$_3$CN) δ 12.4 (bs, 1H), 9.74 (bs, 1H), 7.26-7.16 (m, 2H), 6.96 (t, J=8.62 Hz, 1H), 5.40-5.22 (m, 2H), 4.51 (dd, J=14.6 Hz, J=6.86 Hz, 1H), 4.42 (dd, J=14.6 Hz, J=6.41 Hz, 1H), 4.18-3.92 (m, 3H), 3.78-3.73 (ms, 1H), 3.28-3.18 (m, 3H), 3.01 (s, 3H), 2.95 (s, 3H), 2.93 (s, 3H), 2.21 (s, 3H), 1.30 (t, J=5.97 Hz, 3H). MS (ES) C$_{24}$H$_{31}$FN$_6$O$_5$ requires 502. Found: 503 (M+H$^+$).

N-(8-ethyl-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide has been resolved into its enantiomers by semipreparative chiral SFC using the following conditions: Solvents: CO$_2$, modifier: MeOH 30%, diethylamine 0.2%. Column: Chiracel OD-H 250×10 mm at 9.99 mL/min, P=100 bar, T=35° C. The first eluate is the (+) enantiomer (EtOH, c=0.3, 25° C.) [α]$_D$=(+) 16.0
The second eluate is the (−) enantiomer (EtOH, c=0.3, 25° C.) [α]$_D$=(−) 16.0

Example 19

N-(4-fluorobenzyl)-3-hydroxy-8-methyl-9-{[methyl(methylsulfonyl)amino]methyl}-4-oxo-6,7,8,9-tetrahydro-4H-pyrazino[1,2-a]pyrimidine-2-carboxamide (Entry No. 21 in Table 1)

Step 1: tert-butyl [(2E)-2-amino-1-[(benzyloxy)methyl]-2-(hydroxyimino)ethyl]carbamate Hydroxylamine hydrochloride in methanol was added to an equimolar stirred solution of potassium hydroxide in methanol. The mixture was stirred for 15 minutes and the precipitated potassium chloride was removed by filtration. The filtrate was added to an equimolar amount of tert-butyl [2-(benzyloxy)-1-cyanoethyl]carbamate and the solution was stirred for 5 hours at 45° C. and for 12 hours at room temperature. The reaction mixture was concentrated and the solvent switched to CHCl$_3$. The insoluble material was filtered off and the filtrated was evaporated to afford the title product as a white solid.

$^1$H-NMR (400 MHz, CDCl$_3$) δ 7.27-7.38 (bs, 5H), 5.48 (d, J=7.3 Hz, 1H), 5.26 (bs, 2H), 4.54 (s, 2H), 4.38 (bs, 1H), 3.76 (dd, J=9.5 Hz, J=3.8 Hz, 1H), 3.68 (dd, J=9.5 Hz, J=5.3 Hz, 1H), 1.43 (s, 9H). MS (ES) C$_{15}$H$_{23}$N$_3$O$_4$ requires 309. Found: 310 (M+H$^+$).

Step 2: Methyl 5-(benzoyloxy)-2-{2-(benzyloxy)-1-[(tert-butoxycarbonyl)amino]ethyl}-6-hydroxypyrimidine-4-carboxylate tert-Butyl [(2E)-2-amino-1-[(benzyloxy)methyl]-2-(hydroxyimino)ethyl]carbamate prepared as described in Step 1 was dissolved in chloroform and treated with 1.2 eq. of dimethylacetylenedicarboxylate and the reaction was refluxed for 2.5 hours. After cooling at room temperature, the reaction mixture was concentrated and the solvent switched to xylene. The mixture was heated at 145° C. for 24 hours. After cooling at room temperature, solid material was filtered off and the filtrate was concentrated under reduced pressure. The residue was dissolved in dry CH$_2$Cl$_2$ then dry pyridine was added and finally benzoic anhydride (1.1 eq.). The mixture was stirred at room temperature overnight, then the solvent was removed by rotary evaporation and the residue taken in ethyl acetate was washed with 1 N HCl, sat. NaHCO$_3$ and brine. Organic layer was separated, dried (Na$_2$SO$_4$), filtered and concentrated. The resulting residue was purified by flash chromatography (SiO$_2$, eluting with 60/40 v/v petroleum ether/ethyl acetate), collection and evaporation of appropriate fractions afforded title product.

$^1$H-NMR (400 MHz, CDCl$_3$) δ 11.05 (bs, 1H), 8.21 (d, J=7.9 Hz, 2H), 7.67 (t, J=7.2 Hz, 1H), 7.52 (t, J=7.7 Hz, 2H), 7.23-7.38 (m, 5H), 5.64 (d, J=6.6 Hz, 2H), 4.84 (bs, 1H), 4.56 (s, 2H), 3.99 (m, 1H), 3.84 (s, 3H), 3.77 (dd, J=9.7 Hz, J=5.3 Hz, 1H), 1.46 (s, 9H); MS (ES) C$_{27}$H$_{29}$N$_3$O$_8$ requires 523. Found: 524 (M+H$^+$).

Step 3: 2-[1-amino-2-(benzyloxy)ethyl]-N-(4-fluorobenzyl)-5,6-dihydroxypyrimidine-4-carboxamide To a methanolic solution of methyl 5-(benzoyloxy)-2-{2-(benzyloxy)-1-[(tert butoxycarbonyl)amino]ethyl}-6-hydroxypyrimidine-4-carboxylate prepared as described in Step 2, 4-fluorobenzylamine (2.15 eq.) was added. The resulting solution was refluxed for 24 hours (100% conversion by LC-MS). After cooling to room temperature, the crude was concentrated under reduced pressure and the solvent switched to CH$_2$Cl$_2$. To the solution, trifluoroacetic acid was added and the mixture was stirred at room temperature for 1.5 hours. The reaction mixture was concentrated and diethyl ether (100 mL) was added. The resulting slurry was stirred for 1 hour at room temperature and the product was collected by filtration. The cake was washed with cold diethyl ether and dried under reduced pressure to afford title compound as trifluoroacetic salt. MS (ES) C$_{21}$H$_{21}$FN$_4$O$_4$ requires 412. Found: 413.

Step 4: 2-{2-(benzyloxy)-1-[(2-chloroethyl)amino]ethyl}-N-(4-fluorobenzyl)-5,6-dihydroxypyrimidine-4-carboxamide To a stirred suspension of compound of Step 3 in dry trimethylortoformiate, triethylamine (1.3 eq.) and 1.1 eq. of α-chloroacetaldehyde (1.1 eq.) were added. The resulting solution was aged for 2 hours at room temperature, the solvent was removed by rotary evaporation to afford a residue that was dissolved in MeOH, treated with acetic acid (pH=5) and NaBH$_3$CN (1.1 eq.). The mixture was stirred overnight at room temperature then the solvent was removed by rotary evaporation and the resulting residue was taken in dry toluene and concentrated. This material was used without any purification for the next step. MS (ES) C$_{23}$H$_{24}$ClFN$_4$O$_4$ requires 474. Found: 475.

Step 5: 9-[(benzyloxy)methyl]-2-{[(4-fluorobenzyl)amino]carbonyl}-3-hydroxy-4-oxo-6,7,8,9-tetrahydro-4H-pyrazino[1,2-a]pyrimidin-8-ium trifluoroacetate To a solution of 2-{2-(benzyloxy)-1-[(2-chloroethyl)amino]ethyl}-N-(4-fluorobenzyl)-5,6-dihydroxypyrimidine-4-carboxamide in dry 1,4-dioxane under nitrogen atmosphere potassium tert-butoxide (3 eq.) was added in one portion. The resulting suspension was aged at 120° C. for 2 hours. The reaction mixture was cooled to about 15° C. then acidified with trifluoroacetic acid to pH=3-4. The solvent was removed under reduced pressure and the residue, dissolved in the minimum amount of MeOH, was applied on cation-exchange resin cartridges (Varian MEGA BOND ELUTE SCX), the cartridges washed with MeOH and the crude product was eluted with 1M ammonia in methanol. The pooled eluants were concentrated to dryness under reduced pressure to get 9-[(benzyloxy)methyl]-N-(4-fluorobenzyl)-3-hydroxy-4-oxo-6,7,8,9-tetrahydro-4H-pyrazino[1,2-a]pyrimidine-2-carboxamide as a brown oil (85% yield). The crude product was purified by RP HPLC ($C_{18}$, 5 μM, $H_2O$/MeCN with 1% of TFA as eluant) and product was obtained after freeze drying of appropriate fractions.

$^1$H-NMR (400 MHz, DMSO-$d_6$) δ 12.51 (bs, 1H), 9.46 (t, J=6.5 Hz, 1H), 7.42-7.32 (m, 7H), 7.07 (t, J=8.7 Hz, 2H), 4.76 (bs, 1H), 4.70 (d, J=12.1 Hz, 1H), 4.59 (d, J=12.1 Hz, 1H), 4.58-4.54 (m, 1H), 4.50 (dd, J=15.0 Hz, J=6.3 Hz, 1H), 4.39 (dd, J=10.6 Hz, J=3.4 Hz, 1H), 4.23-4.17 (m, 2H), 4.01 (m, 1H), 3.68 (m, 1H), 3.54 (m, 1H);

MS (ES) $C_{23}H_{23}FN_4O_4$ requires 438. Found: 439 (M+H$^+$).

Step 6: tert-butyl 2-{[(4-fluorobenzyl)amino]carbonyl}-3-hydroxy-9-(hydroxymethyl)-4-oxo-4,6,7,9-tetrahydro-8H-pyrazino[1,2-a]pyrimidine-8-carboxylate To a solution of 9-[(benzyloxy)methyl]-2-{[(4-fluorobenzyl)amino]carbonyl}-3-hydroxy-4-oxo-6,7,8,9-tetrahydro-4H-pyrazino[1,2-a]pyrimidin-8-ium trifluoroacetate in MeOH, $Boc_2O$ (1.2 eq.) was added and the mixture was aged overnight at room temperature. Activated charcoal was added and the mixture was stirred for 30 minutes at room temperature, then was filtered through celite and concentrated under reduced pressure. Required tert-butyl 9-[(benzyloxy)methyl]-2-{[(4-fluorobenzyl)amino]carbonyl}-3-hydroxy-4-oxo-4,6,7,9-tetrahydro-8H-pyrazino[1,2-a]pyrimidine-8-carboxylate was obtained after trituration with ethyl ether and further reacted. MS (ES) $C_{28}H_{31}FN_4O_6$ requires 538. Found: 539 (M+H$^+$). The crude organic product was solubilized in methanol, treated with 1.2 eq. of 1N HCl and the solution was stirred overnight under a hydrogen atmosphere in the presence of catalytic 10% Pd/C. Catalyst was then filtered off through celite, and the filtrate was neutralized with $NaHCO_3$ and concentrated under reduced pressure. The resulting residue was taken in $CHCl_3$, the insoluble material was filtered off and the filtrate was evaporated to afford title compound as a slightly colored solid. MS (ES) $C_{21}H_{25}FN_4O_6$ requires 448. Found: 449 (M+H$^+$).

Step 7: tert-butyl 9-{[benzyl(methyl)amino]methyl}-2-{[(4-fluorobenzyl)amino]carbonyl}-3-hydroxy-4-oxo-4,6,7,9-tetrahydro-8H-pyrazino[1,2-a]pyrimidine-8-carboxylate To a solution of tert-butyl 2-{[(4-fluorobenzyl)amino]carbonyl}-3-hydroxy-9-(hydroxymethyl)-4-oxo-4,6,7,9-tetrahydro-8H-pyrazino[1,2-a]pyrimidine-8-carboxylate in dry $CHCl_3$, triethylamine (2 eq.) was added and mixture was stirred ten minutes at room temperature. Methanesulfonyl chloride (1.5 eq.) was slowly added and the resulting mixture was aged at room temperature for 1.5 hours to afford tert-butyl 2-{[(4-fluorobenzyl)amino]carbonyl}-3-hydroxy-9-{[(methylsulfonyl)oxy]methyl}-4-oxo-4,6,7,9-tetrahydro-8H-pyrazino[1,2-a]pyrimidine-8-carboxylate as the main product (monitored by LC-MS). MS (ES) $C_{22}H_{27}FN_4O_8S$ requires 526. Found: 527 (M+H$^+$). The reaction mixture was concentrated under vacuum at 30° C. and the solvent switched to dry acetonitrile. The insoluble material was filtered off and to the filtrated 5 equivalents of N-benzylmethylamine were added. The mixture was warmed at 110° C. upon microwave irradiation for 30 minutes then stirred at room temperature for further 36 hours. The mixture was concentrated by rotary evaporation and the resulting residue, dissolved in the minimum amount of MeOH, was carefully acidified with some drops of glacial acetic acid applied on cation-exchange resin. The resin was washed with MeOH and the crude product was eluted with 1M ammonia in methanol. The pooled eluants were concentrated to dryness under reduced pressure to get tert-butyl 9-{[benzyl(methyl)amino]methyl}-2-{[(4-fluorobenzyl)amino]carbonyl}-3-hydroxy-4-oxo-4,6,7,9-tetrahydro-8H-pyrazino[1,2-a]pyrimidine-8-carboxylate as a brown oil. MS (ES) $C_{29}H_{34}FN_5O_5$ requires 551. Found: 552 (M+H$^+$).

Step 8: N-(4-fluorobenzyl)-3-hydroxy-9-[(methylamino)methyl]-4-oxo-6,7,8,9-tetrahydro-4H-pyrazino[1,2-a]pyrimidine-2-carboxamide A solution of compound of Step 7 in dry $CH_2Cl_2$/trifluoroacetic acid (8/2 v/v) was stirred at room temperature for 1.5 hours, then evaporated under reduced pressure. MS (ES) $C_{24}H_{26}FN_5O_3$ requires 451. Found: 452 (M+H$^+$). The residue was taken in methanol and the solution was treated with 3 equivalents of triethylamine and stirred for 10 minutes. The mixture was acidified with some drops of acetic acid (pH=5) then treated with formaldehyde (3 eq.) and sodium cyanoborohydride. After over night stirring at room temperature, volatiles were removed by rotary evaporation and the resulting residue, dissolved in the minimum amount of MeOH, was applied on cation-exchange resin. The resin was washed with MeOH and the product was eluted with 1 M ammonia in methanol. The pooled fractions were concentrated to dryness under reduced pressure to get 9-{[benzyl(methyl)amino]methyl}-N-(4-fluorobenzyl)-3-hydroxy-8-methyl-4-oxo-6,7,8,9-tetrahydro-4H-pyrazino[1,2-a]pyrimidine-2-carboxamide as a brown oil. MS (ES) $C_{25}H_{28}FN_5O_3$ requires 465. Found: 466 (M+H$^+$). The crude compound was dissolved in methanol, treated with 2.5 eq. of 1 N HCl and the solution was stirred overnight under a hydrogen atmosphere in the presence of catalytic 10% Pd/C. Catalyst was then filtered off through celite, and the filtrate was evaporated under reduced pressure to afford title compound as hydrochloric salt. MS (ES) $C_{18}H_{22}FN_5O_3$ requires 375. Found: 476 (M+H$^+$).

Step 9: N-(4-fluorobenzyl)-3-hydroxy-8-methyl-9-{[methyl(methylsulfonyl)amino]methyl}-4-oxo-6,7,8,9-tetrahydro-4H-pyrazino[1,2-a]pyrimidine-2-carboxamide N-(4-fluorobenzyl)-3-hydroxy-9-[(methylamino)methyl]-4-oxo-6,7,8,9-tetrahydro-4H-pyrazino[1,2-a]pyrimidine-2-carboxamide was suspended in dry $CH_2Cl_2$ and triethylamine (2.5 eq.), methane sulphonylchloride (1.3 eq.) was slowly added to the solution under nitrogen atmosphere and the reaction mixture was stirred at room temperature overnight. Volatiles were removed under reduced pressure and title product was purified RP HPLC ($C_{18}$, 5 μM, $H_2O$/MeCN with 1% of TFA as eluant). Lyophilization of appropriate fractions gave title compound as trifluoroacetate salt.

$^1$H-NMR (300 MHz, $CD_3CN$) δ 8.52 (bs, 1H), 7.43-7.38 (m, 2H), 7.12 (t, J=8.8 Hz, 2H), 4.67-4.51 (m, 3H), 4.30-4.13 (m, 2H), 4.05 (dd, J=15.7 Hz, J=7.7 Hz, 1H), 3.96-3.68 (m, 3H), 3.10 (s, 3H), 2.94 (s, 3H), 2.89 (s, 3H); MS (ES) $C_{19}H_{24}FN_5O_5S$ requires 453. Found: 454 (M+H$^+$).

Example 20

8-Acetyl-N-(4-fluorobenzyl)-3-hydroxy-4-oxo-4,6,7, 8,9,10-hexahydropyrimido[1,2-d][1,4]diazepine-2-carboxamide (Entry No. 174 in Table 1)

Step 1: Methyl 8-acetyl-3-(acetyloxy)-4-oxo-4,6,7,8, 9,10-hexahydropyrimido[1,2-d][1,4]diazepine-2-carboxylate and methyl 8-acetyl-3-hydroxy-4-oxo-4, 6,7,8,9,10-hexahydropyrimido[1,2-d][1,4]diazepine-2-carboxylate A solution of 8-tert-butyl-2-methyl-3-hydroxy-4-oxo-6,7, 9,10-tetrahydropyrimido[1,2-d][1,4]diazepine-2,8(4H)-dicarboxylate (prepared as described in Example 11, Steps 1-3) in dichloromethane/trifluoroacetic acid (8/2 v/v) was stirred at room temperature for 2 hours. Volatiles were evaporated under reduced pressure and residue after trituration with diethyl ether was taken in dichloromethane and treated with 2.5 equivalents of triethylamine and 2 equivalents of acetic anhydride. The resulting mixture was stirred over night at room temperature. Volatiles were evaporated and residue containing mono- and di-acylated compounds in approximately 1:1 ratio (as evidenced by LC/MS analysis) was taken in the next step. MS (ES) $C_{14}H_{17}N_3O_6$ requires 323. Found: 324 (M+H$^+$); MS (ES) $C_{12}H_{15}N_3O_5$ requires 281. Found: 282 (M+H$^+$).

Step 2: 8-Acetyl-N-(4-fluorobenzyl)-3-hydroxy-4-oxo-4,6,7,8,9,10-hexahydropyrimido[1,2-d][1,4]diazepine-2-carboxamide The mixture of products obtained in Step 1 was taken in methanol and treated with 2.5 equivalents of p-fluorobenzylamine. The resulting mixture was refluxed for 24 hours, then cooled to room temperature and concentrated under reduced pressure. The crude material was purified by R$^P$ HPLC (C$_{18}$, 5 μM, H$_2$O/MeCN with 1% of TFA as eluant). Lyophilization of appropriate fractions gave title compound as a white solid.
$^1$H-NMR (300 MHz, CD$_3$CN) δ 12.19 (bs, 1H), 8.56 (bs, 1H), 7.47-7.42 (m, 2H), 7.17 (t, J=5.75 Hz, 2H), 4.60 (bd, J=5.53, 2H), 4.46-4.37 (m, 2H), 3.86-3.75 (m, 4H), 3.7-3.05 (m, 2H), 2.17 (s, 1.5H), 2.14 (s, 1.5H); MS (ES) $C_{18}H_{19}FN_4O_4$ requires 374. Found: 375 (M+H$^+$).

Example 21

N-(2-{[(4-fluorobenzyl)amino]carbonyl}-3-hydroxy-4-oxo-6,7,9,10-tetrahydro-4H-pyrimido[1,2-d][1,4] oxazepin-10-yl)-N',N'-trimethylethanediamide and the corresponding (+) and (−) enantiomers (Entry Nos. 180 and 181 in Table 1)

Step 1: 1,4-Oxazepane-5-thione 1,4-Oxazepan-5-one, P$_4$S$_{10}$ (0.2 eq.), HMDO (2 eq.) and dichloromethane were combined and stirred magnetically at room temperature for 1 hour. The reaction mixture was then cooled to 0° C. and aqueous K$_2$CO$_3$ solution (1.26 mL of 5.3 M/mmol P$_4$S$_{10}$ taken) was added. A volume of acetone equal to one half of the reaction solvent was added to obtain a stirrable mixture, and the reaction mixture was stirred vigorously for 30 minutes at 0° C. Volatiles were evaporated, water and ethyl acetate were added, layers were separated and the organic phase was washed with water and brine. The organic extract was dried over Na$_2$SO$_4$ and evaporated, to afford crude product in quantitative yield. $^1$H NMR (300 MHz, CDCl$_3$) δ 8.96 (bs, 1H), 3.84-3.77 (m, 4H), 3.57-3.54 (m, 2H), 3.28-3.26 (m, 2H).

Step 2: 1,4-oxazepan-5-one oxime

A solution of NH$_2$OH HCl (2 eq.) in methanol was added to an equimolar methanolic solution of KOH. KCl was filtered off and the filtrate was added to a solution of 1,4-oxazepane-5-thione (1 eq.) in methanol. The mixture was stirred at 55° C. overnight, then cooled to room temperature and the solvent was removed under reduced pressure. The residue was taken in chloroform, washed with brine, dried (Na$_2$SO$_4$) and concentrated under reduced pressure to give, after trituration with ethyl ether, the title compound. $^1$H NMR (300 MHz, CDCl$_3$) δ 8.9 (bs, 1H), 6.15 (bs, 1H), 3.68-3.51 (m, 4H), 3.21-3.19 (m, 2H), 2.38-2.31 (m, 2H); MS (ES) $C_5H_{10}N_2O_2$ requires 130. Found: 131 (M+H$^+$).

Step 3: Methyl 3-hydroxy-4-oxo-6,7,9,10-tetrahydro-4H-pyrimido[1,2-d][1,4]oxazepine-2-carboxylate To a stirred suspension of 1,4-oxazepan-5-one oxime in acetonitrile, dimethylacetylene dicarboxylate (1 eq.) was added in one portion and the mixture was stirred at room temperature for 1 hour. The solvent was removed under reduced pressure and the oily residue was taken in xylene and stirred overnight at 145° C. After cooling to room temperature, the solvent was evaporated under reduced pressure and residue was taken in ethyl acetate and treated with saturated solution of NaHCO$_3$. The aqueous phase was separated, washed with additional ethyl acetate and carefully acidified with 2N HCl. The product was extracted in chloroform, and the organic solution was dried over Na$_2$SO$_4$ and concentrated under reduced pressure to afford title compound as a brown solid. $^1$H NMR (300 MHz, d$_6$-DMSO) δ 10.58 (bs, 1H), 4.57-4.52 (m, 2H), 4.06 (s, 3H), 3.91-3.82 (m, 4H), 3.26-3.18 (m, 2H); MS (ES) $C_{10}H_{12}N_2O_5$ requires 240. Found: 241 (M+H$^+$).

Step 4: Methyl 10-[benzyl(methyl)amino]-3-hydroxy-4-oxo-6,7,9,10-tetrahydro-4H-pyrimido[1,2-d][1,4]oxazepine-2-carboxylate Methyl 3-hydroxy-4-oxo-6,7,9,10-tetrahydro-4H-pyrimido[1,2-d][1,4]oxazepine-2-carboxylate was taken in chloroform and treated with pyridine (3 equivalents) and benzoic anhydride (1.2 eq.). The mixture was stirred overnight at room temperature, then poured in chloroform and washed with 1 N HCl and brine. The organic phase was dried (Na$_2$SO$_4$), filtered and concentrated under reduced pressure to a solid residue. MS (ES) $C_{17}H_{16}N_2O_6$ requires 344. Found: 345 (M+H$^+$). This residue was taken in N,N-dimethylformamide and treated with 0.5 equivalents of benzoyl peroxide and 5 equivalents of N-bromosuccinimide. The mixture was stirred at 100° C. for 1 hour. To allow the reaction to progress further, another aliquot of both reagents was added and stirring continued an additional hour. After cooling to room temperature, mixture was poured in EtOAc, washed with brine, dried (Na$_2$SO$_4$), filtered and concentrated under reduced pressure to an oily residue. This residue was treated with an excess of methylbenzylamine in THF at room temperature for 1 hour. The mixture was applied on cation exchange resin and the resin was extensively washed with methanol, while title compound was eluted with a 1N solution of ammonia in methanol. The pooled fractions were evaporated to dryness. MS (ES) $C_{18}H_{21}N_3O_5$ requires 359. Found: 360 (M+H$^+$).

Step 5: N-(4-fluorobenzyl)-3-hydroxy-10-(methylamino)-4-oxo-6,7,9,10-tetrahydro-4H-pyrimido[1,2-d][1,4]oxazepine-2-carboxamide Crude organic product prepared as described in Step 4 was taken in methanol and reacted with p-fluorobenzylamine (2 equivalents) at 80° C. for 2 hours. Volatiles were evaporated and the residue washed by trituration with diethyl ether. MS (ES) $C_{24}H_{25}FN_4O_4$ requires 452. Found: 453 (M+H$^+$). A solution of this crude material in methanol and 1 N HCl was stirred under a balloon of hydrogen in the presence of 10% Pd/C. After overnight stirring, the mixture was filtered through celite and concentrated under reduced pressure. MS (ES) $C_{17}H_{19}FN_4O_4$ requires 362. Found: 363 (M+H$^+$).

Step 6: N-(2-{[(4-fluorobenzyl)amino]carbonyl}-3-hydroxy-4-oxo-6,7,9,10-tetrahydro-4H-pyrimido[1,2-d][1,4]oxazepin-10-yl)-N,N',N'-trimethylethanediamide To a suspension of N-(4-fluorobenzyl)-3-hydroxy-10-(methylamino)-4-oxo-6,7,9,10-tetrahydro-4H-pyrimido[1,2-d][1,4]oxazepine-2-carboxamide was added triethylamine (2.5 eq.) and methyl chloro(oxo)acetate (2 eq.) and the resulting mixture was stirred one hour at room temperature. Volatiles were evaporated under reduced pressure and residue was taken in methanol and treated with an excess of dimethylamine (2 M solution in methanol). The reaction mixture was stirred overnight at room temperature, evaporated under reduced pressure and purified by RP HPLC (C$_{18}$, 5 μM, H$_2$O/MeCN with 1% of TFA as eluant). Lyophilization of appropriate fractions gave the title compound as a white solid. $^1$H NMR (300 MHz, CD$_3$CN) δ 12.2 (bs, 1H), 9.78 (bs, 1H), 7.48-7.39 (m, 2H), 7.07 (t, J=8.7 Hz, 2H), 5.20-5.12 (m, 1H), 5.1, 4.9 (bs, 1H), 4.61-4.50 (m, 2H), 4.30-4.22 (m, 1H), 4.19-4.08 (m, 2H), 3.80-3.70 (m, 1H), 3.60-3.49 (m, 1H), 3.06 (s, 3H), 2.98 (s, 3H), 2.92 (s, 3H); MS (ES) $C_{21}H_{24}FN_5O_6$ requires 461. Found: 462 (M+H$^+$).

N-(2-{[(4-fluorobenzyl)amino]carbonyl}-3-hydroxy-4-oxo-6,7,9,10-tetrahydro-4H-pyrimido[1,2-d][1,4]oxazepin-10-yl)-N,N',N'-trimethylethanediamide has been resolved into its enantiomers by semipreparative chiral HPLC using the following conditions: Solvents: a mixture 40:60 0.2% TFA in Hexanes: 0.2% TFA in EtOH+3% MeOH. Column: Chiralpack AD 250×46 nm at 10 mL/min, detected by absorption at 300 nm.

The first eluate is the (+) enantiomer (EtOH, c=0.1, 25° C.) $[\alpha]_D$=(+) 12.3

The second eluate is the (−) enantiomer (EtOH, c=0.1, 25° C.) $[\alpha]_D$=(−) 12.0

Example 22

N-(4-fluorobenzyl)-3-hydroxy-9,9-dimethyl-4-oxo-8,9-dihydro-4H-pyrimido[2,1-d][1,2,5]thiadiazine-2-carboxamide 7,7-dioxide (Entry No. 105 in Table 1)

Step 1: 2-(1-{[(chloromethyl)sulfonyl]amino}-1-methylethyl)-4-{[(4-fluorobenzyl)amino]carbonyl}-6-hydroxypyrimidin-5-yl chloromethanesulfonate To a solution of 2-(1-amino-1-methylethyl)-N-(4-fluorobenzyl)-5,6-dihydroxypyrimidine-4-carboxamide hydrochloride (prepared as described in WO2003035076 A1) in dichloromethane, triethylamine (4 eq.) was added and the mixture was cooled down with an ice/salt bath. A solution of chloromethanesulfonyl chloride in dichloromethane was added dropwise to the mixture. After 2 hours further triethylamine (1 eq.) and chloromethanesulfonyl chloride (1 eq.) were added at 0° C. and the reaction mixture was aged at room temperature overnight. To allow complete consumption of starting material, additional Et$_3$N (0.5 eq.) and chloromethanesulfonyl chloride (0.5 eq.) were added at 0° C. After one hour, the mixture was poured in dichloromethane and washed with 1N HCl and brine, dried over Na$_2$SO$_4$, filtered and concentrated under reduced pressure to obtain title compound as yellow oil. $^1$H NMR (300 MHz, d$_6$-DMSO) δ 13.32 (bs, 1H), 9.19 (t, J=6.0 Hz, 1H), 8.03 (s, 1H), 7.37 (dd, J=8.4 Hz, J=5.7 Hz, 2H), 7.15 (t, J=8.5 Hz, 2H), 5.59 (s, 2H), 4.86 (s, 2H), 4.45 (d, J=6.2 Hz, 2H), 1.64 (s, 6H); MS (ES) $C_{17}H_{19}Cl_2FN_4O_7S_2$ requires 545. Found: 546 (M+H$^+$).

Step 2: N-(4-fluorobenzyl)-3-hydroxy-9,9-dimethyl-4-oxo-8,9-dihydro-4H-pyrimido[2,1-d][1,2,5]thiadiazine-2-carboxamide 7,7-dioxide Crude chloride of Step 1 was dissolved in 1,4-dioxane and Cs$_2$CO$_3$ (2 eq.) was added. The reaction mixture was stirred at 100° C. overnight, then cooled down to room temperature, taken up in EtOAc washed with brine, dried over Na$_2$SO$_4$. The solvent was removed under reduced pressure and the resulting brown oil was purified by RP HPLC (C$_{18}$, 5 μM, H$_2$O/MeCN with 1% of TFA as eluant). Lyophilization of appropriate fractions gave title compound as a white solid.

$^1$H NMR (300 MHz, d$_6$-DMSO) δ12.47 (bs, 1H), 9.47 (t, J=6.2 Hz, 1H), 8.24 (s, 1H), 7.38 (dd, J=8.5 Hz, J=5.6 Hz, 2H), 7.17 (t, J=8.9 Hz, 2H), 5.28 (s, 2H), 4.49 (d, J=6.4 Hz, 2H), 1.69 (s, 6H); MS (ES) $C_{16}H_{17}FN_4O_5S$ requires 396. Found: 397 (M+H$^+$).

Example 23

N-(4-fluorobenzyl)-3-hydroxy-7-methyl-4,6-dioxo-6,7,8,9-tetrahydro-4H-pyrimido[1,6-a]pyrimidine-2-carboxamide (Entry No. 104 in Table 1)

Step 1: tert-Butyl [3-amino-3-(hydroxyimino)propyl]benzylcarbamate

Hydroxylamine hydrochloride in methanol was added to an equimolar stirred solution of potassium hydroxide in methanol. The mixture was stirred for 15 minutes and the precipitated potassium chloride is removed by filtration. The filtrate was added to an equimolar amount of the tert-butyl benzyl(2-cyanoethyl)carbamate and the solution was stirred for 2 hours at 60° C. The reaction mixture was concentrated and the solvent switched to CHCl$_3$. The insoluble material was filtered off and the filtrated was evaporated to afford the title product as a white solid. MS (ES) $C_{15}H_{23}N_3O_3$ requires 293. Found: 294 (M+H$^+$).

Step 2: Methyl 2-{2-[benzyl(tert-butoxycarbonyl) amino]ethyl}-5,6-dihydroxypyrimidine-4-carboxylate A solution of tert-butyl [3-amino-3-(hydroxyimino)propyl]benzylcarbamate (prepared as described in Step 1) in chloroform was treated with dimethylacetylene dicarboxylate (1 eq.) and the mixture was stirred at 60° C. for 2 hours. Volatiles were evaporated under reduced pressure and the residue was taken in xylene and stirred for 2 days at 150° C. After cooling to room temperature a brown solid precipitated from xylene and was filtered off and washed with diethyl ether to give crude title compound. MS (ES) $C_{20}H_{25}N_3O_6$ requires 403. Found: 404 (M+H$^+$).

Step 3: tert-Butyl benzyl[2-(4-{[(4-fluorobenzyl) amino]carbonyl}-5,6-dihydroxypyrimidin-2-yl) ethyl]carbamate Crude methyl 2-{2-[benzyl(tert-butoxycarbonyl)amino]ethyl}-5,6-dihydroxypyrimidine-4-carboxylate (prepared as described in Step 2) was dissolved in methanol and treated with p-fluorobenzylamine (2.5 equivalents) at 80° C. for 12 hours. The mixture was then cooled to room temperature, volatiles were evaporated and the residue was poured in EtOAc and washed 0.5 N HCl and brine. The organic phase was dried (Na$_2$SO$_4$), filtered and concentrated to a brown solid residue. MS (ES) $C_{26}H_{29}FN_4O_5$ requires 496. Found: 497 (M+H$^+$).

Step 4: 2-{2-[benzyl(methyl)amino]ethyl}-N-(4-fluorobenzyl)-5,6-dihydroxypyrimidine-4-carboxamide Crude tert-butyl benzyl[2-(4-{[(4-fluorobenzyl)amino]carbonyl}-5,6-dihydroxypyrimidin-2-yl)ethyl]carbamate (prepared as described in Step 3) was taken in dichloromethane/trifluoroacetic acid (8/2 v/v) and the mixture was stirred 1 hour at room temperature. After evaporation of volatiles, the crude organic product was taken in methanol and treated with triethyl amine (1 equivalent), formaldehyde (2 equivalents), sodium cyanoborohydride (1.2 equivalents) and acetic acid (pH=5.5). The mixture was stirred at room temperature for 1 hour. Volatiles were evaporated and product was purified by RP HPLC (C$_{18}$, 5 μM, H$_2$O/MeCN with 1% of TFA as eluant). Lyophilization of appropriate fractions gave the title compound (TFA salt) as a white solid. $^1$H NMR (400 MHz, d$_6$-DMSO) δ 12.78 (bs, 1H), 12.32 (bs, 1H), 9.5-9.4 (m, 2H), 7.48 (s, 5H), 7.42-7.32 (m, 2H), 7.12 (t, J=8.7 Hz, 2H), 4.59-4.45 (m, 3H), 4.23 (bs, 1H), 3.75 (bs, 1H), 3.52 (bs, 1H), 3.08-3.00 (m, 2H), 2.72 (s, 3H); MS (ES) $C_{22}H_{23}FN_4O_3$ requires 410. Found: 411 (M+H$^+$).

Step 5: N-(4-fluorobenzyl)-3-hydroxy-7-methyl-4,6-dioxo-6,7,8,9-tetrahydro-4H-pyrimido[1,6-a]pyrimidine-2-carboxamide A methanolic solution of 2-{2-[benzyl(methyl)amino]ethyl}-N-(4-fluorobenzyl)-5,6-dihydroxypyrimidine-4-carboxamide prepared as described in Step 4 was stirred under H$_2$ atmosphere in the presence of catalytic 10% Pd/C for 2 hours. The reaction mixture was filtered through celite to remove the catalyst then concentrated under reduced pressure. MS (ES) $C_{17}H_{17}FN_4O_3$ requires 320. Found: 321 (M+H$^+$). The crude organic product was treated with carbonyl diimidazole (1.5 equivalents) and potassium tert-butoxide in refluxing dioxane for 1 hour. Title compound was purified by RP HPLC (C$_{18}$, 5 μM, H$_2$O/MeCN with 1% of TFA as eluant). Lyophilization of appropriate fractions gave title compound as a white solid.
$^1$H NMR (400 MHz, d$_6$-DMSO) δ 12.43 (bs, 1H), 9.41 (t, J=6.3 Hz, 1H), 7.38 (m, 2H), 7.17 (t, J=8.7 Hz, 2H), 4.45 (d, J=6.3 Hz, 2H), 3.61 (m, 2H), 3.14 (s, 3H), 3.01 (m, 2H); MS (ES) $C_{16}H_{15}FN_4O_4$ requires 346. Found: 347 (M+H$^+$).

Example 24

N-(4-Fluorobenzyl)-3-hydroxy-9,9-dimethyl-8-[(3-methylisoxazol-5-yl)methyl]-4-oxo-6,7,8,9-tetrahydro-4H-pyrazino[1,2-a]pyrimidine-2-carboxamide (Entry No. 71 in Table 1)

Step 1: 3-(Benzyloxy)-N-(4-fluorobenzyl)-9,9-dimethyl-4-oxo-8-prop-2-yn-1-yl-6,7,8,9-tetrahydro-4H-pyrazino[1,2-a]pyrimidine-2-carboxamide A mixture of 3-(benzyloxy)-N-(4-fluorobenzyl)-9,9-dimethyl-4-oxo-6,7,8,9-tetrahydro-4H-pyrazino[1,2-a]pyrimidine-2-carboxamide (prepared as described in Example 3, Step 1) (1 eq.), K$_2$CO$_3$ (2 eq.), propargyl bromide (2.5 eq.) in DMF was heated at 45° C. overnight and then cooled at room temperature. The solvent was removed under reduced pressure and the residue was taken up in EtOAc and washed with brine, dried (Na$_2$SO$_4$), filtered and concentrated under reduced pressure to yield the titled acetylene. MS (ES) $C_{27}H_{27}FN_4O_3$ requires 474. Found: 475 (M+H$^+$).

Step 2: N-(4-Fluorobenzyl)-3-hydroxy-9,9-dimethyl-8-[(3-methylisoxazol-5-yl)methyl]-4-oxo-6,7,8,9-tetrahydro-4H-pyrazino[1,2-a]pyrimidine-2-carboxamide A solution of EtNO$_2$ (6.5 eq.) and Et$_3$N (catalytic amount) in toluene was added dropwise to a solution of PhNCO (11 eq.) and 3-(benzyloxy)-N-(4-fluorobenzyl)-9,9-dimethyl-4-oxo-8-prop-2-yn-1-yl-6,7,8,9-tetrahydro-4H-pyrazino[1,2-a]pyrimidine-2-carboxamide (1 eq.) in toluene. The reaction mixture was stirred at room temperature for 1 hour, then heated at reflux overnight. The precipitate was filtered off, the filtrate concentrated under reduced pressure and then directly dissolved in MeOH. The mixture was stirred 1 hour under an H$_2$ atmosphere in the presence of 10% Pd/C. Catalyst was then filtered off through celite, and the filtrate was concentrated under reduced pressure and purified by R$^P$ HPLC (C18, 5 μm, H$_2$O/MeCN with 1% of TFA as eluent) to afford the desired isoxazole as a TFA salt after lyophilisation of the desired fractions. $^1$H-NMR (600 MHz, d$_6$-DMSO) δ 12.18 (br. s, 1H), 9.44 (t, J=6.2 Hz, 1H), 7.37 (dd, J=7.9 Hz, J=5.9 Hz, 2H), 7.17 (t, J=8.8 Hz, 2H), 6.32 (s, 1H), 4.47 (d, J=6.2 Hz, 2H), 3.87 (s, 2H), 3.77 (t, J=5.2 Hz, 2H), 2.95 (t, J=5.2 Hz, 2H), 2.21 (s, 3H), 1.55 (s, 6H); MS (ES) $C_{22}H_{24}FN_5O_4$ requires 441. Found: 442 (M+H$^+$).

Example 25

N-(4-Fluorobenzyl)-3-hydroxy-9,9-dimethyl-8-[(3-methyl-1,2,4-oxadiazol-5-yl)methyl]-4-oxo-6,7,8,9-tetrahydro-4H-pyrazino[1,2-a]pyrimidine-2-carboxamide (Entry No. 72 in Table 1)

Step 1: tert-Butyl (3-(benzyloxy)-2-{[(4-fluorobenzyl)amino]carbonyl}-9,9-dimethyl-4-oxo-4,6,7,9-tetrahydro-8H-pyrazino[1,2-a]pyrimidin-8-yl)acetate A mixture of 3-(benzyloxy)-N-(4-fluorobenzyl)-9,9-dimethyl-4-oxo-6,7,8,9-tetrahydro-4H-pyrazino[1,2-a]pyrimidine-2-carboxamide (prepared as described in Example 3, Step 1) (1 eq.), $K_2CO_3$ (2 eq.) and tert-butyl bromoacetate (3 eq.) in DMF was heated for 24 hours at 45° C. and then cooled to room temperature. Solvent was removed under reduced pressure and the residue was taken up in EtOAc and washed with brine, dried ($Na_2SO_4$), filtered and concentrated under reduced pressure to yield the ester. MS (ES) $C_{30}H_{35}FN_4O_5$ requires 550. Found: 551 (M+H$^+$).

Step 2: N-(4-Fluorobenzyl)-3-hydroxy-9,9-dimethyl-8-[(3-methyl-1,2,4-oxadiazol-5-yl)methyl]-4-oxo-6,7,8,9-tetrahydro-4H-pyrazino[1,2-a]pyrimidine-2-carboxamide A mixture of tert-butyl (3-(benzyloxy)-2-{[(4-fluorobenzyl)amino]carbonyl}-9,9-dimethyl-4-oxo-4,6,7,9-tetrahydro-8H-pyrazino[1,2-a]pyrimidin-8-yl)acetate (1 eq.), acetamide oxime (6 eq.) and NaOEt (6 eq.) in EtOH was refluxed overnight to provide a crude which was directly purified by RP HPLC (C18, 5 µm, $H_2O$/MeCN with 1% of TFA as eluant) to afford the desired oxadiazole as TFA salt after lyophilisation of the desired fractions. $^1$H-NMR (400 MHz, d$_6$-DMSO) δ 12.20 (br. s, 1H), 9.44 (t, J=6.3 Hz, 1H), 7.38 (dd, J=8.4 Hz, J=5.8 Hz, 2H), 7.18 (t, J=8.8 Hz, 2H), 4.49 (d, J=6.3 Hz, 2H), 4.09 (s, 2H), 3.77 (t, J=5.3 Hz, 2H), 3.07 (t, J=5.3 Hz, 2H), 2.35 (s, 3H), 1.55 (s, 6H); MS (ES) $C_{21}H_{23}FN_6O_4$ requires 442. Found: 443 (M+H$^+$).

Example 26

N-(4-Fluorobenzyl)-3-hydroxy-9,9-dimethyl-8-(1,3,4-oxadiazol-2-ylmethyl)-4-oxo-6,7,8,9-tetrahydro-4H-pyrazino[1,2-a]pyrimidine-2-carboxamide (Entry No. 82 in Table 1)

Step 1: Methyl (3-(benzyloxy)-2-{[(4-fluorobenzyl)amino]carbonyl}-9,9-dimethyl-4-oxo-4,6,7,9-tetrahydro-8H-pyrazino[1,2-a]pyrimidin-8-yl)acetate A mixture of 3-(benzyloxy)-N-(4-fluorobenzyl)-9,9-dimethyl-4-oxo-6,7,8,9-tetrahydro-4H-pyrazino[1,2-a]pyrimidine-2-carboxamide (prepared as described in Example 3, Step 1) (1 eq.), $K_2CO_3$ (2 eq.), methyl bromoacetate (2 eq.) in DMF was heated for 24 hours at 65° C. and then was cooled to room temperature. The solvent was removed under reduced pressure and the residue was taken up in EtOAc and washed with brine, dried ($Na_2SO_4$), filtered and concentrated under reduced pressure to yield the desired ester as a brown oil. MS (ES) $C_{27}H_{29}FN_4O_5$ requires 508. Found: 509 (M+H$^+$).

Step 2: N-(4-Fluorobenzyl)-3-hydroxy-9,9-dimethyl-8-(1,3,4-oxadiazol-2-ylmethyl)-4-oxo-6,7,8,9-tetrahydro-4H-pyrazino[1,2-a]pyrimidine-2-carboxamide A mixture of methyl (3-(benzyloxy)-2-{[(4-fluorobenzyl)amino]carbonyl}-9,9-dimethyl-4-oxo-4,6,7,9-tetrahydro-8H-pyrazino[1,2-a]pyrimidin-8-yl)acetate (1 eq.), $NH_2NH_2.H_2O$ (10 eq.) in MeOH was refluxed overnight. The volatiles were evaporated under reduced pressure and the residue dissolved in toluene. TsOH (0.2 eq.) and trimethyl orthoformate (ca. 10 eq.) were added and the mixture was heated at 110° C. for 1 hour, then cooled to room temperature and concentrated under reduced pressure. The resulting residue was purified by flash chromatography on silica using 1% MeOH/DCM as eluant. The residue was dissolved in MeOH and the mixture was stirred 1 hour under an $H_2$ atmosphere in the presence of 10% Pd/C. Catalyst was then filtered off using celite and the filtrate was concentrated under reduced pressure and triturated with diethyl ether to yield the desired oxadiazole. $^1$H-NMR (300 MHz, d$_6$-DMSO) δ 12.17 (br. s, 1H), 9.21 (s, 1H), 7.35 (dd, J=8.2 Hz, J=5.8 Hz, 2H), 7.16 (t, J=8.7 Hz, 2H), 4.46 (d, J=6.0 Hz, 2H), 4.05 (s, 2H), 3.75-3.66 (m, 2H), 3.04-2.94 (m, 2H), 1.53 (s, 6H); MS (ES) $C_{20}H_{21}FN_6O_4$ requires 428. Found: 429 (M+H$^+$).

Example 27

N-(4-Fluorobenzyl)-3-hydroxy-9,9-dimethyl-8-[(5-methyl-1,3,4-oxadiazol-2-yl)methyl]-4-oxo-6,7,8,9-tetrahydro-4H-pyrazino[1,2-a]pyrimidine-2-carboxamide (Entry No. 85 in Table 1)

A mixture of methyl (3-(benzyloxy)-2-{[(4-fluorobenzyl)amino]carbonyl}-9,9-dimethyl-4-oxo-4,6,7,9-tetrahydro-8H-pyrazino[1,2-a]pyrimidin-8-yl)acetate (prepared as described in Example 26, Step 1) (1 eq.), $NH_2NH_2.H_2O$ (10 eq.) in MeOH was refluxed overnight, then the volatiles were evaporated under reduced pressure. The residue dissolved in toluene, TsOH (0.2 eq.) and trimethyl orthoacetate (ca. 10 eq.) were added and the mixture was heated at 100° C. for 3 hours, then it was diluted with more toluene and more TsOH (0.2 eq.) was added. After stirring overnight at 100° C., the resulting residue was cooled to room temperature, concentrated under reduced pressure and dissolved in MeOH. The mixture was stirred 1 hour under an $H_2$ atmosphere in the presence of 10% Pd/C. Catalyst was then filtered off through celite and the filtrate was concentrated under reduced pressure and purified by RP HPLC (C18, 5 µm, $H_2O$/MeCN with 1% of TFA as eluant) to afford the desired oxadiazole as TFA salt after lyophilisation of the desired fractions. $^1$H-NMR (300 MHz, d$_6$-DMSO) δ 12.17 (br. s, 1H), 9.43 (t, J=6.2 Hz, 1H), 7.37 (dd, J=8.0 Hz, J=5.8 Hz, 2H), 7.17 (t, J=8.7 Hz, 2H), 4.48 (d, J=6.2 Hz, 2H), 3.97 (s, 2H), 3.75-3.66 (m, 2H), 3.06-2.93 (m, 2H), 2.50 (s, 3H), 1.55 (s, 6H); MS (ES) $C_{21}H_{23}FN_6O_4$ requires 442. Found: 443 (M+H$^+$).

Example 28

N-(4-Fluorobenzyl)-3-hydroxy-9,9-dimethyl-8-[(5-methyl-1,2,4-oxadiazol-3-yl)methyl]-4-oxo-6,7,8,9-tetrahydro-4H-pyrazino[1,2-a]pyrimidine-2-carboxamide (Entry No. 89 in Table 1)

A solution of KOH (2.2 eq.) in MeOH was added to a solution of $NH_2OH.HCl$ (2.2 eq.) in MeOH and the mixture was stirred for 30 minutes, then filtered onto 3-(benzyloxy)-8-(cyanomethyl)-N-(4-fluorobenzyl)-9,9-dimethyl-4-oxo-6,7,8,9-tetrahydro-4H-pyrazino[1,2-a]pyrimidine-2-carboxamide (prepared as described in Example 4, Step 1) (1 eq.). The solution was heated overnight at 60° C., then cooled to room temperature and the solvent was removed under reduced pressure. $Ac_2O$ (3 eq.) was added to a solution of the residue in toluene and the mixture was heated at 65° C. for 30 min and then at 110° C. for 48 hours. The volatiles were removed under reduced pressure and the crude was dissolved in MeOH. The mixture was stirred 1 hour under an $H_2$ atmosphere in the presence of 10% Pd/C. Catalyst was then filtered off through celite and the filtrate was concentrated under reduced pressure and purified by RP HPLC (C18, 5 µm, H$_2$O/MeCN with 1% of TFA as eluant) to afford the oxadiazole as TFA salt after lyophilisation of the desired fractions. $^1$H-NMR (300 MHz, d$_6$-DMSO) δ 12.17 (br. s, 1H), 9.43 (t, J=6.0 Hz, 1H), 7.37 (dd, J=8.4 Hz, J=5.7 Hz, 2H), 7.17 (t, J=8.8 Hz, 2H), 4.48 (d, J=6.2 Hz, 2H), 3.81 (s, 2H), 3.72 (t, J=4.7 Hz, 2H), 3.01 (t, J=5.0 Hz, 2H), 2.58 (s, 3H), 1.56 (s, 6H); MS (ES) C$_{21}$H$_{23}$FN$_6$O$_4$ requires 442. Found: 443 (M+H$^+$).

Example 29

N-(4-Fluorobenzyl)-3-hydroxy-9,9-dimethyl-8-[(1-methyl-1H-1,2,3-triazol-4-yl)methyl]-4-oxo-6,7,8,9-tetrahydro-4H-pyrazino[1,2-a]pyrimidine-2-carboxamide (Entry No. 75 in Table 1) and N-(4-Fluorobenzyl)-3-hydroxy-9,9-dimethyl-8-[(1-methyl-1H-1,2,3-triazol-5-yl)methyl]-4-oxo-6,7,8,9-tetrahydro-4H-pyrazino[1,2-a]pyrimidine-2-carboxamide (Entry No. 76 in Table 1)

To a solution of 3-(benzyloxy)-N-(4-fluorobenzyl)-9,9-dimethyl-4-oxo-8-prop-2-yn-1-yl-6,7,8,9-tetrahydro-4H-pyrazino[1,2-a]pyrimidine-2-carboxamide (prepared as described in Example 24, Step 1) (1 eq.) in toluene was added Me$_3$SiCHN$_2$ (3 eq.) and the mixture was heated at 110° C. overnight. Additional Me$_3$SiCH$_2$N$_3$ (ca. 20 eq.) was added and the mixture was heated further to ensure completion. The solvent was evaporated under reduced pressure and the residue was treated at −78° C. with a 1 M solution of TBAF in THF (0.6 eq.) and the mixture was allowed to warm to room temperature. After evaporation of volatiles under reduced pressure, two isomers were observed and directly separated by RP HPLC (C18, 5 µm, H$_2$O/MeCN with 1% of TFA as eluant) to afford the isomeric triazoles as TFA salts after lyophilisation of the desired fractions.

N-(4-Fluorobenzyl)-3-hydroxy-9,9-dimethyl-8-[(1-methyl-1H-1,2,3-triazol-4-yl)methyl]-4-oxo-6,7,8,9-tetrahydro-4H-pyrazino[1,2-a]pyrimidine-2-carboxamide (more polar): $^1$H-NMR (300 MHz, d$_6$-DMSO) δ12.19 (br. s, 1H), 9.45 (t, J=5.8 Hz, 1H), 8.00 (s, 1H), 7.37 (dd, J=8.3 Hz, J=5.8 Hz, 2H), 7.17 (t, J=8.8 Hz, 2H), 4.48 (d, J=6.2 Hz, 2H), 4.02 (s, 2H), 3.87 (br. s, 3H), 3.79-3.71 (m, 2H), 3.06-2.95 (m, 2H), 1.61 (s, 6H); MS (ES) C$_{21}$H$_{24}$FN$_7$O$_3$ requires 441. Found: 442 (M+H$^+$).

N-(4-Fluorobenzyl)-3-hydroxy-9,9-dimethyl-8-[(1-methyl-1H-1,2,3-triazol-5-yl)methyl]-4-oxo-6,7,8,9-tetrahydro-4H-pyrazino[1,2-a]pyrimidine-2-carboxamide (less polar): $^1$H-NMR (300 MHz, d$_6$-DMSO) δ 12.17 (br. s, 1H), 9.45 (t, J=5.8 Hz, 1H), 7.67 (s, 1H), 7.37 (dd, J=8.3 Hz, J=5.8 Hz, 2H), 7.17 (t, J=8.8 Hz, 2H), 4.49 (d, J=6.2 Hz, 2H), 4.00 (s, 2H), 3.86 (br. s, 3H), 3.77-3.67 (m, 2H), 2.81-2.73 (m, 2H), 1.61 (s, 6H); MS (ES) C$_{21}$H$_{24}$FN$_7$O$_3$ requires 441. Found: 442 (M+H$^+$).

Example 30

N-(4-Fluorobenzyl)-3-hydroxy-9,9-dimethyl-8-[(5-methyl-1,3-oxazol-2-yl)methyl]-4-oxo-6,7,8,9-tetrahydro-4H-pyrazino[1,2-a]pyrimidine-2-carboxamide (Entry No. 91 in Table 1)

Step 1: Lithium (3-(benzyloxy)-2-{[(4-fluorobenzyl)amino]carbonyl}-9,9-dimethyl-4-oxo-4,6,7,9-tetrahydro-8H-pyrazino[1,2-a]pyrimidin-8-yl)acetate To a solution of methyl (3-(benzyloxy)-2-{[(4-fluorobenzyl)amino]carbonyl}-9,9-dimethyl-4-oxo-4,6,7,9-tetrahydro-8H-pyrazino[1,2-a]pyrimidin-8-yl)acetate (prepared as described in Example 26, Step 1) (1 eq.) in THF:H$_2$O (1:1) LiOH (1 eq.) was added and the mixture was stirred for 2 hours at room temperature. The resulting solution was directly lyophilized to afford the desired lithium salt. MS (ES) C$_{26}$H$_{27}$FN$_4$O$_5$ requires 494. Found: 495 (M+H$^+$).

Step 2: N-(4-Fluorobenzyl)-3-hydroxy-9,9-dimethyl-8-[(5-methyl-1,3-oxazol-2-yl)methyl]-4-oxo-6,7,8,9-tetrahydro-4H-pyrazino[1,2-a]pyrimidine-2-carboxamide To a solution of lithium (3-(benzyloxy)-2-{[(4-fluorobenzyl)amino]carbonyl}-9,9-dimethyl-4-oxo-4,6,7,9-tetrahydro-8H-pyrazino[1,2-a]pyrimidin-8-yl)acetate (1 eq.) in CHCl$_3$, propargylamine (1.1), EDC (2 eq.) and HOBt (2 eq.) were added and the reaction mixture was stirred at room temperature for 3 hours. The solvent was removed under reduced pressure and the residue was taken up in EtOAc, washed with brine, dried (Na$_2$SO$_4$), and concentrated under reduced pressure. The resulting crude was directly dissolved in acetic acid and Hg(OAc)$_2$ (0.1 eq.) was added. The mixture was heated at 100° C. overnight and was then concentrated under reduced pressure. The residue was directly purified by RP-HPLC and after lyophilisation of the desired fractions, the O-benzyl protected material was dissolved in MeOH and stirred 1 hour under an H$_2$ atmosphere in the presence of 10% Pd/C. The catalyst was then filtered off through celite, the filtrate was concentrated under reduced pressure and then the residue was dissolved in MeCN and H$_2$O and lyophilized to afford the titled oxazole. $^1$H-NMR (400 MHz, d$_6$-DMSO) δ 12.17 (br. s, 1H), 9.43 (t, J=6.2 Hz, 1H), 7.37 (dd, J=8.1 Hz, J=5.7 Hz, 2H), 7.17 (t, J=8.9 Hz, 2H), 6.77 (s, 1H), 4.47 (d, J=6.2 Hz, 2H), 3.80 (s, 2H), 3.71 (t, J=5.0 Hz, 2H), 3.00 (t, J=5.1 Hz, 2H), 2.27 (s, 3H), 1.53 (s, 6H); MS (ES) C$_{22}$H$_{24}$FN$_5$O$_4$ requires 441. Found: 442 (M+H$^+$).

The following Table 1 lists compounds of the present invention which have been prepared. The table provides the structure and name of each compound and the mass of its molecular ion plus 1 (M+1) as determined via ES-MS. When the compound was prepared as a salt, the identity of the salt is included in parentheses following the compound name for the free base. The synthetic scheme employed to prepare the compound is indicated in parentheses following the compound name.

| Compound (Preparative Method) | Structure | M + 1 |
|---|---|---|
| 1. N-(4-fluorobenzyl)-3'-hydroxy-7'-methyl-4'-oxo-6',7'-dihydro-4'H-spiro[cyclohexane-1,8'-imidazo[1,5-a]pyrimidine]-2'-carboxamide (TFA salt) (Scheme B) | 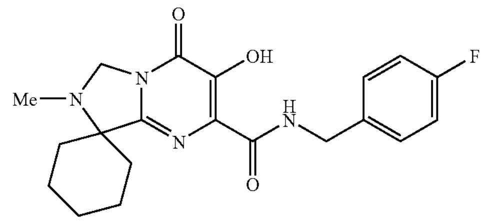 | 387 |
| 2. N-[4-fluoro-2-(methylsulfonyl)benzyl]-3-hydroxy-7,8,8-trimethyl-4-oxo-4,6,7,8-tetrahydroimidazo[1,5-a]pyrimidine-2-carboxamide (TFA salt) (Scheme B) | 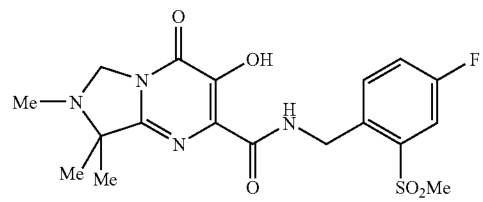 | 425 |
| 3. N-(4-fluorobenzyl)-8-hydroxy-7-oxo-2,3,7,10b-tetrahydro[1,3]thiazolo[3',2':3,4]imidazo[1,5-a]pyrimidine-9-carboxamide (Scheme B) | 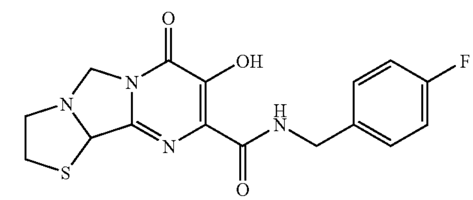 | 363 |
| 4. 3-hydroxy-7,8,8-trimethyl-N-[2-(methylthio)benzyl]-4-oxo-4,6,7,8-tetrahydroimidazo[1,5-a]pyrimidine-2-carboxamide (TFA salt) (Scheme B) | 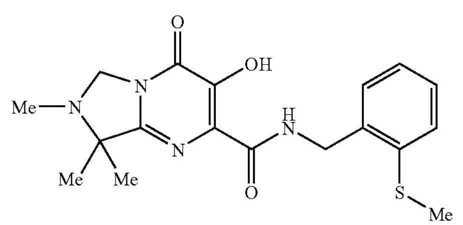 | 375 |
| 5. N-(4-fluorobenzyl)-3-hydroxy-7,8,8-trimethyl-4-oxo-4,6,7,8-tetrahydroimidazo[1,5-a]pyrimidine-2-carboxamide (TFA salt) (Scheme B) | 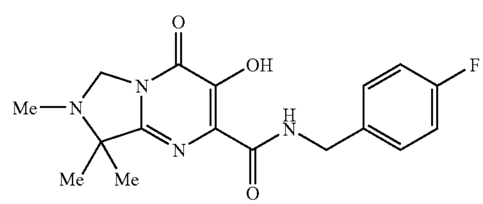 | 347 |
| 6. N-(4-fluorobenzyl)-3-hydroxy-8,8-dimethyl-4-oxo-7-(pyridin-3-ylmethyl)-4,6,7,8-tetrahydroimidazo[1,5-a]pyrimidine-2-carboxamide (TFA salt) (Scheme B) | 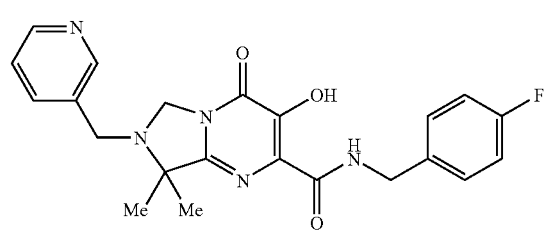 | 424 |
| 7. N-(4-fluorobenzyl)-3-hydroxy-8,8-dimethyl-4,6-dioxo-4,6,7,8-tetrahydroimidazo[1,5-a]pyrimidine-2-carboxamide (Scheme B) | | 347 |

| Compound (Preparative Method) | Structure | M + 1 |
|---|---|---|
| 8. 7-acetyl-N-(4-fluorobenzyl)-3-hydroxy-8,8-dimethyl-4-oxo-4,6,7,8-tetrahydroimidazo[1,5-a]pyrimidine-2-carboxamide (Scheme B) | 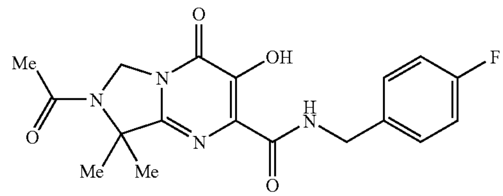 | 375 |
| 9. 9-[(benzyloxy)methyl]-N-(4-fluorobenzyl)-3-hydroxy-4-oxo-6,7,8,9-tetrahydro-4H-pyrazino[1,2-a]pyrimidine-2-carboxamide (TFA salt) (Scheme G) | 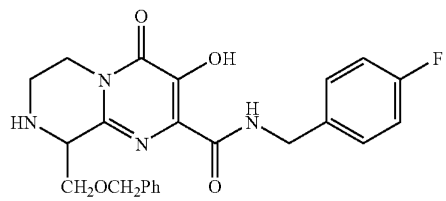 | 439 |
| 10. 8-acetyl-N-(4-fluorobenzyl)-3-hydroxy-9-(hydroxymethyl)-4-oxo-6,7,8,9-tetrahydro-4H-pyrazino[1,2-a]pyrimidine-2-carboxamide (Scheme G) | 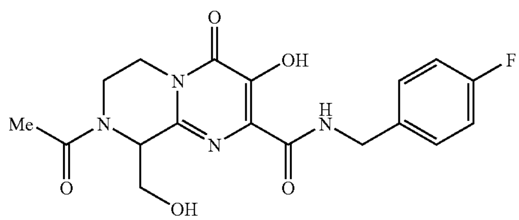 | 391 |
| 11. 9-[(benzyloxy)methyl]-N-(4-fluorobenzyl)-3-hydroxy-8-methyl-4-oxo-6,7,8,9-tetrahydro-4H-pyrazino[1,2-a]pyrimidine-2-carboxamide (TFA salt) (Scheme G) | | 453 |
| 12. 8-acetyl-9-[(benzyloxy)methyl]-N-(4-fluorobenzyl)-3-hydroxy-4-oxo-6,7,8,9-tetrahydro-4H-pyrazino[1,2-a]pyrimidine-2-carboxamide (Scheme G) | 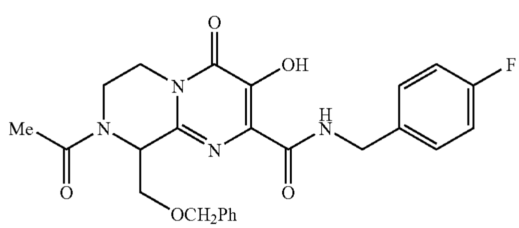 | 481 |
| 13. 9-[(dimethylamino)methyl]-8-[(dimethylamino)(oxo)acetyl]-N-(4-fluorobenzyl)-3-hydroxy-4-oxo-6,7,8,9-tetrahydro-4H-pyrazino[1,2-a]pyrimidine-2-carboxamide (TFA salt) (Scheme G) | 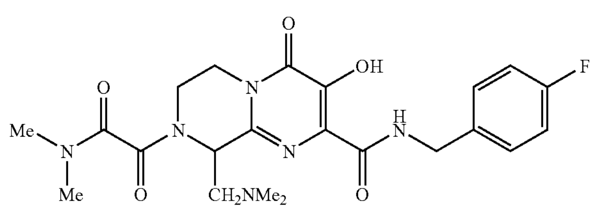 | 475 |
| 14. 8-acetyl-9-[(dimethylamino)methyl]-N-(4-fluorobenzyl)-3-hydroxy-4-oxo-6,7,8,9-tetrahydro-4H-pyrazino[1,2-a]pyrimidine-2-carboxamide (TFA salt) (Scheme G) | 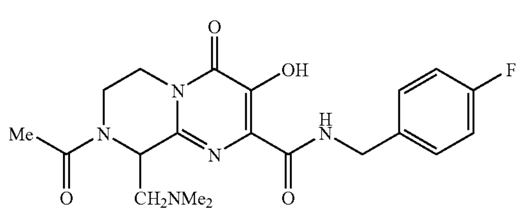 | 418 |

| Compound (Preparative Method) | Structure | M + 1 |
|---|---|---|
| 15. 9-[(dimethylamino)methyl]-N-(4-fluorobenzyl)-3-hydroxy-8-(1,3-oxazol-4-ylmethyl)-4-oxo-6,7,8,9-tetrahydro-4H-pyrazino[1,2-a]pyrimidine-2-carboxamide (TFA salt) (Scheme G) | 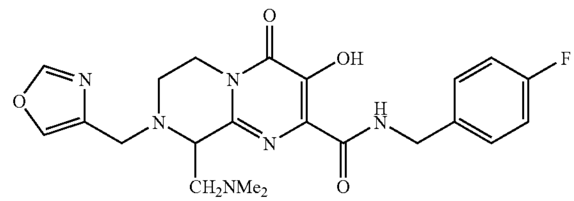 | 457 |
| 16. 9-[(dimethylamino)methyl]-N-(4-fluorobenzyl)-3-hydroxy-8-[(1-methyl-1H-pyrazol-3-yl)methyl]-4-oxo-6,7,8,9-tetrahydro-4H-pyrazino[1,2-a]pyrimidine-2-carboxamide (TFA salt) (Scheme G) | 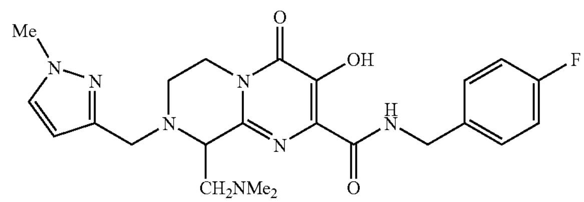 | 470 |
| 17. 9-[(dimethylamino)methyl]-N-(4-fluorobenzyl)-3-hydroxy-8-methyl-4-oxo-6,7,8,9-tetrahydro-4H-pyrazino[1,2-a]pyrimidine-2-carboxamide (TFA salt) (Scheme G) | 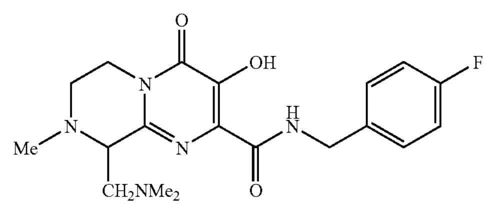 | 390 |
| 18. N-[(2-{[(4-fluorobenzyl)amino]carbonyl}-3-hydroxy-8-methyl-4-oxo-6,7,8,9-tetrahydro-4H-pyrazino[1,2-a]pyrimidin-9-yl)methyl]-N,N',N'-trimethylethanediamide (TFA salt) (Scheme G) | 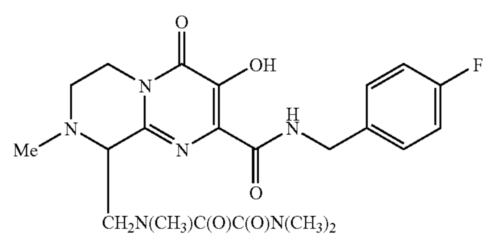 | 475 |
| 19. 9-{[[(dimethylamino)sulfonyl](methyl)amino]methyl}-N-(4-fluorobenzyl)-3-hydroxy-8-methyl-4-oxo-6,7,8,9-tetrahydro-4H-pyrazino[1,2-a]pyrimidine-2-carboxamide (TFA salt) (Scheme G) | | 484 |
| 20. N-(4-fluorobenzyl)-3-hydroxy-8-methyl-9-({methyl[(methylsulfonyl)acetyl]amino}methyl)-4-oxo-6,7,8,9-tetrahydro-4H-pyrazino[1,2-a]pyrimidine-2-carboxamide (TFA salt) (Scheme G) | 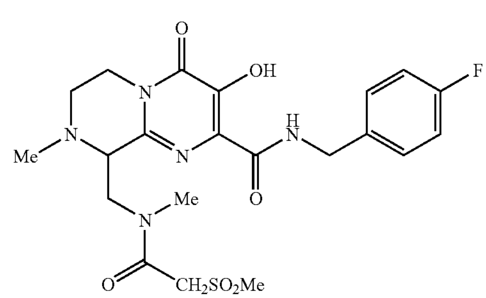 | 496 |

| Compound (Preparative Method) | Structure | M + 1 |
|---|---|---|
| 21. N-(4-fluorobenzyl)-3-hydroxy-8-methyl-9-{[methyl(methylsulfonyl)amino]methyl}-4-oxo-6,7,8,9-tetrahydro-4H-pyrazino[1,2-a]pyrimidine-2-carboxamide (TFA salt) (Scheme G) | 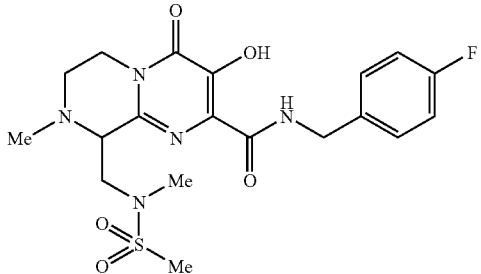 | 454 |
| 22. N-(4-fluorobenzyl)-3-hydroxy-8-methyl-9-{[methyl(pyridin-2-ylcarbonyl)amino]methyl}-4-oxo-6,7,8,9-tetrahydro-4H-pyrazino[1,2-a]pyrimidine-2-carboxamide (TFA salt) (Scheme G) | 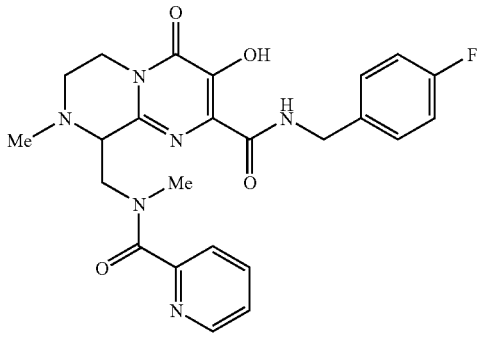 | 482 |
| 23. N-(4-fluorobenzyl)-3-hydroxy-8-methyl-9-({methyl[(1-oxidopyridin-2-yl)carbonyl]amino}methyl)-4-oxo-6,7,8,9-tetrahydro-4H-pyrazino[1,2-a]pyrimidine-2-carboxamide (TFA salt) (Scheme G) | 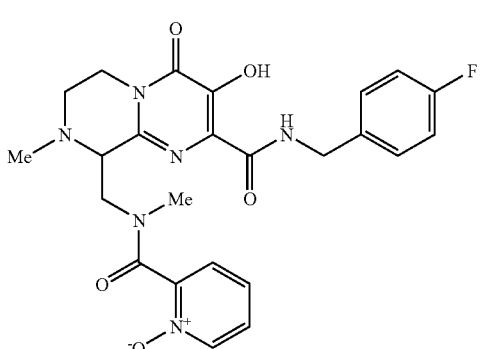 | 498 |
| 24. methyl 9-[(dimethylamino)methyl]-2-{[(4-fluorobenzyl)amino]carbonyl}-3-hydroxy-4-oxo-4,6,7,9-tetrahydro-8H-pyrazino[1,2-a]pyrimidine-8-carboxylate (TFA salt) (Scheme G) | 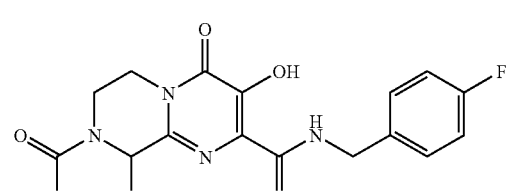 | 434 |
| 25. 9-[(dimethylamino)methyl]-N-(4-fluorobenzyl)-3-hydroxy-8-(methylsulfonyl)-4-oxo-6,7,8,9-tetrahydro-4H-pyrazino[1,2-a]pyrimidine-2-carboxamide (TFA salt) (Scheme G) | 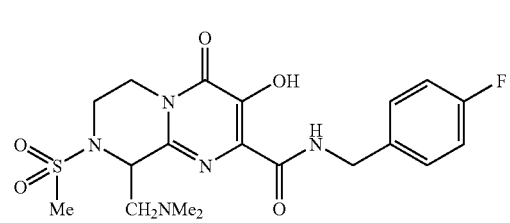 | 454 |

| Compound (Preparative Method) | Structure | M + 1 |
|---|---|---|
| 26. 9-[(dimethylamino)methyl]-N-(4-fluorobenzyl)-3-hydroxy-4-oxo-6,7,8,9-tetrahydro-4H-pyrazino[1,2-a]pyrimidine-2-carboxamide (TFA salt) (Scheme G) | 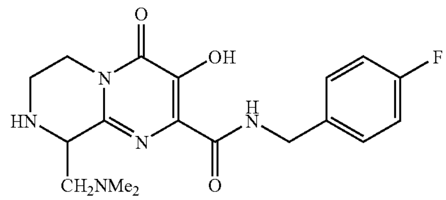 | 376 |
| 27. N-(4-fluorobenzyl)-3-hydroxy-9-[(methylthio)methyl]-4-oxo-6,7,8,9-tetrahydro-4H-pyrazino[1,2-a]pyramidine-2-carboxamide (TFA salt) (Scheme G) | 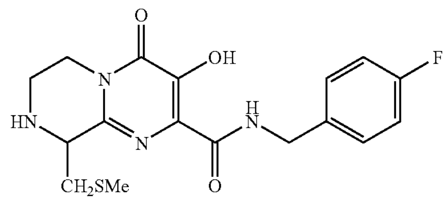 | 379 |
| 28. N-(4-fluorobenzyl)-3-hydroxy-8-methyl-9-[(methylsulfonyl)methyl]-4-oxo-6,7,8,9-tetrahydro-4H-pyrazino[1,2-a]pyrimidine-2-carboxamide (TFA salt) (Scheme G) | 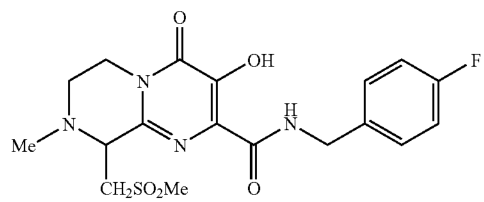 | 425 |
| 29. N-(4-fluorobenzyl)-3'-hydroxy-4'-oxo-2,3,5,6,7',8'-hexahydro-4'H,6'H-spiro[pyran-4,9'-pyrazino[1,2-a]pyrimidine]-2'-carboxamide (TFA salt) (Scheme A) | 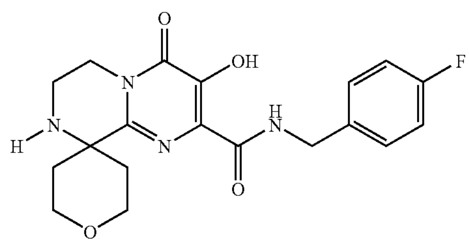 | 389 |
| 30. N-(4-fluorobenzyl)-3'-hydroxy-8'-methyl-4'-oxo-2,3,5,6,7',8'-hexahydro-4'H,6'H-spiro[pyran-4,9'-pyrazino[1,2-a]pyrimidine]-2'-carboxamide (TFA salt) (Scheme A) | 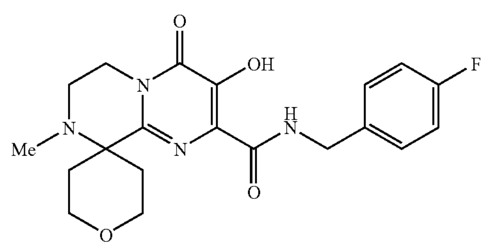 | 403 |
| 31. N-(4-fluorobenzyl)-3-hydroxy-9-methyl-4-oxo-6,7,8,9-tetrahydro-4H-pyrazino[1,2-a]pyrimidine-2-carboxamide (TFA salt) (Scheme A) | 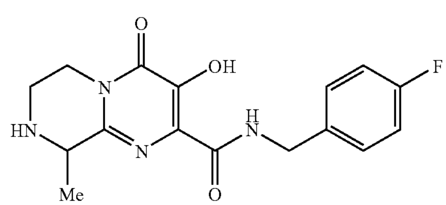 | 333 |
| 32. N-(4-fluorobenzyl)-3-hydroxy-8,9-dimethyl-4-oxo-6,7,8,9-tetrahydro-4H-pyrazino[1,2-a]pyrimidine-2-carboxamide (TFA salt) (Scheme A) | 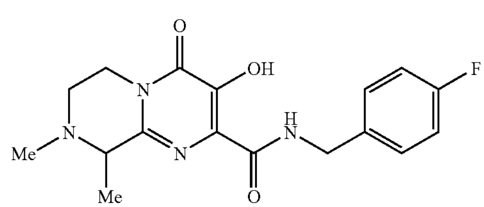 | 347 |

-continued

| Compound (Preparative Method) | Structure | M + 1 |
|---|---|---|
| 33. 8-acetyl-N-(4-fluorobenzyl)-3-hydroxy-9-methyl-4-oxo-6,7,8,9-tetrahydro-4H-pyrazino[1,2-a]pyrimidine-2-carboxamide (Scheme A) | 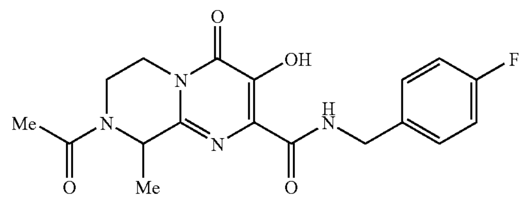 | 375 |
| 34. 8-[(dimethylamino)(oxo)acetyl]-N-(4-fluorobenzyl)-3-hydroxy-9-methyl-4-oxo-6,7,8,9-tetrahydro-4H-pyrazino[1,2-a]pyrimidine-2-carboxamide (Scheme A) | 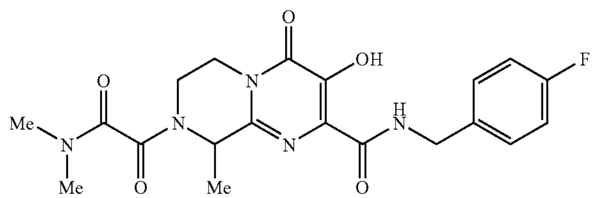 | 432 |
| 35. N-(4-fluorobenzyl)-3-hydroxy-9-methyl-8-[(1-methyl-1H-pyrazol-5-yl)methyl]-4-oxo-6,7,8,9-tetrahydro-4H-pyrazino[1,2-a]pyrimidine-2-carboxamide (TFA salt) (Scheme A) | 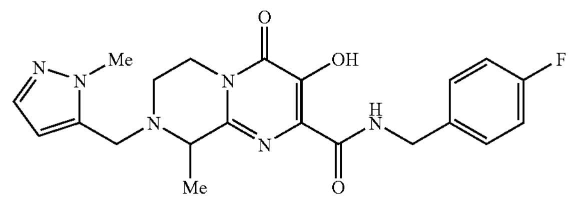 | 427 |
| 36. N-(4-fluorobenzyl)-3-hydroxy-9-methyl-8-(1,3-oxazol-4-ylmethyl)-4-oxo-6,7,8,9-tetrahydro-4H-pyrazino[1,2-a]pyrimidine-2-carboxamide (TFA salt) (Scheme A) | 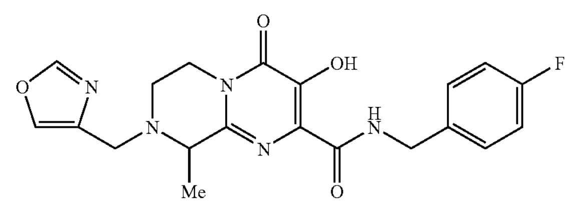 | 414 |
| 37. N-(4-fluorobenzyl)-3'-hydroxy-8'-[(1-methyl-1H-pyrazol-3-yl)methyl]-4'-oxo-2,3,5,6,7',8'-hexahydro-4'H,6'H-spiro[pyran-4,9'-pyrazino[1,2-a]pyrimidine]-2'-carboxamide (TFA salt) (Scheme A) | 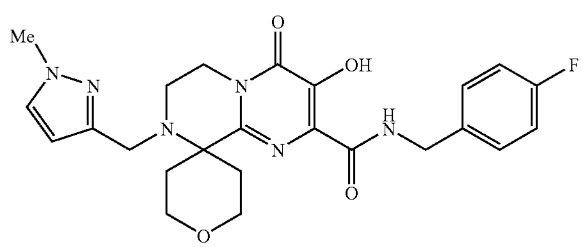 | 484 |
| 38. N-(4-fluorobenzyl)-3'-hydroxy-8'-[(1-methyl-1H-pyrazol-3-yl)methyl]-4'-oxo-7',8'-dihydro-4'H,6'H-spiro[cyclopropane-1,9'-pyrazino[1,2-a]pyrimidine]-2'-carboxamide (TFA salt) (Scheme A) | 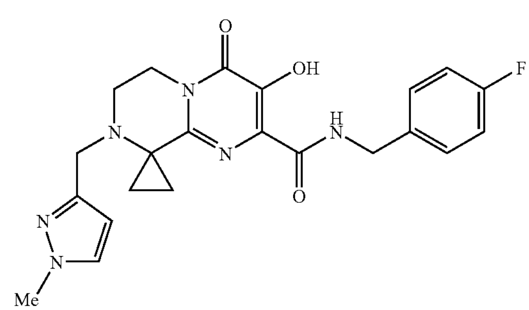 | 439 |
| 39. N-(4-fluorobenzyl)-3'-hydroxy-8'-(1,3-oxazol-4-ylmethyl)-4'-oxo-7',8'-dihydro-4'H,6'H-spiro[cyclopropane-1,9'-pyrazino[1,2-a]pyrimidine]-2'-carboxamide (TFA salt) (Scheme A) | 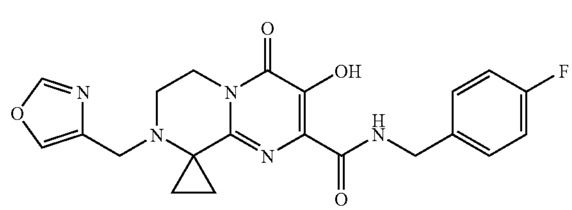 | 426 |

| Compound (Preparative Method) | Structure | M + 1 |
|---|---|---|
| 40. N-(4-fluorobenzyl)-3-hydroxy-9,9-dimethyl-4,7-dioxo-6,7,8,9-tetrahydro-4H-pyrazino[1,2-a]pyrimidine-2-carboxamide (Scheme J) | 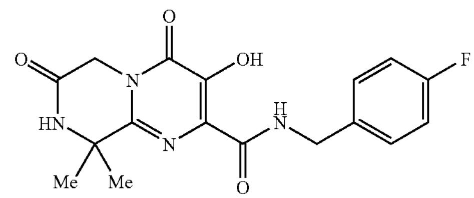 | 361 |
| 41. N-(4-fluorobenzyl)-3-hydroxy-9,9-dimethyl-4-oxo-6,7,8,9-tetrahydro-4H-pyrazino[1,2-a]pyrimidine-2-carboxamide (TFA salt) (Scheme A) | 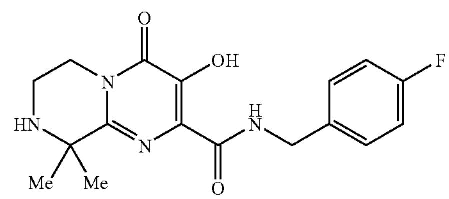 | 347 |
| 42. N-(4-fluorobenzyl)-3-hydroxy-8,9,9-trimethyl-4-oxo-6,7,8,9-tetrahydro-4H-pyrazino[1,2-a]pyrimidine-2-carboxamide (TFA salt) (Scheme A) | 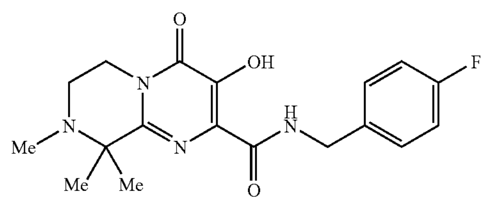 | 361 |
| 43. 8-[(dimethylamino)(oxo)acetyl]-N-(4-fluorobenzyl)-3-hydroxy-9,9-dimethyl-4-oxo-6,7,8,9-tetrahydro-4H-pyrazino[1,2-a]pyrimidine-2-carboxamide (Scheme A) | 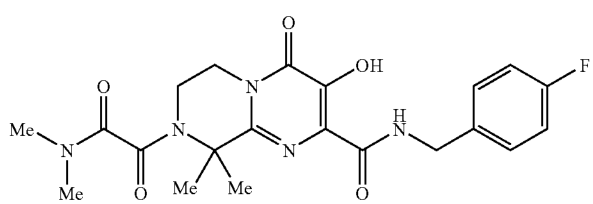 | 446 |
| 44. 8-acetyl-N-(4-fluorobenzyl)-3-hydroxy-9,9-dimethyl-4-oxo-6,7,8,9-tetrahydro-4H-pyrazino[1,2-a]pyrimidine-2-carboxamide (Scheme A) | 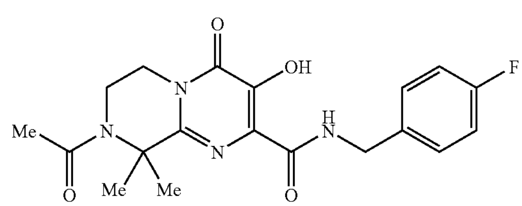 | 389 |
| 45. N-(4-fluorobenzyl)-3-hydroxy-9,9-dimethyl-8-(methylsulfonyl)-4-oxo-6,7,8,9-tetrahydro-4H-pyrazino[1,2-a]pyrimidine-2-carboxamide (Scheme A) | 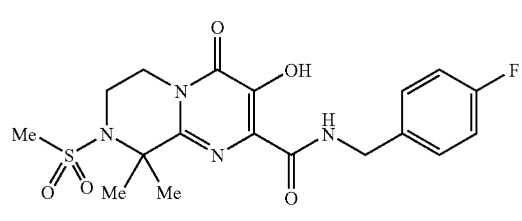 | 425 |
| 46. N-(3-chloro-4-fluorobenzyl)-3-hydroxy-8,9,9-trimethyl-4-oxo-6,7,8,9-tetrahydro-4H-pyrazino[1,2-a]pyrimidine-2-carboxamide (TFA salt) (Scheme A) | 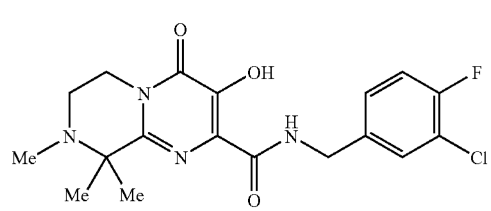 | 395 |

| Compound (Preparative Method) | Structure | M + 1 |
|---|---|---|
| 47. N-[4-fluoro-2-(methylsulfonyl)benzyl]-3-hydroxy-8,9,9-trimethyl-4-oxo-6,7,8,9-tetrahydro-4H-pyrazino[1,2-a]pyrimidine-2-carboxamide (TFA salt) (Scheme A) | 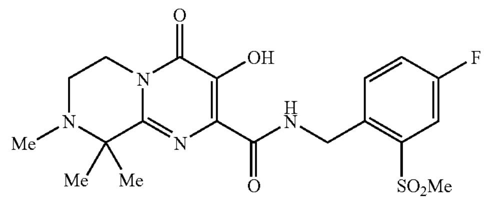 | 439 |
| 48. N-(3-bromo-4-fluorobenzyl)-3-hydroxy-8,9,9-trimethyl-4-oxo-6,7,8,9-tetrahydro-4H-pyrazino[1,2-a]pyrimidine-2-carboxamide (TFA salt) (Scheme A) | 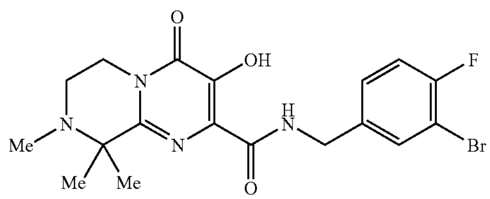 | 439 |
| 49. N-{4-fluoro-2-[(methylamino)carbonyl]benzyl}-3-hydroxy-8,9,9-trimethyl-4-oxo-6,7,8,9-tetrahydro-4H-pyrazino[1,2-a]pyrimidine-2-carboxamide (TFA salt) (Scheme A) | 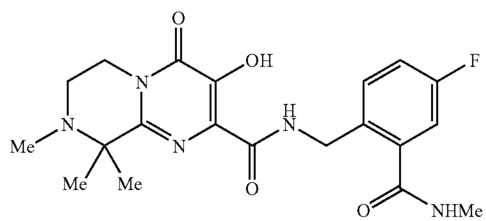 | 418 |
| 50. N-(4-fluorobenzyl)-3-hydroxy-9,9-dimethyl-4-oxo-8-(1H-pyrazol-5-ylmethyl)-6,7,8,9-tetrahydro-4H-pyrazino[1,2-a]pyrimidine-2-carboxamide (TFA salt) (Scheme A) | 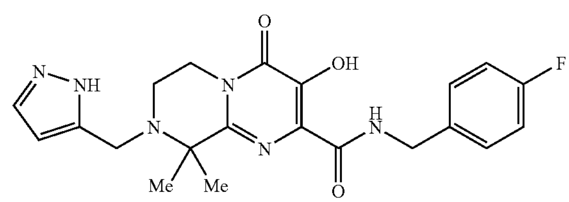 | 427 |
| 51. N-(4-fluorobenzyl)-3-hydroxy-9,9-dimethyl-4-oxo-8-(pyrazin-2-ylmethyl)-6,7,8,9-tetrahydro-4H-pyrazino[1,2-a]pyrimidine-2-carboxamide (TFA salt) (Scheme A) | 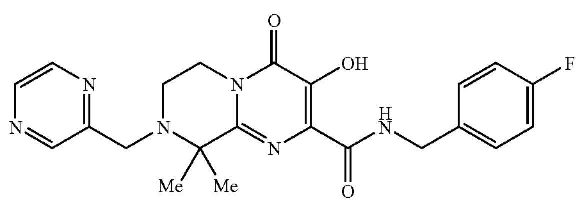 | 439 |
| 52. N-(4-fluorobenzyl)-3-hydroxy-9,9-dimethyl-8-(1,3-oxazol-4-ylmethyl)-4-oxo-6,7,8,9-tetrahydro-4H-pyrazino[1,2-a]pyrimidine-2-carboxamide (TFA salt) (Scheme A) | 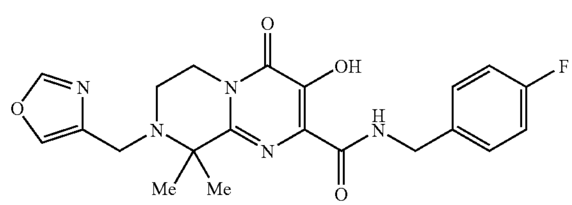 | 428 |
| 53. N-(4-fluorobenzyl)-3-hydroxy-9,9-dimethyl-8-(1,3-oxazol-5-ylmethyl)-4-oxo-6,7,8,9-tetrahydro-4H-pyrazino[1,2-a]pyrimidine-2-carboxamide (TFA salt) (Scheme A) | 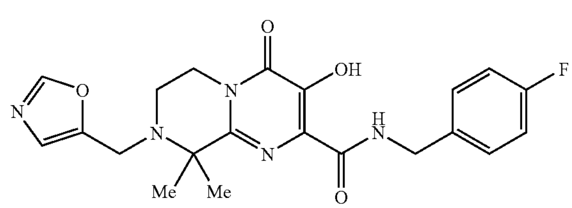 | 428 |

| Compound (Preparative Method) | Structure | M + 1 |
|---|---|---|
| 54. N-(4-fluorobenzyl)-3-hydroxy-9,9-dimethyl-8-(2-morpholin-4-ylethyl)-4-oxo-6,7,8,9-tetrahydro-4H-pyrazino[1,2-a]pyrimidine-2-carboxamide (TFA salt) (Scheme A) | 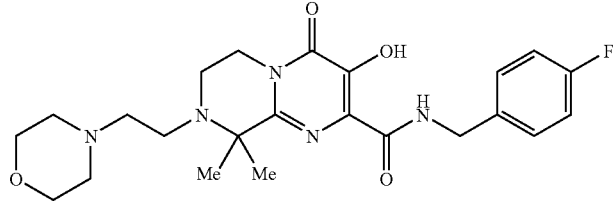 | 460 |
| 55. N-(4-fluorobenzyl)-3-hydroxy-9,9-dimethyl-4-oxo-8-(1H-1,2,3-triazol-5-ylmethyl)-6,7,8,9-tetrahydro-4H-pyrazino[1,2a]pyrimidine-2-carboxamide (Scheme A) | 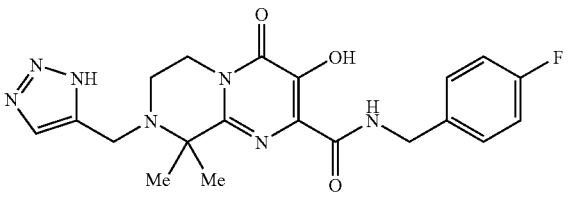 | 428 |
| 56. N8-ethyl-N2-(4-fluorobenzyl)-3-hydroxy-9,9-dimethyl-4-oxo-4,6,7,9-tetrahydro-8H-pyrazino[1,2-a]pyrimidine-2,8-dicarboxamide (Scheme A) | 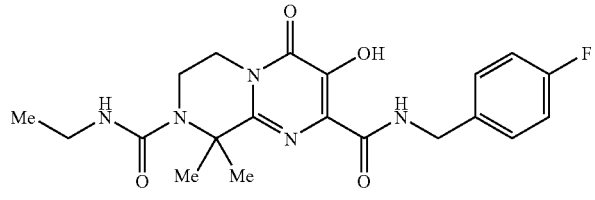 | 418 |
| 57. 8-[(dimethylamino)sulfonyl]-N-(4 fluorobenzyl)-3-hydroxy-9,9-dimethyl-4-oxo-6,7,8,9-tetrahydro-4H-pyrazino[1,2-a]pyrimidine-2-carboxamide (Scheme A) | 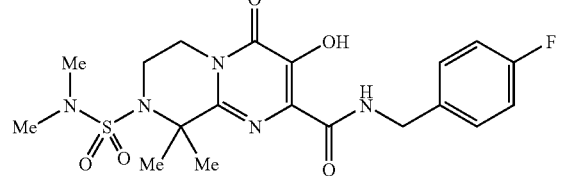 | 454 |
| 58. N-(4-fluorobenzyl)-3-hydroxy-9,9-dimethyl-4-oxo-8-(pyridin-2-ylmethyl)-6,7,8,9-tetrahydro-4H-pyrazino[1,2-a]pyrimidine-2-carboxamide (TFA salt) (Scheme A) | 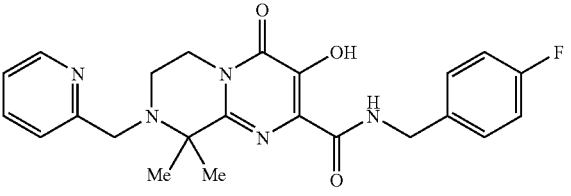 | 438 |
| 59. N-(4-fluorobenzyl)-3-hydroxy-9,9-dimethyl-4-oxo-8-(2-pyridin-2-ylethyl)-6,7,8,9-tetrahydro-4H-pyrazino[1,2-a]pyrimidine-2-carboxamide (TFA salt) (Scheme A) | 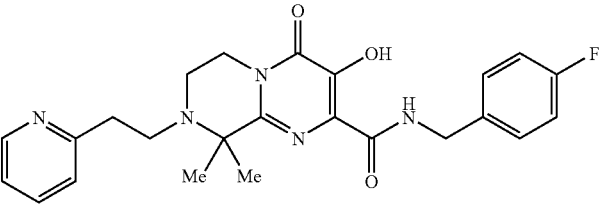 | 452 |
| 60. N-(4-fluorobenzyl)-3-hydroxy-9,9-dimethyl-8-[(1-methyl-1H-pyrazol-5-yl)methyl]-4-oxo-6,7,8,9-tetrahydro-4H-pyrazino[1,2-a]pyrimidine-2-carboxamide (TFA salt) (Scheme A) | 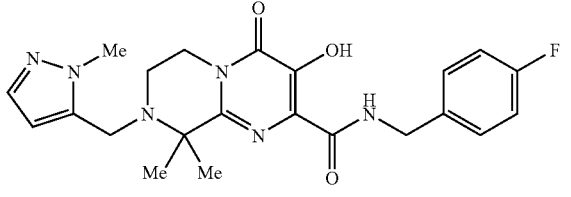 | 441 |

| Compound (Preparative Method) | Structure | M + 1 |
|---|---|---|
| 61. N-(4-fluorobenzyl)-3-hydroxy-9,9-dimethyl-8-[(1-methyl-1H-pyrazol-3-yl)methyl]-4-oxo-6,7,8,9-tetrahydro-4H-pyrazino[1,2a]pyrimidine-2-carboxamide (TFA salt) (Scheme A) | 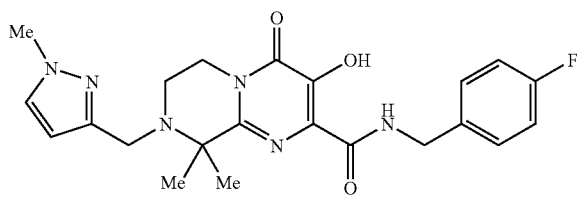 | 441 |
| 62. N-(4-fluorobenzyl)-3-hydroxy-9,9-dimethyl-4-oxo-8-(1H-pyrazol-4-ylmethyl)-6,7,8,9-tetrahydro-4H-pyrazino[1,2-a]pyrimidine-2-carboxamide (TFA salt) (Scheme A) | 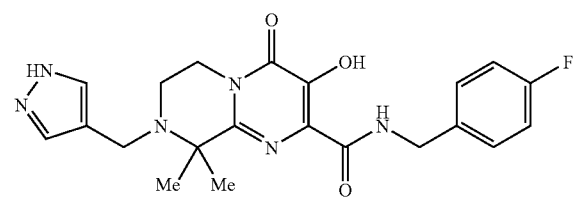 | 427 |
| 63. N-(4-fluorobenzyl)-3-hydroxy-9,9-dimethyl-4-oxo-8-(1,3-thiazol-4-ylmethyl)-6,7,8,9-tetrahydro-4H-pyrazino[1,2-a]pyrimidine-2-carboxamide (TFA salt) (Scheme A) | 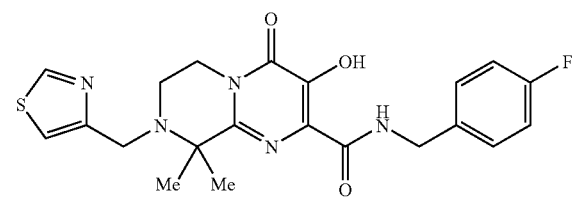 | 444 |
| 64. 8-[2-(dimethylamino)-2-oxoethyl]-N-(4-fluorobenzyl)-3-hydroxy-9,9-dimethyl-4-oxo-6,7,8,9-tetrahydro-4H-pyrazino[1,2-a]pyrimidine-2-carboxamide (TFA salt) (Scheme A) | 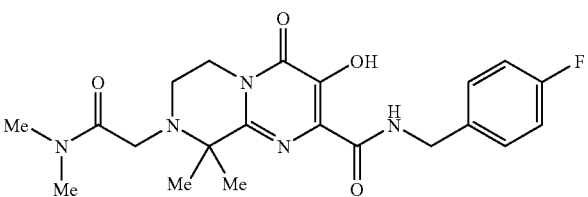 | 432 |
| 65. 8-[2-(dimethylamino)ethyl]-N-(4-fluorobenzyl)-3-hydroxy-9,9-dimethyl-4-oxo-6,7,8,9-tetrahydro-4H-pyrazino[1,2-a]pyrimidine-2-carboxamide (TFA salt) (Scheme A) | 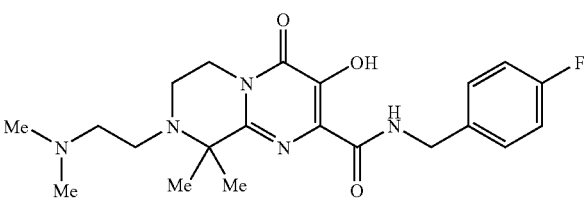 | 418 |
| 66. 8-[2-(dimethylamino)-1-oxoethyl]-N-(4-fluorobenzyl)-3-hydroxy-9,9-dimethyl-4-oxo-6,7,8,9-tetrahydro-4H-pyrazino[1,2-a]pyrimidine-2-carboxamide (TFA salt) (Scheme A) | 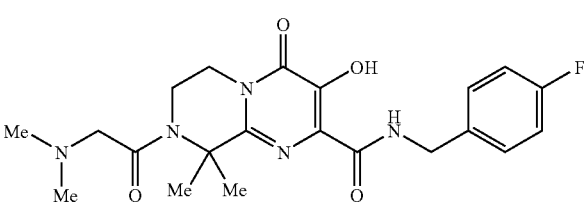 | 432 |
| 67. N-(4-fluorobenzyl)-3-hydroxy-9,9-dimethyl-8-[(5-methylisoxazol-3-yl)methyl]-4-oxo-6,7,8,9-tetrahydro-4H-pyrazino[1,2-a]pyrimidine-2-carboxamide (TFA salt) (Scheme A) | 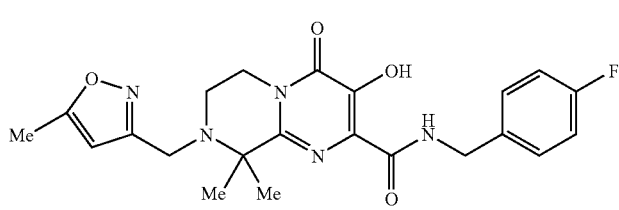 | 442 |

| Compound (Preparative Method) | Structure | M + 1 |
|---|---|---|
| 68. 8-[2-(diethylamino)ethyl]-N-(4-fluorobenzyl)-3-hydroxy-9,9-dimethyl-4-oxo-6,7,8,9-tetrahydro-4H-pyrazino[1,2-a]pyrimidine-2-carboxamide (TFA salt) (Scheme A) | 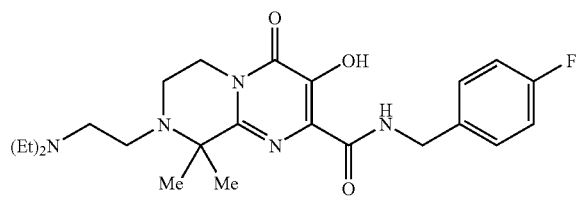 | 446 |
| 69. N-(4-fluorobenzyl)-3-hydroxy-9,9-dimethyl-8-[(1-methyl-1H-1,2,4-triazol-3-yl)methyl]-4-oxo-6,7,8,9-tetrahydro-4H-pyrazino[1,2-a]pyrimidine-2-carboxamide (TFA salt) (Scheme A) | 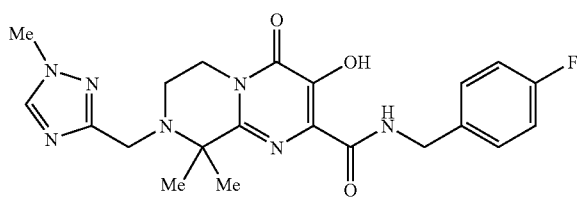 | 442 |
| 70. N-(4-fluorobenzyl)-3-hydroxy-9,9-dimethyl-8-[(2-methyl-1,3-thiazol-4-yl)methyl]-4-oxo-6,7,8,9-tetrahydro-4H-pyrazino[1,2-a]pyrimidine-2-carboxamide (TFA salt) (Scheme A) | 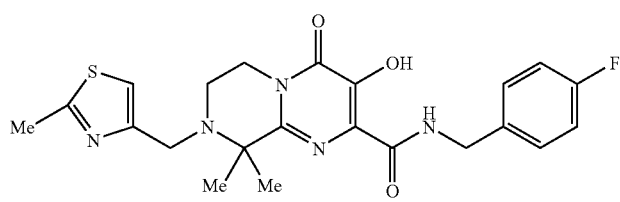 | 458 |
| 71. N-(4-fluorobenzyl)-3-hydroxy-9,9-dimethyl-8-[(3-methylisoxazol-5-yl)methyl]-4-oxo-6,7,8,9-tetrahydro-4H-pyrazino[1,2-a]pyrimidine-2-carboxamide (Scheme A or Scheme M) | 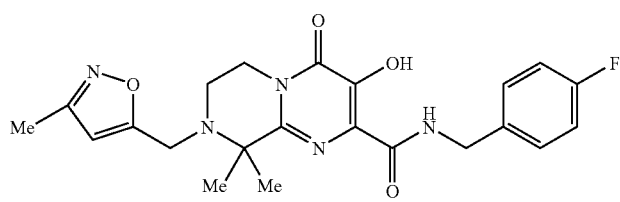 | 442 |
| 72. N-(4-fluorobenzyl)-3-hydroxy-9,9-dimethyl-8-[(3-methyl-1,2,4-oxadiazol-5-yl)methyl]-4-oxo-6,7,8,9-tetrahydro-4H-pyrazino[1,2-a]pyrimidine-2-carboxamide (TFA salt) (Scheme A or Scheme N) | 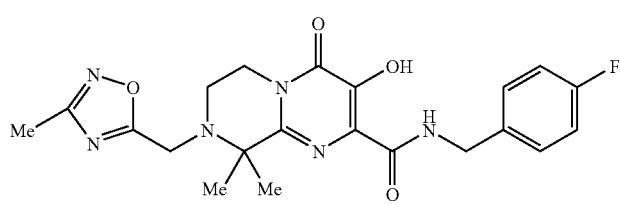 | 443 |
| 73. 8-(cyanomethyl)-N-(4-fluorobenzyl)-3-hydroxy-9,9-dimethyl-4-oxo-6,7,8,9-tetrahydro-4H-pyrazino[1,2-a]pyrimidine-2-carboxamide (TFA salt) (Scheme A or Scheme L) | 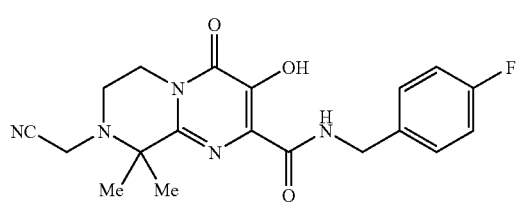 | 386 |
| 74. N-(4-fluorobenzyl)-3-hydroxy-9,9-dimethyl-4-oxo-8-(1H-tetrazol-5-ylmethyl)-6,7,8,9-tetrahydro-4H-pyrazino[1,2-a]pyrimidine-2-carboxamide (TFA salt) (Scheme A or Scheme L) | 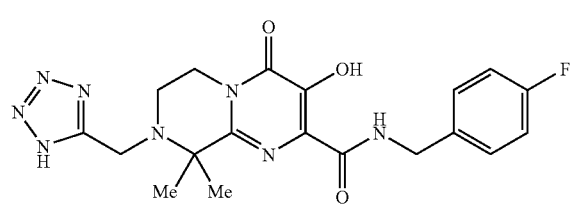 | 429 |

| Compound (Preparative Method) | Structure | M + 1 |
|---|---|---|
| 75. N-(4-fluorobenzyl)-3-hydroxy-9,9-dimethyl-8-[(1-methyl-1H-1,2,3-triazol-4-yl)methyl]-4-oxo-6,7,8,9-tetrahydro-4H-pyrazino[1,2-a]pyrimidine-2-carboxamide (TFA salt) (Scheme A or Scheme M) | 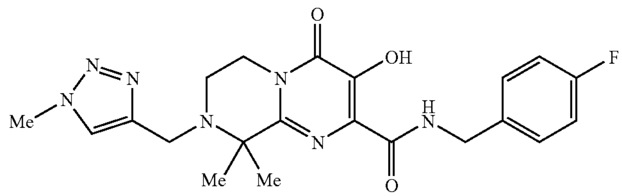 | 442 |
| 76. N-(4-fluorobenzyl)-3-hydroxy-9,9-dimethyl-8-[(1-methyl-1H-1,2,3-triazol-5-yl)methyl]-4-oxo-6,7,8,9-tetrahydro-4H-pyrazino[1,2-a]pyrimidine-2-carboxamide (TFA salt) (Scheme A or Scheme M) | 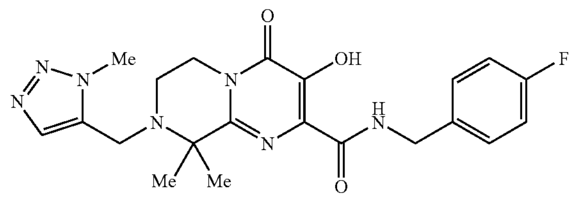 | 442 |
| 77. N-(4-fluorobenzyl)-3-hydroxy-9,9-dimethyl-8-(2-morpholin-4-yl-2-oxoethyl)-4-oxo-6,7,8,9-tetrahydro-4H-pyrazino[1,2-a]pyrimidine-2-carboxamide (TFA salt) (Scheme A or Scheme N) | 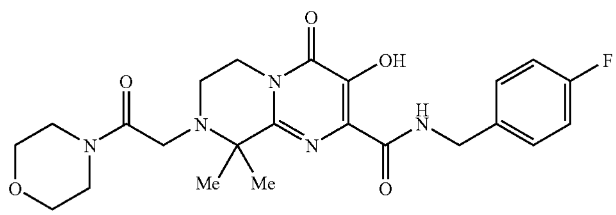 | 474 |
| 78. N-(4-fluorobenzyl)-3-hydroxy-9,9-dimethyl-4-oxo-8-(2-oxo-2-pyrrolidin-1-ylethyl)-6,7,8,9-tetrahydro-4H-pyrazino[1,2-a]pyrimidine-2-carboxamide (TFA salt) (Scheme A or Scheme N) | 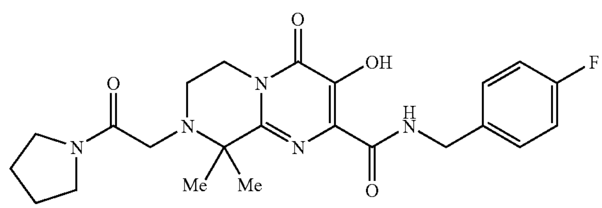 | 458 |
| 79. N-(4-fluorobenzyl)-3-hydroxy-9,9-dimethyl-8-[2-(methylamino)-2-oxoethyl]-4-oxo-6,7,8,9-tetrahydro-4H-pyrazino[1,2-a]pyrimidine-2-carboxamide (TFA salt) (Scheme A or Scheme N) | 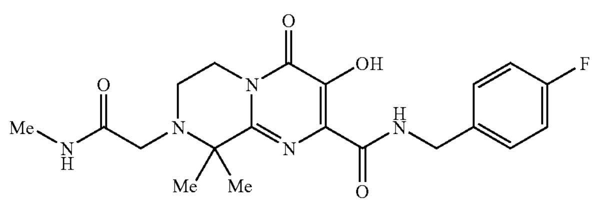 | 418 |
| 80. (2-{[(4-fluorobenzyl)amino]carbonyl}-3-hydroxy-9,9-dimethyl-4-oxo-4,6,7,9-tetrahydro-8H-pyrazino[1,2-a]pyrimidin-8-yl)acetic acid (TFA salt) (Scheme A or Scheme N) | 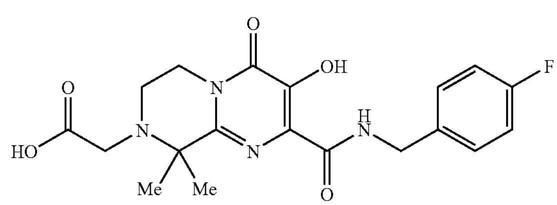 | 405 |
| 81. N-(4-fluorobenzyl)-3-hydroxy-9,9-dimethyl-8-[2-(4-methylpiperazin-1-yl)-2-oxoethyl]-4-oxo-6,7,8,9-tetrahydro-4H-pyrazino[1,2-a]pyrimidine-2-carboxamide (TFA salt) (Scheme A or Scheme N) | 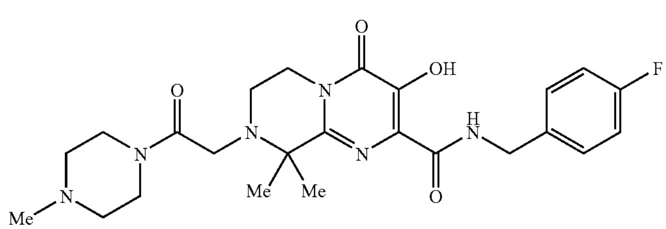 | 487 |

| Compound (Preparative Method) | Structure | M + 1 |
| --- | --- | --- |
| 82. N-(4-fluorobenzyl)-3-hydroxy-9,9-dimethyl-8-(1,3,4-oxadiazol-2-ylmethyl)-4-oxo-6,7,8,9-tetrahydro-4H-pyrazino[1,2-a]pyrimidine-2-carboxamide (Scheme A or Scheme N) | 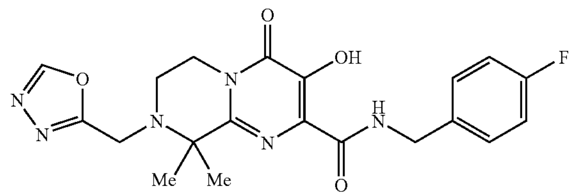 | 429 |
| 83. N-(4-fluorobenzyl)-3-hydroxy-9,9-dimethyl-4-oxo-8-{2-oxo-2-[(pyridin-4-ylmethyl)amino]ethyl}-6,7,8,9-tetrahydro-4H-pyrazino[1,2-a]pyrimidine-2-carboxamide (TFA salt) (Scheme A or Scheme N) | 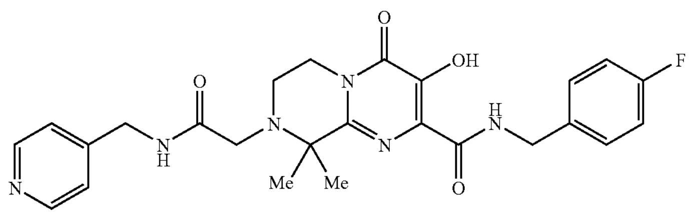 | 495 |
| 84. N-(4-fluorobenzyl)-3-hydroxy-9,9-dimethyl-8-(1,3-oxazol-2-ylmethyl)-4-oxo-6,7,8,9-tetrahydro-4H-pyrazino[1,2-a]pyrimidin-2-carboxamide (TFA salt) (Scheme A) | 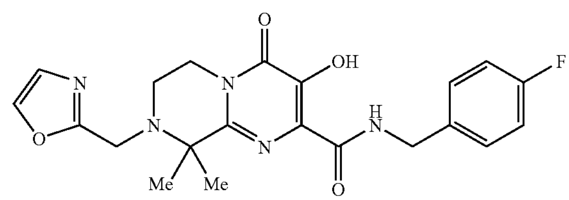 | 428 |
| 85. N-(4-fluorobenzyl)-3-hydroxy-9,9-dimethyl-8-[(5-methyl-1,3,4-oxadiazol-2-yl)methyl]-4-oxo-6,7,8,9-tetrahydro-4H-pyrazino[1,2-a]pyrimidine-2-carboxamide (TFA salt) (Scheme A or Scheme N) | 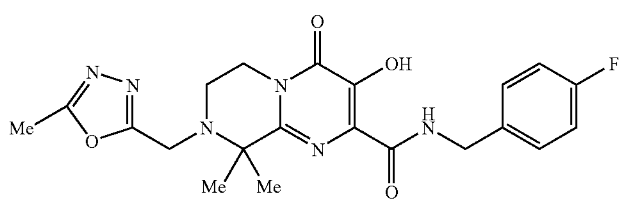 | 443 |
| 86. N-(4-fluorobenzyl)-3-hydroxy-9,9-dimethyl-8-[(1-methyl-1H-tetrazol-5-yl)methyl]-4-oxo-6,7,8,9-tetrahydro-4H-pyrazino[1,2-a]pyrimidine-2-carboxamide (TFA salt) (Scheme A or Scheme L) | 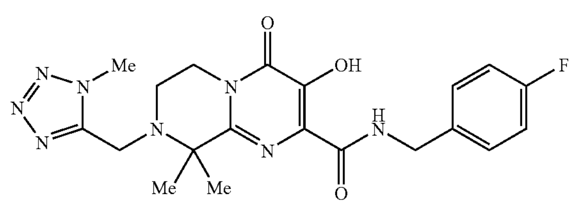 | 443 |
| 87. N-(4-fluorobenzyl)-3-hydroxy-9,9-dimethyl-8-[(2-methyl-1H-tetrazol-5-yl)methyl]-4-oxo-6,7,8,9-tetrahydro-4H-pyrazino[1,2-a]pyrimidine-2-carboxamide (TFA salt) (Scheme A or Scheme L) | 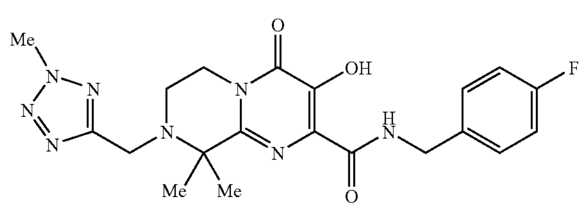 | 443 |
| 88. 8-benzyl-N-{4-fluorobenzyl)-3-hydroxy-9,9-dimethyl-4-oxo-6,7,8,9-tetrahydro-4H-pyrazino[1,2-a]pyrimidine-2-carboxamide (TFA salt) (Scheme A) | 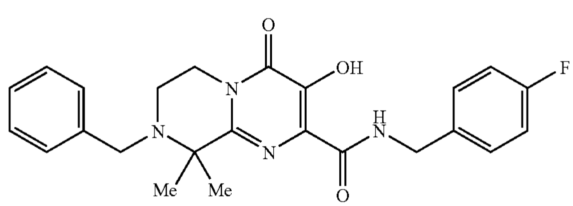 | 437 |

-continued

| Compound (Preparative Method) | Structure | M + 1 |
|---|---|---|
| 89. N-(4-fluorobenzyl)-3-hydroxy-9,9-dimethyl-8-[(5-methyl-1,2,4-oxadiazol-3-yl)methyl]-4-oxo-6,7,8,9-tetrahydro-4H-pyrazino[1,2-a]pyrimidine-2-carboxamide (TFA salt) (Scheme A or Scheme L) | 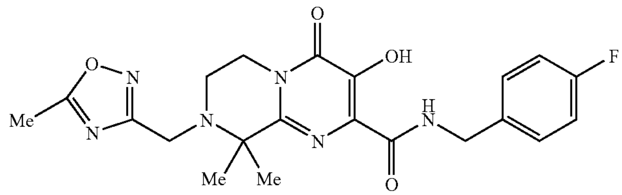 | 443 |
| 90. 8-(2-amino-2-oxoethyl)-N-(4-fluorobenzyl)-3-hydroxy-9,9-dimethyl-4-oxo-6,7,8,9-tetrahydro-4H-pyrazino[1,2-a]pyrimidine-2-carboxamide (TFA salt) (Scheme A or Scheme N) | 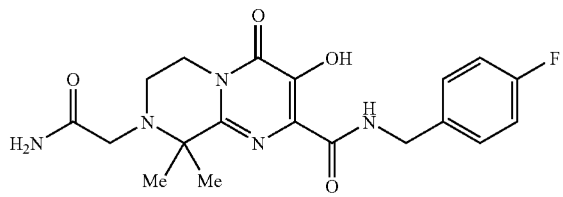 | 404 |
| 91. N-(4-fluorobenzyl)-3-hydroxy-9,9-dimethyl-8-[(5-methyl-1,3-oxazol-2-yl)methyl]-4-oxo-6,7,8,9-tetrahydro-4H-pyrazino[1,2-a]pyrimidine-2-carboxamide (Scheme A or Scheme N) | 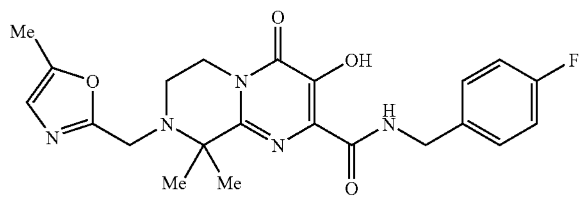 | 442 |
| 92. N-(4-fluorobenzyl)-3-hydroxy-9,9-dimethyl-8-[(4-methyl-1,3-oxazol-2-yl)methyl]-4-oxo-6,7,8,9-tetrahydro-4H-pyrazino[1,2-a]pyrimidine-2-carboxamide (TFA salt) (Scheme A) | 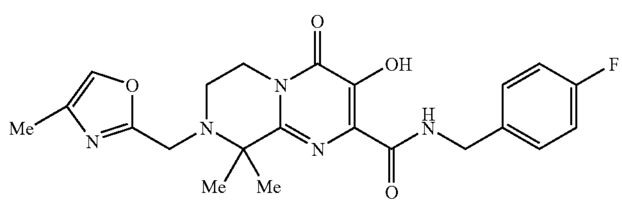 | 442 |
| 93. (2-{[(4-fluorobenzyl)amino]carbonyl}-3-hydroxy-4-oxo-4,6,7,9-tetrahydro-8H-pyrazino[1,2-a]pyrimidin-8-yl)acetic acid (TFA salt) (Scheme A) | 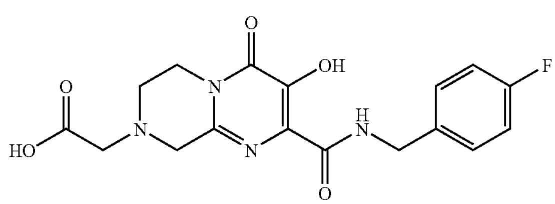 | 377 |
| 94. 8-benzyl-N-(4-fluorobenzyl)-3-hydroxy-4-oxo-6,7,8,9-tetrahydro-4H-pyrazino[1,2-a]pyrimidine-2-carboxamide (TFA salt) (Scheme A) | 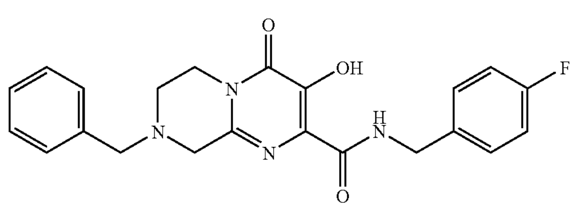 | 409 |
| 95. N-(4-fluorobenzyl)-3-hydroxy-4-oxo-6,7,8,9-tetrahydro-4H-pyrazino[1,2-a]pyrimidine-2-carboxamide (TFA salt) (Scheme A) | 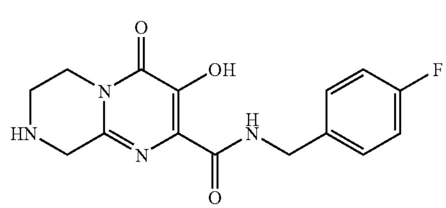 | 319 |

| Compound (Preparative Method) | Structure | M + 1 |
|---|---|---|
| 96. N-(4-fluorobenzyl)-3-hydroxy-4-oxo-8-(1H-1,2,3-triazol-5-ylmethyl)-6,7,8,9-tetrahydro-4H-pyrazino[1,2-a]pyrimidine-2-carboxamide (TFA salt) (Scheme A) | 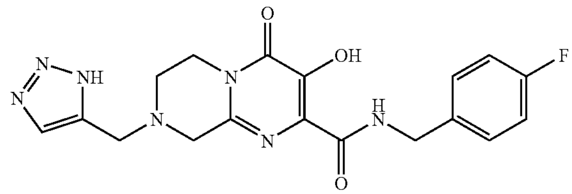 | 400 |
| 97. N-(4-fluorobenzyl)-3-hydroxy-8-methyl-4-oxo-6,7,8,9-tetrahydro-4H-pyrazino[1,2-a]pyrimidine-2-carboxamide (TFA salt) (Scheme A) | 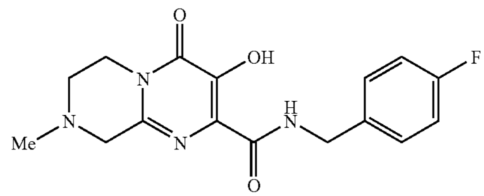 | 333 |
| 98. 8-[(dimethylamino)(oxo)acetyl]-N-(4-fluorobenzyl)-3-hydroxy-4-oxo-6,7,8,9-tetrahydro-4H-pyrazino[1,2-a]pyrimidine-2-carboxamide (Scheme A) | 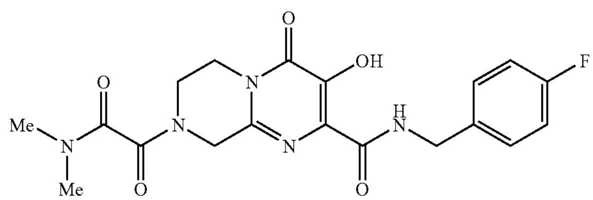 | 418 |
| 99. 8-acetyl-N-(4-fluorobenzyl)-3-hydroxy-4-oxo-6,7,8,9-tetrahydro-4H-pyrazino[1,2-a]pyrimidine-2-carboxamide (Scheme A) | 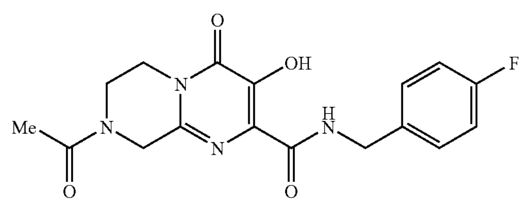 | 361 |
| 100. N-(4-fluorobenzyl)-3-hydroxy-4-oxo-8-(trifluoroacetyl)-6,7,8,9-tetrahydro-4H-pyrazino[1,2-a]pyrimidine-2-carboxamide (Scheme A) | 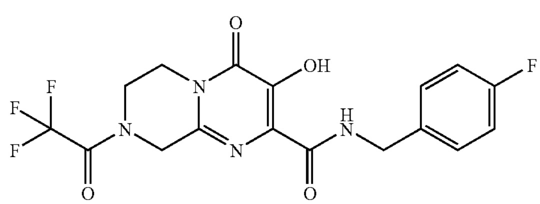 | 415 |
| 101. N-(4-fluorobenzyl)-3-hydroxy-8-[(4-methylphenyl)sulfonyl]-4-oxo-6,7,8,9-tetrahydro-4H-pyrazino[1,2-a]pyrimidine-2-carboxamide (Scheme A) | 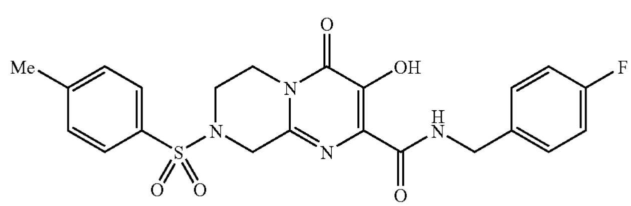 | 473 |
| 102. N-(4-fluorobenzyl)-3-hydroxy-4,7-dioxo-6,7,8,9-tetrahydro-4H-pyrazino[1,2-a]pyrimidine-2-carboxamide (Scheme J) | 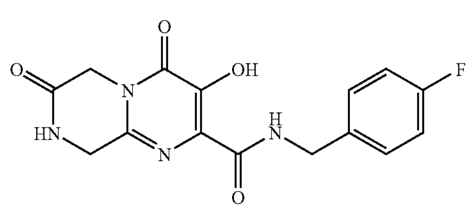 | 333 |

| Compound (Preparative Method) | M + 1 |
|---|---|
| 103. 7-benzyl-N-(4-fluorobenzyl)-3-hydroxy-4,6-dioxo-6,7,8,9-tetrahydro-4H-pyrimido[1,6-a]pyrimidine-2-carboxamide (Scheme K) | 423 |
| 104. N-(4-fluorobenzyl)-3-hydroxy-7-methyl-4,6-dioxo-6,7,8,9-tetrahydro-4H-pyrimido[1,6-a]pyrimidine-2-carboxamide (Scheme K) | 347 |
| 105. N-(4-fluorobenzyl)-3-hydroxy-9,9-dimethyl-4-oxo-8,9-dihydro-4H-pyrimido[2,1-d][1,2,5]thiadiazine-2-carboxamide 7,7-dioxide (Scheme J) | 397 |
| 106. (+) N-[2-{[(4-fluorobenzyl)amino]carbonyl}-3-hydroxy-4-oxo-8-(2-phenylethyl)-4,6,7,8,9,10-hexahydropyrimido[1,2-d][1,4]diazepin-10-yl]-N,N'-N'-trimethylethanediamide (Scheme E) | 566 |
| 107. (−) N-[2-{[(4-fluorobenzyl)amino]carbonyl}-3-hydroxy-4-oxo-8-(2-phenylethyl)-4,6,7,8,9,10-hexahydropyrimido[1,2-d][1,4]diazepin-10-yl]-N,N',N'-trimethylethanediamide (Scheme E) | 566 |
| 108. N-(8-[(dimethylamino)(oxo)acetyl]-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 561 |

| Compound (Preparative Method) | Structure | M + 1 |
|---|---|---|
| 109. N-(cyclohexylmethyl)-N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N',N'-dimethylethanediamide (TFA salt) (Scheme D) | 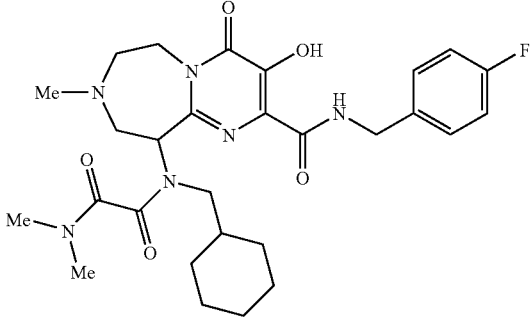 | 557 |
| 110. N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N-benzyl-N',N'-dimethylethanediamide (TFA salt) (Scheme D) | 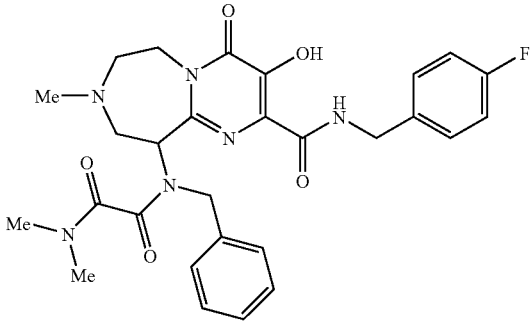 | 551 |
| 111. N-(8-benzyl-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme E) | 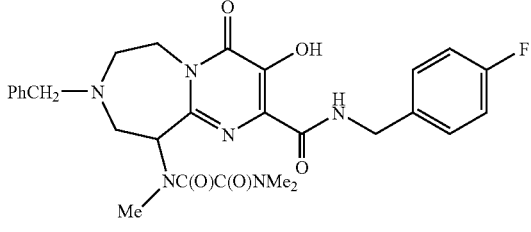 | 552 |
| 112. N-[2-{[(4-fluorobenzyl)amino]carbonyl}-3-hydroxy-8-(methylsulfonyl)-4-oxo-4,6,7,8,9,10-hexahydropyrimido[1,2-d][1,4]diazepin-10-yl]-N,N',N'-trimethylethanediamide (Scheme E) | 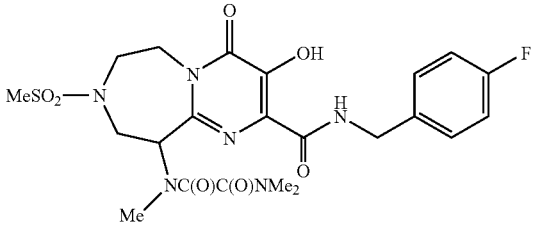 | 540 |
| 113. (+) N-(2-{[(3-chloro-4-fluorobenzyl)amino]carbonyl}-8-cyclopropyl-3-hydroxy-4-oxo-4,6,7,8,9,10-hexahydropyrimido[1,2-d][1,4]diazepin-10-yl)-N,N',N'-trimethylethanediamide (TFA salt) (Scheme D) | 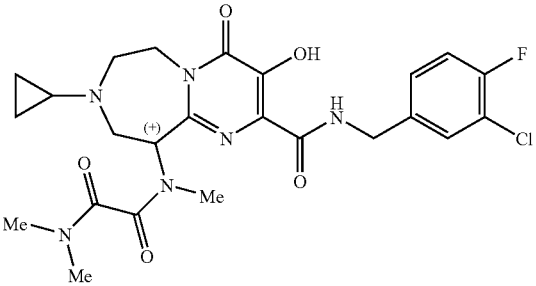 | 535 |

| Compound (Preparative Method) | Structure | M + 1 |
|---|---|---|
| 114. (−) N-(2-{[(3-chloro-4-fluorobenzyl)amino]carbonyl}-8-cyclopropyl-3-hydroxy-4-oxo-4,6,7,8,9,10-hexahydropyrimido[1,2-d][1,4]diazepin-10-yl)-N,N',N'-trimethylethanediamide (TFA salt) (Scheme D) | 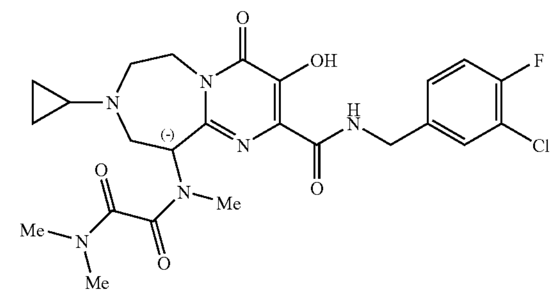 | 535 |
| 115. (+) N-(2-{[(3-chloro-4-methylbenzyl)amino]carbonyl}-8-cyclopropyl-3-hydroxy-4-oxo-4,6,7,8,9,10-hexahydropyrimido[1,2-d][1,4]diazepin-10-yl)-N,N',N'-trimethylethanediamide (TFA salt) (Scheme D) | 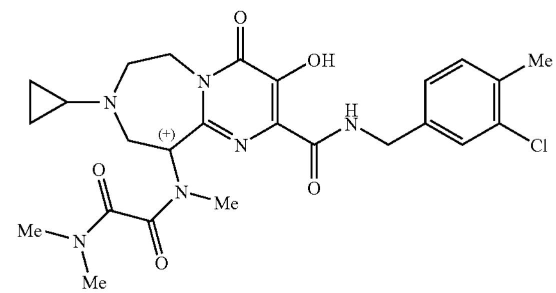 | 531 |
| 116. (−) N-(2-{[(3-chloro-4-methylbenzyl)amino]carbonyl}-8-cyclopropyl-3-hydroxy-4-oxo-4,6,7,8,9,10-hexahydropyrimido[1,2-d][1,4]diazepin-10-yl)-N,N',N'-trimethylethanediamide (TFA salt) (Scheme D) | 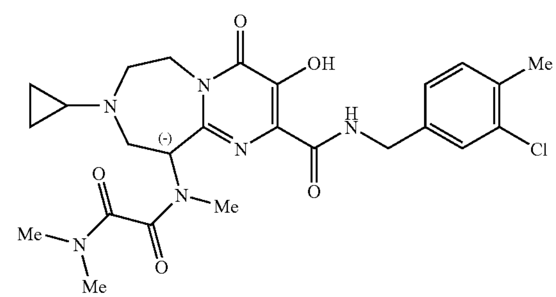 | 531 |
| 117. (+) N-(8-(cyclopropylmethyl)-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 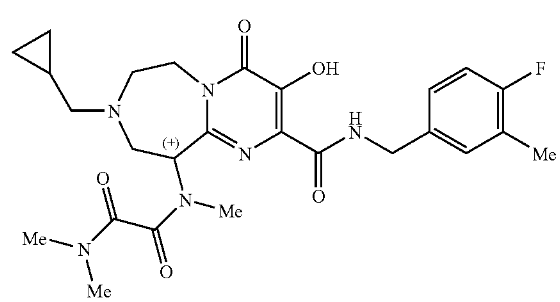 | 530 |
| 118. (−) N-(8-(cyclopropylmethyl)-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 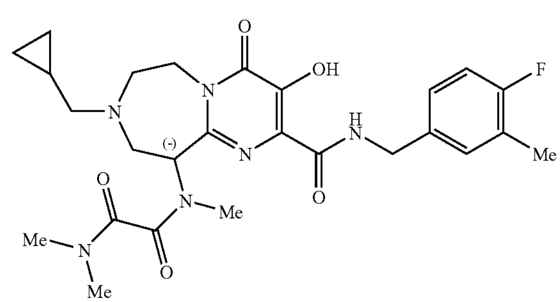 | 530 |

| Compound (Preparative Method) | Structure | M + 1 |
|---|---|---|
| 119. (+) N-(8-cyclopentyl-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 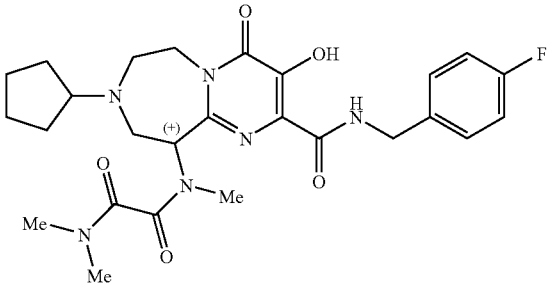 | 530 |
| 120. (−) N-(8-cyclopentyl-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 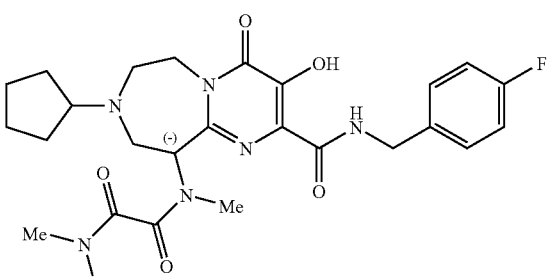 | 530 |
| 121. N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N-isobutyl-N',N'-dimethylethanediamide (TFA salt) (Scheme D) | 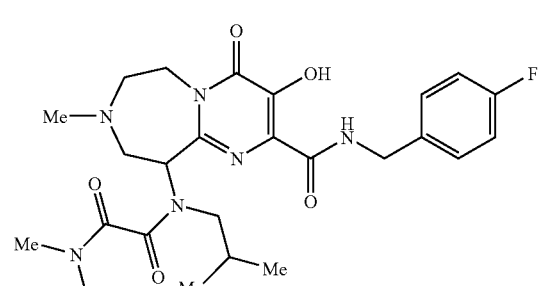 | 518 |
| 122. (+) N-(2-{[(4-fluoro-3-methylbenzyl)amino]carbonyl}-3-hydroxy-8-isopropyl-4-oxo-4,6,7,8,9,10-hexahydropyrimido[1,2-d][1,4]diazepin-10-yl)-N,N',N'-trimethylethanediamide (TFA salt) (Scheme E) | 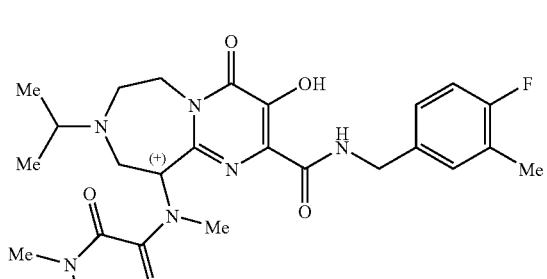 | 518 |
| 123. (−) N-(2-{[(4-fluoro-3-methylbenzyl)amino]carbonyl}-3-hydroxy-8-isopropyl-4-oxo-4,6,7,8,9,10-hexahydropyrimido[1,2-d][1,4]diazepin-10-yl)-N,N',N'-trimethylethanediamide (TFA salt) (Scheme E) | 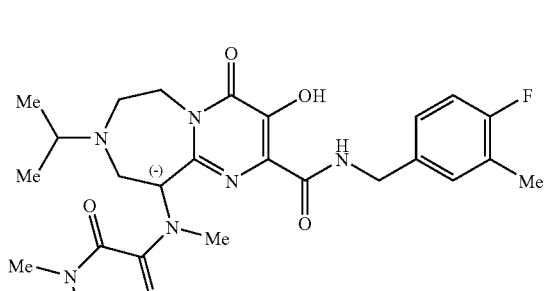 | 518 |

| Compound (Preparative Method) | Structure | M + 1 |
|---|---|---|
| 124. N-(4-fluorobenzyl)-3-hydroxy-8-methyl-10-{methyl[morpholin-4-yl(oxo)acetyl]amino}-4-oxo-4,6,7,8,9,10-hexahydropyrimido[1,2-d][1,4]diazepine-2-carboxamide (TFA salt) (Scheme E) | 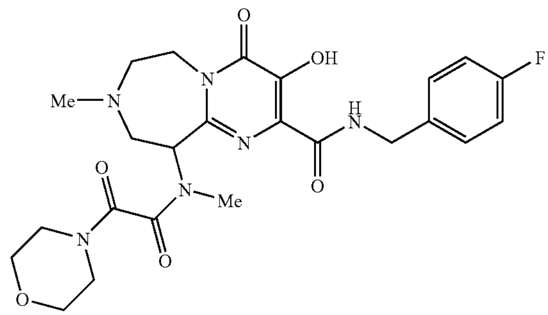 | 517 |
| 125. (+) N-(8-(cyclopropylmethyl)-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 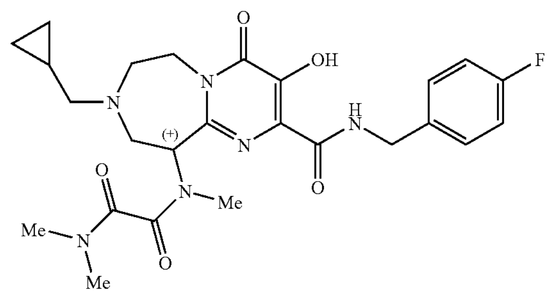 | 516 |
| 126. (−) N-(8-(cyclopropylmethyl)-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 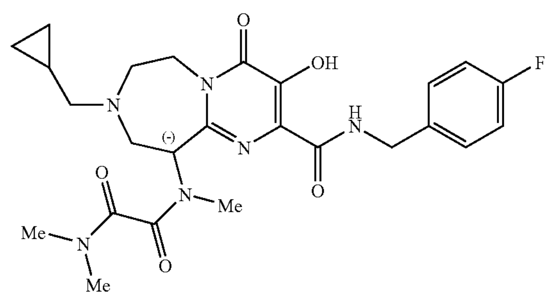 | 516 |
| 127. (+) N-(8-cyclopropyl-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme E) | 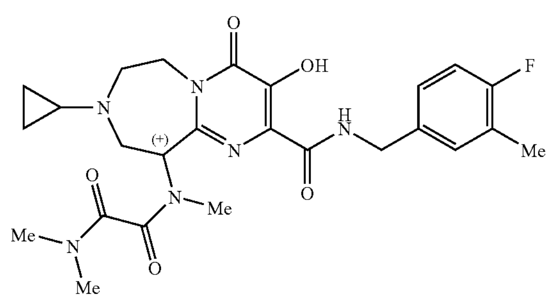 | 515 |
| 128. (−) N-(8-cyclopropyl-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme E) | 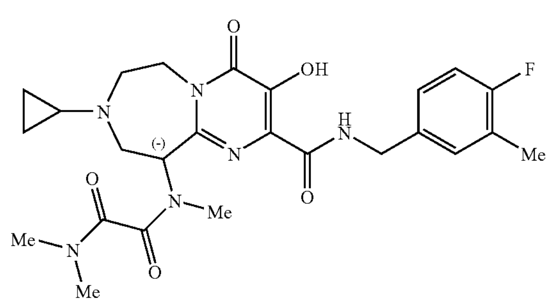 | 515 |

| Compound (Preparative Method) | Structure | M + 1 |
|---|---|---|
| 129. N-(2-{[(3-chloro-4-fluorobenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 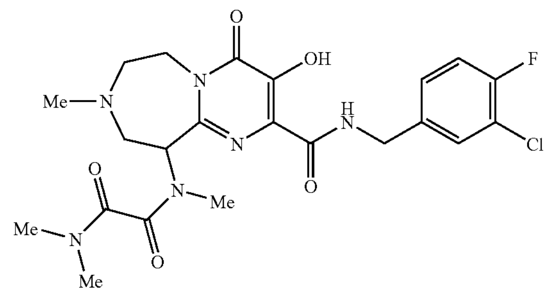 | 510 |
| 130. (+) N-(2-{[(3-chloro-4-methylbenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 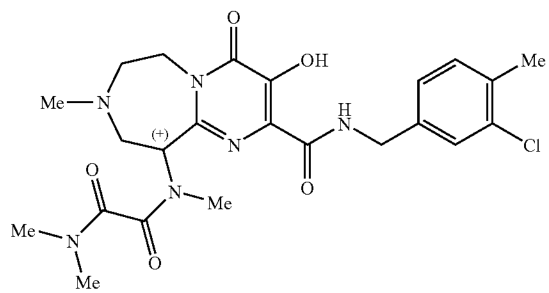 | 505 |
| 131. (−) N-(2-{[(3-chloro-4-methylbenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 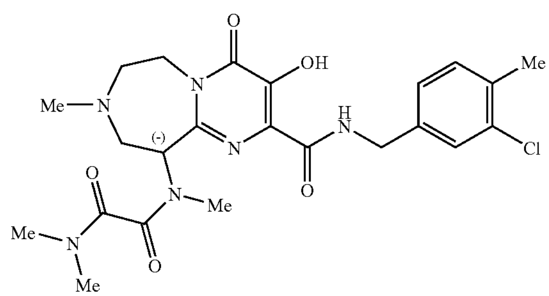 | 505 |
| 132. (+) N-(8-ethyl-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 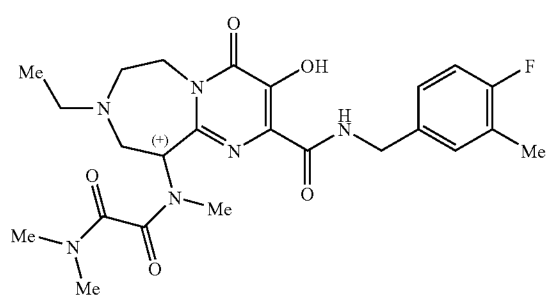 | 503 |
| 133. (−) N-(8-ethyl-2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 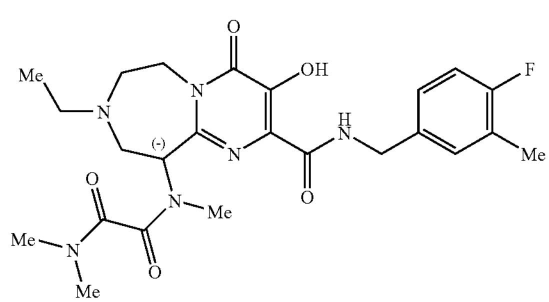 | 503 |

| Compound (Preparative Method) | Structure | M + 1 |
|---|---|---|
| 134. N-ethyl-N-(2-{[(4-fluoro-3-methylbenzyl)amino]carbonyl}-3-hydroxy-8-methyl-4-oxo-4,6,7,8,9,10-hexahydropyrimido[1,2-d][1,4]diazepin-10-yl)-N',N'-dimethylethanediamide (HCl salt) (Scheme E) | 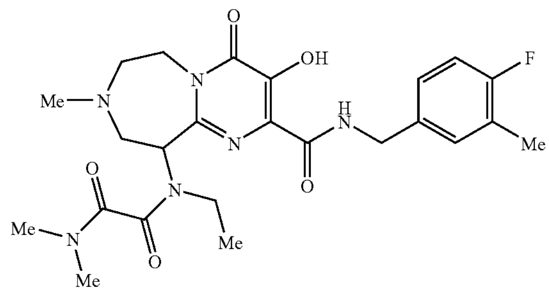 | 504 |
| 135. (+) N-(2-{[(4-fluorobenzyl)amino]carbonyl}-3-hydroxy-8-isopropyl-4-oxo-4,6,7,8,9,10-hexahydropyrimido[1,2-d][1,4]diazepin-10-yl)-N,N',N'-trimethylethanediamide (TFA salt) (Scheme E) | 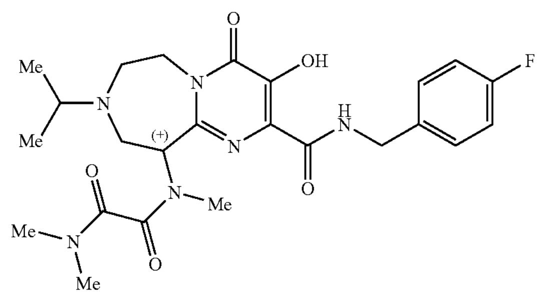 | 504 |
| 136. (−) N-(2-{[(4-fluorobenzyl)amino]carbonyl}-3-hydroxy-8-isopropyl-4-oxo-4,6,7,8,9,10-hexahydropyrimido[1,2-d][1,4]diazepin-10-yl)-N,N',N'-trimethylethanediamide (TFA salt) (Scheme E) | 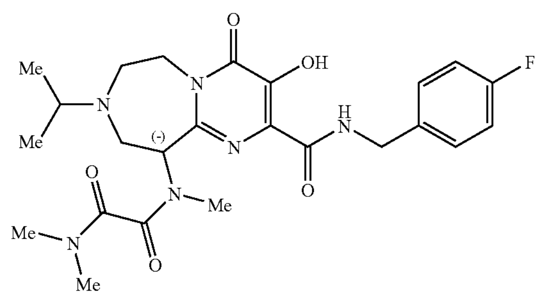 | 504 |
| 137. N-(8-acetyl-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (Scheme E) | 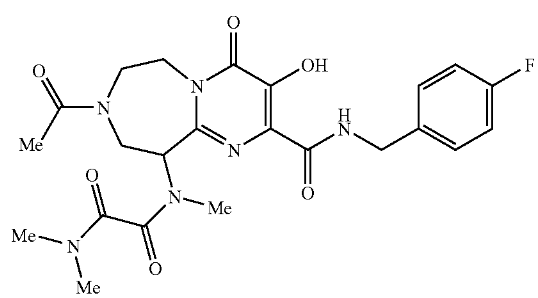 | 503 |
| 138. N-(4-fluorobenzyl)-3-hydroxy-8-methyl-10-{methyl[oxo(pyrrolidin-1-yl)acetyl]amino}-4-oxo-4,6,7,8,9,10-hexahydropyrimido[1,2-d][1,4]diazepine-2-carboxamide (TFA salt) (Scheme D) | 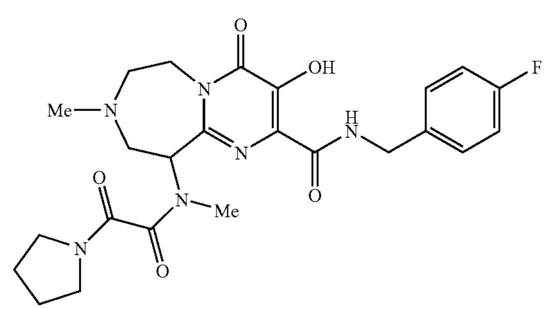 | 502 |

-continued

| Compound (Preparative Method) | Structure | M + 1 |
|---|---|---|
| 139. 10-[acetyl(cyclohexylmethyl)amino]-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 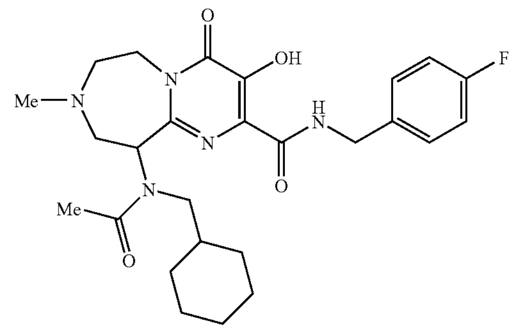 | 501 |
| 140. 10-[acetyl(benzyl)amino]-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 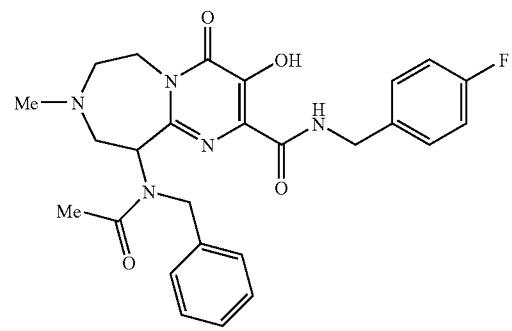 | 494 |
| 141. 8-acetyl-10-[benzyl(methyl)amino]-N-(4-fluorobenzyl)-3-hydroxy-4-oxo-4,6,7,8,9,10-hexahydropyrimido[1,2-d][1,4]diazepine-2-carboxamide (TFA salt) (Scheme D) | 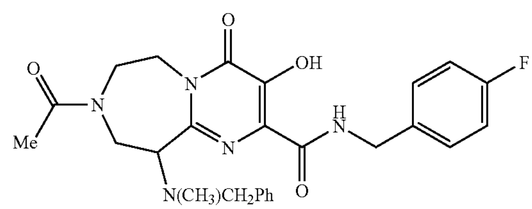 | 494 |
| 142. (+) N-(2-{[(3-chlorobenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 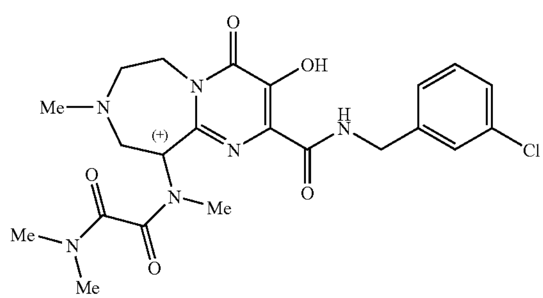 | 491 |
| 143. (−) N-(2-{[(3-chlorobenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 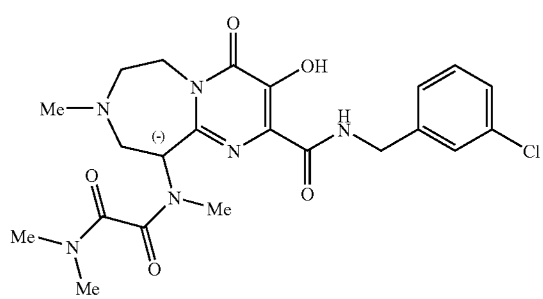 | 491 |

-continued

| Compound (Preparative Method) | Structure | M + 1 |
|---|---|---|
| 144. (+) N-(2-{[(3-chloro-4-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme F) | 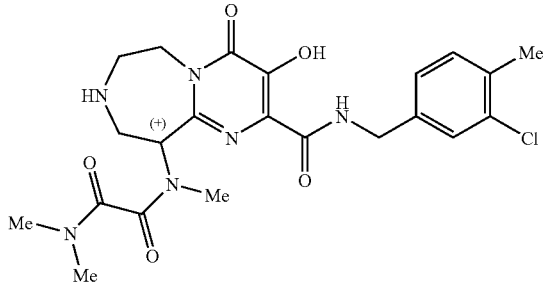 | 490 |
| 145. (−) N-(2-{[(3-chloro-4-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme F) | 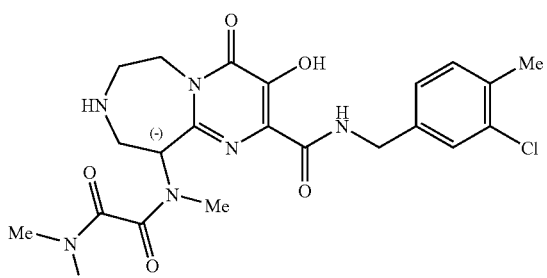 | 490 |
| 146. (−) N-(2-{[(4-fluoro-3-methylbenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 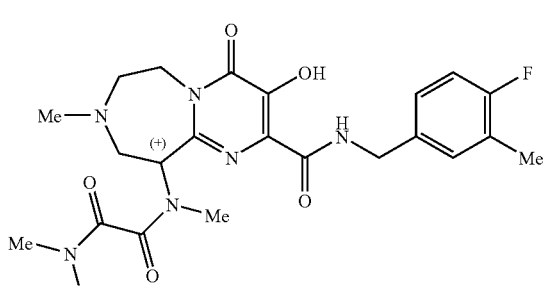 | 489 |
| 147. (+) N-(2-{[(4-fluoro-3-methylbenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 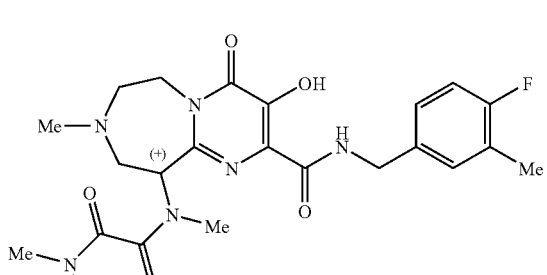 | 489 |
| 148. (+) N-(8-ethyl-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme E) | 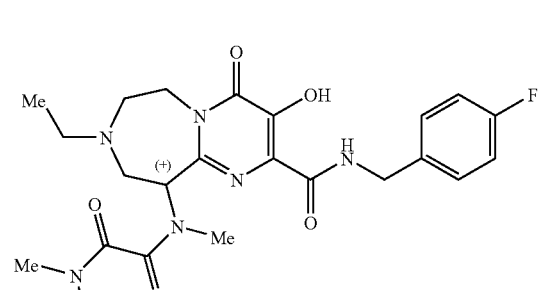 | 490 |

| Compound (Preparative Method) | Structure | M + 1 |
|---|---|---|
| 149. (−) N-(8-ethyl-2-{[(4-fluorobenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme E) | 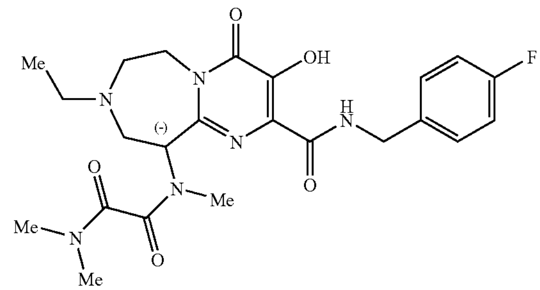 | 490 |
| 150. N-ethyl-N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N,N-dimethylethanediamide (TFA salt) (Scheme E) | 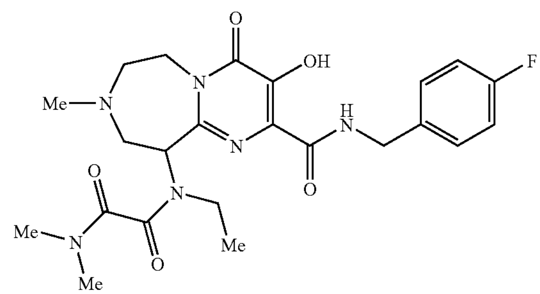 | 490 |
| 151. (−) N-(4-fluorobenzyl)-3-hydroxy-8-methyl-10-{methyl[(5-methyl-1,3,4-oxadiazol-2-yl)carbonyl]amino}-4-oxo-4,6,7,8,9,10-hexahydropyrimido[1,2-d][1,4]diazepine-2-carboxamide (TFA salt) (Scheme E) | 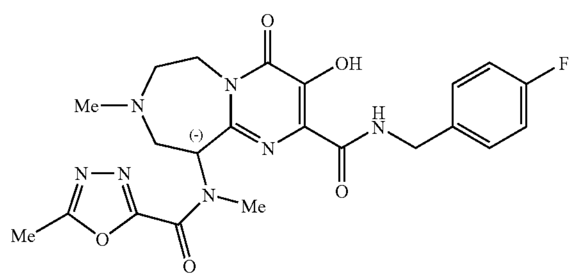 | 486 |
| 152. (+) N-(4-fluorobenzyl)-3-hydroxy-8-methyl-10-{methyl[(5-methyl-1,3,4-oxadiazol-2-yl)carbonyl]amino}-4-oxo-4,6,7,8,9,10-hexahydropyrimido[1,2-d][1,4]diazepine-2-carboxamide (TFA salt) (Scheme E) | 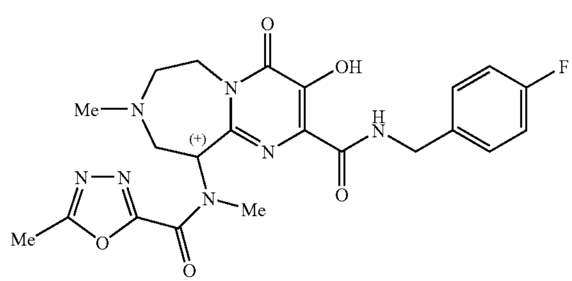 | 486 |
| 153. 10-[[(dimethylamino)sulfonyl](methyl)amino]-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 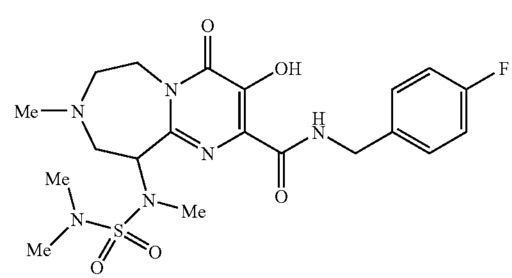 | 484 |

-continued

| Compound (Preparative Method) | Structure | M + 1 |
|---|---|---|
| 154. (+) N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 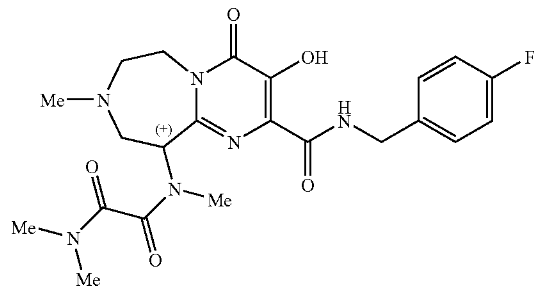 | 475 |
| 155. (−) N-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N,N',N'-trimethylethanediamide (TFA salt) (Scheme E) | 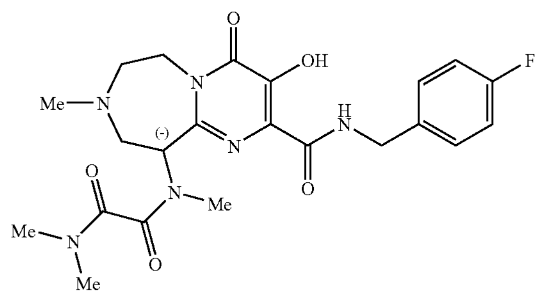 | 475 |
| 156. (+) N-(2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme F) | 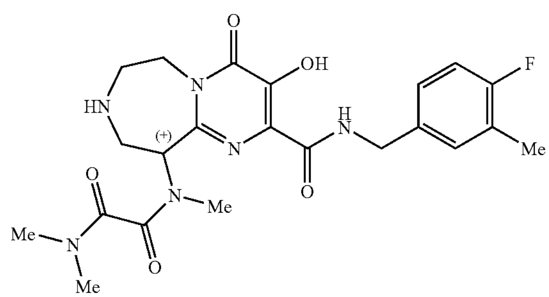 | 475 |
| 157. (−) N-(2-{[(4-fluoro-3-methylbenzyl)amino]carbonyl}-3-hydroxy-4-oxo-4,6,7,8,9,10-hexahydropyrimido[1,2-d][1,4]diazepin-10-yl)-N,N',N'-trimethylethanediamide (TFA salt) (Scheme F) | 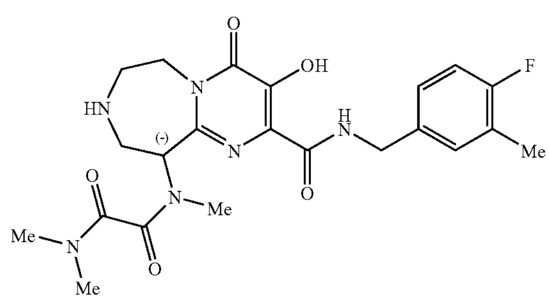 | 475 |
| 158. 11-[(dimethylamino)(oxo)acetyl]-N-(4-fluorobenzyl)-3-hydroxy-4-oxo-6,7,9,10,11,12-hexahydro-4H-8,12-methanopyrimido[1,2-a][1,4,7]triazonine-2-carboxamide (TFA salt) (Scheme E) | 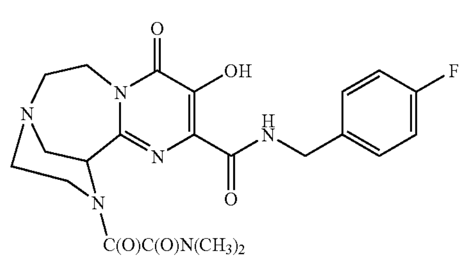 | 473 |

| Compound (Preparative Method) | Structure | M + 1 |
|---|---|---|
| 159. 10-[benzyl(methyl)amino]-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 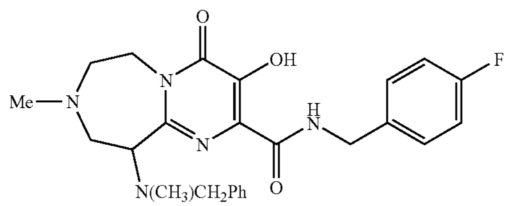 | 467 |
| 160. N'-(2-{[(4-fluorobenzyl)amino]carbonyl}-3-hydroxy-8-methyl-4-oxo-4,6,7,8,9,10-hexahydropyrimido[1,2-d][1,4]diazepin-10-yl)-N,N-dimethylethanediamide (TFA salt) (Scheme D) | 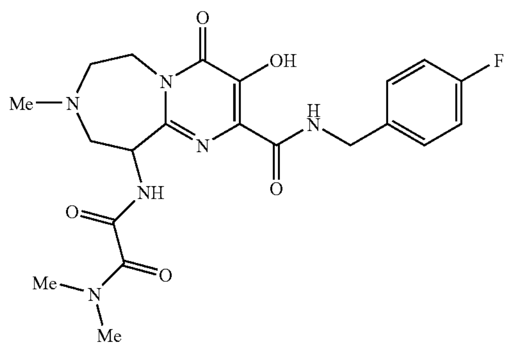 | 461 |
| 161. 10-[acetyl(isobutyl)amino]-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 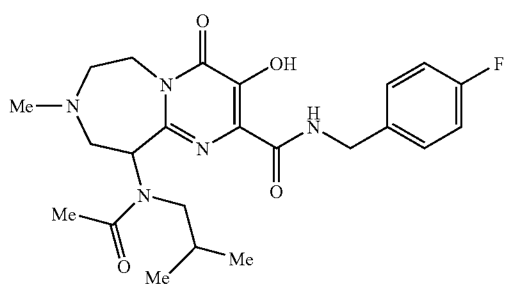 | 461 |
| 162. 10-[(cyclohexylmethyl)amino]-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 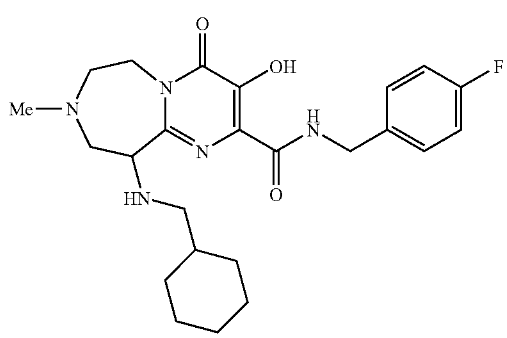 | 459 |
| 163. N-(4-fluorobenzyl)-3-hydroxy-8-methyl-10-[methyl(methylsulfonyl)amino]-4-oxo-4,6,7,8,9,10-hexahydropyrimido[1,2-d][1,4]diazepine-2-carboxamide (TFA salt) (Scheme D) | 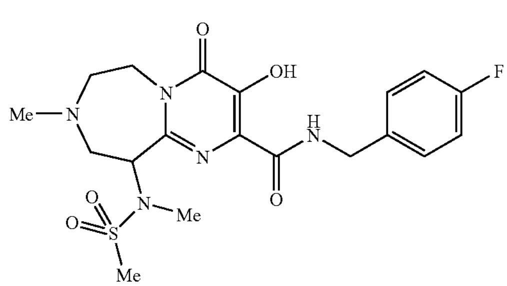 | 454 |

| Compound (Preparative Method) | Structure | M + 1 |
|---|---|---|
| 164. 10-(benzylamino)-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 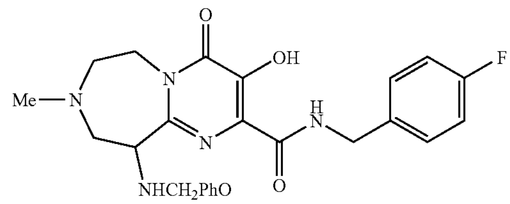 | 452 |
| 165. N-(4-fluorobenzyl)-3-hydroxy-8-methyl-10-[(methylsulfonyl)amino]-4-oxo-4,6,7,8,9,10-hexahydropyrimido[1,2-d][1,4]diazepine-2-carboxamide (TFA salt) (Scheme D) | 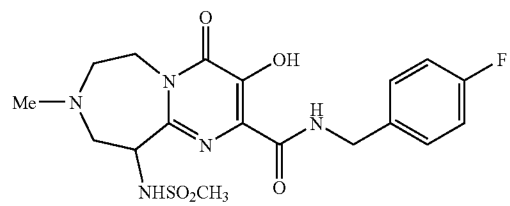 | 440 |
| 166. methyl (2-{[(4-fluorobenzyl)amino]carbonyl}-3-hydroxy-8-methyl-4-oxo-4,6,7,8,9,10-hexahydropyrimido[1,2-d][1,4]diazepin-10-yl)methylcarbamate (TFA salt) (Scheme D) | 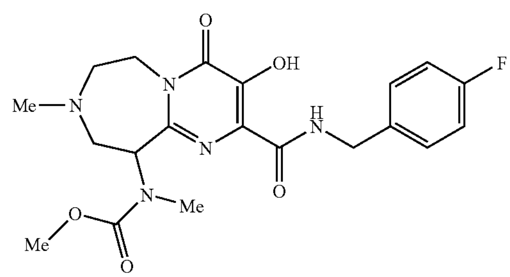 | 434 |
| 167. 8-[(dimethylamino)(oxo)acetyl]-N-(4-fluorobenzyl)-3-hydroxy-4-oxo-4,6,7,8,9,10-hexahydropyrimido[1,2-d][1,4]diazepine-2-carboxamide (Scheme H) | 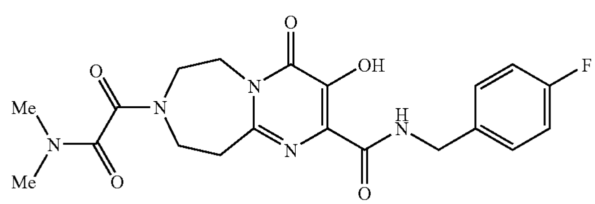 | 432 |
| 168. 8-benzyl-N-(4-fluorobenzyl)-3-hydroxy-4-oxo-4,6,7,8,9,10-hexahydropyrimido[1,2-d][1,4]diazepine-2-carboxamide (TFA salt) (Scheme H) | 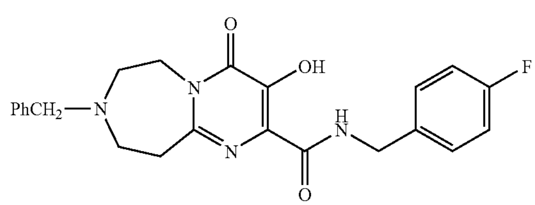 | 423 |
| 169. N-(4-fluorobenzyl)-3-hydroxy-10-(isobutylamino)-8-methyl-4-oxo-4,6,7,8,9,10-hexahydropyrimido[1,2-d][1,4]diazepine-2-carboxamide (TFA salt) (Scheme D) | 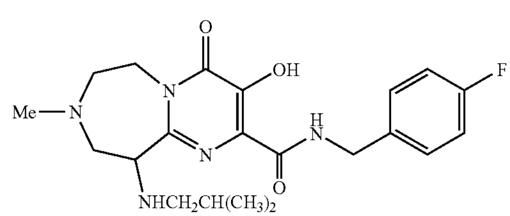 | 418 |

-continued

| Compound (Preparative Method) | Structure | M + 1 |
|---|---|---|
| 170. 10-[acetyl(methyl)amino]-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 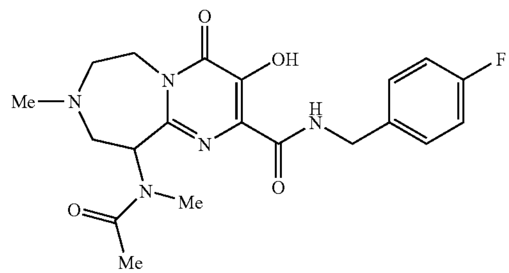 | 418 |
| 171. N-(4-fluorobenzyl)-3-hydroxy-8-(methylsulfonyl)-4-oxo-4,6,7,8,9,10-hexahydropyrimido[1,2-d][1,4]diazepine-2-carboxamide (Scheme H) | 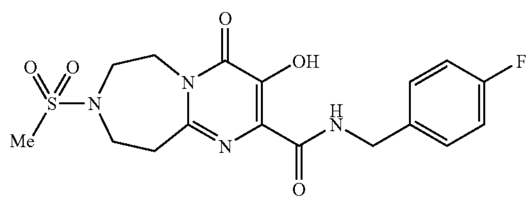 | 411 |
| 172. 10-(acetylamino)-N-(4-fluorobenzyl)-3-hydroxy-8-methyl-4-oxo-4,6,7,8,9,10-hexahydropyrimido[1,2-d][1,4]diazepine-2-carboxamide (TFA salt) (Scheme D) | 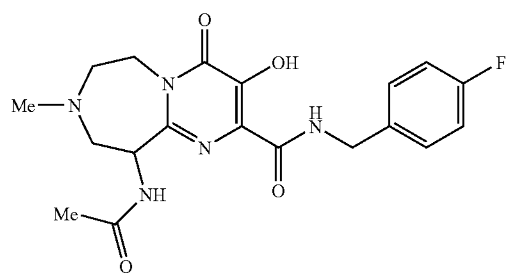 | 404 |
| 173. N-(4-fluorobenzyl)-3-hydroxy-11-methyl-4,10-dioxo-6,7,9,10,11,12-hexahydro-4H-8,12-methanopyrimido[1,2-a][1,4,7]triazonine-2-carboxamide (TFA salt) (Scheme D) | 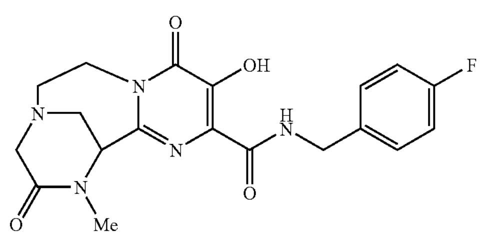 | 402 |
| 174. 8-acetyl-N-(4-fluorobenzyl)-3-hydroxy-4-oxo-4,6,7,8,9,10-hexahydropyrimido[1,2-d][1,4]diazepine-2-carboxamide (Scheme H) | 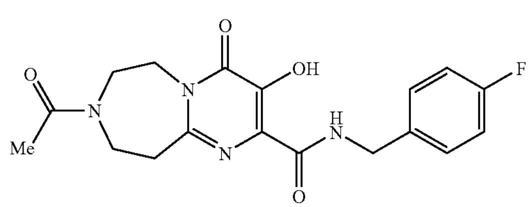 | 375 |
| 175. N-(4-fluorobenzyl)-3-hydroxy-10,10-dimethyl-4-oxo-4,6,7,8,9,10-hexahydropyrimido[1,2-a][1,4]diazepine-2-carboxamide (TFA salt) (Scheme C) | 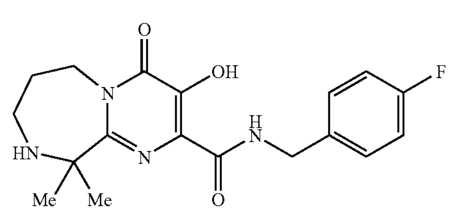 | 361 |

| Compound (Preparative Method) | Structure | M + 1 |
|---|---|---|
| 176. N-(4-fluorobenzyl)-3-hydroxy-9,10,10-trimethyl-4-oxo-4,6,7,8,9,10-hexahydropyrimido[1,2-a][1,4]diazepine-2-carboxamide (TFA salt) (Scheme C) | 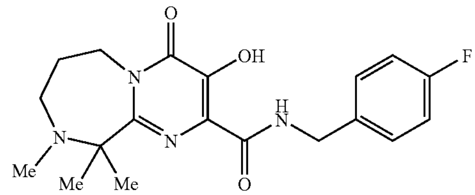 | 375 |
| 177. N-(4-fluorobenzyl)-3-hydroxy-4-oxo-6,7,9,10-tetrahydro-4H-pyrimido[1,2-d][1,4]oxazepine-2-carboxamide (Scheme I) | 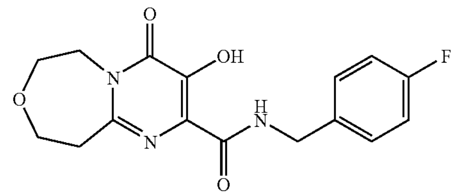 | 334 |
| 178. 10-(dimethylamino)-N-(4-fluorobenzyl)-3-hydroxy-4-oxo-6,7,9,10-tetrahydro-4H-pyrimido[1,2-d][1,4]oxazepine-2-carboxamide (TFA salt) (Scheme I) | 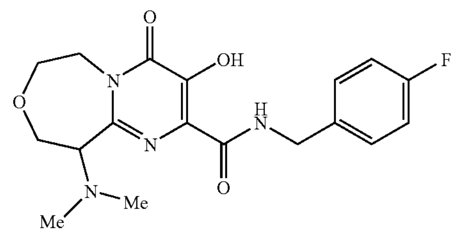 | 377 |
| 179. 10-[acetyl(methyl)amino]-N-(4-fluorobenzyl)-3-hydroxy-4-oxo-6,7,9,10-tetrahydro-4H-pyrimido[1,2-d][1,4]oxazepine-2-carboxamide (Scheme I) | 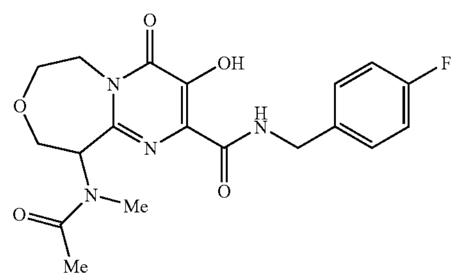 | 405 |
| 180. (+) N-(2-{[(4-fluorobenzyl)amino]carbonyl}-3-hydroxy-4-oxo-6,7,9,10-tetrahydro-4H-pyrimido[1,2-d][1,4]oxazepin-10-yl)-N,N',N'-trimethylethanediamide (Scheme I) | 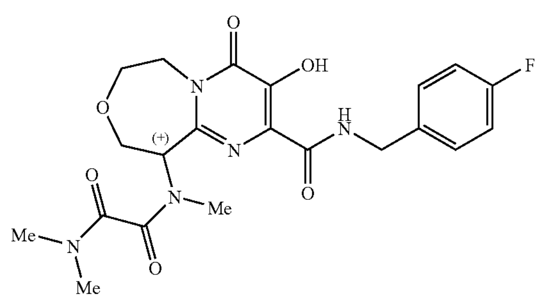 | 462 |
| 181. (−) N-(2-{[(4-fluorobenzyl)amino]carbonyl}-3-hydroxy-4-oxo-6,7,9,10-tetrahydro-4H-pyrimido[1,2-d][1,4]oxazepin-10-yl)-N,N',N'-trimethylethanediamide (Scheme I) | 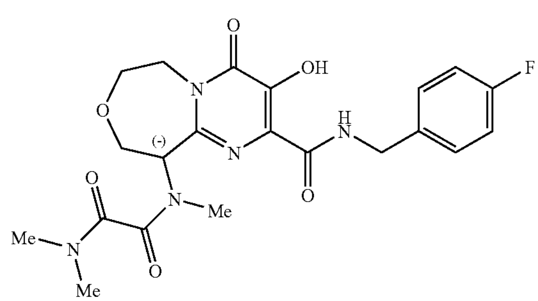 | 462 |

-continued

| Compound (Preparative Method) | Structure | M + 1 |
|---|---|---|
| 182. 10-[[(dimethylamino)sulfonyl](methyl)amino]-N-(4-fluorobenzyl)-3-hydroxy-4-oxo-6,7,9,10-tetrahydro-4H-pyrimido[1,2-d][1,4]oxazepine-2-carboxamide (Scheme I) | 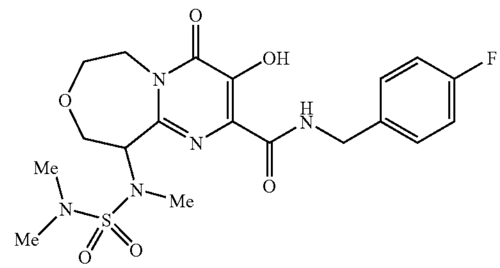 | 470 |
| 183. N-(4-fluorobenzyl)-3-hydroxy-10-{methyl[(5-methyl-1,3,4-oxadiazol-2-yl)carbonyl]amino}-4-oxo-6,7,9,10-tetrahydro-4H-pyrimido[1,2-d][1,4]oxazepine-2-carboxamide (Scheme I) | 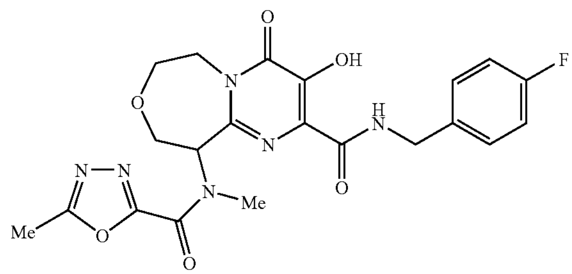 | 473 |
| 184. N-(4-fluorobenzyl)-3-hydroxy-10-{methyl[(4-methylpiperazin-1-yl)(oxo)acetyl]amino}-4-oxo-6,7,9,10-tetrahydro-4H-pyrimido[1,2-d][1,4]oxazepine-2-carboxamide (TFA salt) (Scheme I) | 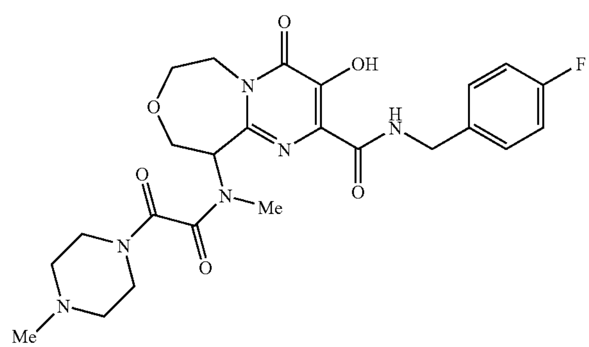 | 518 |
| 185. N-(4-fluorobenzyl)-3-hydroxy-10-{methyl[(4-methylpiperazin-1-yl)sulfonyl]amino}-4-oxo-6,7,9,10-tetrahydro-4H-pyrimido[1,2-d][1,4]oxazepine-2-carboxamide (TFA salt) (Scheme I) | 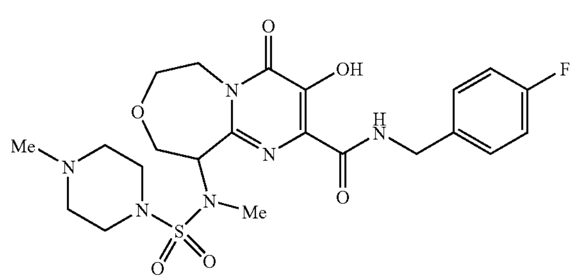 | 526 |

Example 31

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds in Table 1 can be similarly prepared.

Example 32

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds in Table 1 were tested in the integrase assay and found to have $IC_{50}$ values of less than about 10 micromolar.

Further description on conducting the assay using preassembled complexes is found in Wolfe, A. L. et al., J. Virol. 1996, 70: 1424-1432, Hazuda et al., J. Virol. 1997, 71: 7005-7011; Hazuda et al., Drug Design and Discovery 1997, 15: 17-24; and Hazuda et al., Science 2000 287: 646-650.

Example 33

Assay for Inhibition of HIV Replication

Assays for the inhibition of acute HIV infection of T-lymphoid cells (alternatively referred to herein as the "spread assay") were conducted in accordance with Vacca, J. P. et al., Proc. Natl. Acad. Sci. USA 1994, 91: 4096. Representative compounds of the present invention exhibit inhibition of HIV replication in this assay. For example, compounds 1, 2, 5, 6, 9, 27, 29, 30, 32, 35-39, 42-63, 65-92, 106-157, 160, 161, 163, 166, 170, 175, 176 and 179-185 in Table 1 were found to have $CIC_{95}$ values of less than 1 micromolar, and compounds 11, 12, 15-19, 21-23, 28, 64, 105, 159, 169 were found to have $CIC_{95}$ values in a range from 1 to 10 micromolar. The other compounds in Table 1 were tested in the spread assay up to 1 micromolar, but specific $IC_{95}$ values were not obtained; i.e., the $IC_{95}$ values were greater than 1 micromolar. It is believed, however, that the $IC_{95}$ values of these compounds would be less than about 50 micromolar.

Example 34

Cytotoxicity

Cytotoxicity was determined by microscopic examination of the cells in each well in the spread assay, wherein a trained analyst observed each culture for any of the following morphological changes as compared to the control cultures: pH imbalance, cell abnormality, cytostatic, cytopathic, or crystallization (i.e., the compound is not soluble or forms crystals in the well). The toxicity value assigned to a given compound is the lowest concentration of the compound at which one of the above changes is observed. Representative compounds of the present invention that were tested in the spread assay (see Example 33) were examined for cytotoxicity. For example, compounds 11, 12, 15-19, 21-23, 28, 64, 105, 159, 169 in Table 1 were tested up to 10 micromolar and exhibited no toxicity, and the other compounds in Table 1 were tested up to 1 micromolar and exhibited no toxicity.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of formula:

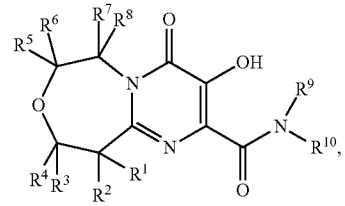

or a pharmaceutically acceptable salt thereof, wherein:
$R^1$ is:
- (1) $C_{1-6}$ haloalkyl,
- (2) $C_{1-6}$ alkyl substituted with V, wherein V is OH, O—$C_{1-6}$ alkyl, O—$C_{1-6}$ haloalkyl, $SR^A$, $S(O)R^A$, $SO_2R^A$, $N(R^D)R^E$, $C(O)N(R^D)R^E$, $N(R^A)$—C(O)C(O)—$N(R^D)R^E$, $N(R^A)$—C(O)$R^B$, $N(R^A)$—$SO_2R^B$, $N(R^A)$—$C_{1-6}$ alkylene-$SO_2R^B$, $N(R^A)C(O)$—$C_{1-6}$ alkylene-$SO_2R^B$, $N(R^A)$—$SO_2N(R^D)R^E$, $N(R^A)$—$CO_2R^B$, or $N(R^A)$—C(O)N(R^D)R^E$,
- (3) $C_{1-6}$ alkyl substituted with W, wherein W is CycA, AryA, HetA, O—$C_{1-6}$ alkylene-CycA, O—$C_{1-6}$ alkylene-AryA, O—$C_{1-6}$ alkylene-HetA, $S(O)_j$—$C_{1-6}$ alkylene-CycA, $S(O)_j$—$C_{1-6}$ alkylene-AryA, $S(O)_j$—$C_{1-6}$ alkylene-HetA, $N(R^A)$—C(O)-AryA, or $N(R^A)$—C(O)—HetA,
- (4) $N(R^A)$—$SO_2R^B$,
- (5) $N(R^A)$—$SO_2N(R^D)R^E$,
- (6) $N(R^A)$—$CO_2R^B$,
- (7) $N(R^D)R^E$,
- (8) $N(R^C)R^A$,
- (9) $N(R^A)$—C(O)$R^B$,
- (10) $N(R^C)$—C(O)$R^A$,
- (11) $S(O)_jR^F$,
- (12) $OR^F$,
- (13) CycA,
- (14) AryA,
- (15) HetA,
- (16) $N(R^A)$—C(O)-CycA,
- (17) $N(R^A)$—C(O)-AryA,
- (18) $N(R^A)$—C(O)—HetA,
- (19) $N(R^A)$—C(O)—$N(R^D)R^E$,
- (20) $N(R^C)$—C(O)-CycA,
- (21) $N(R^C)$—C(O)-AryA,
- (22) $N(R^C)$—C(O)—HetA,
- (23) $N(R^C)$—C(O)—$N(R^D)R^E$,
- (24) $N(R^A)$—C(O)C(O)-CycA,
- (25) $N(R^A)$—C(O)C(O)-AryA,
- (26) $N(R^A)$—C(O)C(O)—HetA,
- (27) $N(R^A)$—C(O)C(O)—$N(R^D)R^E$,
- (28) $N(R^C)$—C(O)C(O)-CycA,
- (29) $N(R^C)$—C(O)C(O)-AryA,
- (30) $N(R^C)$—C(O)C(O)—HetA, or
- (31) $N(R^C)$—C(O)C(O)—$N(R^D)R^E$;

each j is independently an integer equal to zero, 1, or 2;

$R^2$ is H or $C_{1-6}$ alkyl; or alternatively $R^1$ and $R^2$ together with the ring carbon atom to which they are both attached form (i) a 3- to 7-membered saturated carbocyclic ring or (ii) a 4- to 7-membered saturated heterocyclic ring containing 1 or 2 heteroatoms independently selected from N, O and S, where independently each N is optionally substituted with $C_{1-6}$ alkyl and each S is optionally oxidized to S(O) or S(O)$_2$;

$R^3$ is independently H or $C_{1-6}$ alkyl, and $R^4$ is independently H or $C_{1-6}$ alkyl; or alternatively $R^3$ and $R^4$ attached to the same carbon atom together form oxo or thioxo;

$R^5$ is independently H or $C_{1-6}$ alkyl, and $R^6$ is independently H or $C_{1-6}$ alkyl; or alternatively $R^5$ and $R^6$ attached to the same carbon atom together form oxo or thioxo;

$R^7$ is H or $C_{1-6}$ alkyl;

$R^8$ is H or $C_{1-6}$ alkyl; or alternatively $R^7$ and $R^8$ together form oxo or thioxo;

$R^9$ is H or $C_{1-6}$ alkyl;

$R^{10}$ is $C_{1-6}$ alkyl substituted with CycC, AryC or HetC;

each $R^A$ is independently H or $C_{1-6}$ alkyl;

each $R^B$ is independently H or $C_{1-6}$ alkyl;

$R^C$ is $C_{1-6}$ alkyl substituted with CycA, AryA, or HetA;

each $R^D$ and $R^E$ are each independently H or $C_{1-6}$ alkyl, or together with the nitrogen to which they are both attached form a 4- to 7-membered saturated heterocyclic ring optionally containing a heteroatom in addition to the nitrogen attached to $R^D$ and $R^E$ selected from N, O, and S, where the S is optionally oxidized to S(O) or S(O)$_2$, and wherein the saturated heterocyclic ring is optionally substituted with 1 or 2 substituents each of which is independently $C_{1-6}$ alkyl or S(O)$_2$—$C_{1-6}$ alkyl;

$R^F$ is $C_{1-6}$ alkyl;

each CycA is independently $C_{3-8}$ cycloalkyl which is optionally substituted with a total of from 1 to 6 substituents, wherein:
  (i) from zero to 6 substituents are each independently:
    (1) halogen,
    (2) CN
    (3) $C_{1-6}$ alkyl,
    (4) OH,
    (5) O—$C_{1-6}$ alkyl,
    (6) $C_{1-6}$ haloalkyl, or
    (7) O—$C_{1-6}$ haloalkyl, and
  (ii) from zero to 2 substituents are each independently:
    (1) CycD,
    (2) AryD,
    (3) HetD, or
    (4) $C_{1-6}$ alkyl substituted with CycD, AryD, or HetD;

CycC independently has the same definition as CycA;

each AryA is independently aryl which is optionally substituted with a total of from 1 to 5 substituents, wherein:
  (i) from zero to 5 substituents are each independently:
    (1) $C_{1-6}$ alkyl,
    (2) $C_{1-6}$ alkyl substituted with OH, O—$C_{1-6}$ alkyl, O—$C_{1-6}$ haloalkyl, CN, NO$_2$, N($R^A$)$R^B$, C(O)N($R^A$)$R^B$, C(O)$R^A$, CO$_2R^A$, S$R^A$, S(O)$R^A$, S(O)$_2R^A$, S(O)$_2$N($R^A$)$R^B$, N($R^A$)C(O)$R^B$, N($R^A$)CO$_2R^B$, N($R^A$)S(O)$_2R^B$, N($R^A$)S(O)$_2$N($R^A$)$R^B$, OC(O)N($R^A$)$R^B$, N($R^A$)C(O)N($R^A$)$R^B$, or N($R^A$)C(O)C(O)N($R^A$)$R^B$,
    (3) O—$C_{1-6}$ alkyl,
    (4) $C_{1-6}$ haloalkyl,
    (5) O—$C_{1-6}$ haloalkyl,
    (6) OH,
    (7) halogen,
    (8) CN,
    (9) NO$_2$,
    (10) N($R^A$)$R^B$,
    (11) C(O)N($R^A$)$R^B$,
    (12) C(O)$R^A$,
    (13) C(O)—$C_{1-6}$ haloalkyl,
    (14) C(O)O$R^A$,
    (15) OC(O)N($R^A$)$R^B$,
    (16) S$R^A$,
    (17) S(O)$R^A$,
    (18) S(O)$_2R^A$,
    (19) S(O)$_2$N($R^A$)$R^B$,
    (20) N($R^A$)S(O)$_2R^B$,
    (21) N($R^A$)S(O)$_2$N($R^A$)$R^B$,
    (22) N($R^A$)C(O)$R^B$,
    (23) N($R^A$)C(O)N($R^A$)$R^B$,
    (24) N($R^A$)C(O)—C(O)N($R^A$)$R^B$, or
    (25) N($R^A$)CO$_2R^B$, and
  (ii) from zero to 2 substituents are each independently:
    (1) CycD,
    (2) AryD,
    (3) HetD, or
    (4) $C_{1-6}$ alkyl substituted with CycD, AryD, or HetD;

AryC independently has the same definition as AryA;

each HetA is independently a heteroaryl which is optionally substituted with a total of from 1 to 5 substituents, wherein:
  (i) from zero to 5 substituents are each independently:
    (1) $C_{1-6}$ alkyl,
    (2) $C_{1-6}$ alkyl substituted with OH, O—$C_{1-6}$ alkyl, O—$C_{1-6}$ haloalkyl, CN, NO$_2$, N($R^A$)$R^B$, C(O)N($R^A$)$R^B$, C(O)$R^A$, CO$_2R^A$, S$R^A$, S(O)$R^A$, S(O)$_2R^A$, S(O)$_2$N($R^A$)$R^B$, N($R^A$)C(O)$R^B$, N($R^A$)CO$_2R^B$, N($R^A$)S(O)$_2R^B$, N($R^A$)S(O)$_2$N($R^A$)$R^B$, OC(O)N($R^A$)$R^B$, N($R^A$)C(O)N($R^A$)$R^B$, or N($R^A$)C(O)C(O)N($R^A$)$R^B$,
    (3) O—$C_{1-6}$ alkyl,
    (4) $C_{1-6}$ haloalkyl,
    (5) O—$C_{1-6}$ haloalkyl,
    (6) OH,
    (7) oxo,
    (8) halogen,
    (9) CN,
    (10) NO$_2$,
    (11) N($R^A$)$R^B$,
    (12) C(O)N($R^A$)$R^B$,
    (13) C(O)$R^A$,
    (14) C(O)—$C_{1-6}$ haloalkyl,
    (15) C(O)O$R^A$,
    (16) OC(O)N($R^A$)$R^B$,
    (17) S$R^A$,
    (18) S(O)$R^A$,
    (19) S(O)$_2R^A$,
    (20) S(O)$_2$N($R^A$)$R^B$,
    (21) N($R^A$)S(O)$_2R^B$,
    (22) N($R^A$)S(O)$_2$N($R^A$)$R^B$,
    (23) N($R^A$)C(O)$R^B$,
    (24) N($R^A$)C(O)N($R^A$)$R^B$,
    (25) N($R^A$)C(O)—C(O)N($R^A$)$R^B$, or
    (26) N($R^A$)CO$_2R^B$, and
  (ii) from zero to 2 substituents are each independently:
    (1) CycD,
    (2) AryD,
    (3) HetD, or
    (4) $C_{1-6}$ alkyl substituted with CycD, AryD, or HetD;

HetC independently has the same definition as HetA;

each CycD is independently a $C_{3-8}$ cycloalkyl which is optionally substituted with from 1 to 4 substituents each of which is independently halogen, $C_{1-6}$ alkyl, OH, O—$C_{1-6}$ alkyl, or $C_{1-6}$ haloalkyl;

each AryD is independently phenyl or naphthyl, wherein the phenyl or naphthyl is optionally substituted with from 1 to 5 substituents each of which is independently any one of the substituents (1) to (25) as set forth above in part (i) of the definition of AryA;

each HetD is independently a 5- or 6-membered heteroaromatic ring containing from 1 to 4 heteroatoms independently selected from N, O and S, wherein the heteroaromatic ring is optionally substituted with from 1 to 4 substituents each of which is independently halogen, $C_{1-6}$ alkyl, $C_{1-6}$ haloalkyl, O—$C_{1-6}$ alkyl, O—$C_{1-6}$ haloalkyl, or hydroxy;

each aryl is independently (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic;

each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$.

2. A compound according to claim 1 or a pharmaceutically acceptable salt thereof, wherein:

$R^9$ is H; and $R^{10}$ is:
  (1) $CH_2$-phenyl or $CH_2$-HetC, wherein the phenyl is optionally substituted with a total of from 1 to 3 substituents, wherein (i) from zero to 3 substituents are each independently bromo, chloro, fluoro, $C_{1-4}$ alkyl, $CF_3$, $C(O)NH_2$, $C(O)NH(C_{1-4}$ alkyl), $C(O)N(C_{1-4}$ alkyl$)_2$, S—$C_{1-4}$ alkyl, $SO_2$—$C_{1-4}$ alkyl, or $SO_2N(C_{1-4}$ alkyl$)_2$, and (ii) from zero to 1 substituent is a heteroaromatic selected from the group consisting of imidazolyl, triazolyl, oxadiazolyl, pyrrolyl, and pyrazolyl, wherein the heteroaomatic ring is optionally substituted with 1 or 2 substituents each of which is independently Cl, Br, F, $C_{1-4}$ alkyl, $CF_3$, O—$C_{1-4}$ alkyl, $OCF_3$, or OH,
  (2) $CH_2$-HetC, wherein HetC is a heteroaryl which is (i) a 5- or 6-membered heteroaromatic ring containing a total of from 1 to 4 heteroatoms independently selected from 1 to 4N atoms, zero to 1 O atom, and zero to 1 S atom, or (ii) a 9 or 10-membered bicyclic, fused ring system in which one ring is a benzene ring and the other ring is a 5- or 6-membered heteroaromatic ring containing from 1 to 3 heteroatoms independently selected from zero to 3 N atoms, zero to 1 O atom, and zero to 1 S atom, wherein the heteroaryl is optionally substituted with from 1 to 3 substituents each of which is independently Cl, Br, F, or $C_{1-4}$ alkyl.

3. A compound according to claim 1, or a pharmaceutically acceptable salt thereof, wherein:

$R^1$ is:
  (1) $C_{1-4}$ alkyl substituted with V, wherein V is OH, O—$C_{1-4}$ alkyl, $SR^A$, $S(O)R^A$, $SO_2R^A$, $N(R^D)R^E$, $C(O)N(R^D)R^E$, $N(R^A)$—$C(O)C(O)$—$N(R^D)R^E$, $N(R^A)$—$C(O)R^B$, $N(R^A)$—$SO_2R^B$, $N(R^A)$—$C_{1-4}$ alkylene-$SO_2R^B$, $N(R^A)C(O)$—$C_{1-4}$ alkylene-$SO_2R^B$, $N(R^A)$—$SO_2N(R^D)R^E$, or $N(R^A)$—$CO_2R^B$,
  (2) $C_{1-4}$ alkyl substituted with W, wherein W is CycA, AryA, HetA, O—$C_{1-4}$ alkylene-AryA, O—$C_{1-4}$ alkylene-HetA, or $N(R^A)$—$C(O)$—HetA,
  (3) $N(R^A)$—$SO_2R^B$,
  (4) $N(R^A)$—$SO_2N(R^D)R^E$,
  (5) $N(R^A)$—$CO_2R^B$,
  (6) $N(R^D)R^E$,
  (7) $N(R^C)R^A$,
  (8) $N(R^A)$—$C(O)R^B$,
  (9) $N(R^C)$—$C(O)R^A$,
  (10) $SR^F$, $S(O)R^F$, or $S(O)_2R^F$,
  (11) $N(R^A)$—$C(O)$—HetA,
  (12) $N(R^C)$—$C(O)$—$N(R^D)R^E$, or
  (13) $N(R^A)$—$C(O)C(O)$—$N(R^D)R^E$, or
  (14) $N(R^C)$—$C(O)C(O)$—$N(R^D)R^E$;

$R^2$ is H or $C_{1-4}$ alkyl; or alternatively $R^1$ and $R^2$ together with the ring carbon atom to which they are both attached form (i) a 3- to 6-membered saturated carbocyclic ring or (ii) a 6-membered saturated heterocyclic ring containing 1 heteroatom selected from N, O and S, where the N is optionally substituted with $C_{1-4}$ alkyl and the S is optionally oxidized to S(O) or $S(O)_2$;

$R^3$ is independently H or $C_{1-4}$ alkyl, and $R^4$ is independently H or $C_{1-4}$ alkyl; or alternatively $R^3$ and $R^4$ attached to the same carbon atom together form oxo;

$R^5$ is independently H or $C_{1-4}$ alkyl, and $R^6$ is independently H or $C_{1-4}$ alkyl; or alternatively $R^5$ and $R^6$ attached to the same carbon atom together form oxo;

$R^7$ is H or $C_{1-4}$ alkyl;

$R^8$ is H or $C_{1-4}$ alkyl; or alternatively $R^7$ and $R^8$ together form oxo;

$R^9$ is H or $C_{1-4}$ alkyl;

$R^{10}$ is $C_{1-4}$ alkyl substituted with CycC, AryC or HetC;

each $R^A$ is independently H or $C_{1-4}$ alkyl;

each $R^B$ is independently H or $C_{1-4}$ alkyl;

$R^C$ is $C_{1-4}$ alkyl substituted with CycA, AryA, or HetA;

each $R^D$ and $R^E$ are independently H or $C_{1-4}$ alkyl, or together with the nitrogen to which they are both attached form a 5- or 6-membered saturated heterocyclic ring optionally containing a heteroatom in addition to the nitrogen attached to $R^D$ and $R^E$ selected from N, O, and S, where the S is optionally oxidized to S(O) or $S(O)_2$, and wherein the saturated heterocyclic ring is optionally substituted with 1 or 2 substituents each of which is independently $C_{1-4}$ alkyl or $S(O)_2$—$C_{1-4}$ alkyl;

$R^F$ is $C_{1-4}$ alkyl;

each CycA is independently a $C_{3-6}$ cycloalkyl which is optionally substituted with 1 or 2 substituents each of which is independently $C_{1-4}$ alkyl, OH, or O—$C_{1-4}$ alkyl;

CycC is a $C_{3-6}$ cycloalkyl which is optionally substituted with 1 or 2 substituents each of which is independently $C_{1-4}$ alkyl, OH, or O—$C_{1-4}$ alkyl;

each AryA is independently phenyl or naphthyl, wherein the phenyl or naphthyl is optionally substituted with from 1 to 3 substituents each of which is independently:
  (1) $C_{1-4}$ alkyl, which is optionally substituted with OH, O—$C_{1-4}$ alkyl, O—$C_{1-4}$ haloalkyl, CN, $N(R^A)R^B$, $C(O)N(R^A)R^B$, $C(O)R^A$, $CO_2R^A$, $SR^A$, $S(O)R^A$, $SO_2R^A$, or $SO_2N(R^A)R^B$,
  (2) O—$C_{1-4}$ alkyl,
  (3) $C_{1-4}$ haloalkyl,
  (4) O—$C_{1-4}$ haloalkyl, (5) OH,
(6) halogen,
(7) CN,
(8) NO$_2$,
(9) N(R$^A$)R$^B$,
(10) C(O)N(R$^A$)R$^B$,
(11) C(O)R$^A$,
(12) C(O)—C$_{1-4}$ haloalkyl,
(13) CO$_2$R$^A$,
(14) SR$^A$,
(15) S(O)R$^A$,
(16) SO$_2$R$^A$, or
(17) SO$_2$N(R$^A$)R$^B$;

AryC is phenyl or naphthyl, wherein the phenyl or naphthyl is:
(i) optionally substituted with from 1 to 3 substituents each of which is independently any one of the substituents (1) to (17) as set forth above in the definition of AryA, and
(ii) optionally substituted with:
(1) AryD,
(2) HetD,
(3) CycD, or
(4) C$_{1-4}$ alkyl substituted with CycD, AryD or HetD;

each HetA is independently a 5- or 6-membered heteroaromatic ring containing from 1 to 4 heteroatoms independently selected from zero to 4 N atoms, zero or 1 O atom, and zero or 1 S atom, wherein each N is optionally in the form of an oxide, and wherein the heteroaromatic ring is optionally substituted with from 1 to 3 substituents each of which is independently halogen, C$_{1-4}$ alkyl, or OH;

HetC is a 5- or 6-membered heteroaromatic ring containing from 1 to 4 heteroatoms independently selected from zero to 4 N atoms, zero or 1 O atom, and zero or 1 S atom, wherein each N is optionally in the form of an oxide, and wherein the heteroaromatic ring is:
(i) optionally substituted with from 1 to 3 substituents each of which is independently halogen, C$_{1-4}$ alkyl, or OH; and
(ii) optionally substituted with AryD, HetD, CycD, or C$_{1-4}$ alkyl substituted with AryD, HetD or CycD;

each CycD is independently a C$_{3-6}$ cycloalkyl which is optionally substituted with 1 or 2 substituents each of which is independently C$_{1-4}$ alkyl, OH, or O—C$_{1-4}$ alkyl;

each AryD is independently phenyl or naphthyl, wherein the phenyl or naphthyl is optionally substituted with from 1 to 3 substituents each of which is independently any one of the substituents (1) to (17) as set forth above in the definition of AryA; and each HetD is independently a 5- or 6-membered heteroaromatic ring containing from 1 to 4 heteroatoms independently selected from zero to 4N atoms, zero or 1 O atom, and zero or 1 S atom, wherein the heteroaromatic ring is optionally substituted with from 1 to 3 substituents each of which is independently halogen, C$_{1-4}$ alkyl, or OH.

4. A compound according to claim 3, or a pharmaceutically acceptable salt thereof, which is a compound of formula:

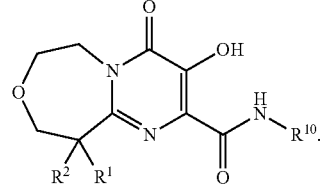

(VII)

5. A compound according to claim 4, or a pharmaceutically acceptable salt thereof, wherein
R$^1$ is N(R$^A$)—C(O)C(O)—N(R$^D$)R$^E$ or N(R$^C$)—C(O)C(O)—N(R$^D$)R$^E$; and
R$^2$ is H.

6. A compound, or a pharmaceutically acceptable salt thereof, which is a compound selected from the group consisting of:
N-(4-fluorobenzyl)-3-hydroxy-4-oxo-6,7,9,10-tetrahydro-4H-pyrimido[1,2-d][1,4]oxazepine-2-carboxamide;
10-(dimethylamino)-N-(4-fluorobenzyl)-3-hydroxy-4-oxo-6,7,9,10-tetrahydro-4H-pyrimido[1,2-d][1,4]oxazepine-2-carboxamide;
10-[acetyl(methyl)amino]-N-(4-fluorobenzyl)-3-hydroxy-4-oxo-6,7,9,10-tetrahydro-4H-pyrimido[1,2-d][1,4]oxazepine-2-carboxamide;
(+) N-(2-{[(4-fluorobenzyl)amino]carbonyl}-3-hydroxy-4-oxo-6,7,9,10-tetrahydro-4H-pyrimido[1,2-d][1,4]oxazepin-10-yl)-N,N',N'-trimethylethanediamide;
(−)N-(2-{[(4-fluorobenzyl)amino]carbonyl}-3-hydroxy-4-oxo-6,7,9,10-tetrahydro-4H-pyrimido[1,2-d][1,4]oxazepin-10-yl)-N,N',N'-trimethylethanediamide;
10-[[(dimethylamino)sulfonyl](methyl)amino]-N-(4-fluorobenzyl)-3-hydroxy-4-oxo-6,7,9,10-tetrahydro-4H-pyrimido[1,2-d][1,4]oxazepine-2-carboxamide;
N-(4-fluorobenzyl)-3-hydroxy-10-{methyl[(5-methyl-1,3,4-oxadiazol-2-yl)carbonyl]amino}-4-oxo-6,7,9,10-tetrahydro-4H-pyrimido[1,2-d][1,4]oxazepine-2-carboxamide;
N-(4-fluorobenzyl)-3-hydroxy-10-{methyl[(4-methylpiperazin-1-yl)(oxo)acetyl]amino}-4-oxo-6,7,9,10-tetrahydro-4H-pyrimido[1,2-d][1,4]oxazepine-2-carboxamide; and
N-(4-fluorobenzyl)-3-hydroxy-10-{methyl[(4-methylpiperazin-1-yl)sulfonyl]amino}-4-oxo-6,7,9,10-tetrahydro-4H-pyrimido[1,2-d][1,4]oxazepine-2-carboxamide.

7. A compound according to claim 6, or a pharmaceutically acceptable salt thereof, which is a compound selected from the group consisting of:
(+) N-(2-{[(4-fluorobenzyl)amino]carbonyl}-3-hydroxy-4-oxo-6,7,9,10-tetrahydro-4H-pyrimido[1,2-d][1,4]oxazepin-10-yl)-N,N',N'-trimethylethanediamide; and
(−)N-(2-{[(4-fluorobenzyl)amino]carbonyl}-3-hydroxy-4-oxo-6,7,9,10-tetrahydro-4H-pyrimido[1,2-d][1,4]oxazepin-10-yl)-N,N',N'-trimethylethanediamide.

8. A pharmaceutical composition comprising an effective amount of a compound according to claim 1, or a pharmaceutically acceptable salt thereof, and a pharmaceutically acceptable carrier.

9. A method for the treatment of infection by HIV or for the treatment or delay in the onset of AIDS in a subject in need thereof, which comprises administering to the subject an effective amount of the compound according to claim 1, or a pharmaceutically acceptable salt thereof.

10. A compound according to claim 3, or a pharmaceutically acceptable salt thereof, wherein $R^1$ is $N(R^A)$—C(O)C(O)—$N(R^D)R^E$ or $N(R^C)$—C(O)C(O)—$N(R^D)R^E$; and $R^2$ is H.

11. A compound according to claim 10, or a pharmaceutically acceptable salt thereof, wherein $R^{10}$ is $C_{1-4}$ alkyl substituted with AryC.

12. A compound according to claim 11, or a pharmaceutically acceptable salt thereof, wherein $R^9$ is H; and $R^{10}$ is 4-fluorobenzyl, 3-chloro-4-fluorobenzyl, 3-chloro-4-methylbenzyl, 4-fluoro-3-methylbenzyl, 3-chlorobenzyl, 4-fluoro-2-methylsulfonylbenzyl, 3-bromo-4-fluorobenzyl, 4-fluoro-2-[(methylamino)carbonyl]benzyl, 2-methylthiobenzyl, or 4-fluoro-2-[(3-methyl)-1,2,4-oxadiazol-5-yl]benzyl.

13. A compound of formula X, or a pharmaceutically acceptable salt thereof, which is:

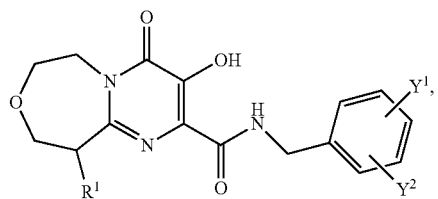
(X)

wherein:
$R^1$ is:
(1) H,
(2) $N(CH_3)$—$SO_2N(CH_3)_2$,
(3) $NH(CH_3)$,
(4) $NH(CH_2CH_3)$,
(5) $NH(CH_2CH(CH_3)_2)$,
(6) $N(CH_3)_2$,
(7) $N(CH_2CH_3)_2$,
(8) $N(CH_3)$—C(O)$CH_3$,
(9) $N(CH_2CH_3)$—C(O)$CH_3$,
(10) $N(CH_2CH(CH_3)_2)$—C(O)$CH_3$,

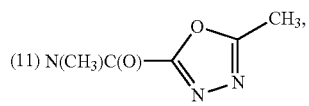

(12) N(H)—C(O)C(O)—$N(CH_3)_2$,
(13) $N(CH_3)$—C(O)C(O)—$N(CH_3)_2$,
(14) $N(CH_2CH_3)$—C(O)C(O)—$N(CH_3)_2$,
(15) $N(CH(CH_3)_2)$—C(O)C(O)—$N(CH_3)_2$,

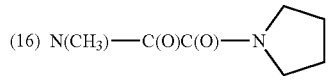
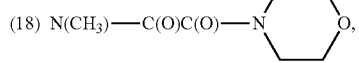
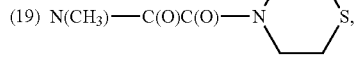
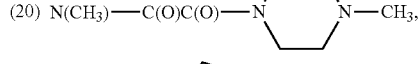
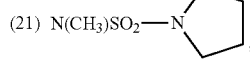
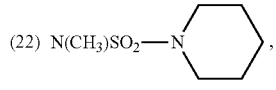
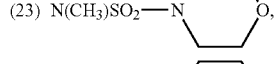
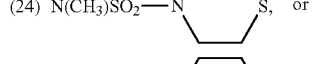
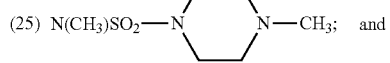

$Y^1$ and $Y^2$ are each independently H, Br, Cl, F, $CH_3$, C(O)$NH(CH_3)$, C(O)$N(CH_3)_2$, $SCH_3$, $SO_2CH_3$, or $SO_2N(CH_3)_2$.

14. A compound according to claim 13, or a pharmaceutically acceptable salt thereof, wherein $R^1$ is other than H.

* * * * *